(12) United States Patent
Lau et al.

(10) Patent No.: US 7,884,210 B2
(45) Date of Patent: Feb. 8, 2011

(54) UREIDO-THIAZOLE GLUCOKINASE ACTIVATORS

(75) Inventors: Jesper Lau, Farum (DK); Anthony Murray, Hellerup (DK); Per Vedso, Vaerlose (DK); Marit Kristiansen, Soborg (DK); Lone Jeppesen, Virum (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 11/994,862

(22) PCT Filed: Jul. 14, 2006

(86) PCT No.: PCT/EP2006/064289

§ 371 (c)(1), (2), (4) Date: Jul. 9, 2008

(87) PCT Pub. No.: WO2007/006814

PCT Pub. Date: Jan. 18, 2007

(65) Prior Publication Data

US 2009/0105482 A1    Apr. 23, 2009

(30) Foreign Application Priority Data

Jul. 14, 2005 (EP) .................... 05106449

(51) Int. Cl.
*C07D 277/00* (2006.01)
(52) U.S. Cl. ..................................... 548/185
(58) Field of Classification Search ................. 548/185
See application file for complete search history.

(56) References Cited

U.S. PATENT DOCUMENTS

| | | |
|---|---|---|
| 3,067,250 A | 12/1962 | Oja |
| 3,152,136 A | 10/1964 | Harris et al. |
| 3,317,534 A | 5/1967 | Nitta et al. |
| 3,551,442 A | 12/1970 | Guillot et al. |
| 3,734,923 A | 5/1973 | Dowding et al. |
| 3,862,163 A | 1/1975 | Boroschewski et al. |
| 3,874,873 A | 4/1975 | Volpp et al. |
| 3,887,709 A | 6/1975 | Brzozowski et al. |
| 3,967,950 A | 7/1976 | Kano et al. |
| 4,153,710 A | 5/1979 | Brzozowski et al. |
| 4,160,833 A | 7/1979 | Diel |
| 4,174,398 A | 11/1979 | Regel et al. |
| 4,175,081 A | 11/1979 | Driscoll |
| 4,183,856 A | 1/1980 | Makisumi et al. |
| 4,241,072 A | 12/1980 | Bolhofer |
| 4,243,404 A | 1/1981 | Kruger et al. |
| 4,405,644 A | 9/1983 | Kabbe et al. |
| 4,694,004 A | 9/1987 | Nakaguti et al. |
| 4,808,722 A | 2/1989 | Henrie |
| 5,262,415 A | 11/1993 | Takemoto et al. |
| 5,371,086 A | 12/1994 | Takemoto et al. |
| 5,556,969 A | 9/1996 | Chambers et al. |
| 5,846,985 A | 12/1998 | Murugesan |
| 5,846,990 A | 12/1998 | Murugesan et al. |
| 5,849,732 A | 12/1998 | Suzuki et al. |
| 5,849,769 A | 12/1998 | Lind et al. |
| 5,891,917 A | 4/1999 | Tang et al. |
| 5,935,993 A | 8/1999 | Tang et al. |
| 6,001,860 A | 12/1999 | Hamanaka |
| 6,140,343 A | 10/2000 | DeNinno et al. |
| 6,180,635 B1 | 1/2001 | Cheshire et al. |
| 6,225,346 B1 | 5/2001 | Tang et al. |
| 6,268,384 B1 | 7/2001 | Novak et al. |
| 6,271,248 B1 | 8/2001 | Murugesan et al. |
| 6,384,220 B2 | 5/2002 | Corbett et al. |
| 6,448,290 B1 | 9/2002 | Ohuchuida et al. |
| 6,486,184 B2 | 11/2002 | Kester et al. |
| 6,489,478 B1 | 12/2002 | DeNinno et al. |
| 6,500,817 B1 | 12/2002 | Fischer et al. |
| 6,559,168 B2 | 5/2003 | Marfat et al. |
| 6,608,218 B2 | 8/2003 | Kester et al. |
| 6,720,347 B2 | 4/2004 | Rawlins et al. |
| 6,720,427 B2 | 4/2004 | Sanner et al. |
| 6,784,198 B1 | 8/2004 | Pevarello et al. |
| 6,863,647 B2 | 3/2005 | Pevarello et al. |
| 6,875,760 B2 | 4/2005 | Lau et al. |
| 6,903,125 B2 | 6/2005 | Kontani et al. |
| 6,916,814 B2 | 7/2005 | Moss et al. |
| 6,936,629 B2 | 8/2005 | Chan Chun Kong et al. |
| 7,056,942 B2 | 6/2006 | Hildesheim et al. |
| 7,196,104 B2 | 3/2007 | Askew et al. |

(Continued)

FOREIGN PATENT DOCUMENTS

AU          29937          12/1972

(Continued)

OTHER PUBLICATIONS

Ferre, T. et al., "Evidence from Transgenic Mice that Glucokinase is Rate Limiting for Glucose Utilization in the Liver", The Faseb Journal, 1996, vol. 10, pp. 1213-1218.

(Continued)

*Primary Examiner*—Yong Chu
*Assistant Examiner*—Valerie Rodriguez-Garcia
(74) *Attorney, Agent, or Firm*—Rosemarie R. Wilk-Orescan

(57) ABSTRACT

The invention provides a compound of general formula (I)

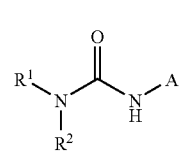

wherein the compounds are of the class ureido-thiazole glucokinase activators, useful for the treatment of various diseases, for example, type 2 diabetes.

26 Claims, No Drawings

U.S. PATENT DOCUMENTS

| | | | |
|---|---|---|---|
| 7,384,967 | B2 | 6/2008 | Polisetti et al. |
| 7,582,769 | B2 | 9/2009 | Murray et al. |
| 2002/0198200 | A1 | 12/2002 | Kester et al. |
| 2003/0171411 | A1 | 9/2003 | Kodra et al. |
| 2003/0220350 | A1 | 11/2003 | Lau et al. |
| 2004/0014789 | A1 | 1/2004 | Lau et al. |
| 2004/0014968 | A1 | 1/2004 | Bizzarro et al. |
| 2007/0054897 | A1 | 3/2007 | Murray et al. |
| 2009/0216013 | A1 | 8/2009 | Murray et al. |

FOREIGN PATENT DOCUMENTS

| | | |
|---|---|---|
| CA | 2416229 | 9/2007 |
| CN | 100506807 C | 7/2009 |
| DE | 1901501 | 8/1969 |
| DE | 2040580 | 4/1971 |
| DE | 2117807 | 10/1971 |
| DE | 2129418 | 12/1971 |
| DE | 2228890 | 12/1972 |
| DE | 2151766 | 4/1973 |
| DE | 2431801 | 1/1975 |
| DE | 2264983 | 10/1975 |
| DE | 2712630 | 9/1978 |
| EP | 0129408 | 12/1984 |
| EP | 0432040 | 6/1991 |
| EP | 0885890 | 12/1998 |
| EP | 0979823 | 2/2000 |
| EP | 1211246 | 6/2002 |
| EP | 1169312 | 10/2004 |
| FR | 2001083 | 9/1969 |
| FR | 7.428 M | 12/1969 |
| FR | 2215967 | 8/1974 |
| GB | 771147 | 3/1957 |
| GB | 1185540 | 3/1970 |
| GB | 1195672 | 6/1970 |
| GB | 1282308 | 7/1972 |
| GB | 1318291 | 5/1973 |
| HU | 0200396 | 7/2002 |
| JP | 01056660 | 3/1989 |
| JP | 64056660 | 3/1989 |
| JP | 4334374 | 11/1992 |
| JP | 6016621 | 1/1994 |
| JP | 6102611 | 4/1994 |
| JP | 2002-536056 | 10/2002 |
| RU | 2021258 | 10/1994 |
| WO | WO 91/04027 | 4/1991 |
| WO | WO 93/24458 | 12/1993 |
| WO | WO 94/14801 | 7/1994 |
| WO | WO 97/24328 | 7/1997 |
| WO | WO 99/24035 | 5/1999 |
| WO | WO 99/24416 * | 5/1999 |
| WO | WO 99/32106 | 7/1999 |
| WO | WO 99/32111 | 7/1999 |
| WO | WO 99/62890 | 12/1999 |
| WO | WO 00/17165 | 3/2000 |
| WO | WO 00/26186 | 5/2000 |
| WO | WO 00/26203 | 5/2000 |
| WO | WO 00/45742 | 8/2000 |
| WO | WO 00/53591 | 9/2000 |
| WO | WO 00/58293 | 10/2000 |
| WO | WO 01/00206 | 4/2001 |
| WO | WO 01/44216 | 6/2001 |
| WO | WO 01/44217 A1 | 6/2001 |
| WO | WO 01/57008 | 8/2001 |
| WO | WO 01/83465 | 11/2001 |
| WO | WO 01/83478 | 11/2001 |
| WO | WO 01/85706 | 11/2001 |
| WO | WO 01/85707 | 11/2001 |
| WO | WO 02/08209 | 1/2002 |
| WO | WO 02/14311 | 2/2002 |
| WO | WO 02/46173 | 6/2002 |
| WO | WO 02/070494 | 9/2002 |
| WO | WO 03/055482 A1 | 7/2003 |
| WO | WO 03/070727 | 8/2003 |
| WO | WO 2004/002481 A1 | 1/2004 |
| WO | WO 2004/085388 A2 | 10/2004 |
| WO | WO 2005/066145 | 7/2005 |
| WO | WO 2005/103050 A2 | 11/2005 |
| WO | WO 2005/103050 A3 | 11/2005 |
| WO | WO 2007/006814 | 1/2007 |
| WO | WO 2008/084043 | 7/2008 |
| WO | WO 2008/084044 | 7/2008 |

OTHER PUBLICATIONS

Glaser, B. et al., "Familial Hyperinsulinism Caused by an Activating Glucokinase Mutation", The New England Journal of Medicine, 1998, No. 338, pp. 226-230.

Grupe, A. et al., "Transgenic Knockouts Reveal a Critical Requirement for Pancreatic β Cell Glucokinase in Maintaining Glucose Homeostasis", Cell, 1995, vol. 83, pp. 69-78.

Meglasson, M. D. et al., "New Perspectives on Pancreatic Islet Glucokinase", American Journal of Physiology, 1984, Vol. 246, pp. E1-E13.

Printz, R.L. et al., "Mammalian Glucokinase", Annual Review of Nutrition, 1993, vol. 13, pp. 463-496.

Chipkin, S. R. et al., "Hormone-Fuel Interrelationships: Fed State, Starvation, and Diabetes Mellitus", Joslin's Diabetes, 1994, pp. 97-115.

Mann, G.V., "The Influence of Obesity on Health", The New England Journal of Medicine, 1974, vol. 291, pp. 226-232.

"Health Implications of Obesity", National Institutes of Health Consensus Development Conference Statement, Annals of Internal Medicine, 1985, vol. 103, pp. 147-151.

Colowick, S. P., "The Hexokinases", Joslin's Diabetes, 1994, pp. 97-115.

Liang, Y. et al., "Variable Effects of Maturity-Onset-Diabetes-of-Youth (MODY)-associated Glucokinase Mutations on Substrate Interactions and Stability of the Enzyme", Biochemistry, 1995, vol. 309, pp. 167-173.

Castelhano, A. L. et al., "Glucokinase-activating Ureas", Bioorganic & Medicinal Chemistry Letters, 2005, vol. 15, pp. 1501-1504.

Atwal et al., 1996, "Cardioselective Antiischemic ATP-Sensitive Potassium Channel Openers 4 Structure-Activity Studies on Benzopyranylcyanoguanidines: Replacement of the Benzopyran Portion," Journal of Medicinal Chemistry 39:304-313.

Decombe, 1932, "Acylacetic Esters," Annali Di Chimica Applicata 18:81-187.

English Translation of Decombe, 1932, "Acylacetic Esters," Annali Di Chimica Applicata 18:81-187.

Evans, et al., 1986, "Design of potent, orally effective, nonpeptidal antagonists of the peptide hormone cholecystokinin," Proceedings of the National Academy of Sciences of the United States of America, vol. 83, No. 13, Juillet 1986, USA pp. 4918-4922 (corresponds to EP0432040 in the foreign patents section).

Gardner, 1948, "The Polyoxyphenol Series III Syntheses of . . . " Canadian Journal of Research 26b:681-693.

Girard et al., 1997, Annual Review of Nutrition 17:325-352.

Grassie et al., 1950, "Preliminary Test on Possible New Stabilizers . . . " Canadian Journal of Research 28b:468-484.

Grupe et al., 1995, "Transgenic Knockouts Reveal . . . " Cell 83:69-78.

Goerdeler et al., 1980, "Acylcarbodiimides. IV. Preparation and Some Reactions of Carbamoylcarboiimides," Hcaplus, Accession No. 585914.

Heitmeier et al., 1964, "Hydroxyphenethylamino Derivatives of Various Nitrogen Heterocycles," Journal of Medicinal Chemistry 7(3):288-293.

Mylari et al., 2003, "Design and Synthesis of a Novel Family of Triazine-Based Inhibitors of Sorbitol Dehydrogenase with Oral Activity: 1-{4-[3R, 5S-Dimethyl-4-(4-methyl-[1,3,5]triazin-2-yl)-piperazin-1-yl]-[1,3,5]triazin-2-yl)-(R) Ethanol," Bioorganic & Medicinal Chemistry 11:4179-4188.

Purchase et al., 1996, "Tetrazole-Substituted Ureas As Inhibitors of Acyl-COA:Cholesterol O-Acyltransferase (ACAT) A Novel Preparation of Ureas From Weakly Nucleophilic Amines," Bioorganic & Medicinal Chemistry Letters 6(15):1753-1758.
Regel, et al., 1977, "Acylierung an C-2 Von Imidazolen Und Benzimidazolen," Liebigs Annalen Der Chemie 1:145-158.
Scheler, 1969, "Heat Developable Diazotype Material," HCAPLUS, Accession No. 444446, Nov. 5, 1968.
Sovetskaya Enthiklopedia, 1983, "Encyclopedic Dictionary," Sovetskaya Enthiklopedia pp. 130-131.
English Translation of Sovetskaya, Enthiklopedia, pp. 130-131 (1983).
Wawer, 1999, Magnetic Resonance in Chemistry 37(3):189-194.
White et al., 1996, "Heterocyclic Ureas: Inhibitors of Acyl-COA:Cholesterol O-Acyltransferase As Hypocholesterolemic Agents," Journal of Medicinal Chemistry 39(22):4382-4395.
Wolff, 1995, "Burger's Medicinal Chemistry and Drug Discovery," Burger's Medicinal Chemistry and Drug Discovery 172-178.
Office Action dated Oct. 17, 2006 from the European Patent Office in EP Application No. 02 787 463.5 filed Dec. 19, 2002 by Novo Nordisk A/S.
Machine Translation of DE2264983, 1975.
Machine Translation of DE2228890, 1972.
Machine Translation of DE2151766, 1973.
Machine Translation of DE2040580, 1970.
English Abstract of EP432040 (correlates to Evans et al.), 1991.
English Abstract of HU200396, 2002.
Machine Translation of JP6102611, 1992.
English Abstract of JP6016621, 1994.
Non-Final Office Action mailed Feb. 28, 2007 in U.S. Appl. No. 10/323,290, filed Dec. 19, 2002 by Kodra et al.
Final Office Action mailed Sep. 14, 2007 in U.S. Appl. No. 10/323,290, filed Dec. 19, 2002 by Kodra et al.
Final Office Action mailed Dec. 6, 2007 in U.S. Appl. No. 10/323,290, filed Dec. 19, 2002 by Kodra et al.
Non-Final Office Action mailed Apr. 1, 2008 in U.S. Appl. No. 10/323,290, filed Dec. 19, 2002 by Kodra et al.
Notice of Allowance mailed Jan. 28, 2009 in U.S. Appl. No. 10/323,290, filed Dec. 19, 2002 by Kodra et al.
Non-Final Office Action mailed May 28, 2009 in U.S. Appl. No. 10/323,290, filed Dec. 19, 2002 by Kodra et al.
Non-Final Office Action mailed Jan. 20, 2010 in U.S. Appl. No. 10/323,290, filed Dec. 19, 2002 by Kodra et al.
Notice of Allowance mailed Oct. 28, 2005 in U.S. Appl. No. 10/679,887, filed Oct. 6, 2003 by Polisetti et al.
Notice of Allowance mailed May 17, 2006 in U.S. Appl. No. 10/679,887, filed Oct. 6, 2003 by Polisetti et al.
Notice of Allowance mailed Aug. 3, 2006 in U.S. Appl. No. 10/679,887, filed Oct. 6, 2003 by Polisetti et al.
Notice of Allowance mailed Nov. 16, 2007 in U.S. Appl. No. 10/679,887, filed Oct. 6, 2003 by Polisetti et al.
Notice of Allowance mailed Jul. 23, 2008 in U.S. Appl. No. 11/365,534, filed Mar. 1, 2006 by Polisetti et al.
Non-Final Office Action mailed Nov. 21, 2008 in U.S. Appl. No. 11/982,248, filed Oct. 31, 2007 by Polisetti et al.
Final Office Action mailed Jul. 24, 2009 in U.S. Appl. No. 11/982,248, filed Oct. 31, 2007 by Polisetti et al.
Notice of Allowance mailed Feb. 25, 2010 in U.S. Appl. No. 11/982,248, filed Oct. 31, 2007 by Polisetti et al.
Notice of Allowance mailed May 11, 2010 in U.S. Appl. No. 11/982,248, filed Oct. 31, 2007 by Polisetti et al.
Non-Final Office Action mailed Jun. 16, 2009 in U.S. Appl. No. 11/981,997, filed Oct. 31, 2007 by Polisetti et al.
Final Office Action mailed Mar. 9, 2010 in U.S. Appl. No. 11/981,997, filed Oct. 31, 2007 by Polisetti et al.
Non-Final Office Action mailed Sep. 27, 2007 in U.S. Appl. No. 11/453,330, filed Jun. 14, 2006 by Murray et al.
Notice of Allowance mailed May 9, 2008 in U.S. Appl. No. 11/453,330, filed Jun. 14, 2006 by Murray et al.
Notice of Allowance mailed Nov. 3, 2008 in U.S. Appl. No. 11/453,330, filed Jun. 14, 2006 by Murray et al.
Notice of Allowance mailed May 28, 2009 in U.S. Appl. No. 11/453,330, filed Jun. 14, 2006 by Murray et al.
Non-Final Office Action mailed Sep. 4, 2009 in U.S. Appl. No. 12/188,402, filed Aug. 8, 2008 by Murray et al.
Notice of Allowance mailed Apr. 19, 2010 in U.S. Appl. No. 12/188,402, filed Aug. 8, 2008 by Murray et al.
Non-Final Office Action mailed Sep. 21, 2009 in U.S. Appl. No. 11/994,718, filed Jul. 9, 2008 by Murray et al.
Final Office Action mailed Jun. 18, 2010 in U.S. Appl. No. 11/994,718, filed Jul. 9, 2008 by Murray et al.
Notice of Allowance mailed Jan. 2, 2009 in U.S. Appl. No. 11/994,728, filed Jul. 9, 2008 by Murray et al.
Notice of Allowance mailed Apr. 7, 2009 in U.S. Appl. No. 11/994,728, filed Jul. 9, 2008 by Murray et al.

* cited by examiner

UREIDO-THIAZOLE GLUCOKINASE ACTIVATORS

CROSS-REFERENCE TO RELATED APPLICATIONS

This application is a 35 U.S.C. §371 national stage application of International Patent Application PCT/EP2006/064289 (published as WO 2007/006814 A1), filed Jul. 14, 2006, which claimed priority of European Patent Application 05106449.1, filed Jul. 14, 2005.

FIELD OF THE INVENTION

This application relates to novel urea glucokinase activators and their use in treatment of assorted diseases.

BACKGROUND OF THE INVENTION

Glucokinase (GK) is one of four hexokinases that are found in mammals [Colowick, S. P., in The Enzymes, Vol. 9 (P. Boyer, ed.) Academic Press, New York, N.Y., pages 1-48, 1973]. The hexokinases catalyze the first step in the metabolism of glucose, i.e., the conversion of glucose to glucose-6-phosphate. Glucokinase has a limited cellular distribution, being found principally in pancreatic β-cells and liver parenchymal cells. In addition, GK is a rate-controlling enzyme for glucose metabolism in these two cell types that are known to play critical roles in whole-body glucose homeostasis [Chipkin, S. R., Kelly, K. L., and Ruderman, N. B. in Joslin's Diabetes (C. R. Khan and G. C. Wier, eds.), Lea and Febiger, Philadelphia, Pa., pages 97-115, 1994]. The concentration of glucose at which GK demonstrates half-maximal activity is approximately 8 mM. The other three hexokinases are saturated with glucose at much lower concentrations (<1 mM). Therefore, the flux of glucose through the GK pathway rises as the concentration of glucose in the blood increases from fasting (5 mM) to postprandial (≈10-15 mM) levels following a carbohydrate-containing meal [Printz, R. G., Magnuson, M. A., and Granner, D. K. in Ann. Rev. Nutrition Vol. 13 (R. E. Olson, D. M. Bier, and D. B. McCormick, eds.), Annual Review, Inc., Palo Alto, Calif., pages 463-496, 1993]. These findings contributed over a decade ago to the hypothesis that GK functions as a glucose sensor in β-cells and hepatocytes (Meglasson, M. D. and Matschinsky, F. M. Amer. J. Physiol. 246, E1-E13, 1984). In recent years, studies in transgenic animals have confirmed that GK does indeed play a critical role in whole-body glucose homeostasis. Animals that do not express GK die within days of birth with severe diabetes while animals overexpressing GK have improved glucose tolerance (Grupe, A., Hultgren, B., Ryan, A. et al., Cell 83, 69-78, 1995; Ferrie, T., Riu, E., Bosch, F. et al., FASEB J., 10, 1213-1218, 1996). An increase in glucose exposure is coupled through GK in β-cells to increased insulin secretion and in hepatocytes to increased glycogen deposition and perhaps decreased glucose production.

The finding that type II maturity-onset diabetes of the young (MODY-2) is caused by loss of function mutations in the GK gene suggests that GK also functions as a glucose sensor in humans (Liang, Y., Kesavan, P., Wang, L. et al., Biochem. J. 309, 167-173, 1995). Additional evidence supporting an important role for GK in the regulation of glucose metabolism in humans was provided by the identification of patients that express a mutant form of GK with increased enzymatic activity. These patients exhibit a fasting hypoglycemia associated with an inappropriately elevated level of plasma insulin (Glaser, B., Kesavan, P., Heyman, M. et al., New England J. Med. 338, 226-230, 1998). While mutations of the GK gene are not found in the majority of patients with type 2 diabetes, compounds that activate GK and, thereby, increase the sensitivity of the GK sensor system will still be useful in the treatment of the hyperglycemia characteristic of all type 2 diabetes. Glucokinase activators will increase the flux of glucose metabolism in β-cells and hepatocytes, which will be coupled to increased insulin secretion. Such agents would be useful for treating type II diabetes. Several GK activators are known, see, for example, US 2004/0014968 (Hofmann-La Roche Inc.), WO 2003/055482 (Novo Nordisk A/S) and WO 2004/002481 (Novo Nordisk A/S). Diabetes is characterised by an impaired glucose metabolism manifesting itself among other things by an elevated blood glucose level in the diabetic patients. Underlying defects lead to a classification of diabetes into two major groups: Type 1 diabetes, or insulin demanding diabetes mellitus (IDDM), which arises when patients lack β-cells producing insulin in their pancreatic glands, and type 2 diabetes, or non-insulin dependent diabetes mellitus (NIDDM), which occurs in patients with an impaired β-cell function besides a range of other abnormalities.

Type 1 diabetic patients are currently treated with insulin, while the majority of type 2 diabetic patients are treated either with sulphonylureas that stimulate β-cell function or with agents that enhance the tissue sensitivity of the patients towards insulin or with insulin. Among the agents applied to enhance tissue sensitivity towards insulin metformin is a representative example.

Even though sulphonylureas are widely used in the treatment of NIDDM this therapy is, in most instances, not satisfactory: In a large number of NIDDM patients sulphonylureas do not suffice to normalise blood sugar levels and the patients are, therefore, at high risk for acquiring diabetic complications. Also, many patients gradually lose the ability to respond to treatment with sulphonylureas and are thus gradually forced into insulin treatment. This shift of patients from oral hypoglycaemic agents to insulin therapy is usually ascribed to exhaustion of the β-cells in NIDDM patients.

In normal subjects as well as in diabetic subjects, the liver produces glucose in order to avoid hypoglycemia. This glucose production is derived either from the release of glucose from glycogen stores or from gluconeogenesis, which is a de novo intracellular synthesis of glucose. In type 2 diabetes, however, the regulation of hepatic glucose output is poorly controlled and is increased, and may be doubled after an overnight fast. Moreover, in these patients there exists a strong correlation between the increased fasting plasma glucose levels and the rate of hepatic glucose production. Similarly, hepatic glucose production will be increased in type 1 diabetes, if the disease is not properly controlled by insulin treatment. Since existing forms of therapy of diabetes does not lead to sufficient glycaemic control and therefore are unsatisfactory, there is a great demand for novel therapeutic approaches. Atherosclerosis, a disease of the arteries, is recognized to be the leading cause of death in the United States and Western Europe. The pathological sequence leading to atherosclerosis and occlusive heart disease is well known. The earliest stage in this sequence is the formation of "fatty streaks" in the carotid, coronary and cerebral arteries and in the aorta. These lesions are yellow in colour due to the presence of lipid deposits found principally within smooth-muscle cells and in macrophages of the intima layer of the arteries and aorta. Further, it is postulated that most of the cholesterol found within the fatty streaks, in turn, give rise to development of the "fibrous plaque", which consists of accumulated intimal smooth muscle cells laden with lipid and surrounded by extra-cellular lipid, collagen, elastin and proteoglycans. The cells plus matrix form a fibrous cap that covers a deeper deposit of cell debris and more extracellular lipid. The lipid is primarily free and esterified cholesterol. The fibrous plaque forms slowly, and is likely in time to become calcified and necrotic, advancing to the "complicated lesion" which accounts for the arterial occlusion and tendency toward mural thrombosis and arterial muscle spasm that characterize advanced atherosclerosis. Epidemiological evidence has firmly established hyperlipidemia as a primary risk factor in causing cardiovascular disease (CVD) due to atherosclerosis. In recent years, leaders of the medical profession have placed renewed emphasis on lowering plasma cholesterol levels, and low density lipoprotein cholesterol in particular, as an essential step in prevention of CVD. The upper limits of "normal" are now known to be significantly lower than heretofore appreciated. As a result, large segments of Western populations are now realized to be at particular high risk. Independent risk factors include glucose intolerance, left ventricular hypertrophy, hypertension, and being of the male sex. Cardiovascular disease is especially prevalent among diabetic subjects, at least in part because of the existence of multiple independent risk factors in this population. Successful treatment of hyperlipidemia in the general population, and in diabetic subjects in particular, is therefore of exceptional medical importance.

Hypertension (or high blood pressure) is a condition, which occurs in the human population as a secondary symptom to various other disorders such as renal artery stenosis, pheochromocytoma, or endocrine disorders. However, hypertension is also evidenced in many patients in whom the causative agent or disorder is unknown. While such "essential" hypertension is often associated with disorders such as obesity, diabetes, and hypertriglyceridemia, the relationship between these disorders has not been elucidated. Additionally, many patients display the symptoms of high blood pressure in the complete absence of any other signs of disease or disorder.

It is known that hypertension can directly lead to heart failure, renal failure, and stroke (brain haemorrhaging). These conditions are capable of causing short-term death in a patient. Hypertension can also contribute to the development of atherosclerosis and coronary disease. These conditions gradually weaken a patient and can lead to long-term death.

The exact cause of essential hypertension is unknown, though a number of factors are believed to contribute to the onset of the disease. Among such factors are stress, uncontrolled emotions, unregulated hormone release (the renin, angiotensin aldosterone system), excessive salt and water due to kidney malfunction, wall thickening and hypertrophy of the vasculature resulting in constricted blood vessels and genetic factors.

The treatment of essential hypertension has been undertaken bearing the foregoing factors in mind. Thus a broad range of beta-blockers, vasoconstrictors, angiotensin converting enzyme inhibitors and the like have been developed and marketed as antihypertensives. The treatment of hypertension utilizing these compounds has proven beneficial in the prevention of short-interval deaths such as heart failure, renal failure, and brain hemorrhaging. However, the development of atherosclerosis or heart disease due to hypertension over a long period of time remains a problem. This implies that although high blood pressure is being reduced, the underlying cause of essential hypertension is not responding to this treatment. Hypertension has been associated with elevated blood insulin levels, a condition known as hyperinsulinemia. Insulin, a peptide hormone whose primary actions are to promote glucose utilization, protein synthesis and the formation and storage of neutral lipids, also acts to promote vascular cell growth and increase renal sodium retention, among other things. These latter functions can be accomplished without affecting glucose levels and are known causes of hypertension. Peripheral vasculature growth, for example, can cause constriction of peripheral capillaries, while sodium retention increases blood volume. Thus, the lowering of insulin levels in hyperinsulinemics can prevent abnormal vascular growth and renal sodium retention caused by high insulin levels and thereby alleviates hypertension.

Cardiac hypertrophy is a significant risk factor in the development of sudden death, myocardial infarction, and congestive heart failure. Theses cardiac events are due, at least in part, to increased susceptibility to myocardial injury after ischemia and reperfusion, which can occur in out-patient as well as perioperative settings. There is an unmet medical need to prevent or minimize adverse myocardial perioperative outcomes, particularly perioperative myocardial infarction. Both non-cardiac and cardiac surgery are associated with substantial risks for myocardial infarction or death. Some 7 million patients undergoing non-cardiac surgery are considered to be at risk, with incidences of perioperative death and serious cardiac complications as high as 20-25% in some series. In addition, of the 400,000 patients undergoing coronary bypass surgery annually, perioperative myocardial infarction is estimated to occur in 5% and death in 1-2%. There is currently no drug therapy in this area, which reduces damage to cardiac tissue from perioperative myocardial ischemia or enhances cardiac resistance to ischemic episodes. Such a therapy is anticipated to be life-saving and reduce hospitalizations, enhance quality of life and reduce overall health care costs of high risk patients. Obesity is a well-known risk factor for the development of many very common diseases such as atherosclerosis, hypertension, and diabetes. The incidence of obese people and thereby also these diseases is increasing throughout the entire industrialised world. Except for exercise, diet and food restriction no convincing pharmacological treatment for reducing body weight effectively and acceptably currently exists. However, due to its indirect but important effect as a risk factor in mortal and common diseases it will be important to find treatment for obesity and/or means of appetite regulation.

The term obesity implies an excess of adipose tissue. In this context obesity is best viewed as any degree of excess adiposity that imparts a health risk. The cut off between normal and obese individuals can only be approximated, but the health risk imparted by the obesity is probably a continuum with increasing adiposity. The Framingham study demonstrated that a 20% excess over desirable weight clearly imparted a health risk (Mann G V N. Engl. J. Med 291:226, 1974). In the United States a National Institutes of Health consensus panel on obesity agreed that a 20% increase in relative weight or a body mass index (BMI=body weight in kilograms divided by the square of the height in meters) above the 85th percentile for young adults constitutes a health risk. By the use of these criteria 20 to 30 percent of adult men and 30 to 40 percent of adult women in the United States are obese. (NIH, Ann Intern Med 103:147, 1985).

Even mild obesity increases the risk for premature death, diabetes, hypertension, atherosclerosis, gallbladder disease, and certain types of cancer. In the industrialised western world the prevalence of obesity has increased significantly in the past few decades. Because of the high prevalence of obesity and its health consequences, its prevention and treatment should be a high public health priority.

When energy intake exceeds expenditure, the excess calories are stored in adipose tissue, and if this net positive balance is prolonged, obesity results, i.e. there are two components to weight balance, and an abnormality on either side (intake or expenditure) can lead to obesity. The regulation of eating behaviour is incompletely understood. To some extent appetite is controlled by discrete areas in the hypothalamus: a feeding centre in the ventrolateral nucleus of the hypothalamus (VLH) and a satiety centre in the ventromedial hypothalamus (VMH). The cerebral cortex receives positive signals from the feeding centre that stimulate eating, and the satiety centre modulates this process by sending inhibitory impulses to the feeding centre. Several regulatory processes may influence these hypothalamic centres. The satiety centre may be activated by the increases in plasma glucose and/or insulin that follow a meal. Meal induced gastric distension is another possible inhibitory factor. Additionally the hypothalamic centres are sensitive to catecholamines, and beta adrenergic stimulation inhibits eating behaviour. Ultimately, the cerebral cortex controls eating behaviour, and impulses from the feeding centre to the cerebral cortex are only one input. Psychological, social, and genetic factors also influence food intake.

At present a variety of techniques are available to effect initial weight loss. Unfortunately, initial weight loss is not an optimal therapeutic goal. Rather, the problem is that most obese patients eventually regain their weight. An effective means to establish and/or sustain weight loss is the major challenge in the treatment of obesity today.

SUMMARY OF THE INVENTION

The invention provides a compound of general formula (I)

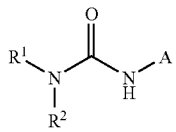

(I)

wherein the substituents are defined below, as well as further embodiments hereof described in the attached embodiments.

The present invention also provides use of the compounds of the invention for preparation of a medicament for the treatment of various diseases, e.g. for the treatment of type 2 diabetes.

DEFINITIONS

In the structural formulas given herein and throughout the present specification, the following terms have the indicated meaning:

The term "optionally substituted" as used herein means that the moiety which is optionally substituted is either unsubstituted or substituted with one or more of the substituents specified. When the moiety in question is substituted with more than one substituent, the substituent may be the same or different.

The term "adjacent" as used herein regards the relative positions of two atoms or variables, these two atoms or variables sharing a bond or one variable preceding or succeeding the other in a variable specification. By way of example, "atom A adjacent to atom B" means that the two atoms A and B share a bond.

The term "halogen" or "halo" means fluorine, chlorine, bromine or iodine.

The term "perhalomethyl" means trifluoromethyl, trichloromethyl, tribromomethyl, or triiodomethyl.

The use of prefixes of this structure: $C_{x-y}$-alkyl, $C_{x-y}$-alkenyl, $C_{x-y}$-alkynyl, $C_{x-y}$-cycloalkyl or $C_{x-y}$-cycloalkyl-$C_{x-y}$-alkenyl- and the like designates radical of the designated type having from x to y carbon atoms.

The term "alkyl" as used herein, alone or in combination, refers to a straight or branched chain saturated monovalent hydrocarbon radical having from one to ten carbon atoms, for example $C_{1-8}$-alkyl or $C_{1-6}$-alkyl. Typical $C_{1-8}$-alkyl groups and $C_{1-6}$-alkyl groups include, but are not limited to e.g. methyl, ethyl, n-propyl, isopropyl, n-butyl, sec-butyl, isobutyl, tert-butyl, n-pentyl, 2-methylbutyl, 3-methylbutyl, 4-methylpentyl, neopentyl, n-pentyl, n-hexyl, 1,2-dimethylpropyl, 2,2-dimethylpropyl, 1,2,2-trimethylpropyl and the like. The term "$C_{1-8}$-alkyl" as used herein also includes secondary $C_{3-8}$-alkyl and tertiary $C_{4-8}$-alkyl. The term "$C_{1-6}$-alkyl" as used herein also includes secondary $C_{3-6}$-alkyl and tertiary $C_{4-6}$-alkyl.

The term "alkenyl" as used herein, alone or in combination, refers to a straight or branched chain monovalent hydrocarbon radical containing from two to ten carbon atoms and at least one carbon-carbon double bond, for example $C_{2-8}$-alkenyl or $C_{2-6}$-alkenyl. Typical $C_{2-8}$-alkenyl groups and $C_{2-6}$-alkenyl groups include, but are not limited to, vinyl, 1-propenyl, 2-propenyl, iso-propenyl, 1,3-butadienyl, 1-butenyl, 2-butenyl, 3-butenyl, 2-methyl-1-propenyl, 1-pentenyl, 2-pentenyl, 3-pentenyl, 4-pentenyl, 3-methyl-2-butenyl, 1-hexenyl, 2-hexenyl, 3-hexenyl, 2,4-hexadienyl, 5-hexenyl and the like.

The term "alkynyl" as used herein alone or in combination, refers to a straight or branched monovalent hydrocarbon radical containing from two to ten carbon atoms and at least one triple carbon-carbon bond, for example $C_{2-8}$-alkynyl or $C_{2-6}$-alkynyl. Typical $C_{2-8}$-alkynyl groups and $C_{2-6}$-alkynyl groups include, but are not limited to, ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 5-hexynyl, 2,4-hexadienyl and the like.

The term "cycloalkyl" as used herein, alone or in combination, refers to a saturated mono-, bi-, or tricarbocyclic radical having from three to twelve carbon atoms, for example $C_{3-8}$-cycloalkyl. Typical $C_{3-8}$-cycloalkyl groups include, but are not limited to, cyclopropyl, cyclobutyl, cyclopentyl, cyclohexyl, cycloheptyl, cyclooctyl, bicyclo[3.2.1]octyl, bicyclo[2.2.1]heptyl, norpinyl, norbonyl, norcaryl, adamantyl and the like.

The term "cycloalkenyl" as used herein, alone or in combination, refers to an non-aromatic unsaturated mono-, bi-, or tricarbocyclic radical having from three to twelve carbon atoms, for example $C_{3-8}$-cycloalkenyl. Typical $C_{3-8}$-cycloalkyl groups include, but are not limited to cyclohexene, cycloheptene and cyclopentene, and the like.

The term "heterocyclic" or the term "heterocyclyl" as used herein, alone or in combination, refers to a saturated mono-, bi-, or tricarbocyclic group having three to twelve carbon atoms and one or two additional heteroatoms or groups selected from nitrogen, oxygen, sulphur, SO or $SO_2$, for example $C_{3-8}$-heterocyclyl. Typical $C_{3-8}$-heterocyclyl groups include, but are not limited to, tetrahydrofuryl, tetrahydrothienyl, tetrahydropyranyl, tetrahydrothiopyranyl, 1,4-dioxanyl, 1,3-dioxanyl, piperidyl, pyrrolidinyl, morpholinyl, piperazinyl, and the like.

The term "heterocycloalkenyl" as used herein, alone or in combination, refers to a non-aromatic unsaturated mono-, bi-, or tricyclic radical having from three to twelve carbon atoms, and one or two additional heteroatoms or groups selected from nitrogen, oxygen, sulphur, SO or $SO_2$, for example $C_{3-8}$-hetereocycloalkenyl. Typical $C_{3-8}$-hetreocycloalkenyl groups include, but are not limited to tetrahydropyridine, azacycloheptene, 2-pyrroline, 3-pyrroline, 2-pyrazoline, imidazoline, 4H-pyran, and the like.

The terms "alkoxy" or "alkyloxy", which are interchangeable terms herein, as used herein, alone or in combination, refers to the monovalent radical $R^aO$—, where $R^a$ is alkyl as defined above, for example $C_{1-8}$-alkyl giving $C_{1-8}$-alkoxy. Typical $C_{1-8}$-alkoxy groups include, but are not limited to, methoxy, ethoxy, n-propoxy, isopropoxy, butoxy, sec-butoxy, tert-butoxy, pentoxy, isopentoxy, hexoxy, isohexoxy and the like.

The term "alkenyloxy", as used herein, alone or in combination, refers to the monovalent radical $R^aO$—, where $R^a$ is alkenyl as defined above, for example $C_{2-8}$-alkyl giving $C_{2-8}$-alkenyloxy. Typical $C_{2-8}$-alkenyloxy groups include, but are not limited to, vinyloxy, propenyloxy, 2-methyl-propenyloxy, butenyloxy, and the like.

The term "alkenylthio", as used herein, alone or in combination, refers to the monovalent radical $R^aS$—, where $R^a$ is alkenyl as defined above, for example $C_{2-8}$-alkyl giving $C_{2-8}$-alkenylthio. Typical $C_{2-8}$-alkenyloxy groups include, but are not limited to, vinylthio, propenylthio, 2-methyl-propenylthio, and the like.

The term "alkylthio" as used herein, alone or in combination, refers to a straight or branched monovalent radical comprising an alkyl group as described above linked through a divalent sulphur atom having its free valence bond from the sulphur atom, for example $C_{1-6}$-alkylthio. Typical $C_{1-6}$-alkylthio groups include, but are not limited to, methylthio, ethylthio, propylthio, butylthio, pentylthio, hexylthio and the like.

The term "alkoxycarbonyl" as used herein refers to the monovalent radical $R^aOC(O)$—, where $R^a$ is alkyl as described above, for example $C_{1-8}$-alkoxycarbonyl. Typical $C_{1-8}$-alkoxycarbonyl groups include, but are not limited to, methoxycarbonyl, ethoxycarbonyl, propoxycarbonyl, isopropoxycarbonyl, n-butoxycarbonyl, sec-butoxycarbonyl, tertbutoxycarbonyl, 3-methylbutoxycarbonyl, n-hexoxycarbonyl and the like.

The term "aryl" as used herein refers to a carbocyclic aromatic ring radical or to an aromatic ring system radical. Aryl is also intended to include the partially hydrogenated derivatives of the carbocyclic systems.

The term "heteroaryl", as used herein, alone or in combination, refers to an aromatic ring radical with for instance 5 to 7 member atoms, or to a aromatic ring system radical with for instance from 7 to 18 member atoms, containing one or more heteroatoms selected from nitrogen, oxygen, or sulphur heteroatoms, wherein N-oxides and sulphur monoxides and sulphur dioxides are permissible heteroaromatic substitutions; such as e.g. furanyl, thienyl, thiophenyl, pyrrolyl, imidazolyl, pyrazolyl, triazolyl, tetrazolyl, thiazolyl, oxazolyl, isoxazolyl, oxadiazolyl, thiadiazolyl, isothiazolyl, pyridinyl, pyridazinyl, pyrazinyl, pyrimidinyl, quinolinyl, isoquinolinyl, benzofuranyl, benzothiophenyl, indolyl, and indazolyl, and the like. Heteroaryl is also intended to include the partially hydrogenated derivatives of the heterocyclic systems enumerated below.

Examples of "aryl" and "heteroaryl" includes, but are not limited to, phenyl, biphenyl, indene, fluorene, naphthyl (1-naphthyl, 2-naphthyl), anthracene (1-anthracenyl, 2-anthracenyl, 3-anthracenyl), thiophene (2-thienyl, 3-thienyl), furyl (2-furyl, 3-furyl), indolyl, oxadiazolyl, isoxazolyl, thiadiazolyl, oxatriazolyl, thiatriazolyl, quinazolin, fluorenyl, xanthenyl, isoindanyl, benzhydryl, acridinyl, thiazolyl, pyrrolyl (1-pyrrolyl, 2-pyrrolyl, 3-pyrrolyl), pyrazolyl (1-pyrazolyl, 3-pyrazolyl, 4-pyrazolyl, 5-pyrazolyl), imidazolyl (1-imidazolyl, 2-imidazolyl, 4-imidazolyl, 5-imidazolyl), triazolyl (1,2,3-triazol-1-yl, 1,2,3-triazol-4-yl 1,2,3-triazol-5-yl, 1,2,4-triazol-3-yl, 1,2,4-triazol-5-yl), oxazolyl (2-oxazolyl, 4-oxazolyl, 5-oxazolyl), isooxazolyl (isooxazo-3-yl, isooxazo-4-yl, isooxaz-5-yl), isothiazolyl (isothiazo-3-yl, isothiazo-4-yl, isothiaz-5-yl)thiazolyl (2-thiazolyl, 4-thiazolyl, 5-thiazolyl), pyridyl (2-pyridyl, 3-pyridyl, 4-pyridyl), pyrimidinyl (2-pyrimidinyl, 4-pyrimidinyl, 5-pyrimidinyl, 6-pyrimidinyl), pyrazinyl, pyridazinyl (3-pyridazinyl, 4-pyridazinyl, 5-pyridazinyl), quinolyl (2-quinolyl, 3-quinolyl, 4-quinolyl, 5-quinolyl, 6-quinolyl, 7-quinolyl, 8-quinolyl), isoquinolyl (1-isoquinolyl, 3-isoquinolyl, 4-isoquinolyl, 5-isoquinolyl, 6-isoquinolyl, 7-isoquinolyl, 8-isoquinolyl), benzo[b]furanyl (2-benzo[b]furanyl, 3-benzo[b]furanyl, 4-benzo[b]furanyl, 5-benzo[b]furanyl, 6-benzo[b]furanyl, 7-benzo[b]furanyl), 2,3-dihydro-benzo[b]furanyl (2-(2,3-dihydro-benzo[b]furanyl), 3-(2,3-dihydro-benzo[b]furanyl), 4-(2,3-dihydro-benzo[b]furanyl), 5-(2,3-dihydro-benzo[b]furanyl), 6-(2,3-dihydro-benzo[b]furanyl), 7-(2,3-dihydro-benzo[b]furanyl)), benzo[b]thiophenyl (benzo[b]thiophen-2-yl, benzo[b]thiophen-3-yl, benzo[b]thiophen-4-yl, benzo[b]thiophen-5-yl, benzo[b]thiophen-6-yl, benzo[b]thiophen-7-yl), 2,3-dihydro-benzo[b]thiophenyl (2,3-dihydrobenzo[b]thiophen-2-yl, 2,3-dihydro-benzo[b]thiophen-3-yl, 2,3-dihydro-benzo[b]thiophen-4-yl, 2,3-dihydro-benzo[b]thiophen-5-yl, 2,3-dihydro-benzo[b]thiophen-6-yl, 2,3-dihydrobenzo[b]thiophen-7-yl), indolyl (1-indolyl, 2-indolyl, 3-indolyl, 4-indolyl, 5-indolyl, 6-indolyl, 7-indolyl), indazole (1-indazolyl, 3-indazolyl, 4-indazolyl, 5-indazolyl, 6-indazolyl, 7-indazolyl), benzimidazolyl (1-benzimidazolyl, 2-benzimidazolyl, 4-benzimidazolyl, 5-benzimidazolyl, 6-benzimidazolyl, 7-benzimidazolyl, 8-benzimidazolyl), benzoxazolyl (2-benzoxazolyl, 3-benzoxazolyl, 4-benzoxazolyl, 5-benzoxazolyl, 6-benzoxazolyl, 7-benzoxazolyl), benzothiazolyl (2-benzothiazolyl, 4-benzothiazolyl, 5-benzothiazolyl, 6-benzothiazolyl, 7-benzothiazolyl), carbazolyl (1-carbazolyl, 2-carbazolyl, 3-carbazolyl, 4-carbazolyl), 5H-dibenz[b,f]azepine (5H-dibenz[b,f]azepin-1-yl, 5H-dibenz[b,f]azepine-2-yl, 5H-dibenz[b,f]azepine-3-yl, 5H-dibenz[b,f]azepine-4-yl, 5H-dibenz[b,f]azepine-5-yl), 10,11-dihydro-5H-dibenz[b,f]azepine (10,11-dihydro-5H-dibenz[b,f]azepine-1-yl, 10,11-dihydro-5H-dibenz[b,f]azepine-2-yl, 10,11-dihydro-5H-dibenz[b,f]azepine-3-yl, 10,11-dihydro-5H-dibenz[b,f]azepine-4-yl, 10,11-dihydro-5H-dibenz[b,f]azepine-5-yl), benzo[1,3]dioxole (2-benzo[1,3]dioxole, 4-benzo[1,3]dioxole, 5-benzo[1,3]dioxole, 6-benzo[1,3]dioxole, 7-benzo[1,3]dioxole), purinyl, and tetrazolyl (5-tetrazolyl, N-tetrazolyl).

The present invention also relates to partly or fully saturated analogues of the ring systems mentioned above.

When two or more of the above defined terms are used in combination, such as in aryl-alkyl, heteroaryl-alkyl, cycloalkyl-$C_{1-6}$-alkyl and the like, it is to be understood that the first mentioned radical is a substituent on the latter mentioned radical, where the point of substitution, i.e. the point of attachment to another part of the molecule, is on the latter of the radicals, for example aryl-alkyl-:

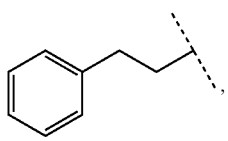

cycloalkyl-alkyl-:

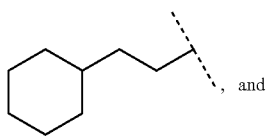, and aryl-alkoxy-:

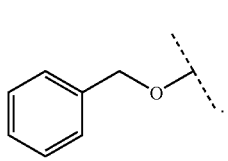.

The term "fused arylcycloalkyl", as used herein, refers to an aryl group, as defined above, fused to a cycloalkyl group, as defined above and having the indicated number of carbon atoms, the aryl and cycloalkyl groups having two atoms in common, and wherein the cycloalkyl group is the point of substitution. Examples of "fused arylcycloalkyl" used herein include 1-indanyl, 2-indanyl, 1-(1,2,3,4-tetrahydronaphthyl),

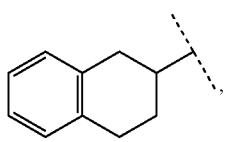, and the like.

The term "fused heteroarylcycloalkyl", as used herein, refers to a heteroaryl group, as defined above, fused to a cycloalkyl group, as defined above and having the indicated number of carbon atoms, the aryl and cycloalkyl groups having two atoms in common, and wherein the cycloalkyl group is the point of substitution. Examples of fused heteroarylcycloalkyl used herein include 6,7-dihydro-5H-cyclopenta[b]pyridine, 5,6,7,8-tetrahydroquinoline, 5,6,7,8-tetrahydroisoquinoline, 5,6,7,8-tetrahydroquinazoline and the like The term "alkylsulfanyl", as used herein, refers to the group $R^aS-$, where $R^a$ is alkyl as described above.

The term "alkylsulfenyl", as used herein, refers to the group $R^aS(O)-$, where $R^a$ is alkyl as described above.

The term "alkylsulfonyl", as used herein, refers to the group $R^aSO_2-$, where $R^a$ is alkyl as described above.

The term "alkylsulfamoyl", as used herein, refers to the group $R^aNHSO_2-$, where $R^a$ is alkyl as described above.

The term "dialkylsulfamoyl", as used herein, refers to the group $R^aR^bNSO_2-$, where $R^a$ and $R^b$ are alkyl as described above.

The term "alkylsulfinamoyl", as used herein, refers to the group $R^aNHSO-$, where $R^a$ is alkyl as described above.

The term "dialkylsulfinamoyl", as used herein, refers to the group $R^aR^bNSO-$, where $R^a$ and $R^b$ are alkyl as described above.

The term "alkylamino", as used herein, refers to the group $R^aNH-$, where $R^a$ is alkyl as described above.

The term "acyl", as used herein, refers to the group $R^aC(O)-$, where $R^a$ is alkyl, alkenyl, alkynyl, cycloalkyl, cycloalkenyl, or heterocyclyl as described above.

The term "heteroaryloxy" as used herein, alone or in combination, refers to the monovalent radical $R^aO-$, where $R^a$ is heteroaryl as defined above.

The term "aryloxycarbonyl", as used herein, refers to the group $R^a-O-C(O)-$, where $R^a$ is aryl as described above.

The term "acyloxy", as used herein, refers to the group $R^aC(O)O-$, where $R^a$ is alkyl, alkenyl, alkynyl, cycloalkyl, cycloalkenyl, or heterocyclyl as described above.

The term "aryloxy", as used herein refers to the group $R^aC(O)O-$, where $R^a$ is aryl as described above.

The term "aroyloxy", as used herein, refers to the group $R^aC(O)O-$, where $R^a$ is aryl as described above.

The term "heteroaroyloxy", as used herein, refers to the group $R^aC(O)O-$, where $R^a$ is heteroaryl as described above.

Whenever the terms "alkyl", "cycloalkyl", "aryl", "heteroaryl" or the like or either of their prefix roots appear in a name of a substituent (e.g. arylalkoxyaryloxy) they shall be interpreted as including those limitations given above for "alkyl" and "aryl".

As used herein, the term "oxo" shall refer to the substituent $=O$.

As used herein, the term "mercapto" shall refer to the substituent $-SH$.

As used herein, the term "carboxy" shall refer to the substituent $-C(O)OH$.

As used herein, the term "cyano" shall refer to the substituent $-CN$.

As used herein, the term "nitro" shall refer to the substituent $-NO_2$.

As used herein, the term "aminosulfonyl" shall refer to the substituent $-SO_2NH_2$.

As used herein, the term "sulfanyl" shall refer to the substituent $-S-$.

As used herein, the term "sulfenyl" shall refer to the substituent $-S(O)-$.

As used herein, the term "sulfonyl" shall refer to the substituent $-S(O)_2-$.

As used herein, the term "direct bond", where part of a structural variable specification, refers to the direct joining of the substituents flanking (preceding and succeeding) the variable taken as a "direct bond".

The term "lower", as used herein, refers to an group having between one and six carbons, and may be indicated with the prefix $C_{x-6}-$. Lower alkyl may thus be indicated as $C_{1-6}$-alkyl, while lower alkylene may be indicated as $C_{2-6}$-alkylene.

A radical such as $C_{x-y}$-cycloalkyl-$C_{a-b}$-alkenyl shall designate that the radical's point of attachment is in part of the radical mentioned last.

As used herein, the term "optionally" means that the subsequently described event(s) may or may not occur, and includes both event(s) which occur and events that do not occur.

As used herein, the term "substituted" refers to substitution with the named substituent or substituents, multiple degrees of substitution being allowed unless otherwise stated.

As used herein, the term "attached" or "—" (e.g. —C(O)R$^{11}$ which indicates the carbonyl attachment point to the scaffold) signifies a stable covalent bond.

As used herein, the terms "contain" or "containing" can refer to in-line substitutions at any position along the above defined alkyl, alkenyl, alkynyl or cycloalkyl substituents with one or more of any of O, S, SO, $SO_2$, N, or N-alkyl, including, for example, —$CH_2$—O—$CH_2$—, —$CH_2$—$SO_2$—$CH_2$—, —$CH_2$—NH—$CH_3$ and so forth.

Certain of the above defined terms may occur more than once in the structural formulae, and upon such occurrence each term shall be defined independently of the other.

As used herein, the term "solvate" is a complex of variable stoichiometry formed by a solute (in this invention, a compound of formula (I)) and a solvent. Such solvents for the purpose of the present invention may not interfere with the biological activity of the solute. Solvents may be, by way of example, water, ethanol, or acetic acid.

As used herein, the term "biohydrolyzable ester" is an ester of a drug substance (in this invention, a compound of formula (I)) which either a) does not interfere with the biological activity of the parent substance but confers on that substance advantageous properties in vivo such as duration of action, onset of action, and the like, or b) is biologically inactive but is readily converted in vivo by the subject to the biologically active principle. The advantage is that, for example, the biohydrolyzable ester is orally absorbed from the gut and is transformed to (I) in plasma. Many examples of such are known in the art and include by way of example lower alkyl esters (e.g., $C_{1-4}$), lower acyloxyalkyl esters, lower alkoxyacyloxyalkyl esters, alkoxyacyloxy esters, alkyl acylamino alkyl esters, and choline esters.

As used herein, the term "biohydrolyzable amide" is an amide of a drug substance (in this invention, a compound of general formula (I)) which either a) does not interfere with the biological activity of the parent substance but confers on that substance advantageous properties in vivo such as duration of action, onset of action, and the like, or b) is biologically inactive but is readily converted in vivo by the subject to the biologically active principle. The advantage is that, for example, the biohydrolyzable amide is orally absorbed from the gut and is transformed to (I) in plasma. Many examples of such are known in the art and include by way of example lower alkyl amides, α-amino acid amides, alkoxyacyl amides, and alkylaminoalkylcarbonyl amides.

As used herein, the term "prodrug" includes biohydrolyzable amides and biohydrolyzable esters and also encompasses a) compounds in which the biohydrolyzable functionality in such a prodrug is encompassed in the compound of formula (I) and b) compounds which may be oxidized or reduced biologically at a given functional group to yield drug substances of formula (I). Examples of these functional groups include, but are not limited to, 1,4-dihydropyridine, N-alkylcarbonyl-1,4-dihydropyridine, 1,4-cyclohexadiene, tert-butyl, and the like.

The term "pharmacologically effective amount" or shall mean that amount of a drug or pharmaceutical agent that will elicit the biological or medical response of a tissue, animal or human that is being sought by a researcher or clinician. This amount can be a therapeutically effective amount. The term "therapeutically effective amount" shall mean that amount of a drug or pharmaceutical agent that will elicit the therapeutic response of an animal or human that is being sought.

The term "treatment" and "treating" as used herein means the management and care of a patient for the purpose of combating a disease, disorder or condition. The term is intended to include the full spectrum of treatments for a given disorder from which the patient is suffering, such as the delaying of the progression of the disease, disorder or condition, the alleviation or relief of symptoms and complications, the prevention of the disease and/or the cure or elimination of the disease, disorder or condition. The patient to be treated is preferably a mammal, in particular a human being.

The term "pharmaceutically acceptable salt" as used herein includes pharmaceutically acceptable acid addition salts, pharmaceutically acceptable base addition salts, pharmaceutically acceptable metal salts, ammonium salts, and alkylated ammonium salts. Acid addition salts include salts of inorganic acids as well as organic acids. Representative examples of suitable inorganic acids include hydrochloric, hydrobromic, hydroiodic, phosphoric, sulfuric, and nitric acids. Representative examples of suitable organic acids include formic, acetic, trichloroacetic, trifluoroacetic, propionic, benzoic, cinnamic, citric, fumaric, glycolic, lactic, maleic, malic, malonic, mandelic, oxalic, picric, pyruvic, salicylic, succinic, methanesulfonic, ethanesulfonic, tartaric, ascorbic, pamoic, bismethylene salicylic, ethanedisulfonic, gluconic, citraconic, aspartic, stearic, palmitic, EDTA, glycolic, p-aminobenzoic, glutamic, benzenesulfonic, p-toluenesulfonic acids, sulphates, nitrates, phosphates, perchlorates, borates, acetates, benzoates, hydroxynaphthoates, glycerophosphates, and ketoglutarates. Further examples of pharmaceutically acceptable inorganic or organic acid addition salts include the pharmaceutically acceptable salts listed in J. Pharm. Sci. 1977, 66, 2, which is incorporated herein by reference. Examples of metal salts include lithium, sodium, potassium, magnesium, zinc, and calcium salts. Examples of amines and organic amines include ammonium, methylamine, dimethylamine, trimethylamine, ethylamine, diethylamine, propylamine, butylamine, tetramethylamine, ethanolamine, diethanolamine, triethanolamine, meglumine, ethylenediamine, choline, N,N'-dibenzylethylenediamine, N-benzylphenylethylamine, N-methyl-D-glucamine, and guanidine. Examples of cationic amino acids include lysine, arginine, and histidine.

The pharmaceutically acceptable salts are prepared by reacting the compound of formula I with 1 to 4 equivalents of a base such as sodium hydroxide, sodium methoxide, sodium hydride, potassium t-butoxide, calcium hydroxide, and magnesium hydroxide, in solvents such as ether, THF, methanol, t-butanol, dioxane, isopropanol, ethanol etc. Mixture of solvents may be used. Organic bases such as lysine, arginine, diethanolamine, choline, guandine and their derivatives etc. may also be used. Alternatively, acid addition salts wherever applicable are prepared by treatment with acids such as hydrochloric acid, hydrobromic acid, nitric acid, sulfuric acid, phosphoric acid, p-toluenesulphonic acid, methanesulfonic acid, acetic acid, citric acid, maleic acid salicylic acid, hydroxynaphthoic acid, ascorbic acid, palmitic acid, succinic acid, benzoic acid, benzenesulfonic acid, and tartaric acid in solvents such as ethyl acetate, ether, alcohols, acetone, THF, dioxane etc. Mixture of solvents may also be used. The term "combination therapy", "combined", "in combination with", and the like, as used herein refers to the administration of a single pharmaceutical dosage formulation which comprises the glucokinase activator compound of the present invention and another active agent(s), as well as administration of each active agent(s) in its own separate pharmaceutical dosage formulation. Where separate dosage formulations are used, the compound of the present invention and another active agent(s) can be administered to the patient at essentially the same time, i.e. concurrently, or at separate staggered times, i.e. sequentially. When given by different dosage formulations, the route of administration may be the same or different for each agent. Any route of administration known or contemplated for the individual agents is acceptable for the practice of the present invention.

DESCRIPTION OF THE INVENTION

In an embodiment 1 the invention provides a compound of general formula (I)

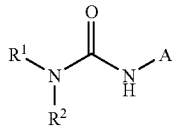

wherein $R^1$ is $C_{1-8}$-alkyl, $C_{2-8}$-alkenyl, $C_{2-8}$-alkynyl, aryl, heteroaryl, $C_{3-8}$-cycloalkyl-$C_{1-6}$-alkyl, $C_{3-8}$-cycloalkyl-$C_{2-6}$-alkenyl, $C_{3-8}$-cycloalkyl-$C_{2-6}$-alkynyl, $C_{3-8}$-cycloalkenyl-$C_{1-6}$-alkyl, $C_{3-8}$-cycloalkenyl-$C_{2-6}$-alkenyl, $C_{3-8}$-cycloalkenyl-$C_{2-6}$-alkynyl, $C_{3-8}$-heterocyclyl-$C_{1-6}$-alkyl, $C_{3-8}$-heterocyclyl-$C_{2-6}$-alkenyl, $C_{3-8}$-heterocyclyl-$C_{2-6}$-alkynyl, $C_{3-8}$-heterocycloalkenyl-$C_{1-6}$-alkyl, $C_{3-8}$-heterocycloalkenyl-$C_{2-6}$-alkenyl, $C_{3-8}$-heterocycloalkenyl-$C_{2-6}$-alkynyl, aryl-$C_{1-6}$-alkyl, aryl-$C_{2-6}$-alkenyl, aryl-$C_{2-6}$-alkynyl, heteroaryl-$C_{1-6}$-alkyl, heteroaryl-$C_{2-6}$-alkenyl, heteroaryl-$C_{2-6}$-alkynyl, (fused aryl-$C_{3-8}$-cycloalkyl)-$C_{1-6}$-alkyl, (fused aryl-$C_{3-8}$-cycloalkyl)-$C_{2-6}$-alkenyl, (fused aryl-$C_{3-8}$-cycloalkyl)-$C_{2-6}$-alkynyl, (fused heteroaryl-$C_{3-8}$-cycloalkyl)-$C_{1-6}$-alkyl, (fused heteroaryl-$C_{3-8}$-cycloalkyl)-$C_{2-6}$-alkenyl or (fused heteroaryl-$C_{3-8}$-cycloalkyl-$C_{2-6}$-alkynyl) each of which is optionally substituted with one or more substituents $R^3$, $R^4$, $R^5$ and $R^6$;

$R^2$ is $C_{1-8}$-alkyl, $C_{3-8}$-cycloalkyl, $C_{3-8}$-cycloalkyl-$C_{1-8}$-alkyl, $C_{3-8}$-cycloalkenyl, $C_{3-8}$-heterocyclyl, $C_{3-8}$-heterocycloalkenyl, fused aryl-$C_{3-8}$-cycloalkyl, or fused heteroaryl-$C_{3-8}$-cycloalkyl, each of which is optionally substituted with one or more substituents $R^{30}$, $R^{31}$, $R^{32}$ and $R^{33}$;

$R^3$, $R^4$, $R^5$, $R^6$, $R^{30}$, $R^{31}$, $R^{32}$ and $R^{33}$ are independently selected from the group consisting of halogen, nitro, cyano, hydroxy, oxo, carboxy, —$CF_3$; or —$NR^{10}R^{11}$; or $C_{1-6}$-alkyl, $C_{2-6}$-alkenyl, $C_{2-6}$-alkynyl, $C_{3-8}$-cycloalkyl, $C_{3-8}$-cycloalkyl-$C_{1-6}$-alkyl, $C_{3-8}$-cycloalkyl-$C_{3-6}$-alkenyl, aryl, aryl-$C_{1-6}$-alkyl, aryl-$C_{2-6}$-alkenyl, heteroaryl-$C_{1-6}$-alkyl, heteroaryl-$C_{2-6}$-alkenyl, heterocyclyl-$C_{1-6}$-alkyl, heterocyclyl-$C_{2-6}$-alkenyl, $C_{1-6}$-alkoxy, $C_{3-6}$-alkenyloxy, $C_{3-8}$-cycloalkoxy, $C_{3-8}$-cycloalkyl-$C_{1-6}$-alkoxy, $C_{3-8}$-cycloalkenyl-$C_{1-6}$-alkoxy, $C_{3-8}$-heterocyclyl-$C_{1-6}$-alkoxy, fused aryl-$C_{3-8}$-cycloalkenyl-$C_{1-6}$-alkoxy, $C_{3-8}$-cycloalkyl-$C_{3-6}$-alkenyloxy, $C_{3-8}$-cycloalkenyl-$C_{3-6}$-alkenyloxy, $C_{3-8}$-heterocyclyl-$C_{3-6}$-alkenyloxy, fused $C_{3-8}$-cycloalkyl-aryloxy, fused heterocyclyl-aryloxy, fused aryl-$C_{3-8}$-cycloalkenyl-$C_{3-6}$-alkenyloxy, aryl-$C_{1-6}$-alkoxy, aryl-$C_{3-6}$-alkenyloxy, heteroaryl, heteroaryl-$C_{1-6}$-alkoxy, heteroaryl-$C_{3-6}$-alkenyloxy, aryloxy, heteroaryloxy, $C_{1-6}$-alkylthio, $C_{3-6}$-alkenylthio, $C_{3-6}$-cycloalkyl-$C_{1-6}$-alkylthio, $C_{3-8}$-cycloalkenyl-$C_{1-6}$-alkylthio, $C_{3-8}$-heterocyclyl-$C_{1-6}$-alkylthio, fused aryl-$C_{3-8}$-cycloalkenyl-$C_{1-6}$-alkylthio, $C_{3-8}$-cycloalkyl-$C_{3-6}$-alkenylthio, $C_{3-8}$-cycloalkenyl-$C_{3-6}$-alkenylthio, $C_{3-8}$-heterocyclyl-$C_{3-6}$-alkenylthio, fused aryl-$C_{3-8}$-cycloalkenyl-$C_{3-6}$-alkenylthio, aryl-$C_{1-6}$-alkylthio, aryl-$C_{3-6}$-alkenylthio, heteroaryl-$C_{1-6}$-alkylthio, heteroaryl-$C_{3-6}$-alkenylthio, arylthio, heteroarylthio amino-$C_{1-6}$-alkyl, $C_{1-6}$-alkylamino-$C_{1-6}$-alkyl, di-($C_{1-6}$-alkyl)amino-$C_{1-6}$-alkyl, $C_{1-6}$-alkylsulfamoyl, di($C_{1-6}$-alkyl)sulfamoyl, $C_{1-6}$-alkylsulfinamoyl or di($C_{1-6}$-alkyl)sulfinamoyl each of which is optionally substituted with one or more substituents independently selected from $R^{12}$; or —C(O)—$R^{27}$, —S(O)$_2$—$R^{27}$, —C(O)—$NR^{13}R^{14}$, —S(O)$_2$—$NR^{13}R^{14}$, —$C_{1-6}$-alkyl-C(O)—$NR^{13}R^{14}$; or two substituents selected from $R^3$, $R^4$, $R^5$ and $R^6$ or $R^{30}$, $R^{31}$, $R^{32}$ and $R^{33}$ attached to the same or adjacent atoms together may form a radical —O—(CH$_2$)$_{1-3}$—O—;

$R^{10}$ and $R^{11}$ independently represent hydrogen, $C_{1-6}$-alkyl, —C(O)—$C_{1-6}$-alkyl, —C(O)—O—$C_{1-6}$-alkyl, —C(O)—$C_{3-8}$-cycloalkyl, carboxy-$C_{1-6}$-alkyl, —C(O)—$C_{1-6}$-alkyl-C(O)OH, —S(O)$_2$—$C_{1-6}$-alkyl, or aryl, each of which is optionally substituted with one or more halogens;

$R^{27}$ is $C_{1-6}$-alkyl, $C_{1-6}$-alkoxy, $C_{2-6}$-alkenyl, $C_{2-6}$-alkynyl, $C_{3-8}$-cycloalkyl, $C_{3-8}$-cycloalkyl-$C_{1-6}$-alkyl, $C_{3-8}$-cycloalkyl-$C_{2-6}$-alkenyl, aryl, aryl-$C_{1-6}$-alkyl, aryloxy-$C_{1-6}$-alkyl, aryl-$C_{2-6}$-alkenyl, heteroaryl, $C_{3-8}$-heterocyclyl, heteroaryl-$C_{1-6}$-alkyl, $C_{3-8}$-heterocyclyl-$C_{1-6}$-alkyl, heteroaryloxy-$C_{1-6}$-alkyl, carboxy-$C_{1-6}$-alkyl, carboxy-$C_{2-6}$-alkenyl, $C_{1-6}$-alkoxy-$C_{1-6}$-alkyl, $C_{1-6}$-alkoxy-$C_{2-6}$-alkenyl, $C_{1-6}$-alkylthio-$C_{1-6}$-alkyl, $R^{10}$HN—$C_{1-6}$-alkyl, $R^{10}R^{11}$—N—$C_{1-6}$-alkyl, $R^{10}R^{11}$—N—$C_{2-6}$-alkenyl, $R^{10}R^{11}$—N—S(O)$_2$—$C_{1-6}$-alkyl, $R^{10}R^{11}$—N—C(O)—$C_{1-6}$-alkyl, $C_{1-6}$-alkyl-C(O)—NH—$C_{1-6}$-alkyl, aryl-C(O)—NH—$C_{1-6}$-alkyl, heteroaryl-C(O)—NH—$C_{1-6}$-alkyl, $C_{3-8}$-cycloalkyl-C(O)—NH—$C_{1-6}$-alkyl, $C_{1-6}$-alkyl-S(O)$_2$—NH—$C_{1-6}$-alkyl, aryl-S(O)$_2$—NH—$C_{1-6}$-alkyl, heteroaryl-S(O)$_2$—NH—$C_{1-6}$-alkyl, or $C_{3-8}$-cycloalkyl-S(O)$_2$—NH—$C_{1-6}$-alkyl, each of which is optionally substituted with one or more substituents independently selected from $R^{12}$;

$R^{12}$ is halogen, cyano, hydroxy, —C(O)—O—$C_{1-6}$-alkyl, carboxy, —$CF_3$, $C_{1-6}$-alkyl, aryl, heteroaryl, $C_{1-6}$-alkoxy, $C_{2-6}$-alkenyloxy, $C_{3-8}$-cycloalkyloxy, $C_{3-8}$-cycloalkenyloxy, $C_{3-8}$-heterocyclyloxy, aryloxy, heteroaryloxy, aryl-$C_{1-6}$-alkoxy, aryl-$C_{1-6}$-alkenyloxy, heteroaryl-$C_{1-6}$-alkoxy, heteroaryl-$C_{1-6}$-alkenyloxy, $C_{3-8}$-cycloalkyl-$C_{1-6}$-alkoxy, $C_{3-8}$-cycloalkyl-$C_{1-6}$-alkenyloxy, $C_{3-8}$-heterocyclyl-$C_{1-6}$-alkoxy, $C_{3-8}$-heterocyclyl-$C_{1-6}$-alkenyloxy, fused aryl-$C_{3-8}$-cycloalkyl-$C_{1-6}$-alkoxy, fused aryl-$C_{3-8}$-cycloalkyl-$C_{1-6}$-alkenyloxy, $C_{1-6}$-alkylthio, $C_{2-6}$-alkenylthio, $C_{3-8}$-cycloalkylthio, $C_{3-8}$-cycloalkenylthio, $C_{3-8}$-heterocyclylthio, arylthio, heteroarylthio, aryl-$C_{1-6}$-alkylthio, aryl-$C_{1-6}$-alkenylthio, heteroaryl-$C_{1-6}$-alkylthio, heteroaryl-$C_{1-6}$-alkenylthio, $C_{3-8}$-cycloalkyl-$C_{1-6}$-alkylthio, $C_{3-8}$-cycloalkyl-$C_{1-6}$-alkenylthio, $C_{3-8}$-heterocyclyl-$C_{1-6}$-alkylthio, $C_{3-8}$-heterocyclyl-$C_{1-6}$-alkenylthio, fused aryl-$C_{3-8}$-cycloalkyl-$C_{1-6}$-alkylthio, fused aryl-$C_{3-8}$-cycloalkyl-$C_{1-6}$-alkenylthio, —$NR^{10}R^{11}$, —S(O)$_2$CH$_3$, —S(O)$_2$CF$_3$ or —S(O)$_2$NH$_2$ each of which is optionally substituted with one or more substituents independently selected from $R^{38}$;

$R^{13}$ and $R^{14}$ are independently selected from the group consisting of hydrogen, $C_{1-6}$-alkyl, hydroxy-$C_{1-6}$-alkyl, carboxy-$C_{1-6}$-alkyl, aryl, or heteroaryl, each of which is optionally substituted with one or more substituents independently selected from $R^{15}$; or $R^{13}$ and $R^{14}$ together with the nitrogen to which they are attached form a 3 to 8 membered heterocyclic ring with the said nitrogen atom, the heterocyclic ring optionally containing one or two further heteroatoms selected from nitrogen, oxygen and sulphur;

$R^{15}$ is halogen, cyano, hydroxy, carboxy, —$CF_3$, $C_{1-6}$-alkyl, —$S(O)_2CH_3$, or —$S(O)_2NH_2$;

$R^{38}$ is halogen or $C_{1-6}$-alkyl;

A is heteroaryl which is substituted with at least one substituent independently selected from $R^7$, $R^8$ and $R^9$; wherein $R^7$, $R^8$ and $R^9$ are independently selected from $C_{1-6}$-alkyl, $C_{1-6}$-alkoxy, $C_{1-6}$-alkylthio, $C_{3-6}$-cycloalkylthio, $C_{1-6}$-alkylamino, $C_{1-6}$-alkylsulfanyl, —$C_{1-6}$-alkyl-O—C(O)—$C_{1-6}$-alkyl, —NH—C(O)—$C_{1-6}$-alkyl, —$C_{1-6}$-alkoxy-$C_{1-6}$-alkyl, —$C_{1-6}$-alkyl-S—$C_{1-6}$-alkyl or hydroxy-$C_{1-6}$-alkyl, each of which is substituted with one or more substituents independently selected from $R^{34}$; or —$C_{1-6}$-alkyl-$NR^{19}R^{20}$, —$C_{2-6}$-alkenyl-$NR^{19}R^{20}$, —$C_{1-6}$-alkyl-S—$R^{21}$, —$C_{1-6}$-alkyl-S(O)—$R^{21}$, —$C_{1-6}$-alkyl-$S(O)_2$—$R^{21}$, —$S(O)_2$—$R^{21}$, —$S(O)_2$—$N(R^{19})(C_{1-6}$-alkyl)-C(O)—$NR^{22}R^{23}$ or —$S(O)_2$—$NR^{19}R^{20}$, each of which is substituted with one or more substituents independently selected from $R^{25}$; or —$C(O)NR^{22}R^{23}$, —$C_{1-6}$-alkyl-$C(O)NR^{22}R^{23}$ each of which is substituted with one or more substituents independently selected from $R^{25}$; or two of $R^7$, $R^8$ and $R^9$ can be taken together to form a $C_{2-5}$-alkylene bridge; the $C_{2-5}$-alkylene bridge is optionally substituted with one or more substituents independently selected from $R^{16}$; or carboxy, nitro, hydroxy, —SCN; or $C_{2-6}$-alkenyl, $C_{2-6}$-alkynyl, $C_{1-6}$-alkenyloxy, $C_{2-6}$-alkenylthio, $C_{3-6}$-cycloalkyl, $C_{3-6}$-cycloalkyl-$C_{1-6}$-alkyl, $C_{3-6}$-cycloalkoxy, $C_{3-6}$-cycloalkyl-$C_{1-6}$-alkylthio, —C(O)—O—$C_{1-6}$-alkyl, formyl, —C(O)—$C_{1-6}$-alkyl, —$C_{1-6}$-alkyl-C(O)—O—$C_{1-6}$-alkyl, carboxy-$C_{1-6}$-alkyl each of which is optionally substituted with one or more substituents independently selected from $R^{16}$; or heteroaryl, heteroaryl-$C_{1-6}$-alkyl, heteroaryl-$C_{1-6}$-alkoxy, heteroaryl-$C_{1-6}$-alkylthio, heteroaryl-thio-$C_{1-6}$-alkyl, heteroaryl-oxy-$C_{1-6}$-alkyl, heteroaryloxy, heteroarylthio, —C(O)-aryl, or —C(O)-heteroaryl, each of which is optionally substituted on the aryl or heteroaryl part with one or more substituents independently selected from $R^{17}$; or $C_{3-8}$-cycloalkyl, $C_{3-8}$-cycloalkenyl, $C_{3-8}$-cycloalkylthio, $C_{3-8}$-cycloalkyl-$C_{1-6}$-alkyl, $C_{3-8}$-cycloalkenyl-$C_{1-6}$-alkyl, $C_{3-6}$-cycloalkyl-$C_{1-6}$-alkoxy, $C_{3-6}$-cycloalkyl-$C_{1-6}$-alkylthio, each of which is optionally substituted on the cycloalkyl part with one or more substituents independently selected from $R^{18}$; or $C_{3-8}$-heterocyclyl, $C_{3-8}$-heterocyclyl-$C_{1-6}$-alkyl, $C_{3-8}$-heterocyclyl-$C_{1-6}$-alkylthio, $C_{3-8}$-heterocyclylthio, $C_{3-8}$-heterocyclyl-amino-$C_{1-6}$-alkyl, or —C(O)—$C_{3-8}$-heterocyclyl, each of which is optionally substituted with one or more substituents independently selected from $R^{16}$; or —$C_{1-6}$-alkyl-$NR^{36}R^{37}$, —$C_{2-6}$-alkenyl-$NR^{36}R^{37}$ or —$S(O)_2$—$NR^{36}R^{37}$, each optionally substituted with one or more substituents independently selected from $R^{25}$; or —$C(O)NR^{36}R^{37}$, —$C_{1-6}$-alkyl-C(O)$NR^{36}R^{37}$, —$C_{1-6}$-alkyl-NH—$NR^{22}R^{23}$, —$C_{1-6}$-alkyl-NH—C(O)—$C_{1-6}$-alkyl-$NR^{22}R^{23}$, each optionally substituted with one or more substituents independently selected from $R^{26}$;

If more than one substituent $R^7$, $R^8$ and $R^9$ is present on A that additional $R^7$, $R^8$ and $R^9$ may be selected from halogen or $C_{1-6}$-alkyl;

$R^{16}$, $R^{17}$, and $R^{18}$ are independently $C_{1-6}$-alkyl, halogen, nitro, cyano, hydroxy, carboxy, oxo, —$CF_3$, carboxy-$C_{1-6}$-alkyl, hydroxy-$C_{1-6}$-alkyl, —$C_{1-6}$-alkyl-C(O)—O—$C_{1-6}$-alkyl, —$C_{1-6}$-alkyl-C(O)—$NR^{19}R^{20}$, —C(O)—O—$C_{1-6}$-alkyl, —C(O)—$C_{1-6}$-alkyl-C(O)—$C_{1-6}$-alkyl, —$NR^{19}R^{20}$, —$NHS(O)_2C_{1-6}$-alkyl, —$NHS(O)_2CF_3$, —$C(O)NR^{19}R^{20}$, —$S(O)_2C_{1-6}$-alkyl, —$S(O)_2CF_3$, —$S(O)_2CH_2CF_3$ or —$S(O)_2NR^{19}R^{20}$;

$R^{34}$ is halogen, nitro, cyano, hydroxy, carboxy, —$CF_3$; or carboxy-$C_{1-6}$-alkyl, —$C_{1-6}$-alkyl-C(O)—O—$C_{1-6}$-alkyl, —C(O)—O—$C_{1-6}$-alkyl or —C(O)—$C_{1-6}$-alkyl-C(O)—$C_{1-6}$-alkyl each optionally substituted with one or more halogens;

$R^{19}$ and $R^{20}$ independently represent hydrogen, $C_{1-6}$-alkyl, $C_{2-6}$-alkenyl, hydroxy-$C_{1-6}$-alkyl, carboxy-$C_{1-6}$-alkyl, aryl, heteroaryl, $C_{3-8}$-cycloalkyl, $C_{3-8}$-cycloalkyl-$C_{1-6}$-alkyl, $C_{3-8}$-heterocyclyl, aryl-$C_{1-6}$-alkyl, $C_{3-8}$-heterocyclyl-$C_{1-6}$-alkyl, —C(O)—O—$C_{1-6}$-alkyl, —$C_{1-6}$-alkyl-C(O)—O—$C_{1-6}$-alkyl, —$C_{1-6}$-alkyl-$NR^{22}R^{23}$, or —$S(O)_2$—$C_{1-6}$-alkyl, each of which is optionally substituted with one or more substituents independently selected from $R^{24}$, or $R^{19}$ and $R^{20}$ together with the nitrogen to which they are attached form a 3 to 8 membered heterocyclic ring with the said nitrogen atom, the heterocyclic ring optionally containing one or two further heteroatoms selected from nitrogen, oxygen and sulphur, the heterocyclic ring is optionally substituted with one or more substituents independently selected from $R^{24}$;

$R^{21}$ is selected from $C_{1-6}$-alkyl, $C_{2-6}$-alkenyl, carboxy-$C_{1-6}$-alkyl, $C_{1-6}$-alkylamino-$C_{1-6}$-alkyl or hydroxy-$C_{1-6}$-alkyl, —$C_{1-6}$-alkyl-$NR^{22}R^{23}$; or aryl, heteroaryl, aryl-$C_{1-6}$-alkyl, or heteroaryl-$C_{1-6}$-alkyl, wherein the aryl or heteroaryl part is optionally substituted with one or more substituents independently selected from $R^{24}$; or $C_{3-8}$-cycloalkyl, $C_{3-8}$-cycloalkenyl, $C_{3-8}$-cycloalkyl-$C_{1-6}$-alkyl, $C_{3-8}$-cycloalkenyl-$C_{1-6}$-alkyl;

$R^{22}$ and $R^{23}$ are independently selected from hydrogen, $C_{1-6}$-alkyl, carboxy-$C_{1-6}$-alkyl, —$C_{1-6}$-alkyl-C(O)—O—$C_{1-6}$-alkyl, —C(O)—O—$C_{1-6}$-alkyl, —$C_{1-6}$-alkyl-$S(O)_2$—$C_{1-6}$-alkyl, —$C_{1-6}$-alkyl-$S(O)_3H$, $C_{3-8}$-cycloalkyl, aryl, or heteroaryl; or $R^{22}$ and $R^{23}$ together with the nitrogen to which they are attached form a 3 to 8 membered heterocyclic ring with the said nitrogen atom, the heterocyclic ring optionally containing one or two further heteroatoms selected from nitrogen, oxygen and sulphur, the heterocyclic ring is optionally substituted with one or more substituents independently selected from $R^{24}$;

$R^{36}$ and $R^{37}$ are independently selected from carboxy-$C_{1-6}$-alkyl, —$C_{1-6}$-alkyl-C(O)—O—$C_{1-6}$-alkyl, —C(O)—O—$C_{1-6}$-alkyl, —$C_{1-6}$-alkyl-$S(O)_2$—$C_{1-6}$-alkyl, $C_{3-8}$-cycloalkyl, aryl, or heteroaryl; or $R^{36}$ and $R^{37}$ together with the nitrogen to which they are attached form a 3 to 8 membered heterocyclic ring with the said nitrogen atom, the heterocyclic ring optionally containing one or two further heteroatoms selected from nitrogen, oxygen and sulphur, the heterocyclic ring is optionally substituted with one or more substituents independently selected from $R^{24}$;

$R^{24}$ is halogen, nitro, cyano, hydroxy, carboxy, oxo, —$CF_3$, $C_{1-6}$-alkyl, hydroxy-$C_{1-6}$-alkyl, carboxy-$C_{1-6}$-alkyl, —C(O)—$C_{1-6}$-alkyl, —C(O)—$C_{3-8}$-cycloalkyl, —C(O)-aryl, —C(O)-heteroaryl, —C(O)—$C_{3-8}$-heterocyclyl —C(O)—O—$C_{1-6}$-alkyl, —$C_{1-6}$-alkyl-C(O)—O—$C_{1-6}$-alkyl, aryl, heteroaryl, aryl-$C_{1-6}$-alkyl, heteroaryl-$C_{1-6}$-alkyl, $C_{3-8}$-cycloalkyl, $C_{3-8}$-heterocyclyl, $C_{3-8}$-cycloalkyl-$C_{1-6}$-alkyl, $C_{3-8}$-heterocyclyl-$C_{1-6}$-alkyl, —$C_{1-6}$-alkyl-C(O)—$C_{3-8}$-heterocyclyl, —C(O)—O—$C_{1-6}$-alkyl-aryl, —NH—S $-(O)_2R^{28}$, or $-S(O)_2R^{28}$, wherein each cyclic moiety is optionally substituted with one or more substituents independently selected from $R^{29}$;

$R^{25}$ and $R^{26}$ are independently $C_{1-6}$-alkyl, halogen, nitro, cyano, hydroxy, $-C(O)-O-C_{1-6}$-alkyl, carboxy, $-C_{1-6}$-alkyl-$C(O)-O-C_{1-6}$-alkyl, carboxy-$C_{1-6}$-alkyl, carboxy-$C_{3-8}$-cycloalkyl, $-CF_3$, $-S(O)_2CH_3$, or $-S(O)_2NH_2$;

$R^{28}$ is $C_{1-6}$-alkyl, carboxy-$C_{1-6}$-alkyl, $-C_{1-6}$-alkyl-$C(O)-O-C_{1-6}$-alkyl, $C_{3-8}$-cycloalkyl, aryl, aryl-$C_{1-6}$-alkyl, heteroaryl optionally substituted with $C_{1-6}$-alkyl, $-NH_2$, or $-N(CH_3)_2$;

$R^{29}$ is halogen, nitro, cyano, hydroxy, carboxy, oxo, $-CF_3$, $C_{1-6}$-alkyl, or $C_{1-6}$-alkoxy;

$R^{35}$ is halogen, nitro, cyano, hydroxy, $-C(O)-O-C_{1-6}$-alkyl, carboxy, $-C_{1-6}$-alkyl-$C(O)-O-C_{1-6}$-alkyl, carboxy-$C_{1-6}$-alkyl, $-CF_3$, $-S(O)_2CH_3$, or $-S(O)_2NH_2$;

as well as any salt hereof with a pharmaceutically acceptable acid or base, or any optical isomer or mixture of optical isomers, including a racemic mixture, or any tautomeric forms.

Embodiment 2. A compound according to embodiment 1 wherein $R^1$ is $C_{1-8}$-alkyl, $C_{2-8}$-alkenyl, aryl, heteroaryl, $C_{3-8}$-cycloalkyl-$C_{1-6}$-alkyl, $C_{3-8}$-cycloalkyl-$C_{2-6}$-alkenyl, $C_{3-8}$-cycloalkenyl-$C_{1-6}$-alkyl, $C_{3-8}$-cycloalkenyl-$C_{2-6}$-alkenyl, $C_{3-8}$-heterocyclyl-$C_{1-6}$-alkyl, $C_{3-8}$-heterocyclyl-$C_{2-6}$-alkenyl, $C_{3-8}$-heterocycloalkenyl-$C_{1-6}$-alkyl, $C_{3-8}$-heterocycloalkenyl-$C_{2-6}$-alkenyl, aryl-$C_{1-6}$-alkyl, or aryl-$C_{2-6}$-alkenyl, each of which is optionally substituted with one or more substituents $R^3$, $R^4$, $R^5$ and $R^6$.

Embodiment 3. A compound according to embodiment 2 wherein $R^1$ is $C_{1-8}$-alkyl, $C_{2-8}$-alkenyl, aryl, heteroaryl, $C_{3-8}$-cycloalkyl-$C_{1-6}$-alkyl, $C_{3-8}$-cycloalkyl-$C_{2-6}$-alkenyl, $C_{3-8}$-cycloalkenyl-$C_{1-6}$-alkyl, $C_{3-8}$-cycloalkenyl-$C_{2-6}$-alkenyl, aryl-$C_{1-6}$-alkyl, or aryl-$C_{2-6}$-alkenyl, each of which is optionally substituted with one or more substituents $R^3$, $R^4$, $R^5$ and $R^6$.

Embodiment 4. A compound according to embodiment 3 wherein $R^1$ is $C_{1-8}$-alkyl, $C_{2-8}$-alkenyl, aryl, heteroaryl, $C_{3-8}$-cycloalkyl-$C_{1-6}$-alkyl, $C_{3-8}$-cycloalkenyl-$C_{1-6}$-alkyl, or aryl-$C_{1-6}$-alkyl, each of which is optionally substituted with one or more substituents $R^3$, $R^4$, $R^5$ and $R^6$.

Embodiment 5. A compound according to embodiment 4 wherein $R^1$ is $C_{1-8}$-alkyl, $C_{2-8}$-alkenyl, phenyl, pyridinyl, benzo[1,3]dioxolyl, $C_{3-8}$-cycloalkyl-$C_{1-6}$-alkyl, $C_{3-8}$-cycloalkenyl-$C_{1-6}$-alkyl, or phenyl-$C_{1-6}$-alkyl, each of which is optionally substituted with one or more substituents $R^3$, $R^4$, $R^5$ and $R^6$.

Embodiment 6. A compound according to embodiment 5 wherein $R^1$ is methyl, ethyl, propyl, butyl, 3-methyl-butyl, 2,2-dimethylpropyl, 1,3,-dimethylbutyl, isopropyl, 3-methyl-but-2-enyl, ethenyl, propenyl, butenyl, cyclopropyl-methyl, cyclopropyl-ethyl, cyclopropyl-propyl, cyclobutyl-methyl, cyclobutyl-ethyl, cyclobutyl-propyl, cyclopentyl-methyl, cyclopentyl-ethyl, cyclopentyl-propyl, cyclohexyl-methyl, cyclohexyl-ethyl, cyclohexyl-propyl, cycloheptyl-methyl, cycloheptyl-ethyl, cycloheptyl-propyl, cyclohexenyl-methyl, cyclohexenyl-ethyl, cyclohexenyl-propyl, cycloheptenyl-methyl, cycloheptenyl-ethyl, phenyl, pyridinyl, benzo[1,3]dioxolyl, benzyl, phenethyl, phenyl-propyl, bicyclo[2.2.1]heptenyl-methyl or bicyclo[2.2.1]heptyl-methyl, each of which is optionally substituted with one or more substituents $R^3$, $R^4$, $R^5$ and $R^6$.

Embodiment 7. A compound according to embodiment 6 wherein $R^1$ is methyl, ethyl, propyl, butyl, 3-methyl-butyl, 2,2-dimethylpropyl, 1,3,-dimethylbutyl, isopropyl, 3-methyl-but-2-enyl, ethenyl, cyclohexyl-methyl, cyclohexyl-ethyl, cyclohexyl-propyl, cyclohexenyl-methyl, cyclohexenyl-ethyl, cyclohexenyl-propyl, cycloheptenyl-methyl, cycloheptenyl-ethyl, phenyl, pyridinyl, benzo[1,3]dioxolyl, benzyl, phenethyl, phenylpropyl, bicyclo[2.2.1]heptenyl-methyl or bicyclo[2.2.1]heptyl-methyl, each of which is optionally substituted with one or more substituents $R^3$, $R^4$, $R^5$ and $R^6$.

Embodiment 8. A compound according to embodiment 7 wherein $R^1$ is methyl, ethyl, propyl, isopropyl, butyl or 3-methyl-butyl, each of which is optionally substituted with one or more substituents $R^3$, $R^4$, $R^5$ and $R^6$.

Embodiment 9. A compound according to embodiment 7 wherein $R^1$ is benzyl, phenethyl or phenylpropyl, optionally substituted with one or more substituents $R^3$, $R^4$, $R^5$ and $R^6$.

Embodiment 10. A compound according to embodiment 7 wherein $R^1$ is phenyl, optionally substituted with one or more substituents $R^3$, $R^4$, $R^5$ and $R^6$.

Embodiment 11. A compound according to any one of the embodiments 1 to 10 wherein $R^2$ is $C_{1-8}$-alkyl, $C_{3-8}$-cycloalkyl, $C_{3-8}$-cycloalkyl-$C_{1-8}$-alkyl or $C_{3-8}$-cycloalkenyl, each of which is optionally substituted with one or more substituents $R^{30}$, $R^{31}$, $R^{32}$ and $R^{33}$.

Embodiment 12. A compound according to embodiment 11 wherein $R^2$ is $C_{3-8}$-cycloalkyl or $C_{3-8}$-cycloalkyl-$C_{1-8}$-alkyl optionally substituted with one or more substituents $R^{30}$, $R^{31}$, $R^{32}$ and $R^{33}$.

Embodiment 13. A compound according to embodiment 12 wherein $R^2$ is $C_{3-8}$-cycloalkyl optionally substituted with one or more substituents $R^{30}$, $R^{31}$, $R^{32}$ and $R^{33}$.

Embodiment 14. A compound according to embodiment 11 wherein $R^2$ is methyl, ethyl, propyl, butyl, pentyl, hexyl, 3-methylbutyl, 3,3-dimethylbutyl, cyclopropyl, cyclobutyl, cyclopentyl, cyclohexyl, cycloheptyl, methylcyclopropyl, methylcyclobutyl, methylcyclopentyl, methylcyclohexyl, or ethylcyclopentyl, each of which may optionally be substituted with $R^{30}$.

Embodiment 15. A compound according to embodiment 14 wherein $R^2$ is methylcyclopentyl or methylcyclohexyl, each of which may optionally be substituted with $R^{30}$.

Embodiment 16. A compound according to embodiment 14 wherein $R^2$ is cyclohexyl optionally substituted with $R^{30}$.

Embodiment 17. A compound according to any one of the embodiments 1 to 16 which is

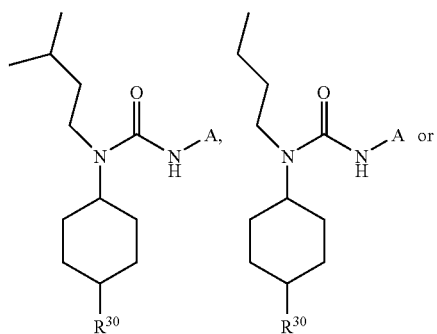

-continued

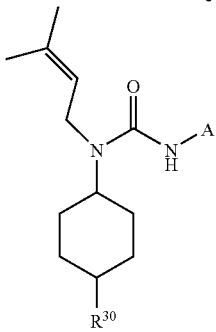

wherein A and R³⁰ are as defined in embodiment 1.

Embodiment 18. A compound according to any one of the embodiments 1 to 16 which is

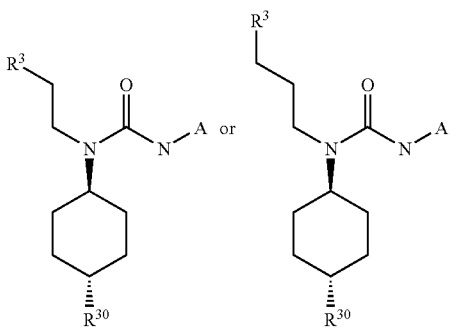

wherein A, R³ and R³⁰ are as defined in embodiment 1.

Embodiment 19. A compound according to any one of the embodiments 1 to 16 which is

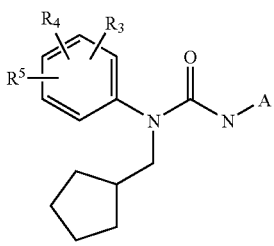

wherein A, R³, R⁴, R⁵ and R³⁰ are as defined in embodiment 1.

Embodiment 20. A compound according to any one of the embodiments 1 to 19 wherein R³, R⁴, R⁵ and R⁶ are independently selected from the group consisting of halogen, hydroxy, carboxy, —CF₃; or
—NR¹⁰R¹¹; or
C$_{1-6}$-alkyl, C$_{2-6}$-alkenyl, C$_{1-6}$-alkoxy, C$_{3-6}$-alkenyloxy, C$_{3-8}$-cycloalkyl, C$_{3-8}$-cycloalkoxy, C$_{3-8}$-cycloalkyl-C$_{1-6}$-alkyl, C$_{3-6}$-cycloalkyl-C$_{1-6}$-alkoxy, C$_{3-8}$-cycloalkenyl-C$_{1-6}$-alkoxy, phenyl-C$_{1-6}$-alkoxy, each of which is optionally substituted with one or more substituents independently selected from R¹²; or
Phenyl, phenoxy, benzyloxy, indanyloxy, benzo[1,3]dioxolyloxy, phenylthio, or benzylthio; or
—C(O)—R²⁷, —S(O)₂—R²⁷, —C(O)—NR¹³R¹⁴, or —S(O)₂—NR¹³R¹⁴; or
two substituents selected from R³, R⁴, R⁵ and R⁶ attached to the same or adjacent atoms together may form a radical —O—(CH₂)$_{1-3}$—O—.

Embodiment 21. A compound according to embodiment 20 wherein R³, R⁴, R⁵ and R⁶, are independently selected from the group consisting of halogen, —CF₃, C$_{1-6}$-alkyl, C$_{2-6}$-alkenyl, C$_{1-6}$-alkoxy, phenyl, phenoxy, benzyloxy, indanyloxy, benzo[1,3]dioxolyloxy, phenylthio, benzylthio, phenyl-C$_{1-6}$-alkoxy, C$_{3-8}$-cycloalkyl, C$_{3-8}$-cycloalkoxy, or C$_{3-6}$-cycloalkyl-C$_{1-6}$-alkoxy, each of which is optionally substituted with one or more substituents independently selected from R¹²; or —NR¹⁰R¹¹, —C(O)—R²⁷, —S(O)₂—R²⁷, —C(O)—NR¹³R¹⁴, or —S(O)₂—NR¹³R¹⁴.

Embodiment 22. A compound according to embodiment 21 wherein R³, R⁴, R⁵ and R⁶ are independently selected from the group consisting of halogen, CF₃, C$_{1-6}$-alkyl, C$_{1-6}$-alkoxy, phenoxy, benzyloxy, phenylthio, benzylthio, C$_{3-8}$-cycloalkyl, C$_{3-8}$-cycloalkoxy, or C$_{3-6}$-cycloalkyl-C$_{1-6}$-alkoxy, each of which is optionally substituted with one or more substituents independently selected from R¹²; or —NR¹⁰R¹¹, —C(O)—R²⁷, —S(O)₂—R²⁷, —C(O)—NR¹³R¹⁴, or —S(O)₂—NR¹³R¹⁴.

Embodiment 23. A compound according to embodiment 21 wherein R³, R⁴, R⁵ and R⁶ are independently selected from the group consisting of F, Cl, Br, —CF₃, methyl, ethyl, propyl, butyl, isopropyl, tert-butyl, ethenyl, propenyl, butenyl, cyclopropyl, cyclobutyl, cyclopentyl, cyclohexyl, phenyl, methoxy, ethoxy, propoxy, butoxy, isopropoxy, isobutoxy, tert-butoxy, cyclohexyloxy, phenoxy, benzyloxy, indanyloxy, benzo[1,3]dioxolyloxy, cyclopropyl-methoxy, cyclopropyl-ethoxy, cyclopropyl-propoxy, cyclobutyl-methoxy, cyclobutyl-ethoxy, cyclobutyl-propoxy, cyclopentyl-methoxy, cyclopentyl-ethoxy, cyclopentyl-propoxy, cyclohexyl-methoxy, cyclohexyl-ethoxy, cyclohexyl-propoxy, cycloheptyl-methoxy, cycloheptyl-ethoxy, cycloheptyl-propoxy, phenylethoxy, phenylthio or benzylthio, each of which is optionally substituted with one or more substituents independently selected from R¹²; or —NR¹⁰R¹¹, —C(O)—R²⁷, —S(O)₂—R⁷, —C(O)—NR¹³R¹⁴, or —S(O)₂—NR¹³R¹⁴.

Embodiment 24. A compound according to embodiment 23 wherein R³, R⁴, R⁵ and R⁶ are independently selected from the group consisting of F, Cl, Br, —CF₃, methyl, ethyl, propyl, methoxy, ethoxy, propoxy, butoxy, isopropoxy, isobutoxy, tert-butoxy, cyclohexyloxy, phenoxy, benzyloxy, indanyloxy, benzo[1,3]dioxolyloxy, phenylmethoxy, phenylethoxy, phenylthio or benzylthio, each of which is optionally substituted with one or more substituents independently selected from R¹²; or —NR¹⁰R¹¹, —C(O)—R²⁷, —S(O)₂—R²⁷, —C(O)—NR¹³R¹⁴, or —S(O)₂—NR¹³R¹⁴.

Embodiment 25. A compound according to embodiment 24 wherein R³, R⁴, R⁵ and R⁶ are independently selected from the group consisting of F, Cl, Br, —CF₃, methyl, methoxy, ethoxy, propoxy, butoxy, phenoxy, benzyloxy, phenylthio or benzylthio, each of which is optionally substituted with one or more substituents independently selected from R¹².

Embodiment 26. A compound according to embodiment 25 wherein R³, R⁴, R⁵ and R⁶ are independently selected from the group consisting of phenoxy and benzyloxy, each of which is optionally substituted with one or more substituents independently selected from R¹².

Embodiment 27. A compound according to embodiment 25 wherein R³, R⁴, R⁵ and R⁶ are independently selected from the group consisting of F, Cl, Br or —CF₃.

Embodiment 28. A compound according to any one of the embodiments 1 to 27 wherein $R^{30}$, $R^{31}$, $R^{32}$ and $R^{33}$ are independently selected from the group consisting of halogen, hydroxy, carboxy, —$CF_3$; or
—$NR^{10}R^{11}$; or
$C_{1-6}$-alkyl, $C_{2-6}$-alkenyl, $C_{1-6}$-alkoxy, $C_{3-6}$-alkenyloxy, $C_{3-8}$-cycloalkyl, $C_{3-8}$-cycloalkoxy, $C_{3-8}$-cycloalkyl-$C_{1-6}$-alkyl, $C_{3-6}$-cycloalkyl-$C_{1-6}$-alkoxy, $C_{3-8}$-cycloalkenyl-$C_{1-6}$-alkoxy, each of which is optionally substituted with one or more substituents independently selected from $R^{12}$; or
Phenyl, phenoxy, benzyloxy, indanyloxy, benzo[1,3]dioxolyloxy, phenylthio, or benzylthio; or
—$C(O)$—$R^{27}$, —$S(O)_2$—$R^{27}$, —$C(O)$—$NR^{13}R^{14}$, or —$S(O)_2$—$NR^{13}R^{14}$; or
two substituents selected from $R^{30}$, $R^{31}$, $R^{32}$ or $R^{33}$ attached to the same or adjacent atoms together may form a radical —O—$(CH_2)$1-3-O—.

Embodiment 29. A compound according to embodiment 28 wherein $R^{30}$, $R^{31}$, $R^{32}$ and $R^{33}$ are independently selected from the group consisting of halogen, —$CF_3$, $C_{1-6}$-alkyl, $C_{2-6}$-alkenyl, $C_{1-6}$-alkoxy, phenoxy, phenyl, benzyloxy, phenylthio, benzylthio, $C_{3-8}$-cycloalkyl, $C_{3-8}$-cycloalkoxy, or $C_{3-6}$-cycloalkyl-$C_{1-6}$-alkoxy, each of which is optionally substituted with one or more substituents independently selected from $R^{12}$; or —$C(O)$—$R^{27}$, —$S(O)_2$—$R^{27}$, —$C(O)$—$NR^{13}R^{14}$, or —$S(O)_2$—$NR^{13}R^{14}$.

Embodiment 30. A compound according to embodiment 28 wherein $R^{30}$, $R^{31}$, $R^{32}$ and $R^{33}$ are independently selected from the group consisting of F, Cl, Br, —$CF_3$, methyl, ethyl, propyl, butyl, isopropyl, tert-butyl, ethenyl, propenyl, butenyl, cyclopropyl, cyclobutyl, cyclopentyl, cyclohexyl, phenyl, methoxy, ethoxy, propoxy, butoxy, tert-butoxy, cyclohexyloxy, phenoxy, benzyloxy, indanyloxy, benzo[1,3]dioxolyloxy, cyclopropyl-methoxy, cyclopropyl-ethoxy, cyclopropyl-propoxy, cyclobutyl-methoxy, cyclobutyl-ethoxy, cyclobutyl-propoxy, cyclopentyl-methoxy, cyclopentyl-ethoxy, cyclopentyl-propoxy, cyclohexyl-methoxy, cyclohexyl-ethoxy, cyclohexyl-propoxy, cycloheptyl-methoxy, cycloheptyl-ethoxy, cycloheptyl-propoxy, phenylthio or benzylthio, each of which is optionally substituted with one or more substituents independently selected from $R^{12}$; or —$C(O)$—$R^{27}$, —$S(O)_2$—$R^{27}$, —$C(O)$—$NR^{13}R^{14}$, or —$S(O)_2$—$NR^{13}R^{14}$.

Embodiment 31. A compound according to embodiment 30 wherein $R^{30}$, $R^{31}$, $R^{32}$ and $R^{33}$ are independently selected from the group consisting of methyl, ethyl, propyl, butyl, isopropyl, tert-butyl, cyclopropyl, cyclobutyl, cyclopentyl, cyclohexyl, methoxy, ethoxy, propoxy, butoxy, tert-butoxy, phenyl, phenoxy, benzyloxy, cyclopropyl-methoxy, cyclopropyl-ethoxy, cyclobutyl-methoxy, cyclobutyl-ethoxy, cyclopentyl-methoxy, cyclopentyl-ethoxy, cyclohexyl-methoxy, cyclohexyl-ethoxy, each of which is optionally substituted with one or more substituents independently selected from $R^{12}$.

Embodiment 32. A compound according to embodiment 31 wherein $R^{30}$, $R^{31}$, $R^{32}$ and $R^{33}$ are independently selected from the group consisting of methyl, ethyl, propyl, isopropyl, tertbutyl, cyclopropyl, cyclobutyl, cyclopentyl, cyclohexyl, phenyl, methoxy, ethoxy, propoxy, butoxy, tert-butoxy, benzyloxy, or cyclopropyl-methoxy, each of which is optionally substituted with one or more substituents independently selected from $R^{12}$.

Embodiment 33. A compound according to embodiment 32 wherein $R^{30}$, $R^{31}$, $R^{32}$ and $R^{33}$ are independently selected from the group consisting of methyl or ethyl, each of which is optionally substituted with one or more substituents independently selected from $R^{12}$.

Embodiment 34. A compound according to embodiment 32 wherein $R^{30}$, $R^{31}$, $R^{32}$ and $R^{33}$ are independently selected from the group consisting of cyclopentyl or cyclohexyl optionally substituted with one or more substituents independently selected from $R^{12}$.

Embodiment 35. A compound according to any one of the embodiments 1 to 34 wherein $R^{10}$ and $R^{11}$ independently represent hydrogen, $C_{1-6}$-alkyl, —$C(O)$—$C_{1-6}$-alkyl, carboxy-$C_{1-6}$-alkyl, —$C(O)$—$C_{3-8}$-cycloalkyl, or —$S(O)_2$—$C_{1-6}$-alkyl.

Embodiment 36. A compound according to embodiment 35 wherein $R^{10}$ and $R^{11}$ independently represent hydrogen, —$C(O)$—$C_{1-6}$-alkyl, —$C(O)$—$C_{3-8}$-cycloalkyl, or —$S(O)_2$—$C_{1-6}$-alkyl.

Embodiment 37. A compound according to embodiment 35 wherein $R^{10}$ and $R^{11}$ independently represent hydrogen, methyl, ethyl, propyl, butyl, —$C(O)$-methyl, —$C(O)$-ethyl, —$C(O)$-propyl, —$C(O)$-isopropyl, —$C(O)$-butyl, —$C(O)$-cyclopentyl, —$S(O)_2$-methyl, carboxy-ethyl, carboxy-propyl or carboxy-butyl.

Embodiment 38. A compound according to any one of the embodiments 1 to 37 wherein $R^{27}$ is $C_{1-6}$-alkyl, $C_{1-6}$-alkoxy, $C_{2-6}$-alkenyl, $C_{2-6}$-alkynyl, $C_{3-8}$-cycloalkyl, $C_{3-8}$-cycloalkyl-$C_{1-6}$-alkyl, aryl, aryl-$C_{1-6}$-alkyl, aryl-$C_{2-6}$-alkenyl, heteroaryl, heteroaryl-$C_{1-6}$-alkyl, carboxy-$C_{1-6}$-alkyl, $C_{1-6}$-alkoxy-$C_{1-6}$-alkyl, $C_{1-6}$-alkylthio-$C_{1-6}$-alkyl, $R^{10}HN$—$C_{1-6}$-alkyl, $R^{10}R^{11}N$—$C_{1-6}$-alkyl, $R^{10}R^{11}N$—$S(O)_2$—$C_{1-6}$-alkyl, or $R^{10}R^{11}N$—$C(O)$—$C_{1-6}$-alkyl, each of which is optionally substituted with one or more substituents independently selected from $R^{12}$.

Embodiment 39. A compound according to embodiment 38 wherein $R^{27}$ is $C_{1-6}$-alkyl, $C_{1-6}$-alkoxy, $C_{3-8}$-cycloalkyl, $C_{3-8}$-cycloalkyl-$C_{1-6}$-alkyl, aryl-$C_{1-6}$-alkyl, aryl-$C_{2-6}$-alkenyl, aryl, heteroaryl, heteroaryl-$C_{1-6}$-alkyl, carboxy-$C_{1-6}$-alkyl, $C_{1-6}$-alkoxy-$C_{1-6}$-alkyl, $R^{10}HN$—$C_{1-6}$-alkyl, $R^{10}R^{11}N$—$C_{1-6}$-alkyl, $R^{10}R^{11}N$—$S(O)_2$—$C_{1-6}$-alkyl, or $R^{10}R^{11}N$—$C(O)$—$C_{1-6}$-alkyl, each of which is optionally substituted with one or more substituents independently selected from $R^{12}$.

Embodiment 40. A compound according to embodiment 39 wherein $R^{27}$ is $C_{1-6}$-alkyl, $C_{1-6}$-alkoxy, $C_{3-8}$-cycloalkyl, $C_{3-8}$-cycloalkyl-$C_{1-6}$-alkyl, aryl, heteroaryl-$C_{1-6}$-alkyl, aryl-$C_{1-6}$-alkyl, $C_{1-6}$-alkoxy-$C_{1-6}$-alkyl, carboxy-$C_{1-6}$-alkyl, or heteroaryl, each of which is optionally substituted with one or more substituents independently selected from $R^{12}$.

Embodiment 41. A compound according to embodiment 40 wherein $R^{27}$ is methyl, ethyl, propyl, n-butyl, isobutyl, cyclopropyl, cyclopentyl, cyclopropylmethyl, phenyl, pyridyl, thiophene, imidazole, or thiazole, each of which is optionally substituted with one or more substituents independently selected from $R^{12}$.

Embodiment 42. A compound according to embodiment 41 wherein $R^{27}$ is methyl, ethyl, propyl, n-butyl, isobutyl, cyclopropyl, cyclopentyl, cyclopropylmethyl, phenyl, pyridyl, thiophene, imidazole, orthiazole.

Embodiment 43. A compound according to embodiment 42 wherein $R^{27}$ is methyl, ethyl, or propyl.

Embodiment 44. A compound according to any one of the embodiments 1 to 43 wherein $R^{12}$ is halogen, —$CF_3$, —CN, $C_{1-6}$-alkyl, $C_{1-6}$-alkoxy, $C_{1-6}$-alkylthio, $C_{2-6}$-alkenyloxy, $C_{3-8}$-cycloalkyloxy, $C_{3-8}$-cycloalkenyloxy, aryloxy, aryl-$C_{1-6}$-alkoxy, aryl-$C_{1-6}$-alkenyloxy, $C_{3-8}$-cycloalkyl-$C_{1-6}$-alkoxy, $C_{3-8}$-cycloalkyl-$C_{1-6}$-alkenyloxy, $C_{3-8}$-heterocyclyl-$C_{1-6}$-alkoxy, or $C_{3-8}$-heterocyclyl-$C_{1-6}$-alkenyloxy, each of which is optionally substituted with one or more substituents independently selected from $R^{38}$; or $NR^{10}R^{11}$, or —$S(O)_2$—$C_{1-6}$-alkyl.

Embodiment 45. A compound according to embodiment 44 wherein $R^{12}$ is halogen, —$CF_3$, —CN, $C_{1-6}$-alkyl, $C_{1-6}$-alkoxy, $C_{1-6}$-alkylthio, $C_{3-8}$-cycloalkyloxy, aryloxy, aryl-$C_{1-6}$-alkoxy, $C_{3-8}$-cycloalkyl-$C_{1-6}$-alkoxy, or $C_{3-8}$-heterocyclyl-$C_{1-6}$-alkoxy, each of which is optionally substituted with one or more substituents independently selected from $R^{38}$; or $NR^{10}R^{11}$, or —$S(O)_2$—$C_{1-6}$-alkyl.

Embodiment 46. A compound according to embodiment 45 wherein $R^{12}$ is F, Cl, Br, —$CF_3$, —CN, methyl, ethyl, propyl, butyl, isopropyl, tert-butyl, methoxy, methylthio, ethoxy, propoxy, butoxy, phenoxy, benzyloxy, cyclopropyl-methoxy, cyclopropyl-ethoxy, cyclobutyl-methoxy, cyclobutyl-ethoxy, cyclopentyl-methoxy, cyclopentyl-ethoxy, cyclohexyl-methoxy, cyclohexyl-ethoxy, —$NHC(O)CH_3$, or —$S(O)_2$—$CH_3$.

Embodiment 47. A compound according to embodiment 46 wherein $R^{12}$ is F, Cl, Br, —$CF_3$, —CN, methyl, ethyl, isopropyl, tert-butyl, methoxy, methylthio, ethoxy, cyclopropyl-methoxy, —$NHC(O)CH_3$, or —$S(O)_2$—$CH_3$.

Embodiment 48. A compound according to embodiment 47 wherein $R^{12}$ is F, Cl, Br, methyl or ethyl.

Embodiment 49. A compound according to any one of the embodiments 1 to 48 wherein $R^{13}$ and $R^{14}$ are independently selected from hydrogen and $C_{1-6}$-alkyl; or $R^{13}$ and $R^{14}$ together with the nitrogen to which they are attached form a 3 to 8 membered heterocyclic ring with the said nitrogen atom.

Embodiment 50. A compound according to any one of the embodiments 1 to 49 wherein $R^{15}$ is selected from F, Cl, Br, hydroxy, carboxy, —$CF_3$, or $C_{1-6}$-alkyl.

Embodiment 51. A compound according to any one of the embodiments 1 to 50 wherein $R^{38}$ is F, Cl, Br, methyl or ethyl.

Embodiment 52. A compound according to any one of the embodiments 1 to 51 wherein A is

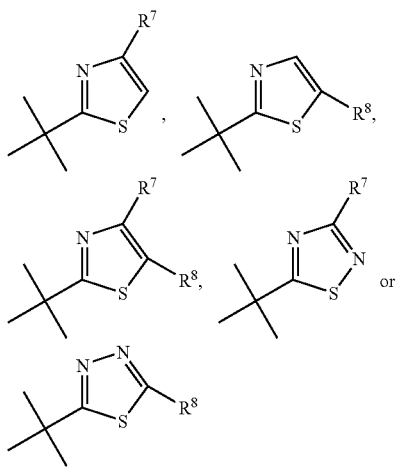

Embodiment 53. A compound according to embodiment 52 wherein A is

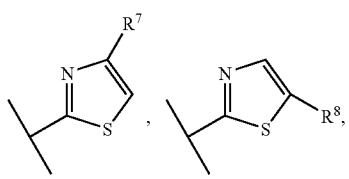

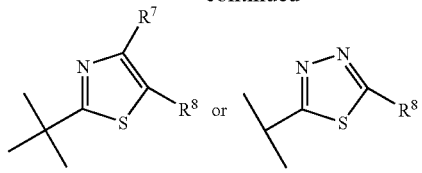

Embodiment 54. A compound according to embodiment 53 wherein A is

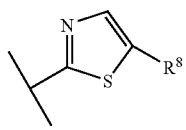

Embodiment 55. A compound according to any one of the embodiments 1 to 54 wherein A is substituted with at least one substituent $R^7$, $R^8$ or $R^9$ independently selected from $C_{1-6}$-alkyl, $C_{1-6}$-alkylthio, $C_{3-6}$-cycloalkylthio, each of which is substituted with one or more substituents independently selected from $R^{34}$; or —$C_{1-6}$-alkyl-$NR^{19}R^{20}$, —$S(O)_2$—$R^{21}$, —$S(O)_2$—$NR^{19}R^{20}$ or —$S(O)_2$—$N(R^{19})(C_{1-6}alkyl)$-$C(O)$—$NR^{22}R^{23}$, each of which is substituted with one or more substituents independently selected from $R^{25}$; or —$C(O)$—$O$—$C_{1-6}$-alkyl, $C_{3-6}$-cycloalkyl-$C_{1-6}$-alkylthio, or carboxy-$C_{1-6}$-alkyl, each of which is optionally substituted with one or more substituents independently selected from $R^{16}$; or $C_{3-8}$-cycloalkyl or $C_{3-8}$-cycloalkylthio, each of which is optionally substituted on the cycloalkyl part with one or more substituents independently selected from $R^{18}$; or —$C_{1-6}$-alkyl-$NR^{36}R^{37}$, or —$S(O)_2$—$NR^{36}R^{37}$, each optionally substituted with one or more substituents independently selected from $R^{25}$; or —$C_{1-6}$-alkyl-$C(O)NR^{36}R^{37}$, or —$C_{1-6}$-alkyl-NH—$C(O)$—$C_{1-6}$-alkyl-$NR^{22}R^{23}$, each optionally substituted with one or more substituents independently selected from $R^{26}$.

Embodiment 56. A compound according to embodiment 55 wherein A is substituted with at least one substituent $R^7$, $R^8$ or $R^9$ independently selected from $C_{1-6}$-alkyl, $C_{1-6}$-alkylthio substituted with one or more substituents independently selected from $R^{34}$; or —$S(O)_2$—$R^{21}$, —$S(O)_2$—$NR^{19}R^{20}$, or —$S(O)_2$—$N(R^{19})(C_{1-6}$-alkyl)-$C(O)$—$NR^{22}R^{23}$; or —$C(O)$—$O$—$C_{1-6}$-alkyl, which is optionally substituted with one or more substituents independently selected from $R^{16}$.

Embodiment 57. A compound according to embodiment 56 wherein A is substituted with at least one substituent $R^7$, $R^8$ or $R^9$ independently selected from methylthio, ethylthio, propylthio, isopropylthio, butylthio or 2-methylpropylthio, each of which is substituted with one or more substituents independently selected from $R^{34}$; or —$S(O)_2$—$R^{21}$, —$S(O)_2$—$NR^{19}R^{20}$, or —$S(O)_2$—$N(R^{19})$—$CH_2$—$C(O)$—$NR^{22}R^{23}$.

Embodiment 58. A compound according to embodiment 57 wherein A is substituted with at least one substituent $R^7$, $R^8$ or $R^9$ independently selected from methylthio, isopropylthio, ethylthio, or 2-methylpropylthio each of which is substituted with one or more substituents independently selected from $R^{34}$.

Embodiment 59. A compound according to embodiment 57 wherein $R^7$, $R^8$ or $R^9$ are independently selected from —S(O)$_2$—$R^{21}$.

Embodiment 60. A compound according to any one of the embodiments 1 to 59 wherein if more than one substituent $R^7$, $R^8$ and $R^9$ is present on A that additional $R^7$, $R^8$ and $R^9$ may be selected from methyl, ethyl, propyl, butyl, Cl, F, or Br.

Embodiment 61. A compound according to any one of the embodiments 1 to 60 wherein $R^{16}$, $R^{17}$, and $R^{18}$ are independently halogen, carboxy, or carboxy-$C_{1-6}$-alkyl.

Embodiment 62. A compound according to any one of the embodiments 1 to 61 wherein $R^{34}$ is carboxy, carboxy-$C_{1-6}$-alkyl, or —C(O)—O—$C_{1-6}$-alkyl.

Embodiment 63. A compound according to embodiment 62 wherein $R^{34}$ is carboxy.

Embodiment 64. A compound according to any one of the embodiments 1 to 63 wherein $R^{19}$ and $R^{20}$ independently represent hydrogen, $C_{1-6}$-alkyl or carboxy-$C_{1-6}$-alkyl, or $R^{19}$ and $R^{20}$ together with the nitrogen to which they are attached form a 3 to 8 membered heterocyclic ring with the said nitrogen atom, the heterocyclic ring optionally containing one or two further heteroatoms selected from nitrogen, oxygen and sulphur, the heterocyclic ring is optionally substituted with one or more substituents independently selected from $R^{24}$.

Embodiment 65. A compound according to any one of the embodiments 1 to 64 wherein $R^{21}$ is selected from $C_{1-6}$-alkyl or carboxy-$C_{1-6}$-alkyl.

Embodiment 66. A compound according to any one of the embodiments 1 to 65 wherein $R^{22}$ and $R^{23}$ are independently selected from $C_{1-6}$-alkyl.

Embodiment 67. A compound according to any one of the embodiments 1 to 66 wherein $R^{36}$ and $R^{37}$ are independently selected from carboxy-$C_{1-6}$-alkyl.

Embodiment 68. A compound according to any one of the embodiments 1 to 67 wherein $R^{24}$ is carboxy or carboxy-$C_{1-6}$-alkyl.

Embodiment 69. A compound according to any one of the embodiments 1 to 68 wherein $R^{25}$ and $R^{26}$ are independently selected from carboxy or carboxy-$C_{1-6}$-alkyl.

Embodiment 70. A compound according to any one of the embodiments 1 to 69 wherein $R^{28}$ is $C_{1-6}$-alkyl, carboxy-$C_{3-8}$-cycloalkyl or carboxy-$C_{1-6}$-alkyl.

Embodiment 71. A compound according to any one of the embodiments 1 to 70 wherein $R^{29}$ is F, Cl, Br or carboxy.

Embodiment 72. A compound according to any one of the embodiments 1 to 71 wherein $R^{35}$ is F, Cl, Br or carboxy.

In another embodiment, the present invention provides a novel compound wherein the compound is selected from the following:

[2-(3-Cyclohexyl-3-phenethyl-ureido)-thiazol-5-ylsulfanyl]-acetic acid;
[2-(3-Butyl-3-cyclohexyl-ureido)-thiazol-5-ylsulfanyl]-acetic acid;
{2-[3-Cyclohexyl-3-(3-methyl-butyl)-ureido]-thiazol-5-ylsulfanyl}-acetic acid;
{2-[3-Cyclohexyl-3-(2,2-dimethyl-propyl)-ureido]-thiazol-5-ylsulfanyl}-acetic acid;
{2-[3-(2-Cyclohex-1-enyl-ethyl)-3-cyclohexyl-ureido]-thiazol-5-ylsulfanyl}-acetic acid;
[2-(3-Bicyclo[2.2.1]hept-2-ylmethyl-3-cyclohexyl-ureido)-thiazol-5-ylsulfanyl]-acetic acid;
[2-(3-Bicyclo[2.2.1]hept-5-en-2-ylmethyl-3-cyclohexyl-ureido)-thiazol-5-ylsulfanyl]-acetic acid;
{2-[3-Cyclohexyl-3-(2-cyclohexyl-ethyl)-ureido]-thiazol-5-ylsulfanyl}-acetic acid;
3-[2-(3-Cyclohexyl-3-phenethyl-ureido)-thiazol-5-ylsulfanyl]-propionic acid;
3-[2-(3-Butyl-3-cyclohexyl-ureido)-thiazol-5-ylsulfanyl]-propionic acid;
3-{2-[3-Cyclohexyl-3-(3-methyl-butyl)-ureido]-thiazol-5-ylsulfanyl}-propionic acid;
3-{2-[3-(trans-4-Methyl-cyclohexyl)-3-phenethyl-ureido]-thiazol-5-ylsulfanyl}-propionic acid;
3-{2-[3-Butyl-3-(trans-4-methyl-cyclohexyl)-ureido]-thiazol-5-ylsulfanyl}-propionic acid;
3-{2-[3-(3-Methyl-butyl)-3-(trans-4-methyl-cyclohexyl)-ureido]-thiazol-5-ylsulfanyl}-propionic acid;
3-{2-[3-(2-Cyclohex-1-enyl-ethyl)-3-cyclohexyl-ureido]-thiazol-5-ylsulfanyl}-propionic acid;
{2-[3-(3-Methyl-butyl)-3-(trans-4-methyl-cyclohexyl)-ureido]-thiazol-5-ylsulfanyl}-acetic acid;
{2-[3-(trans-4-Methyl-cyclohexyl)-3-phenethyl-ureido]-thiazol-5-ylsulfanyl}-acetic acid;
{2-[3-(2-Cyclohex-1-enyl-ethyl)-3-(trans-4-methyl-cyclohexyl)-ureido]-thiazol-5-ylsulfanyl}-acetic acid;
{2-[3-(3-Methyl-but-2-enyl)-3-(trans-4-methyl-cyclohexyl)-ureido]-thiazol-5-ylsulfanyl}-acetic acid;
3-{2-[3-(3-Methyl-but-2-enyl)-3-(trans-4-methyl-cyclohexyl)-ureido]-thiazol-5-ylsulfanyl}-propionic acid;
{2-[3-(4-trans-Ethyl-cyclohexyl)-3-(3-methyl-butyl)-ureido]-thiazol-5-ylsulfanyl}-acetic acid;
{2-[3-(4-trans-Ethyl-cyclohexyl)-3-phenethyl-ureido]-thiazol-5-ylsulfanyl}-acetic acid;
{2-[3-(2-Cyclohexyl-ethyl)-3-(4-trans-ethyl-cyclohexyl)-ureido]-thiazol-5-ylsulfanyl}-acetic acid;
3-{2-[3-(4-trans-Ethyl-cyclohexyl)-3-(3-methyl-butyl)-ureido]-thiazol-5-ylsulfanyl}-propionic acid;
3-{2-[3-(4-trans-Ethyl-cyclohexyl)-3-phenethyl-ureido]-thiazol-5-ylsulfanyl}-propionic acid;
3-{2-[3-(2-Cyclohexyl-ethyl)-3-(4-trans-ethyl-cyclohexyl)-ureido]-thiazol-5-ylsulfanyl}-propionic acid;
2-{2-[3-(4-trans-Ethyl-cyclohexyl)-3-(3-methyl-butyl)-ureido]-thiazol-5-ylsulfanyl}-2-methyl-propionic acid;
2-{2-[3-(4-trans-Ethyl-cyclohexyl)-3-phenethyl-ureido]-thiazol-5-ylsulfanyl}-2-methyl-propionic acid;
{2-[3-(3-Methyl-butyl)-3-(trans-4-methyl-cyclohexyl)-ureido]-thiazole-5-sulfonylamino}-acetic acid;
3-{2-[3-(3-Methyl-butyl)-3-(trans-4-methyl-cyclohexyl)-ureido]-thiazole-5-sulfonylamino}-propionic acid;
(Methyl-{2-[3-(3-methyl-butyl)-3-(trans-4-methyl-cyclohexyl)-ureido]-thiazole-5-sulfonyl}-amino)-acetic acid;
(S)-1-{2-[3-(3-Methyl-butyl)-3-(trans-4-methyl-cyclohexyl)-ureido]-thiazole-5-sulfonyl}-pyrrolidine-2-carboxylic acid;
{2-[3-(4-trans-tert-Butyl-cyclohexyl)-3-(3-methyl-butyl)-ureido]-thiazol-5-ylsulfanyl}-acetic acid;
{2-[3-(4-trans-Isopropyl-cyclohexyl)-3-(3-methyl-butyl)-ureido]-thiazol-5-ylsulfanyl}-acetic acid;
3-{2-[3-(4-trans-tert-Butyl-cyclohexyl)-3-(3-methyl-butyl)-ureido]-thiazol-5-ylsulfanyl}-propionic acid;
3-{2-[3-(4-trans-Isopropyl-cyclohexyl)-3-(3-methyl-butyl)-ureido]-thiazol-5-ylsulfanyl}-propionic acid;
{2-[3-(4-Methyl-cyclohexyl)-3-(3-phenyl-propyl)-ureido]-thiazol-5-ylsulfanyl}-acetic acid;
{2-[3-(3-Methyl-butyl)-3-(trans-4-propoxy-cyclohexyl)-ureido]-thiazol-5-ylsulfanyl}-acetic acid;
{2-[3-(trans-4-tert-Butoxy-cyclohexyl)-3-(3-methyl-butyl)-ureido]-thiazol-5-ylsulfanyl}-acetic acid;
{2-[3-(trans-4-Cyclopropylmethoxy-cyclohexyl)-3-(3-methyl-butyl)-ureido]-thiazol-5-ylsulfanyl}-acetic acid;

{2-[3-[trans-4-(2-Methoxy-ethoxy)-cyclohexyl]-3-(3-methyl-butyl)-ureido]-thiazol-5-ylsulfanyl}-acetic acid;
{2-[3-(trans-4-Benzyloxy-cyclohexyl)-3-(3-methyl-butyl)-ureido]-thiazol-5-ylsulfanyl}-acetic acid;
{2-[3-(trans-4-Methoxymethyl-cyclohexyl)-3-(3-methyl-butyl)-ureido]-thiazol-5-ylsulfanyl}-acetic acid;
{2-[3-(trans-4-Ethoxymethyl-cyclohexyl)-3-(3-methyl-butyl)-ureido]-thiazol-5-ylsulfanyl}-acetic acid;
{2-[3-(trans-4-Cyclopropylmethoxymethyl-cyclohexyl)-3-(3-methyl-butyl)-ureido]-thiazol-5-ylsulfanyl}-acetic acid;
{2-[3-Butyl-3-(trans-4-methyl-cyclohexyl)-ureido]-thiazol-5-ylsulfanyl}-acetic acid;
{2-[3,3-Bis-(3-methyl-butyl)-ureido]-thiazol-5-ylsulfanyl}-acetic acid;
{2-[3-Butyl-3-(3-methyl-butyl)-ureido]-thiazol-5-ylsulfanyl}-acetic acid;
3-{2-[3,3-Bis-(3-methyl-butyl)-ureido]-thiazol-5-ylsulfanyl}-propionic acid;
2-[3-(4-trans-Ethyl-cyclohexyl)-3-(2-phenoxy-ethyl)-ureido]-thiazol-5-ylsulfanyl}-acetic acid;
{2-[3-(4-trans-Ethyl-cyclohexyl)-3-(4-phenoxy-butyl)-ureido]-thiazol-5-ylsulfanyl}-acetic acid;
3-{2-[3-Butyl-3-(3-methyl-butyl)-ureido]-thiazol-5-ylsulfanyl}-propionic acid;
2-Methyl-2-{2-[3-(3-methyl-butyl)-3-(4-trans-methyl-cyclohexyl)-ureido]-thiazol-5-ylsulfanyl}-propionic acid;
2-{2-[3-Cyclohexyl-3-(3-methyl-butyl)-ureido]-thiazol-5-ylsulfanyl}-2-methyl-propionic acid;
5-[3-(3-Methyl-butyl)-3-(4-trans-methyl-cyclohexyl)-ureido]-1,3,4-thiadiazole-2-carboxylic acid ethyl ester;
{5-[3-(3-Methyl-butyl)-3-(4-trans-methyl-cyclohexyl)-ureido]-1,3,4-thiadiazol-2-ylsulfanyl}-acetic acid ethyl ester;
2-Methyl-2-{5-[3-(3-methyl-butyl)-3-(4-trans-methyl-cyclohexyl)-ureido]-1,3,4-thiadiazol-2-ylsulfanyl}-propionic acid;
{5-[3-(3-Methyl-butyl)-3-(4-trans-methyl-cyclohexyl)-ureido]-1,3,4-thiadiazol-2-ylsulfanyl}-acetic acid;
3-{5-[3-(3-Methyl-butyl)-3-(4-trans-methyl-cyclohexyl)-ureido]-1,3,4-thiadiazol-2-ylsulfanyl}-propionic acid ethyl ester;
3-{5-[3-(3-Methyl-butyl)-3-(4-trans-methyl-cyclohexyl)-ureido]-1,3,4-thiadiazol-2-yl}-propionic acid methyl ester;
{2-[3-(1,3-Dimethyl-butyl)-3-(4-trans-methyl-cyclohexyl)-ureido]-thiazol-5-ylsulfanyl}-acetic acid;
2-{2-[3-(1,3-Dimethyl-butyl)-3-(4-trans-methyl-cyclohexyl)-ureido]-thiazol-5-ylsulfanyl}-2-methyl-propionic acid;
3-{2-[3-(1,3-Dimethyl-butyl)-3-(4-trans-methyl-cyclohexyl)-ureido]-thiazol-5-ylsulfanyl}-propionic acid;
3-{5-[3-(3-Methyl-butyl)-3-(4-trans-methyl-cyclohexyl)-ureido]-1,3,4-thiadiazol-2-ylsulfanyl}-propionic acid;
3-{5-[3-(3-Methyl-butyl)-3-(4-trans-methyl-cyclohexyl)-ureido]-1,3,4-thiadiazol-2-yl}-propionic acid;
{2-[3-(2-Benzyloxy-ethyl)-3-(4-trans-methyl-cyclohexyl)-ureido]-thiazol-5-ylsulfanyl}-acetic acid;
{2-[3-(2-Isopropoxy-ethyl)-3-(4-trans-methyl-cyclohexyl)-ureido]-thiazol-5-ylsulfanyl}-acetic acid;
{2-[3-(2-tert-Butoxy-ethyl)-3-(4-trans-methyl-cyclohexyl)-ureido]-thiazol-5-ylsulfanyl}-acetic acid;
{2-[3-(2-Cyclohexyloxy-ethyl)-3-(4-trans-methyl-cyclohexyl)-ureido]-thiazol-5-ylsulfanyl}-acetic acid;
(2-{3-(4-trans-methyl-cyclohexyl)-3-[2-(2,2,2-trifluoro-1-trifluoromethyl-ethoxy)-ethyl]-ureido}-thiazol-5-ylsulfanyl)-acetic acid;
{2-[3-(2-Ethoxy-ethyl)-3-(4-trans-methyl-cyclohexyl)-ureido]-thiazol-5-ylsulfanyl}-acetic acid;
{2-[3-(2-Iso-butoxy-ethyl)-3-(4-trans-methyl-cyclohexyl)-ureido]-thiazol-5-ylsulfanyl}-acetic acid;
(2-{3-(4-trans-methyl-cyclohexyl)-3-[2-(2,2,2-trifluoro-ethoxy)-ethyl]-ureido}-thiazol-5-ylsulfanyl)-acetic acid;
{2-[3-(3-Methoxy-3-methyl-butyl)-3-(4-trans-methyl-cyclohexyl)-ureido]-thiazol-5-ylsulfanyl}-acetic acid;
3-{2-[3-(2-Benzyloxy-ethyl)-3-(4-trans-methyl-cyclohexyl)-ureido]-thiazol-5-ylsulfanyl}-propionic acid;
3-{2-[3-(2-Iso-propoxy-ethyl)-3-(4-trans-methyl-cyclohexyl)-ureido]-thiazol-5-ylsulfanyl}-propionic acid;
3-{2-[3-(2-tert-Butoxy-ethyl)-3-(4-trans-methyl-cyclohexyl)-ureido]-thiazol-5-ylsulfanyl}-propionic acid;
3-{2-[3-(2-Cyclohexyloxy-ethyl)-3-(4-trans-methyl-cyclohexyl)-ureido]-thiazol-5-ylsulfanyl}-propionic acid;
3-(2-{3-(4-trans-methyl-cyclohexyl)-3-[2-(2,2,2-trifluoro-1-trifluoromethyl-ethoxy)-ethyl]-ureido}-thiazol-5-ylsulfanyl)-propionic acid;
3-{2-[3-(2-Iso-butoxy-ethyl)-3-(4-trans-methyl-cyclohexyl)-ureido]-thiazol-5-ylsulfanyl}-propionic acid;
3-(2-{3-(4-trans-methyl-cyclohexyl)-3-[2-(2,2,2-trifluoro-ethoxy)-ethyl]-ureido}-thiazol-5-ylsulfanyl)-propionic acid;
3-{2-[3-(3-Methoxy-3-methyl-butyl)-3-(4-trans-methyl-cyclohexyl)-ureido]-thiazol-5-ylsulfanyl}-propionic acid;
{2-[3-(4-trans-methyl-cyclohexyl)-3-(2-phenoxy-ethyl)-ureido]-thiazol-5-ylsulfanyl}-acetic acid;
{2-[3-(3-Ethoxy-propyl)-3-(4-trans-methyl-cyclohexyl)-ureido]-thiazol-5-ylsulfanyl}-acetic acid;
{2-[3-(3-Methoxy-butyl)-3-(4-trans-methyl-cyclohexyl)-ureido]-thiazol-5-ylsulfanyl}-acetic acid;
{2-[3-(3-Benzyloxy-propyl)-3-(4-trans-methyl-cyclohexyl)-ureido]-thiazol-5-ylsulfanyl}-acetic acid;
3-{2-[3-(4-trans-methyl-cyclohexyl)-3-(2-phenoxy-ethyl)-ureido]-thiazol-5-ylsulfanyl}-propionic acid;
3-{2-[3-(3-Ethoxy-propyl)-3-(4-trans-methyl-cyclohexyl)-ureido]-thiazol-5-ylsulfanyl}-propionic acid;
{2-[3-(2-Benzyloxy-1-methyl-ethyl)-3-(4-trans-methyl-cyclohexyl)-ureido]-thiazol-5-ylsulfanyl}-acetic acid;
{2-[3-(4-trans-methyl-cyclohexyl)-3-(3-phenoxy-propyl)-ureido]-thiazol-5-ylsulfanyl}-acetic acid;
3-{2-[3-(2-Benzyloxy-1-methyl-ethyl)-3-(4-trans-methyl-cyclohexyl)-ureido]-thiazol-5-ylsulfanyl}-propionic acid;
3-{2-[3-(4-trans-methyl-cyclohexyl)-3-(3-phenoxy-propyl)-ureido]-thiazol-5-ylsulfanyl}-propionic acid;
{2-[3-[2-(2-Chloro-phenyl)-ethyl]-3-(4-trans-methyl-cyclohexyl)-ureido]-thiazol-5-ylsulfanyl}-acetic acid;
{2-[3-[2-(3-Chloro-phenyl)-ethyl]-3-(4-trans-methyl-cyclohexyl)-ureido]-thiazol-5-ylsulfanyl}-acetic acid;
{2-[3-[2-(4-Chloro-phenyl)-ethyl]-3-(4-trans-methyl-cyclohexyl)-ureido]-thiazol-5-ylsulfanyl}-acetic acid;
{2-[3-[2-(2-Methoxy-phenyl)-ethyl]-3-(4-trans-methyl-cyclohexyl)-ureido]-thiazol-5-ylsulfanyl}-acetic acid;
{2-[3-[2-(3-Methoxy-phenyl)-ethyl]-3-(4-trans-methyl-cyclohexyl)-ureido]-thiazol-5-ylsulfanyl}-acetic acid;
{2-[3-[2-(4-Methoxy-phenyl)-ethyl]-3-(4-trans-methyl-cyclohexyl)-ureido]-thiazol-5-ylsulfanyl}-acetic acid;
(2-{3-(4-trans-methyl-cyclohexyl)-3-[2-(1-phenyl-ethoxy)-ethyl]-ureido}-thiazol-5-ylsulfanyl)-acetic acid;
(2-{3-(4-trans-methyl-cyclohexyl)-3-[2-(2-trifluoromethyl-sulfanyl-benzyloxy)-ethyl]-ureido}-thiazol-5-ylsulfanyl)-acetic acid;
{2-[3-[2-(2-Cyano-benzyloxy)-ethyl]-3-(4-trans-methyl-cyclohexyl)-ureido]-thiazol-5-ylsulfanyl}-acetic acid;

{2-[3-[2-(4-Fluoro-2-trifluoromethyl-benzyloxy)-ethyl]-3-(4-trans-methyl-cyclohexyl)-ureido]-thiazol-5-ylsulfanyl}-acetic acid;

{2-[3-[2-(4-Fluoro-phenyl)-ethyl]-3-(4-trans-methyl-cyclohexyl)-ureido]-thiazol-5-ylsulfanyl}-acetic acid;

{2-[3-[2-(2-Fluoro-6-trifluoromethyl-benzyloxy)-ethyl]-3-(4-trans-methyl-cyclohexyl)-ureido]-thiazol-5-ylsulfanyl}-acetic acid;

{2-[3-(4-trans-methyl-cyclohexyl)-3-(2-phenyl-propyl)-ureido]-thiazol-5-ylsulfanyl}-acetic acid;

{2-[3-[2-(2-Chloro-4-fluoro-benzyloxy)-ethyl]-3-(4-trans-methyl-cyclohexyl)-ureido]-thiazol-5-ylsulfanyl}-acetic acid;

{2-[3-[2-(3,4-Dimethoxy-phenyl)-ethyl]-3-(4-trans-methyl-cyclohexyl)-ureido]-thiazol-5-ylsulfanyl}-acetic acid;

{2-[3-(4-trans-methyl-cyclohexyl)-3-(2-p-tolyl-ethyl)-ureido]-thiazol-5-ylsulfanyl}-acetic acid;

{2-[3-(4-trans-methyl-cyclohexyl)-3-(2-pentafluorophenyl-methoxy-ethyl)-ureido]-thiazol-5-ylsulfanyl}-acetic acid;

(2-{3-(4-trans-methyl-cyclohexyl)-3-[2-(4-trifluoromethyl-phenyl)-ethyl]-ureido}-thiazol-5-ylsulfanyl)-acetic acid;

{2-[3-[2-(4-Ethoxy-phenyl)-ethyl]-3-(4-trans-methyl-cyclohexyl)-ureido]-thiazol-5-ylsulfanyl}-acetic acid;

{2-[3-[2-(4-Isopropoxy-phenyl)-ethyl]-3-(4-trans-methyl-cyclohexyl)-ureido]-thiazol-5-ylsulfanyl}-acetic acid;

(2-{3-(4-trans-methyl-cyclohexyl)-3-[2-(4-propoxy-phenyl)-ethyl]-ureido}-thiazol-5-ylsulfanyl)-acetic acid;

{2-[3-[2-(2-Fluoro-phenyl)-ethyl]-3-(4-trans-methyl-cyclohexyl)-ureido]-thiazol-5-ylsulfanyl}-acetic acid;

{2-[3-[2-(3-Fluoro-phenyl)-ethyl]-3-(4-trans-methyl-cyclohexyl)-ureido]-thiazol-5-ylsulfanyl}-acetic acid;

{2-[3-[2-(4-Isopropyl-phenyl)-ethyl]-3-(4-trans-methyl-cyclohexyl)-ureido]-thiazol-5-ylsulfanyl}-acetic acid;

{2-[3-[2-(3-Fluoro-4-methoxy-phenyl)-ethyl]-3-(4-trans-methyl-cyclohexyl)-ureido]-thiazol-5-ylsulfanyl}-acetic acid;

{2-[3-[2-(3-Fluoro-benzyloxy)-ethyl]-3-(4-trans-methyl-cyclohexyl)-ureido]-thiazol-5-ylsulfanyl}-acetic acid;

(2-{3-(4-trans-methyl-cyclohexyl)-3-[2-(3-trifluoromethyl-benzyloxy)-ethyl]-ureido}-thiazol-5-ylsulfanyl)-acetic acid;

{2-[3-[2-(4-Methanesulfonyl-benzyloxy)-ethyl]-3-(4-trans-methyl-cyclohexyl)-ureido]-thiazol-5-ylsulfanyl}-acetic acid;

(2-{3-(4-trans-methyl-cyclohexyl)-3-[2-(4-trifluoromethyl-benzyloxy)-ethyl]-ureido}-thiazol-5-ylsulfanyl)-acetic acid;

(2-{3-(4-trans-methyl-cyclohexyl)-3-[2-(2-trifluoromethyl-benzyloxy)-ethyl]-ureido}-thiazol-5-ylsulfanyl)-acetic acid;

{2-[3-[2-(2-Methoxy-benzyloxy)-ethyl]-3-(4-trans-methyl-cyclohexyl)-ureido]-thiazol-5-ylsulfanyl}-acetic acid;

{2-[3-[2-(4-tert-Butyl-benzyloxy)-ethyl]-3-(4-trans-methyl-cyclohexyl)-ureido]-thiazol-5-ylsulfanyl}-acetic acid;

(2-{3-(4-trans-methyl-cyclohexyl)-3-[2-(4-trifluoromethoxy-benzyloxy)-ethyl]-ureido}-thiazol-5-ylsulfanyl)-acetic acid;

{2-[3-[2-(2,4-Difluoro-benzyloxy)-ethyl]-3-(4-trans-methyl-cyclohexyl)-ureido]-thiazol-5-ylsulfanyl}-acetic acid;

{2-[3-[2-(4-Isopropyl-benzyloxy)-ethyl]-3-(4-trans-methyl-cyclohexyl)-ureido]-thiazol-5-ylsulfanyl}-acetic acid;

{2-[3-[2-(4-Fluoro-benzyloxy)-ethyl]-3-(4-trans-methyl-cyclohexyl)-ureido]-thiazol-5-ylsulfanyl}-acetic acid;

(2-{3-(4-trans-methyl-cyclohexyl)-3-[2-(3-trifluoromethoxy-benzyloxy)-ethyl]-ureido}-thiazol-5-ylsulfanyl)-acetic acid;

{2-[3-[2-(2-Fluoro-benzyloxy)-ethyl]-3-(4-trans-methyl-cyclohexyl)-ureido]-thiazol-5-ylsulfanyl}-acetic acid;

{2-[3-[2-(2-Chloro-benzyloxy)-ethyl]-3-(4-trans-methyl-cyclohexyl)-ureido]-thiazol-5-ylsulfanyl}-acetic acid;

{2-[3-[2-(2,3-Difluoro-benzyloxy)-ethyl]-3-(4-trans-methyl-cyclohexyl)-ureido]-thiazol-5-ylsulfanyl}-acetic acid;

{2-[3-[2-(2,6-Difluoro-benzyloxy)-ethyl]-3-(4-trans-methyl-cyclohexyl)-ureido]-thiazol-5-ylsulfanyl}-acetic acid;

{2-[3-(4-trans-methyl-cyclohexyl)-3-(3-o-tolyloxy-propyl)-ureido]-thiazol-5-ylsulfanyl}-acetic acid;

{2-[3-[3-(4-Methoxy-phenoxy)-propyl]-3-(4-trans-methyl-cyclohexyl)-ureido]-thiazol-5-ylsulfanyl}-acetic acid;

{2-[3-[3-(4-Fluoro-phenoxy)-propyl]-3-(4-trans-methyl-cyclohexyl)-ureido]-thiazol-5-ylsulfanyl}-acetic acid;

{2-[3-[3-(Indan-5-yloxy)-propyl]-3-(4-trans-methyl-cyclohexyl)-ureido]-thiazol-5-ylsulfanyl}-acetic acid;

{2-[3-[3-(3,4-Difluoro-phenoxy)-propyl]-3-(4-trans-methyl-cyclohexyl)-ureido]-thiazol-5-ylsulfanyl}-acetic acid;

{2-[3-[3-(2,4-Difluoro-phenoxy)-propyl]-3-(4-trans-methyl-cyclohexyl)-ureido]-thiazol-5-ylsulfanyl}-acetic acid;

{2-[3-[3-(4-tert-Butyl-phenoxy)-propyl]-3-(4-trans-methyl-cyclohexyl)-ureido]-thiazol-5-ylsulfanyl}-acetic acid;

{2-[3-[3-(4-Isopropyl-phenoxy)-propyl]-3-(4-trans-methyl-cyclohexyl)-ureido]-thiazol-5-ylsulfanyl}-acetic acid;

{2-[3-[3-(3-Acetylamino-phenoxy)-propyl]-3-(4-trans-methyl-cyclohexyl)-ureido]-thiazol-5-ylsulfanyl}-acetic acid;

{2-[3-[3-(2-Fluoro-phenoxy)-propyl]-3-(4-trans-methyl-cyclohexyl)-ureido]-thiazol-5-ylsulfanyl}-acetic acid;

{2-[3-[3-(3-Isopropyl-phenoxy)-propyl]-3-(4-trans-methyl-cyclohexyl)-ureido]-thiazol-5-ylsulfanyl}-acetic acid;

{2-[3-[3-(Benzo[1,3]dioxol-5-yloxy)-propyl]-3-(4-trans-methyl-cyclohexyl)-ureido]-thiazol-5-ylsulfanyl}-acetic acid;

(2-{3-(4-trans-methyl-cyclohexyl)-3-[3-(4-trifluoromethoxy-phenoxy)-propyl]-ureido}-thiazol-5-ylsulfanyl)-acetic acid;

(2-{3-(4-trans-methyl-cyclohexyl)-3-[3-(3-trifluoromethoxy-phenoxy)-propyl]-ureido}-thiazol-5-ylsulfanyl)-acetic acid;

{2-[3-[3-(3-Fluoro-phenoxy)-propyl]-3-(4-trans-methyl-cyclohexyl)-ureido]-thiazol-5-ylsulfanyl}-acetic acid;

3-{2-[3-[3-(2-Chloro-phenoxy)-propyl]-3-(4-trans-methyl-cyclohexyl)-ureido]-thiazol-5-ylsulfanyl}-propionic acid;

3-{2-[3-[3-(4-Chloro-phenoxy)-propyl]-3-(4-trans-methyl-cyclohexyl)-ureido]-thiazol-5-ylsulfanyl}-propionic acid;

{2-[3-Cyclopentylmethyl-3-(3,4-difluoro-phenyl)-ureido]-thiazol-4-yl}-acetic acid;

{2-[3-Cyclopentylmethyl-3-(3,4-difluoro-phenyl)-ureido]-thiazol-5-ylsulfanyl}-acetic acid;

2-{2-[3-Cyclopentylmethyl-3-(3,4-difluoro-phenyl)-ureido]-thiazol-5-ylsulfanyl}-2-methyl-propionic acid;

2-({2-[3-Cyclopentylmethyl-3-(3,4-difluoro-phenyl)-ureido]-thiazole-5-sulfonyl}-methyl-amino)-N,N-diethyl-acetamide;

(S)-1-{2-[3-Cyclopentylmethyl-3-(3,4-difluoro-phenyl)-ureido]-thiazole-5-sulfonyl}-pyrrolidine-2-carboxylic acid;

{2-[3-Cyclopentylmethyl-3-(3,4-difluoro-phenyl)-ureido]-thiazole-5-sulfonylamino}-acetic acid;

3-{2-[3-Cyclopentylmethyl-3-(3,4-difluoro-phenyl)-ureido]-thiazole-5-sulfonylamino}-propionic acid;

{2-[3-Cyclopentylmethyl-3-(4-methanesulfonyl-phenyl)-ureido]-thiazol-4-yl}-acetic acid;
{2-[3-Cyclopentylmethyl-3-(4-methanesulfonyl-phenyl)-ureido]-thiazol-5-ylsulfanyl}-acetic acid;
2-{2-[3-Cyclopentylmethyl-3-(4-methanesulfonyl-phenyl)-ureido]-thiazol-5-ylsulfanyl}-2-methyl-propionic acid;
(S)-1-{2-[3-Cyclopentylmethyl-3-(4-methanesulfonyl-phenyl)-ureido]-thiazole-5-sulfonyl}-pyrrolidine-2-carboxylic acid;
{2-[3-Cyclopentylmethyl-3-(4-methanesulfonyl-phenyl)-ureido]-thiazole-5-sulfonylamino}-acetic acid;
3-{2-[3-Cyclopentylmethyl-3-(4-methanesulfonyl-phenyl)-ureido]-thiazole-5-sulfonylamino}-propionic acid;
3-{2-[3-Cyclopentylmethyl-3-(3,4-difluoro-phenyl)-ureido]-thiazol-5-ylsulfanyl}-propionic acid;
3-{2-[3-Cyclopentylmethyl-3-(4-methanesulfonyl-phenyl)-ureido]-thiazol-5-ylsulfanyl}-propionic acid;
{2-[3-(3-Acetylamino-phenyl)-3-cyclopentylmethyl-ureido]-thiazol-5-ylsulfanyl}-acetic acid;
3-{2-[3-(3-Acetylamino-phenyl)-3-cyclopentylmethyl-ureido]-thiazol-5-ylsulfanyl}-propionic acid;
{2-[3-Cyclopentylmethyl-3-(3-dimethylcarbamoyl-phenyl)-ureido]-thiazol-5-ylsulfanyl}-acetic acid;
3-{2-[3-Cyclopentylmethyl-3-(3-dimethylcarbamoyl-phenyl)-ureido]-thiazol-5-ylsulfanyl}-propionic acid;
{2-[3-(3-Carbamoyl-phenyl)-3-cyclopentylmethyl-ureido]-thiazol-5-ylsulfanyl}-acetic acid;
3-{2-[3-(3-Carbamoyl-phenyl)-3-cyclopentylmethyl-ureido]-thiazol-5-ylsulfanyl}-propionic acid;
{2-[3-Cyclopentylmethyl-3-(3-methylcarbamoyl-phenyl)-ureido]-thiazol-5-ylsulfanyl}-acetic acid;
3-{2-[3-Cyclopentylmethyl-3-(3-methylcarbamoyl-phenyl)-ureido]-thiazol-5-ylsulfanyl}-propionic acid;
{2-[3-Cyclopentylmethyl-3-(3-trifluoromethyl-phenyl)-ureido]-thiazol-5-ylsulfanyl}-acetic acid;
{2-[3-Cyclopentylmethyl-3-(4-sulfamoyl-phenyl)-ureido]-thiazol-5-ylsulfanyl}-acetic acid;
{2-[3-Cyclopentylmethyl-3-(4-fluoro-3-trifluoromethyl-phenyl)-ureido]-thiazol-5-ylsulfanyl}-acetic acid;
{2-[3-Cyclopentylmethyl-3-(4-trifluoromethyl-phenyl)-ureido]-thiazol-5-ylsulfanyl}-acetic acid;
{2-[3-Cyclopentylmethyl-3-(4-trifluoromethoxy-phenyl)-ureido]-thiazol-5-ylsulfanyl}-acetic acid;
{2-[3-Cyclopentylmethyl-3-(3-sulfamoyl-phenyl)-ureido]-thiazol-5-ylsulfanyl}-acetic acid;
[2-(3-Benzo[1,3]dioxol-5-yl-3-cyclopentylmethyl-ureido)-thiazol-5-ylsulfanyl]-acetic acid;
{2-[3-Cyclopentylmethyl-3-(3-trifluoromethoxy-phenyl)-ureido]-thiazol-5-ylsulfanyl}-acetic acid;
{2-[3-Cyclopentylmethyl-3-(6-methoxy-pyridin-3-yl)-ureido]-thiazol-5-ylsulfanyl}-acetic acid;
{2-[3-(6-Acetylamino-pyridin-3-yl)-3-cyclopentylmethyl-ureido]-thiazol-5-ylsulfanyl}-acetic acid;
{2-[3-(3-Acetylamino-phenyl)-3-pentyl-ureido]-thiazol-5-ylsulfanyl}-acetic acid;
{2-[3-(3-Acetylamino-phenyl)-3-cyclohexylmethyl-ureido]-thiazol-5-ylsulfanyl}-acetic acid;
{2-[3-(3-Acetylamino-phenyl)-3-(3-methyl-butyl)-ureido]-thiazol-5-ylsulfanyl}-acetic acid;
{2-[3-(3-Acetylamino-phenyl)-3-hexyl-ureido]-thiazol-5-ylsulfanyl}-acetic acid;
{2-[3-(3-Acetylamino-phenyl)-3-cyclopropylmethyl-ureido]-thiazol-5-ylsulfanyl}-acetic acid;
{2-[3-(3-Acetylamino-phenyl)-3-(3,3-dimethyl-butyl)-ureido]-thiazol-5-ylsulfanyl}-acetic acid;
{2-[3-Cyclohexylmethyl-3-(3,4-difluoro-phenyl)-ureido]-thiazol-5-ylsulfanyl}-acetic acid;
[2-(3-Benzo[1,3]dioxol-5-yl-3-cyclohexyl methyl-ureido)-thiazol-5-ylsulfanyl]-acetic acid;
{2-[3-Cyclohexylmethyl-3-(6-methoxy-pyridin-3-yl)-ureido]-thiazol-5-ylsulfanyl}-acetic acid;
{2-[3-Cyclopentylmethyl-3-(3-ethylcarbamoyl-phenyl)-ureido]-thiazol-5-ylsulfanyl}-acetic acid;
{2-[3-Cyclobutylmethyl-3-(3,4-difluoro-phenyl)-ureido]-thiazol-5-ylsulfanyl}-acetic acid;
{2-[3-Cyclopentylmethyl-3-(3-isopropylcarbamoyl-phenyl)-ureido]-thiazol-5-ylsulfanyl}-acetic acid;
(2-{3-[3-(Azetidine-1-carbonyl)-phenyl]-3-cyclopentylmethyl-ureido}-thiazol-5-ylsulfanyl)-acetic acid;
{2-[3-(3,4-Difluoro-phenyl)-3-(4-methyl-cyclohexylmethyl)-ureido]-thiazol-5-ylsulfanyl}-acetic acid;
{2-[3-(3,4-Difluoro-phenyl)-3-(4-trifluoromethyl-cyclohexylmethyl)-ureido]-thiazol-5-ylsulfanyl}-acetic acid;
{2-[3-(4-tert-Butyl-cyclohexylmethyl)-3-(3,4-difluoro-phenyl)-ureido]-thiazol-5-ylsulfanyl}-acetic acid;
{2-[3-Cyclopentylmethyl-3-(2,3,4-trifluoro-phenyl)-ureido]-thiazol-5-ylsulfanyl}-acetic acid;
{2-[3-(3-Chloro-4-fluoro-phenyl)-3-cyclopentylmethyl-ureido]-thiazol-5-ylsulfanyl}-acetic acid;
{2-[3-Cyclopentylmethyl-3-(2,4-difluoro-phenyl)-ureido]-thiazol-5-ylsulfanyl}-acetic acid;
{2-[3-Cyclopentylmethyl-3-(2,3-dichloro-phenyl)-ureido]-thiazol-5-ylsulfanyl}-acetic acid;
{2-[3-Cyclopentylmethyl-3-(3-fluoro-4-methoxy-phenyl)-ureido]-thiazol-5-ylsulfanyl}-acetic acid;
{2-[3-(3-Acetylamino-phenyl)-3-benzyl-ureido]-thiazol-5-ylsulfanyl}-acetic acid;
{2-[3-(3-Acetylamino-phenyl)-3-phenethyl-ureido]-thiazol-5-ylsulfanyl}-acetic acid;
{2-[3-(2-Cyclopentylethyl)-3-(3,4-difluoro-phenyl)-ureido]-thiazol-5-ylsulfanyl}-acetic acid;
{2-[3-(3,4-Difluoro-phenyl)-3-(trans-4-methyl-cyclohexylmethyl)-ureido]-thiazol-5-ylsulfanyl}-acetic acid;
{2-[3-(3-Acetylamino-4-fluoro-phenyl)-3-cyclopentylmethyl-ureido]-thiazol-5-ylsulfanyl}-acetic acid;
{2-[3-Cyclopentylmethyl-3-(3-propionylamino-phenyl)-ureido]-thiazol-5-ylsulfanyl}-acetic acid;
{2-[3-Cyclopentylmethyl-3-(3-isobutyrylamino-phenyl)-ureido]-thiazol-5-ylsulfanyl}-acetic acid;
(2-{3-[3-(Cyclopentanecarbonyl-amino)-phenyl]-3-cyclopentylmethyl-ureido}-thiazol-5-ylsulfanyl)-acetic acid;
{2-[3-(trans-4-Methyl-cyclohexylmethyl)-3-(2,3,4-trifluoro-phenyl)-ureido]-thiazol-5-ylsulfanyl}-acetic acid;
{2-[3-Cyclohexylmethyl-3-(2,3,4-trifluoro-phenyl)-ureido]-thiazol-5-ylsulfanyl}-acetic acid;
{2-[3-Cyclopentylmethyl-3-(2,3-difluoro-phenyl)-ureido]-thiazol-5-ylsulfanyl}-acetic acid;
{2-[3-Cyclopentylmethyl-3-(4-methoxy-phenyl)-ureido]-thiazol-5-ylsulfanyl}-acetic acid;
{2-[3-(3-Chloro-4-methoxy-phenyl)-3-cyclopentylmethyl-ureido]-thiazol-5-ylsulfanyl}-acetic acid,
{2-[3-Cyclopentylmethyl-3-(2,2-difluoro-benzo[1,3]dioxol-5-yl)-ureido]-thiazol-5-ylsulfanyl}-acetic acid;
{2-[3-Cyclopentylmethyl-3-(3-methanesulfonylamino-phenyl)-ureido]-thiazol-5-ylsulfanyl}-acetic acid;
{2-[3-Cyclopentylmethyl-3-(2,4,6-trifluoro-phenyl)-ureido]-thiazol-5-ylsulfanyl}-acetic acid;
{2-[3-(3-Chloro-2-fluoro-phenyl)-3-cyclopentylmethyl-ureido]-thiazol-5-ylsulfanyl}-acetic acid,
{2-[3-Cyclopentylmethyl-3-(4-fluoro-3-methoxy-phenyl)-ureido]-thiazol-5-ylsulfanyl}-acetic acid;
{2-[3-Cyclopentylmethyl-3-(2,3-difluoro-4-methoxy-phenyl)-ureido]-thiazol-5-ylsulfanyl}-acetic acid;

{2-[3-Cyclopentylmethyl-3-(4-isopropoxy-phenyl)-ureido]-thiazol-5-ylsulfanyl}-acetic acid;
{2-[3-Cyclopentylmethyl-3-(3-fluoro-2-methyl-phenyl)-ureido]-thiazol-5-ylsulfanyl}-acetic acid;
{2-[3-(3-Chloro-2-methoxy-phenyl)-3-cyclopentylmethyl-ureido]-thiazol-5-ylsulfanyl}-acetic acid;
{2-[3-(3-Chloro-2-methyl-phenyl)-3-cyclopentylmethyl-ureido]-thiazol-5-ylsulfanyl}-acetic acid;
{2-[3-Cyclopentylmethyl-3-(2-fluoro-3-methyl-phenyl)-ureido]-thiazol-5-ylsulfanyl}-acetic acid;
{2-[3-[2-(3,4-Difluoro-phenyl)-ethyl]-3-(4-trans-methyl-cyclohexyl)-ureido]-thiazol-5-ylsulfanyl}-acetic acid;
(2-{3-(4-trans-Methyl-cyclohexyl)-3-[2-(3,4,5-trifluoro-phenyl)-ethyl]-ureido}-thiazol-5-ylsulfanyl)-acetic acid;
(2-{3-(4-trans-Methyl-cyclohexyl)-3-[2-(2,4,5-trifluoro-phenyl)-ethyl]-ureido}-thiazol-5-ylsulfanyl)-acetic acid;
(2-{3-(4-trans-Methyl-cyclohexyl)-3-[2-(2,3,4-trifluoro-phenyl)-ethyl]-ureido}-thiazol-5-ylsulfanyl)-acetic acid;
2-{2-[3-[2-(2-Chloro-benzyloxy)-ethyl]-3-(4-trans-methyl-cyclohexyl)-ureido]-thiazol-5-ylsulfanyl}-2-methyl-propionic acid;
2-{2-[3-[2-(2-Fluoro-benzyloxy)-ethyl]-3-(4-trans-methyl-cyclohexyl)-ureido]-thiazol-5-ylsulfanyl}-2-methyl-propionic acid;
{2-[3-(2-Chloro-3-fluoro-phenyl)-3-cyclopentylmethyl-ureido]-thiazol-5-ylsulfanyl}-acetic acid;
{2-[3-(3-Bromo-phenyl)-3-cyclopentylmethyl-ureido]-thiazol-5-ylsulfanyl}-acetic acid;
{2-[3-(4-Bromo-2-fluoro-phenyl)-3-cyclopentylmethyl-ureido]-thiazol-5-ylsulfanyl}-acetic acid;
{2-[3-(2-Bromo-phenyl)-3-cyclopentylmethyl-ureido]-thiazol-5-ylsulfanyl}-acetic acid;
{2-[3-Cyclopentylmethyl-3-(3-methoxy-5-trifluoromethyl-phenyl)-ureido]-thiazol-5-ylsulfanyl}-acetic acid;
{2-[3-(3-Acetyl-phenyl)-3-cyclopentylmethyl-ureido]-thiazol-5-ylsulfanyl}-acetic acid;
{2-[3-(1-Acetyl-2,3-dihydro-1H-indol-6-yl)-3-cyclopentylmethyl-ureido]-thiazol-5-ylsulfanyl}-acetic acid;
{2-[3-(2-Benzyloxy-ethyl)-3-(4-methyl-cyclohexyl)-ureido]-thiazole-5-sulfonyl}-acetic acid;
{2-[3-[2-(2-Methyl-benzyloxy)-ethyl]-3-(4-methyl-cyclohexyl)-ureido]-thiazole-5-sulfonyl}-acetic acid;
{2-[3-[2-(2-Fluoro-benzyloxy)-ethyl]-3-(4-methyl-cyclohexyl)-ureido]-thiazole-5-sulfonyl}-acetic acid;
{2-[3-[2-(2-Chloro-benzyloxy)-ethyl]-3-(4-methyl-cyclohexyl)-ureido]-thiazole-5-sulfonyl}-acetic acid;
(2-{3-(4-Methyl-cyclohexyl)-3-[2-(2-trifluoromethyl-benzyloxy)-ethyl]-ureido}-thiazole-5-sulfonyl)-acetic acid;
{2-[3-[2-(4-Fluoro-2-trifluoromethyl-benzyloxy)-ethyl]-3-(4-methyl-cyclohexyl)-ureido]-thiazole-5-sulfonyl}-acetic acid;
{2-[3-[2-(2-Chloro-4-fluoro-benzyloxy)-ethyl]-3-(4-methyl-cyclohexyl)-ureido]-thiazole-5-sulfonyl}-acetic acid;
{2-[3-[2-(2,4-Difluoro-benzyloxy)-ethyl]-3-(4-methyl-cyclohexyl)-ureido]-thiazole-5-sulfonyl}-acetic acid;
2-{2-[3-(2-Benzyloxy-ethyl)-3-(4-methyl-cyclohexyl)-ureido]-thiazole-5-sulfonyl}-2-methyl-propionic acid;
2-Methyl-2-{2-[3-[2-(2-methyl-benzyloxy)-ethyl]-3-(4-methyl-cyclohexyl)-ureido]-thiazole-5-sulfonyl}-propionic acid;
2-{2-[3-[2-(2-Fluoro-benzyloxy)-ethyl]-3-(4-methyl-cyclohexyl)-ureido]-thiazole-5-sulfonyl}-2-methyl-propionic acid;
2-{2-[3-[2-(2-Chloro-benzyloxy)-ethyl]-3-(4-methyl-cyclohexyl)-ureido]-thiazole-5-sulfonyl}-2-methyl-propionic acid;
2-Methyl-2-(2-{3-(4-methyl-cyclohexyl)-3-[2-(2-trifluoromethyl-benzyloxy)-ethyl]-ureido}-thiazole-5-sulfonyl)-propionic acid;
2-{2-[3-[2-(4-Fluoro-2-trifluoromethyl-benzyloxy)-ethyl]-3-(4-methyl-cyclohexyl)-ureido]-thiazole-5-sulfonyl}-2-methyl-propionic acid;
2-{2-[3-[2-(2,4-Difluoro-benzyloxy)-ethyl]-3-(4-methyl-cyclohexyl)-ureido]-thiazole-5-sulfonyl}-2-methyl-propionic acid;
{2-[3-(4-Methyl-cyclohexyl)-3-(3-phenoxy-propyl)-ureido]-thiazole-5-sulfonyl}-acetic acid;
2-Methyl-2-{2-[3-(4-methyl-cyclohexyl)-3-(3-phenoxy-propyl)-ureido]-thiazole-5-sulfonyl}-propionic acid;
{2-[3-(4-Methyl-cyclohexyl)-3-phenethyl-ureido]-thiazole-5-sulfonyl}-acetic acid;
{2-[3-[2-(4-Methoxy-phenyl)-ethyl]-3-(4-methyl-cyclohexyl)-ureido]-thiazole-5-sulfonyl}-acetic acid;
{2-[3-[2-(3-Fluoro-4-methoxy-phenyl)-ethyl]-3-(4-methyl-cyclohexyl)-ureido]-thiazole-5-sulfonyl}-acetic acid;
{2-[3-[2-(4-Ethoxy-phenyl)-ethyl]-3-(4-methyl-cyclohexyl)-ureido]-thiazole-5-sulfonyl}-acetic acid;
2-Methyl-2-{2-[3-(4-methyl-cyclohexyl)-3-phenethyl-ureido]-thiazole-5-sulfonyl}-propionic acid;
2-{2-[3-[2-(4-Methoxy-phenyl)-ethyl]-3-(4-methyl-cyclohexyl)-ureido]-thiazole-5-sulfonyl}-2-methyl-propionic acid;
2-{2-[3-[2-(3-Fluoro-4-methoxy-phenyl)-ethyl]-3-(4-methyl-cyclohexyl)-ureido]-thiazole-5-sulfonyl}-2-methyl-propionic acid;
2-{2-[3-[2-(3-Fluoro-4-methoxy-phenyl)-ethyl]-3-(4-methyl-cyclohexyl)-ureido]-thiazole-5-sulfonyl}-2-methyl-propionic acid;
3-{2-[3-(2-Benzyloxy-ethyl)-3-(4-methyl-cyclohexyl)-ureido]-thiazol-5-ylsulfanyl}-2,2-dimethyl-propionic acid;
3-{2-[3-[2-(2-Fluoro-benzyloxy)-ethyl]-3-(4-methyl-cyclohexyl)-ureido]-thiazol-5-ylsulfanyl}-2,2-dimethyl-propionic acid;
2,2-Dimethyl-3-{2-[3-[2-(2-methyl-benzyloxy)-ethyl]-3-(4-methyl-cyclohexyl)-ureido]-thiazol-5-ylsulfanyl}-propionic acid;
3-{2-[3-[2-(2-Chloro-benzyloxy)-ethyl]-3-(4-methyl-cyclohexyl)-ureido]-thiazol-5-ylsulfanyl}-2,2-dimethyl-propionic acid;
2,2-Dimethyl-3-(2-{3-(4-methyl-cyclohexyl)-3-[2-(2-trifluoromethyl-benzyloxy)-ethyl]-ureido}-thiazol-5-ylsulfanyl)-propionic acid;
2,2-Dimethyl-3-{2-[3-(4-methyl-cyclohexyl)-3-(3-phenoxy-propyl)-ureido]-thiazol-5-ylsulfanyl}-propionic acid;
3-{2-[3-[3-(2-Chloro-phenoxy)-propyl]-3-(4-methyl-cyclohexyl)-ureido]-thiazol-5-ylsulfanyl}-2,2-dimethyl-propionic acid;
3-{2-[3-[3-(3-Chloro-phenoxy)-propyl]-3-(4-methyl-cyclohexyl)-ureido]-thiazol-5-ylsulfanyl}-2,2-dimethyl-propionic acid;
3-{2-[3-[3-(4-Chloro-phenoxy)-propyl]-3-(4-methyl-cyclohexyl)-ureido]-thiazol-5-ylsulfanyl}-2,2-dimethyl-propionic acid;
2,2-Dimethyl-3-{2-[3-(4-methyl-cyclohexyl)-3-phenethyl-ureido]-thiazol-5-ylsulfanyl}-propionic acid;
3-{2-[3-[2-(4-Methoxy-phenyl)-ethyl]-3-(4-methyl-cyclohexyl)-ureido]-thiazol-5-ylsulfanyl}-2,2-dimethyl-propionic acid;
3-{2-[3-[2-(4-Ethoxy-phenyl)-ethyl]-3-(4-methyl-cyclohexyl)-ureido]-thiazol-5-ylsulfanyl}-2,2-dimethyl-propionic acid;

3-{2-[3-[2-(3-Fluoro-4-methoxy-phenyl)-ethyl]-3-(4-methyl-cyclohexyl)-ureido]-thiazol-5-ylsulfanyl}-2,2-dimethyl-propionic acid;
{2-[3-(2-Benzylsulfanyl-ethyl)-3-(4-methyl-cyclohexyl)-ureido]-thiazol-5-ylsulfanyl}-acetic acid;
2-{2-[3-(2-Benzylsulfanyl-ethyl)-3-(4-methyl-cyclohexyl)-ureido]-thiazol-5-ylsulfanyl}-2-methyl-propionic acid;
{2-[3-(2-Benzylsulfanyl-ethyl)-3-(4-methyl-cyclohexyl)-ureido]-thiazole-5-sulfonyl}-acetic acid;
2-{2-[3-(2-Benzylsulfanyl-ethyl)-3-(4-methyl-cyclohexyl)-ureido]-thiazole-5-sulfonyl}-2-methyl-propionic acid;
3-{2-[3-(2-Benzylsulfanyl-ethyl)-3-(4-methyl-cyclohexyl)-ureido]-thiazol-5-ylsulfanyl}-2,2-dimethyl-propionic acid;
3-{2-[3-(2-Benzylsulfanyl-ethyl)-3-(4-methyl-cyclohexyl)-ureido]-thiazole-5-sulfonyl}-2,2-dimethyl-propionic acid;
2,2-Dimethyl-3-{2-[3-(4-methyl-cyclohexyl)-3-(3-phenylsulfanyl-propyl)-ureido]-thiazol-5-ylsulfanyl}-propionic acid;
2,2-Dimethyl-3-{2-[3-(4-methyl-cyclohexyl)-3-(3-phenylsulfanyl-propyl)-ureido]-thiazole-5-sulfonyl}-propionic acid;
{2-[3-(4-Methyl-cyclohexyl)-3-(3-phenylsulfanyl-propyl)-ureido]-thiazol-5-ylsulfanyl}-acetic acid;
2-Methyl-2-{2-[3-(4-methyl-cyclohexyl)-3-(3-phenylsulfanyl-propyl)-ureido]-thiazol-5-ylsulfanyl}-propionic acid;
{2-[3-(4-Methyl-cyclohexyl)-3-(3-phenylsulfanyl-propyl)-ureido]-thiazole-5-sulfonyl}-acetic acid;
2-Methyl-2-{2-[3-(4-methyl-cyclohexyl)-3-(3-phenylsulfanyl-propyl)-ureido]-thiazole-5-sulfonyl}-propionic acid;

or a pharmaceutically acceptable salt thereof.

In another embodiment, the present invention provides a novel pharmaceutical composition, comprising: a pharmaceutically acceptable carrier and a compound of the present invention, or a pharmaceutically acceptable salt thereof.

In another embodiment, the present invention provides a novel method of treating type 2 diabetes, comprising: administering to a subject in need thereof a therapeutically effective amount of a compound of the present invention.

In one aspect the invention provides a method of preventing hypoglycemia comprising administration of a compound according to the present invention.

In another aspect the invention provides the use of a compound according to the present invention for the preparation of a medicament for the prevention of hypoglycemia.

In another aspect the invention provides a compound as described herein, which is an agent useful for the treatment of an indication selected from the group consisting of hyperglycemia, IGT, insulin resistance syndrome, syndrome X, type 2 diabetes, type 1 diabetes, dyslipidemia, hypertension, and obesity.

In another aspect the invention provides a compound as described herein for use as a medicament.

In another aspect the invention provides a compound as described herein for treatment of hyperglycemia, for treatment of IGT, for treatment of Syndrome X, for treatment of type 2 diabetes, for treatment of type 1 diabetes, for treatment of dyslipidemia, for treatment of hyperlipidemia, for treatment of hypertension, for treatment of obesity, for lowering of food intake, for appetite regulation, for regulating feeding behaviour, or for enhancing the secretion of enteroincretins, such as GLP-1.

In another aspect the invention provides a pharmaceutical composition comprising, as an active ingredient, at least one compound as described herein together with one or more pharmaceutically acceptable carriers or excipients.

In one embodiment such a pharmaceutical composition may be in unit dosage form, comprising from about 0.05 mg to about 1000 mg, preferably from about 0.1 mg to about 500 mg and especially preferred from about 0.5 mg to about 200 mg of the compound according to the present invention.

In another aspect the invention provides the use of a compound according to the invention for increasing the activity of glucokinase.

In another aspect the invention provides the use of a compound according to the invention for the preparation of a medicament for the treatment of metabolic disorders, for blood glucose lowering, for the treatment of hyperglycemia, for the treatment of IGT, for the treatment of Syndrome X, for the treatment of impaired fasting glucose (IFG), for the treatment of type 2 diabetes, for the treatment of type 1 diabetes, for delaying the progression of impaired glucose tolerance (IGT) to type 2 diabetes, for delaying the progression of non-insulin requiring type 2 diabetes to insulin requiring type 2 diabetes, for the treatment of dyslipidemia, for the treatment of hyperlipidemia, for the treatment of hypertension, for lowering of food intake, for appetite regulation, for the treatment of obesity, for regulating feeding behaviour, or for enhancing the secretion of enteroincretins. In another aspect the invention provides the use of a compound according to the invention for the preparation of a medicament for the adjuvant treatment of type 1 diabetes for preventing the onset of diabetic complications.

In another aspect the invention provides the use of a compound according to the invention for the preparation of a medicament for increasing the number and/or the size of beta cells in a mammalian subject, for treatment of beta cell degeneration, in particular apoptosis of beta cells, or for treatment of functional dyspepsia, in particular irritable bowel syndrome. In one embodiment the invention provides any of the above uses in a regimen which comprises treatment with a further antidiabetic agent.

In a further aspect the invention provides the use of a compound according to the invention or a pharmaceutical composition as described above for the treatment of metabolic disorders, for blood glucose lowering, for the treatment of hyperglycemia, for treatment of IGT, for treatment of Syndrome X, for the treatment of impaired fasting glucose (IFG), for treatment of type 2 diabetes, for treatment of type 1 diabetes, for delaying the progression of impaired glucose tolerance (IGT) to type 2 diabetes, for delaying the progression of non-insulin requiring type 2 diabetes to insulin requiring type 2 diabetes, for treatment of dyslipidemia, for treatment of hyperlipidemia, for treatment of hypertension, for the treatment or prophylaxis of obesity, for lowering of food intake, for appetite regulation, for regulating feeding behaviour, or for enhancing the secretion of enteroincretins.

In a further aspect the invention provides the use of a compound according to the invention or a pharmaceutical composition as described above for the adjuvant treatment of type 1 diabetes for preventing the onset of diabetic complications.

In a further aspect the invention provides the use of a compound according to the invention or a pharmaceutical composition as described above for increasing the number and/or the size of beta cells in a mammalian subject, for treatment of beta cell degeneration, in particular apoptosis of beta cells, or for treatment of functional dyspepsia, in particular irritable bowel syndrome.

In another embodiment the invention provides a for the treatment of a glucokinase-deficiency mediated condition/disease which is caused by a glucokinase mutation.

In another embodiment the invention provides a method wherein the glucokinase-deficiency mediated condition/disease is Maturity-Onset Diabetes of the Young, Neonatal Diabetes Mellitus, or Persistent Neonatal Diabetes Mellitus.

In another embodiment the invention provides a method for preventing or ameliorating the development of diabetes in subjects exhibiting symptoms of Impaired Glucose Tolerance, Gestational Diabetes Mellitus, Polycystic Ovarian Syndrome, Cushings syndrome or Metabolic Syndrome comprising administering to a subject in need of such treatment a compound according to the invention or pharmaceutical composition thereof, wherein blood glucose normalization occurs with reduced risk of hypoglycemia.

In another embodiment the invention provides a method for preventing or ameliorating microvascular diseases comprising administering to a subject in need of such treatment a compound according to the invention or pharmaceutical composition thereof.

In another embodiment the invention provides a method for preventing macrovascular diseases in subjects exhibiting symptoms of Impaired Glucose Tolerance, Gestational Diabetes Mellitus, or Metabolic Syndrome, comprising administering to a subject in need of such treatment a compound according to the invention or pharmaceutical composition thereof, alone or in combination with lipid-lowering drugs, wherein blood glucose normalization occurs with reduced risk of hypoglycemia.

In another embodiment the invention provides a method for the preservation of beta-cell mass and function comprising administering to a subject in need of such treatment a compound according to the invention or pharmaceutical composition thereof, wherein blood glucose normalization occurs with reduced risk of hypoglycemia.

In another embodiment the invention provides a method for preventing amyloid beta peptide induced cell death comprising administering to a subject in need of such treatment a compound according to the invention or pharmaceutical composition thereof, wherein blood glucose normalization occurs with reduced risk of hypoglycemia.

In another embodiment the invention provides a method wherein the subject is a veterinary subject.

In another embodiment the invention provides a method wherein a compound according to the invention is administered as a food additive.

In another embodiment the invention provides a method for the treatment of hepatic conditions benefiting from blood glucose normalization comprising administering to a subject in need of such treatment a compound according to the invention or pharmaceutical composition thereof, wherein blood glucose normalization occurs with reduced risk of hypoglycemia.

In another embodiment the invention provides a method for the treatment of hepatic conditions benefiting from improved liver function comprising administering to a subject in need of such treatment a compound according to the invention or pharmaceutical composition thereof.

In another embodiment the invention provides a method for the treatment of hyperglycemic conditions that result from critical illness, or as a consequence of therapeutic intervention comprising administering to a subject in need of such treatment a compound according to the invention or pharmaceutical composition thereof, wherein blood glucose normalization occurs with reduced risk of hypoglycemia.

In another embodiment the invention provides a method for the treatment of hepatic conditions that result from critical illness like cancer, or are a consequence of therapy, for example cancer therapy or HIV-treatment, comprising administering to a subject in need of such treatment a compound according to the invention or pharmaceutical composition thereof.

In another embodiment the invention provides a method of treatment adjuvant to insulin in insulin-requiring diabetes type 2, or as replacement for insulin comprising administering to a subject in need of such treatment a compound according to the invention or pharmaceutical composition thereof, wherein blood glucose normalization occurs with reduced risk of hypoglycemia.

In another embodiment the invention provides a method for the treatment of lipodistrophy comprising administering to a subject in need of such treatment a compound according to the invention or pharmaceutical composition thereof, wherein blood glucose normalization occurs with reduced risk of hypoglycemia.

In another embodiment the invention provides a method for the treatment of hyperglycemia resulting from severe physical stress without signs of liver failure comprising administering to a subject in need of such treatment a compound according to the invention or pharmaceutical composition thereof, wherein blood glucose normalization occurs with reduced risk of hypoglycemia.

In another embodiment the invention provides a method wherein the severe physical stress is multiple trauma, or diabetic ketoacidosis.

In another embodiment the invention provides a method for preventing apoptotic liver damage comprising administering to a subject in need of such treatment a compound according to the invention or pharmaceutical composition thereof.

In another embodiment the invention provides a method for preventing hypoglycemia comprising administering to a subject in need of such treatment a compound according to the invention or pharmaceutical composition thereof, wherein blood glucose normalization occurs with reduced risk of hypoglycemia.

In another embodiment the invention provides a method for increasing beta-cell mass and function comprising administering to a subject in need of such treatment a compound according to the invention or pharmaceutical composition thereof, wherein blood glucose normalization occurs with reduced risk of hypoglycemia.

In another embodiment the invention provides a method of preventing type 1 diabetes comprising administering to a subject in need of such treatment a compound according to the invention or pharmaceutical composition thereof, wherein blood glucose normalization occurs with reduced risk of hypoglycemia.

In another embodiment the invention provides a method of preserving and/or increasing beta-cell mass and function in patients having undergone pancreatic islet transplantation comprising administering to a subject in need of such treatment a compound according to the invention or pharmaceutical composition thereof.

In another embodiment the invention provides a method of improving glucose control during and after surgery comprising administering to a subject in need of such treatment a compound according to the invention or pharmaceutical composition thereof.

In another embodiment the invention provides a method of improving liver function and/or survival in patients undergoing liver transplantation comprising administering to a subject in need of such treatment a compound according to the invention or pharmaceutical composition thereof. In another embodiment hereof the invention provides a method wherein the administration occurs before, during or after transplantation, or any combination thereof.

In another embodiment the invention provides a method of obtaining blood glucose normalization comprising administering to a subject in need of such treatment a compound according to the invention or pharmaceutical composition thereof, wherein blood glucose normalization occurs with reduced risk of hypoglycemia.

In another embodiment the invention provides a method of preventing or ameliorating diabetic late complications comprising administering to a subject in need of such treatment a compound according to the invention or pharmaceutical composition thereof.

In another embodiment the invention provides a method of treating type 1 or 2 diabetes comprising administering to a subject in need of such treatment a compound according to the invention or pharmaceutical composition thereof, wherein the treatment does not result in a weight gain.

In another embodiment the invention provides a method of preventing diabetic ketoacidosis comprising administering to a subject in need of such treatment a compound according to the invention or pharmaceutical composition thereof.

Combination Treatment

In a further aspect of the present invention the present compounds are administered in combination with one or more further active substances in any suitable ratios. Such further active agents may be selected from antidiabetic agents, antihyperlipidemic agents, antiobesity agents, antihypertensive agents and agents for the treatment of complications resulting from or associated with diabetes.

Suitable antidiabetic agents include insulin, GLP-1 (glucagon like peptide-1) derivatives such as those disclosed in WO 98/08871 (Novo Nordisk A/S), which is incorporated herein by reference, as well as orally active hypoglycemic agents.

Suitable orally active hypoglycemic agents preferably include imidazolines, sulfonylureas, biguanides, meglitinides, oxadiazolidinediones, thiazolidinediones, insulin sensitizers, α-glucosidase inhibitors, agents acting on the ATP-dependent potassium channel of the pancreatic β-cells eg potassium channel openers such as those disclosed in WO 97/26265, WO 99/03861 and WO 00/37474 (Novo Nordisk A/S) which are incorporated herein by reference, potassium channel openers, such as ormitiglinide, potassium channel blockers such as nateglinide or BTS-67582, glucagon antagonists such as those disclosed in WO 99/01423 and WO 00/39088 (Novo Nordisk A/S and Agouron Pharmaceuticals, Inc.), all of which are incorporated herein by reference, GLP-1 agonists such as those disclosed in WO 00/42026 (Novo Nordisk A/S and Agouron Pharmaceuticals, Inc.), which are incorporated herein by reference, DPP-IV (dipeptidyl peptidase-IV) inhibitors, PTPase (protein tyrosine phosphatase) inhibitors, inhibitors of hepatic enzymes involved in stimulation of gluconeogenesis and/or glycogenolysis, glucose uptake modulators, GSK-3 (glycogen synthase kinase-3) inhibitors, compounds modifying the lipid metabolism such as antihyperlipidemic agents and antilipidemic agents, compounds lowering food intake, and PPAR (peroxisome proliferator-activated receptor) and RXR (retinoid X receptor) agonists such as ALRT-268, LG-1268 or LG-1069.

In one embodiment of the present invention, the present compounds are administered in combination with a sulphonylurea eg tolbutamide, chlorpropamide, tolazamide, glibenclamide, glipizide, glimepiride, glicazide or glyburide.

In one embodiment of the present invention, the present compounds are administered in combination with a biguanide eg metformin.

In one embodiment of the present invention, the present compounds are administered in combination with a meglitinide eg repaglinide or senaglinide/nateglinide.

In one embodiment of the present invention, the present compounds are administered in combination with a thiazolidinedione insulin sensitizer eg troglitazone, ciglitazone, pioglitazone, rosiglitazone, isaglitazone, darglitazone, englitazone, CS-011/CI-1037 or T 174 or the compounds disclosed in WO 97/41097 (DRF-2344), WO 97/41119, WO 97/41120, WO 00/41121 and WO 98/45292 (Dr. Reddy's Research Foundation), which are incorporated herein by reference.

In one embodiment of the present invention the present compounds may be administered in combination with an insulin sensitizer eg such as GI 262570, YM-440, MCC-555, JTT-501, AR-H039242, KRP-297, GW-409544, CRE-16336, AR-H049020, LY510929, MBX-102, CLX-0940, GW-501516 or the compounds disclosed in WO 99/19313 (NN622/DRF-2725), WO 00/50414, WO 00/63191, WO 00/63192, WO 00/63193 (Dr. Reddy's Research Foundation) and WO 00/23425, WO 00/23415, WO 00/23451, WO 00/23445, WO 00/23417, WO 00/23416, WO 00/63153, WO 00/63196, WO 00/63209, WO 00/63190 and WO 00/63189 (Novo Nordisk A/S), which are incorporated herein by reference.

In one embodiment of the present invention the present compounds are administered in combination with an α-glucosidase inhibitor eg voglibose, emiglitate, miglitol or acarbose. In one embodiment of the present invention the present compounds are administered in combination with a glycogen phosphorylase inhibitor eg the compounds described in WO 97/09040 (Novo Nordisk A/S).

In one embodiment of the present invention the present compounds are administered in combination with an agent acting on the ATP-dependent potassium channel of the pancreatic β-cells eg tolbutamide, glibenclamide, glipizide, glicazide, BTS-67582 or repaglinide. In one embodiment of the present invention the present compounds are administered in combination with nateglinide.

In one embodiment of the present invention the present compounds are administered in combination with an antihyperlipidemic agent or a antilipidemic agent eg cholestyramine, colestipol, clofibrate, gemfibrozil, lovastatin, pravastatin, simvastatin, probucol or dextrothyroxine.

Furthermore, the compounds according to the invention may be administered in combination with one or more antiobesity agents or appetite regulating agents.

Such agents may be selected from the group consisting of CART (cocaine amphetamine regulated transcript) agonists, NPY (neuropeptide Y) antagonists, MC3 (melanocortin 3) agonists, MC4 (melanocortin 4) agonists, orexin antagonists, TNF (tumor necrosis factor) agonists, CRF (corticotropin releasing factor) agonists, CRF BP (corticotropin releasing factor binding protein) antagonists, urocortin agonists, β3 adrenergic agonists such as CL-316243, AJ-9677, GW-0604, LY362884, LY377267 or AZ-40140, MSH (melanocyte-stimulating hormone) agonists, MCH (melanocyte-concentrating hormone) antagonists, CCK (cholecystokinin) agonists, serotonin reuptake inhibitors (fluoxetine, seroxat or citalopram), serotonin and norepinephrine reuptake inhibitors, 5HT (serotonin) agonists, bombesin agonists, galanin antagonists, growth hormone, growth factors such as prolactin or placental lactogen, growth hormone releasing compounds, TRH (thyreotropin releasing hormone) agonists, UCP 2 or 3 (uncoupling protein 2 or 3) modulators, leptin agonists, DA (dopamine) agonists (bromocriptin, doprexin), lipase/amylase inhibitors, PPAR modulators, RXR modulators, TR β agonists, adrenergic CNS stimulating agents, AGRP (agouti related protein) inhibitors, H3 histamine antagonists such as those disclosed in WO 00/42023, WO 00/63208 and WO 00/64884, which are incorporated herein by reference, exendin-4, GLP-1 agonists, ciliary neurotrophic factor, and oxyntomodulin. Further antiobesity agents are bupropion (antidepressant), topiramate (anticonvulsant), ecopipam (dopamine D1/D5 antagonist) and naltrexone (opioid antagonist).

In one embodiment of the present invention the antiobesity agent is leptin.

In one embodiment of the present invention the antiobesity agent is a serotonin and norepinephrine reuptake inhibitor eg sibutramine.

In one embodiment of the present invention the antiobesity agent is a lipase inhibitor eg orlistat.

In one embodiment of the present invention the antiobesity agent is an adrenergic CNS stimulating agent eg dexamphetamine, amphetamine, phentermine, mazindol phendimetrazine, diethylpropion, fenfluramine or dexfenfluramine.

Furthermore, the present compounds may be administered in combination with one or more antihypertensive agents. Examples of antihypertensive agents are β-blockers such as alprenolol, atenolol, timolol, pindolol, propranolol and metoprolol, ACE (angiotensin converting enzyme) inhibitors such as benazepril, captopril, enalapril, fosinopril, lisinopril, quinapril and ramipril, calcium channel blockers such as nifedipine, felodipine, nicardipine, isradipine, nimodipine, diltiazem and verapamil, and β-blockers such as doxazosin, urapidil, prazosin and terazosin. Further reference can be made to Remington: The Science and Practice of Pharmacy, 19th Edition, Gennaro, Ed., Mack Publishing Co., Easton, Pa., 1995.

In one embodiment of the present invention, the present compounds are administered in combination with insulin, insulin derivatives or insulin analogues.

In one embodiment of the invention the insulin is an insulin derivative is selected from the group consisting of B29-N$^\epsilon$-myristoyl-des(B30) human insulin, B29-N$^\epsilon$-palmitoyl-des(B30) human insulin, B29-N$^\epsilon$-myristoyl human insulin, B29-N$^\epsilon$-palmitoyl human insulin, B28-N$^\epsilon$-myristoyl Lys$^{B28}$ Pro$^{B29}$ human insulin, B28-N$^\epsilon$-palmitoyl Lys$^{B28}$ Pro$^{B29}$ human insulin, B30-N$^\epsilon$-myristoyl-Thr$^{B29}$Lys$^{B30}$ human insulin, B30-N$^\epsilon$-palmitoyl-Thr$^{B29}$Lys$^{B30}$ human insulin, B29-N$^\epsilon$-(N-palmitoyl-γ-glutamyl)-des(B30) human insulin, B29-N$^\epsilon$-(N-lithocholyl-γ-glutamyl)-des(B30) human insulin, B29-N$^\epsilon$-(ω-carboxyheptadecanoyl)-des(B30) human insulin and B29-N$^\epsilon$-(ω-carboxyheptadecanoyl) human insulin.

In another embodiment of the invention the insulin derivative is B29-N$^\epsilon$-myristoyl-des(B30) human insulin.

In a further embodiment of the invention the insulin is an acid-stabilised insulin. The acid-stabilised insulin may be selected from analogues of human insulin having one of the following amino acid residue substitutions:
A21G
A21G, B28K, B29P
A21G, B28D
A21G, B28E
A21G, B3K, B29E
A21G, desB27
A21G, B9E
A21G, B9D
A21G, B10E insulin.

In a further embodiment of the invention the insulin is an insulin analogue. The insulin analogue may be selected from the group consisting of An analogue wherein position B28 is Asp, Lys, Leu, Val, or Ala and position B29 is Lys or Pro; and des(B28-B30), des(B27) or des(B30) human insulin.

In another embodiment the analogue is an analogue of human insulin wherein position B28 is Asp or Lys, and position B29 is Lys or Pro.

In another embodiment the analogue is des(B30) human insulin.

In another embodiment the insulin analogue is an analogue of human insulin wherein position B28 is Asp.

In another embodiment the analogue is an analogue wherein position B3 is Lys and position B29 is Glu or Asp.

In another embodiment the GLP-1 derivative to be employed in combination with a compound of the present invention refers to GLP-1 (1-37), exendin-4(1-39), insulinotropic fragments thereof, insulinotropic analogues thereof and insulinotropic derivatives thereof. Insulinotropic fragments of GLP-1 (1-37) are insulinotropic peptides for which the entire sequence can be found in the sequence of GLP-1 (1-37) and where at least one terminal amino acid has been deleted. Examples of insulinotropic fragments of GLP-1 (1-37) are GLP-1 (7-37) wherein the amino acid residues in positions 1-6 of GLP-1 (1-37) have been deleted, and GLP-1 (7-36) where the amino acid residues in position 1-6 and 37 of GLP-1 (1-37) have been deleted. Examples of insulinotropic fragments of exendin-4(1-39) are exendin-4(1-38) and exendin-4(1-31). The insulinotropic property of a compound may be determined by in vivo or in vitro assays well known in the art. For instance, the compound may be administered to an animal and monitoring the insulin concentration over time. Insulinotropic analogues of GLP-1(1-37) and exendin-4(1-39) refer to the respective molecules wherein one or more of the amino acids residues have been exchanged with other amino acid residues and/or from which one or more amino acid residues have been deleted and/or from which one or more amino acid residues have been added with the proviso that said analogue either is insulinotropic or is a prodrug of an insulinotropic compound. Examples of insulinotropic analogues of GLP-1(1-37) are e.g. Met$^8$-GLP-1 (7-37) wherein the alanine in position 8 has been replaced by methionine and the amino acid residues in position 1 to 6 have been deleted, and Arg$^{34}$-GLP-1(7-37) wherein the valine in position 34 has been replaced with arginine and the amino acid residues in position 1 to 6 have been deleted. An example of an insulinotropic analogue of exendin-4(1-39) is Ser$^2$Asp$^3$-exendin-4 (1-39) wherein the amino acid residues in position 2 and 3 have been replaced with serine and aspartic acid, respectively (this particular analogue also being known in the art as exendin-3). Insulinotropic derivatives of GLP-1(1-37), exendin-4 (1-39) and analogues thereof are what the person skilled in the art considers to be derivatives of these peptides, i.e. having at least one substituent which is not present in the parent peptide molecule with the proviso that said derivative either is insulinotropic or is a prodrug of an insulinotropic compound. Examples of substituents are amides, carbohydrates, alkyl groups and lipophilic substituents. Examples of insulinotropic derivatives of GLP-1(1-37), exendin-4(1-39) and analogues thereof are GLP-1(7-36)-amide, Arg$^{34}$, Lys$^{26}$(N$^\epsilon$-(γ-Glu(N$^\alpha$-hexadecanoyl)))-GLP-1(7-37) and Tyr$^{31}$-exendin-4 (1-31)-amide. Further examples of GLP-1(1-37), exendin-4 (1-39), insulinotropic fragments thereof, insulinotropic analogues thereof and insulinotropic derivatives thereof are described in WO 98/08871, WO 99/43706, U.S. Pat. No. 5,424,286 and WO 00/09666.

In another aspect of the present invention, the present compounds are administered in combination with more than one of the above-mentioned compounds e.g. in combination with metformin and a sulphonylurea such as glyburide; a sulphonylurea and acarbose; nateglinide and metformin; acarbose and metformin; a sulfonylurea, metformin and troglitazone; insulin and a sulfonylurea; insulin and metformin; insulin, metformin and a sulfonylurea; insulin and troglitazone; insulin and lovastatin; etc.

It should be understood that any suitable combination of the compounds according to the invention with diet and/or exercise, one or more of the above-mentioned compounds and optionally one or more other active substances are considered to be within the scope of the present invention. In one embodiment of the present invention, the pharmaceutical composition according to the present invention comprises e.g. a compound of the invention in combination with metformin and a sulphonylurea such as glyburide; a compound of the invention in combination with a sulphonylurea and acarbose; nateglinide and metformin; acarbose and metformin; a sulfonylurea, metformin and troglitazone; insulin and a sulfonylurea; insulin and metformin; insulin, metformin and a sulfonylurea; insulin and troglitazone; insulin and lovastatin; etc.

Pharmaceutical Compositions

The compounds of the present invention may be administered alone or in combination with pharmaceutically acceptable carriers or excipients, in either single or multiple doses. The pharmaceutical compositions according to the invention may be formulated with pharmaceutically acceptable carriers or diluents as well as any other known adjuvants and excipients in accordance with conventional techniques such as those disclosed in Remington: The Science and Practice of Pharmacy, 19$^{th}$ Edition, Gennaro, Ed., Mack Publishing Co., Easton, Pa., 1995.

The pharmaceutical compositions may be specifically formulated for administration by any suitable route such as the oral, rectal, nasal, pulmonary, topical (including buccal and sublingual), transdermal, intracisternal, intraperitoneal, vaginal and parenteral (including subcutaneous, intramuscular, intrathecal, intravenous and intradermal) route, the oral route being preferred. It will be appreciated that the preferred route will depend on the general condition and age of the subject to be treated, the nature of the condition to be treated and the active ingredient chosen.

Pharmaceutical compositions for oral administration include solid dosage forms such as hard or soft capsules, tablets, troches, dragees, pills, lozenges, powders and granules. Where appropriate, they can be prepared with coatings such as enteric coatings or they can be formulated so as to provide controlled release of the active ingredient such as sustained or prolonged release according to methods well known in the art.

Liquid dosage forms for oral administration include solutions, emulsions, aqueous or oily suspensions, syrups and elixirs.

Pharmaceutical compositions for parenteral administration include sterile aqueous and non-aqueous injectable solutions, dispersions, suspensions or emulsions as well as sterile powders to be reconstituted in sterile injectable solutions or dispersions prior to use. Depot injectable formulations are also contemplated as being within the scope of the present invention.

Other suitable administration forms include suppositories, sprays, ointments, cremes, gels, inhalants, dermal patches, implants etc.

A typical oral dosage is in the range of from about 0.001 to about 100 mg/kg body weight per day, preferably from about 0.01 to about 50 mg/kg body weight per day, and more preferred from about 0.05 to about 10 mg/kg body weight per day administered in one or more dosages such as 1 to 3 dosages. The exact dosage will depend upon the frequency and mode of administration, the sex, age, weight and general condition of the subject treated, the nature and severity of the condition treated and any concomitant diseases to be treated and other factors evident to those skilled in the art.

The formulations may conveniently be presented in unit dosage form by methods known to those skilled in the art. A typical unit dosage form for oral administration one or more times per day such as 1 to 3 times per day may contain from 0.05 to about 1000 mg, preferably from about 0.1 to about 500 mg, and more preferred from about 0.5 mg to about 200 mg. For parenteral routes such as intravenous, intrathecal, intramuscular and similar administration, typically doses are in the order of about half the dose employed for oral administration.

The compounds of this invention are generally utilized as the free substance or as a pharmaceutically acceptable salt thereof. Examples are an acid addition salt of a compound having the utility of a free base and a base addition salt of a compound having the utility of a free acid. The term "pharmaceutically acceptable salts" refers to non-toxic salts of the compounds of this invention which are generally prepared by reacting the free base with a suitable organic or inorganic acid or by reacting the acid with a suitable organic or inorganic base. When a compound according to the present invention contains a free base such salts are prepared in a conventional manner by treating a solution or suspension of the compound with a chemical equivalent of a pharmaceutically acceptable acid. When a compound according to the present invention contains a free acid such salts are prepared in a conventional manner by treating a solution or suspension of the compound with a chemical equivalent of a pharmaceutically acceptable base. Physiologically acceptable salts of a compound with a hydroxy group include the anion of said compound in combination with a suitable cation such as sodium or ammonium ion. Other salts which are not pharmaceutically acceptable may be useful in the preparation of compounds of the present invention and these form a further aspect of the present invention.

For parenteral administration, solutions of the novel compounds of the formula (I) in sterile aqueous solution, aqueous propylene glycol or sesame or peanut oil may be employed. Such aqueous solutions should be suitably buffered if necessary and the liquid diluent first rendered isotonic with sufficient saline or glucose. The aqueous solutions are particularly suitable for intravenous, intramuscular, subcutaneous and intraperitoneal administration. The sterile aqueous media employed are all readily available by standard techniques known to those skilled in the art.

Suitable pharmaceutical carriers include inert solid diluents or fillers, sterile aqueous solution and various organic solvents. Examples of solid carriers are lactose, terra alba, sucrose, cyclodextrin, talc, gelatine, agar, pectin, acacia, magnesium stearate, stearic acid and lower alkyl ethers of cellulose. Examples of liquid carriers are syrup, peanut oil, olive oil, phospholipids, fatty acids, fatty acid amines, polyoxyethylene and water. Similarly, the carrier or diluent may include any sustained release material known in the art, such as glyceryl monostearate or glyceryl distearate, alone or mixed with a wax. The pharmaceutical compositions formed by combining the novel compounds of the present invention and the pharmaceutically acceptable carriers are then readily administered in a variety of dosage forms suitable for the disclosed routes of administration. The formulations may conveniently be presented in unit dosage form by methods known in the art of pharmacy.

Formulations of the present invention suitable for oral administration may be presented as discrete units such as capsules or tablets, each containing a predetermined amount of the active ingredient, and which may include a suitable excipient. Furthermore, the orally available formulations may be in the form of a powder or granules, a solution or suspension in an aqueous or non-aqueous liquid, or an oil-in-water or water-in-oil liquid emulsion. Compositions intended for oral use may be prepared according to any known method, and such compositions may contain one or more agents selected from the group consisting of sweetening agents, flavoring agents, coloring agents, and preserving agents in order to provide pharmaceutically elegant and palatable preparations. Tablets may contain the active ingredient in admixture with non-toxic pharmaceutically-acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example corn starch or alginic acid; binding agents, for example, starch, gelatin or acacia; and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in U.S. Pat. Nos. 4,356,108; 4,166,452; and 4,265,874, incorporated herein by reference, to form osmotic therapeutic tablets for controlled release. Formulations for oral use may also be presented as hard gelatin capsules where the active ingredient is mixed with an inert solid diluent, for example, calcium carbonate, calcium phosphate or kaolin, or a soft gelatin capsules wherein the active ingredient is mixed with water or an oil medium, for example peanut oil, liquid paraffin, or olive oil.

Aqueous suspensions may contain the active compounds in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; dispersing or wetting agents may be a naturally-occurring phosphatide such as lecithin, or condensation products of an alkylene oxide with fatty acids, for example polyoxyethylene stearate, or condensation products of ethylene oxide with long chain aliphatic alcohols, for example, heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as a liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active compound in admixture with a dispersing or wetting agent, suspending agent and one or more preservatives. Suitable dispersing or wetting agents and suspending agents are exemplified by those already mentioned above. Additional excipients, for example, sweetening, flavoring, and coloring agents may also be present. The pharmaceutical compositions of the present invention may also be in the form of oil-in-water emulsions. The oily phase may be a vegetable oil, for example, olive oil or arachis oil, or a mineral oil, for example a liquid paraffin, or a mixture thereof. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of said partial esters with ethylene oxide, for example polyoxyethylene sorbitan monooleate. The emulsions may also contain sweetening and flavoring agents. Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleaginous suspension. This suspension may be formulated according to the known methods using suitable dispersing or wetting agents and suspending agents described above. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution, and isotonic sodium chloride solution. In addition, sterile, fixed oils are conveniently employed as solvent or suspending medium. For this purpose, any bland fixed oil may be employed using synthetic mono- or diglycerides. In addition, fatty acids such as oleic acid find use in the preparation of injectables.

The compositions may also be in the form of suppositories for rectal administration of the compounds of the present invention. These compositions can be prepared by mixing the drug with a suitable non-irritating excipient which is solid at ordinary temperatures but liquid at the rectal temperature and will thus melt in the rectum to release the drug. Such materials include cocoa butter and polyethylene glycols, for example.

For topical use, creams, ointments, jellies, solutions of suspensions, etc., containing the compounds of the present invention are contemplated. For the purpose of this application, topical applications shall include mouth washes and gargles.

The compounds of the present invention may also be administered in the form of liposome delivery systems, such as small unilamellar vesicles, large unilamellar vesicles, and multilamellar vesicles. Liposomes may be formed from a variety of phospholipids, such as cholesterol, stearylamine, or phosphatidylcholines.

In addition, some of the compounds of the present invention may form solvates with water or common organic solvents. Such solvates are also encompassed within the scope of the present invention.

Thus, in a further embodiment, there is provided a pharmaceutical composition comprising a compound according to the present invention, or a pharmaceutically acceptable salt, solvate, or prodrug thereof, and one or more pharmaceutically acceptable carriers, excipients, or diluents.

If a solid carrier is used for oral administration, the preparation may be tableted, placed in a hard gelatine capsule in powder or pellet form or it can be in the form of a troche or lozenge. The amount of solid carrier will vary widely but will usually be from about 25 mg to about 1 g. If a liquid carrier is used, the preparation may be in the form of a syrup, emulsion, soft gelatine capsule or sterile injectable liquid such as an aqueous or non-aqueous liquid suspension or solution.

A typical tablet that may be prepared by conventional tabletting techniques may contain:

| Core: | |
|---|---|
| Active compound (as free compound or salt thereof) | 5.0 mg |
| Lactosum Ph. Eur. | 67.8 mg |
| Cellulose, microcryst. (Avicel) | 31.4 mg |
| Amberlite ®IRP88* | 1.0 mg |
| Magnesii stearas Ph. Eur. | q.s. |
| Coating: | |
| Hydroxypropyl methylcellulose | approx. 9 mg |
| Mywacett 9-40 T** | approx. 0.9 mg |

*Polacrillin potassium NF, tablet disintegrant, Rohm and Haas.
**Acylated monoglyceride used as plasticizer for film coating.

If desired, the pharmaceutical composition of the present invention may comprise a compound according to the present invention in combination with further active substances such as those described in the foregoing.

The present invention also provides a method for the synthesis of compounds useful as intermediates in the preparation of compounds of formula (I) along with methods for the preparation of compounds of formula (I). The compounds can be prepared readily according to the following reaction Schemes (in which all variables are as defined before, unless so specified) using readily available starting materials, reagents and conventional synthesis procedures. In these reactions, it is also possible to make use of variants which are themselves known to those of ordinary skill in this art, but are not mentioned in greater detail.

Pharmacological Methods

Glucokinase Activity Assay (I)

Glucokinase activity is assayed spectrometrically coupled to glucose 6-phosphate dehydrogenase to determine compound activation of glucokinase. The final assay contains 50 mM Hepes, pH 7.1, 50 mM KCl, 5 mM $MgCl_2$, 2 mM dithiothreitol, 0.6 mM NADP, 1 mM ATP, 0.195 µM G-6-P dehydrogenase (from Roche, 127 671), 15 nM recombinant human glucokinase. The glucokinase is human liver glucokinase N-terminally truncated with an N-terminal His-tag (($His)_8$-VEQILA . . . Q466) and is expressed in *E. coli* as a soluble protein with enzymatic activity comparable to liver extracted GK.

The purification of His-tagged human glucokinase (hGK) was performed as follows: The cell pellet from 50 ml *E. coli* culture was resuspended in 5 ml extraction buffer A (25 mM HEPES, pH 8.0, 1 mM $MgCl_2$, 150 mM NaCl, 2 mM mercaptoethanol) with addition of 0.25 mg/ml lysozyme and 50 µg/ml sodium azide. After 5 minutes at room temperature 5 ml of extraction buffer B (1.5 M NaCl, 100 mM $CaCl_2$, 100 mM $MgCl_2$, 0.02 mg/ml DNase 1, protease inhibitor tablet (Complete® 1697498): 1 tablet pr. 20 ml buffer) was added. The extract was then centrifugated at 15,000 g for 30 minutes. The resulting supernatant was loaded on a 1 ml Metal Chelate Affinity Chromatography (MCAC) Column charged with $Ni^{2+}$. The column is washed with 2 volumes buffer A containing 20 mM imidazole and the bound his-tagged hGK is subsequently eluted using a 20 minute gradient of 20 to 500 mM imididazol in buffer A. Fractions are examined using SDS-gel-electrophoresis, and fractions containing hGK (MW: 52 KDa) are pooled. Finally a gel filtration step is used for final polishing and buffer exchange. hGK containing fractions are loaded onto a Superdex 75 (16/60) gel filtration column and eluted with Buffer B (25 mM HEPES, pH 8.0, 1 mM $MgCl_2$, 150 mM NaCl, 1 mM Dithiothreitol). The purified hGK is examined by SDS-gel electrophoresis and MALDI mass spectrometry and finally 20% glycerol is added before freezing. The yield from 50 ml *E. coli* culture is generally approximately 2-3 mg hGK with a purity>90%.

The compound to be tested is added into the well in final 2.5% DMSO concentration in an amount sufficient to give a desired concentration of compound, for instance 1, 5, 10, 25 or 50 µM. The reaction starts after glucose is added to a final concentration of 2, 5, 10 or 15 mM. The assay uses a 96-well UV plate and the final assay volume used is 200 µl/well. The plate is incubated at 25° C. for 5 min and kinetics is measured at 340 nm in SpectraMax every 30 seconds for 5 minutes. Results for each compound are expressed as the fold activation of the glucokinase activity compared to the activation of the glucokinase enzyme in an assay without compound after having been subtracted from a "blank", which is without glucokinase enzyme and without compound. The compounds in each of the Examples exhibits activation of glucokinase in this assay. A compound, which at a concentration of at or below 30 µM gives 1.5-fold higher glucokinase activity than the result from the assay without compound, is deemed to be an activator of glucokinase.

The glucose sensitivity of the compounds are measured at a compound concentration of 10 µM and at glucose concentrations of 5 and 15 mM.

Glucokinase Activity Assay (II)

Determination of Glycogen Deposition in Isolated Rat Hepatocytes:

Hepatocytes are isolated from rats fed ad libitum by a two-step perfusion technique. Cell viability, assessed by trypan blue exclusion, is consistently greater than 80%. Cells are plated onto collagen-coated 96-well plates in basal medium (Medium 199 (5.5 mM glucose) supplemented with 0.1 µM dexamethasone, 100 units/ml penicillin, 100 mg/ml streptomycin, 2 mM L-glutamine and 1 nM insulin) with 4% FCS at a cell density of 30,000 cells/well. The medium is replaced with basal medium 1 hour after initial plating in order to remove dead cells. Medium is changed after 24 hours to basal medium supplemented with 9.5 mM glucose and 10 nM insulin to induce glycogen synthesis, and experiments are performed the next day. The hepatocytes are washed twice with prewarmed (37° C.) buffer A (117.6 mM NaCl, 5.4 mM KCl, 0.82 mM $Mg_2SO_4$, 1.5 mM $KH_2PO_4$, 20 mM HEPES, 9 mM $NaHCO_3$, 0.1% w/v HSA, and 2.25 mM $CaCl_2$, pH 7.4 at 37° C.) and incubated in 100 µl buffer A containing 15 mM glucose and increasing concentrations of the test compound, such as for instance 1, 5, 10, 25, 50 or 100 µM, for 180 minutes. Glycogen content is measured using standard procedures (Agius, L. et al, Biochem J. 266, 91-102 (1990). A compound, which when used in this assay gives an significant increase in glycogen content compared to the result from the assay without compound, is deemed to have activity in this assay.

Glucokinase Activity Assay (III)

Stimulation of Insulin Secretion by Glucokinase Activators in INS-1E Cells

The glucose responsive β-cell line INS-1E is cultivated as described by Asfari M et al., Endocrinology, 130, 167-178 (1992). The cells are then seeded into 96 well cell culture plates and grown to a density of approximately $5 \times 10^4$ per well. Stimulation of glucose dependent insulin secretion is tested by incubation for 2 hours in Krebs Ringer Hepes buffer at glucose concentrations from 2.5 to 15 mM with or without addition of glucokinase activating compounds in concentrations of for instance 1, 5, 10, 25, 50 or 100 µM, and the supernatants collected for measurements of insulin concentrations by ELISA (n=4). A compound, which when used in this assay gives an significant increase in insulin secretion in response to glucose compared to the result from the assay without compound, is deemed to have activity in this assay.

While the invention has been described and illustrated with reference to certain preferred embodiments thereof, those skilled in the art will appreciate that various changes, modifications and substitutions can be made therein without departing from the spirit and scope of the present invention. For example, effective dosages other than the preferred dosages as set forth herein may be applicable as a consequence of variations in the responsiveness of the mammal being treated for glucokinase-deficiency mediated disease(s). Likewise, the specific pharmacological responses observed may vary according to and depending on the particular active compound selected or whether there are present pharmaceutical carriers, as well as the type of formulation and mode of administration employed, and such expected variations or differences in the results are contemplated in accordance with the objects and practices of the present invention.

EXAMPLES

Abbreviations used in the Schemes and Examples are as follows:
d=day(s)
g=gram(s)
h=hour(s)
MHz=mega hertz
L=liter(s)
M=molar
mg=milligram(s)
min=minute(s)
mL=milliliter(s)
mM=millimolar
mmol=millimole(s)
mol=mole(s)
N=normal
ppm=parts per million
i.v.=intravenous
m/z=mass to charge ratio
mp=melting point
MS=mass spectrometry
HPLC=high pressure liquid chromatography
HPLC-MS=high pressure liquid chromatography-mass spectrometry
NMR=nuclear magnetic resonance spectroscopy
p.o.=per oral
$R_t$=retention time
rt=room temperature
s.c.=subcutaneous
TLC=thin layer chromatography
BuOK=Potassium tert-butoxide
Boc=tert-Butyloxcarbonyl
CDI=carbonyldiimidazole
DBU=1,8-Diazabicyclo[5.4.0]-undec-7-en
DCM ($CH_2Cl_2$)=dichloromethane, methylenechloride
DHOBt=3,4-Dihydro-3-hydroxy-4-oxo-1,2,3-benzotriazine
DIC=1,3-Diisopropyl carbodiimide
DCC=1,3-Dicyclohexyl carbodiimide
DIEA=N,N-diisopropylethylamine
DIPEA=N,N-diisopropylethylamine
DMA=N,N-dimethylacetamide
DMAP=4-(N,N-dimethylamino)pyridine
DMF=N,N-dimethylformamide
DMF=N,N-dimethylformamide
DMPU=NN'-dimethylpropyleneurea, 1,3-dimethyl-2-oxohexahydropyrimidine
EDAC=1-(3-Dimethylaminopropyl)-3-ethyl-carbodiimide hydrochloride
$Et_2O$=diethyl ether
EtOAc=ethyl acetate
HMPA=hexamethylphosphoric acid triamide
HOBt=N-Hydroxybenzotriazole
HOAt=7-Aza-1-Hydroxybenzotriazole
LAH, ($LiAlH_4$)=Lithiumaluminium hydride
LDA=lithium diisopropylamide
MeCN=acetonitrile
MeOH=methanol
NMP=N-methylpyrrolidin-2-one
NaH=Sodium Hydride
$NH_2OH$=Hydroxylamine
PyBroP=Bromotrispyrrolidinophosphonium hexafluorophosphate
TEA ($Et_3N$)=triethylamine
TFA=trifluoroacetic acid
THF=tetrahydrofuran
$CDCl_3$=deuterio chloroform
$CD_3OD$=tetradeuterio methanol
DMSO-$d_6$=hexadeuterio dimethylsulfoxide

HPLC-MS

The RP-analysis was performed on an Agilent HPLC system (1100 degasser, 1100 pump, 1100 injector and a 1100 DAD) fitted with an Agilent MS detector system Model SL (MW 0-3000) and a S.E.D.E.R.E Model Sedex 75 ELS detector system using a Waters X-terra MS C18 column (5 µm, 3.0 mm×50 mm) with gradient elution, 5% to 100% solvent B (0.05% TFA in acetonitrile) in solvent A (0.05% TFA in water) within 6.75 min, 1.5 mL/min.

Preparative HPLC

The RP-purification was performed on a Gilson system (3 Gilson 306 pumps, Gilson 170 DAD detector and a Gilson 215 liquid handler) using a Waters X-terra RP (10 µm, 30 mm×150 mm) with gradient elution, 5% to 95% solvent B (0.05% TFA in acetonitrile) in solvent A (0.05% TFA in water) within 15 min, 40 mL/min, detection at 210 nm, temperature rt. The pooled fractions are either evaporated to dryness in vacuo, or evaporated in vacuo until the acetonitrile is removed, and then frozen and freeze dried.

NMR

Proton NMR spectra were recorded at ambient temperature using a Brucker Avance DPX 400 (400 MHz) with tetramethylsilane as an internal standard. Chemical shifts (δ) are given in ppm General The following examples and general procedures refer to intermediate compounds and final products for general formula (I) identified in the specification and in the synthesis schemes. The preparation of the compounds of general formula (I) of the present invention is described in detail using the following examples. Occasionally, the reaction may not be applicable as described to each compound included within the disclosed scope of the invention. The compounds for which this occurs will be readily recognised by those skilled in the art. In these cases the reactions can be successfully performed by conventional modifications known to those skilled in the art, which is, by appropriate protection of interfering groups, by changing to other conventional reagents, or by routine modification of reaction conditions. Alternatively, other reactions disclosed herein or otherwise conventional will be applicable to the preparation of the corresponding compounds of the invention. In all preparative methods, all starting materials are known or may be prepared by a person skilled in the art in analogy with the preparation of similar known compounds or by the General procedures A through K described herein.

The structures of the compounds are confirmed by either by nuclear magnetic resonance (NMR) and/or by HPLS-MS.

General Procedure (A)

Compounds of the formula (Ia) according to the invention wherein $R^1$, $R^2$ and A are as defined for formula (I) can be prepared as outlined below:

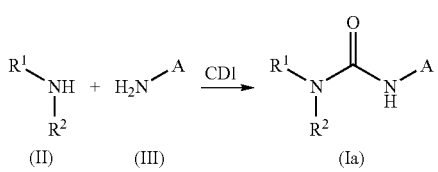

Step 1.

The aminoheterocycle ($NH_2A$) (III) wherein A is as defined for formula (I), can be converted using standard literature procedures (for example WO 2004/002481) to an acyl imidazonium intermediate with carbonyl diimidazole (CDI) or an equivalent of this in a solvent such as dichloromethane, dichloroethane, tetrahydrofuran, or DMF. Treatment with $R^1R^2NH$ (II), wherein $R^1$ and $R^2$ are as defined above, gives the compound of formula (Ia). The aminoheterocycle ($NH_2A$) or secondary amine ($R^1R^2NH$) can be either commercially available compounds or compounds that can be prepared following procedures described in the literature or prepared as described in the relevant example and general procedures.

Step 2.

In some cases it might be more convenient to generate the final substituents on $R^1$, $R^2$ and A after the urea formation. If in example the substituent on A in formula (Ia) contains an ester functionality this can be hydrolysed to the corresponding carboxylic acid using standard conditions for hydrolysis of esters. Suitable bases for the hydrolysis are NaOH and LiOH or equivalents of these in solvents like dioxane, THF, EtOH, MeOH and water or mixtures of these. The reactions can be performed at room temperature or at elevated temperatures.

Other examples are described in general procedure I and J.

General Procedure (B)

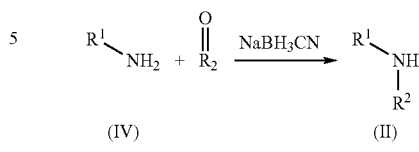

The desired amines $R^1R^2NH$ described in General procedure (A) can in example be prepared by a reductive amination with a suitable primary amine and a ketone or an aldehyde. The reaction can be performed in THF-MeOH or similar solvents in the presence of molecular sieves (4 Å) or with 10% AcOH, using $NaBH_3CN$ or suitable equivalents of this as reducing agent. The primary amine, ketone and aldehyde can be either commercially available compounds or compounds that can be prepared following procedures described in the literature or prepared as described in the relevant example and general procedures.

General Procedure (C)

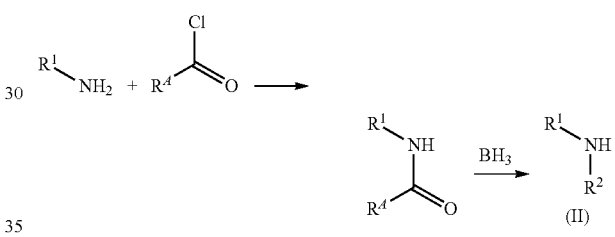

In case the primary amines ($R^1NH_2$) are not sufficiently reactive to undergo reductive amination (general procedure B), the desired secondary amines can be prepared by initial formation of a secondary amide using a primary amine and an acid chloride or an equivalent thereof and subsequent reduction of the amide. The amide reduction can be performed in THF or similar solvents using borane or suitable equivalents. The primary amine and the acid chloride can be either commercially available compounds or compounds that can be pre-pared following procedures described in the literature or prepared as described in the relevant example and general procedures.

General Procedure (D)

Preparation of trans-alkoxymethylcyclohexylamine and the Like

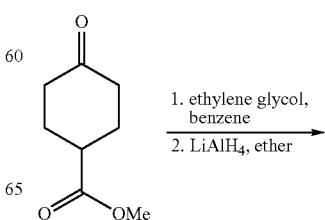

1. ethylene glycol, benzene
2. LiAlH$_4$, ether

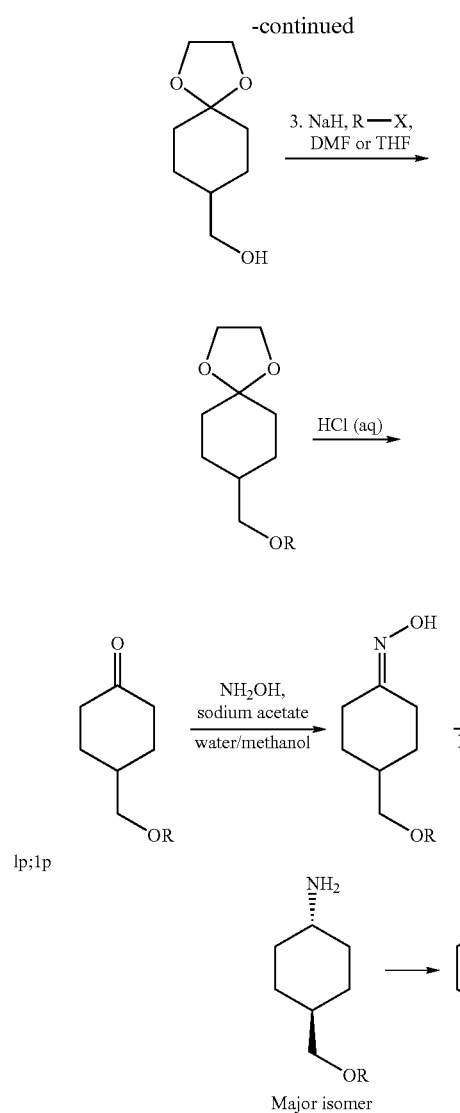

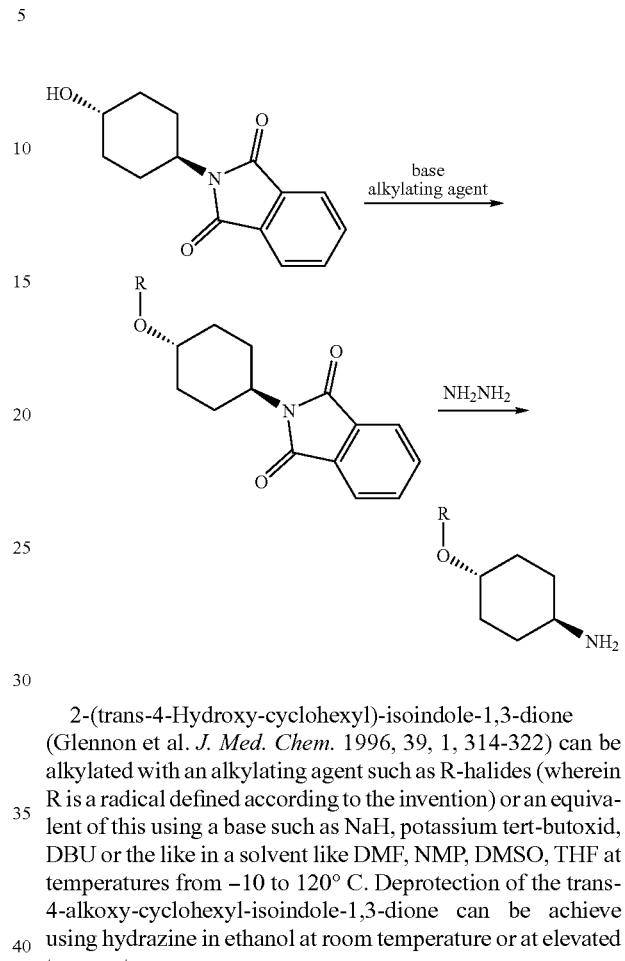

General Procedure (E)

Preparation of trans-4-alkoxy-cyclohexylamine and the Like 2-(trans-4-Hydroxy-cyclohexyl)-isoindole-1,3-dione (Glennon et al. *J. Med. Chem.* 1996, 39, 1, 314-322) can be alkylated with an alkylating agent such as R-halides (wherein R is a radical defined according to the invention) or an equivalent of this using a base such as NaH, potassium tert-butoxid, DBU or the like in a solvent like DMF, NMP, DMSO, THF at temperatures from −10 to 120° C. Deprotection of the trans-4-alkoxy-cyclohexyl-isoindole-1,3-dione can be achieve using hydrazine in ethanol at room temperature or at elevated temperatures.

General Procedure (F)

Preparation of trans-4-alkyl-cyclohexylamines and the Like

The carbonyl group of 4-oxo-cyclohexanone carboxylic acid methyl ester can be protected as ketal by reaction with ethylene glycol in benzene with azeotropic removal of water. The ester group can then be reduced with lithium aluminium hydride in a suitable solvent such as diethyl ether or tetrahydrofuran. The alcohol can be alkylated using sodium hydride and a suitable alkyl halide (R—X, wherein R is an appropriate radical defined according to the invention) in a solvent such as tetrahydrofuran or DMF. Ketal deprotection of the product under standard acidic conditions gives the corresponding ketone, which can be converted to the corresponding oxime upon treatment with hydroxylamine and a suitable base (for example sodium acetate). Reduction of the oxime using sodium in ethanol affords the trans-4-alkoxymethyl-cyclohexylamine as the major isomer, which, if necessary can be purified by recrystallisation of the corresponding HCl salt.

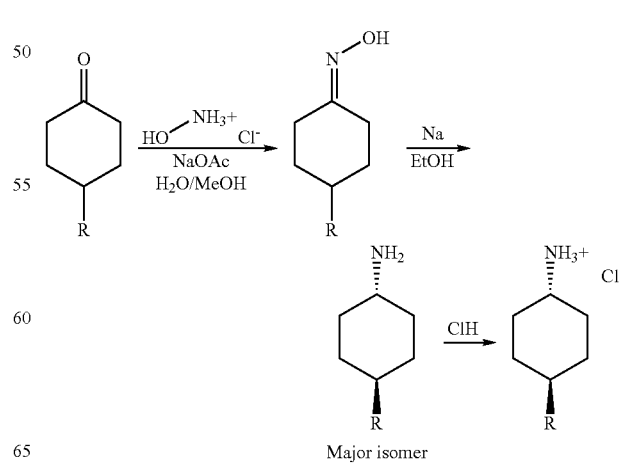

A 4-substituted cyclohexanone (wherein R is a radical defined according to the invention) can be converted to the corresponding oxime upon treatment with hydroxylamine hydrochloride and a suitable base such as sodium acetate in a solvent mixture such as water/MeOH at elevated temperature. Reduction of the oxime using sodium in ethanol at elevated temperatures affords the trans-4-alkyl/aryl-cyclohexylamine as the major isomer, which, if necessary can be purified by recrystallisation of the corresponding HCl salt.

General Procedure (G)

Preparation of alkyl-(trans-4-alkyl-cyclohexyl)-amine and the Like

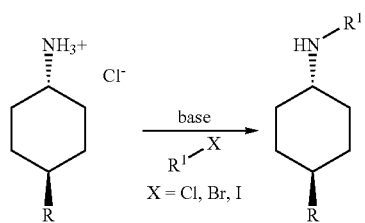

To a mixture of a 4-trans-substituted cyclohexylamine (wherein R is a radical defined according to the invention), hydrochloride in DMF, NMP, MeCN or a similar solvent was added potassium carbonate, NaOH or an equivalent of such a base. The alkyl halide (wherein $R^1$ is defined according to the invention) was added and the reaction mixture was heated until completion of the reaction. The crude product can be used as such for subsequent reactions or alternatively it can be purified before further reactions.

General Procedure (H)

Preparation of 2-Amino-thiazole-5-sulfonic acid amides

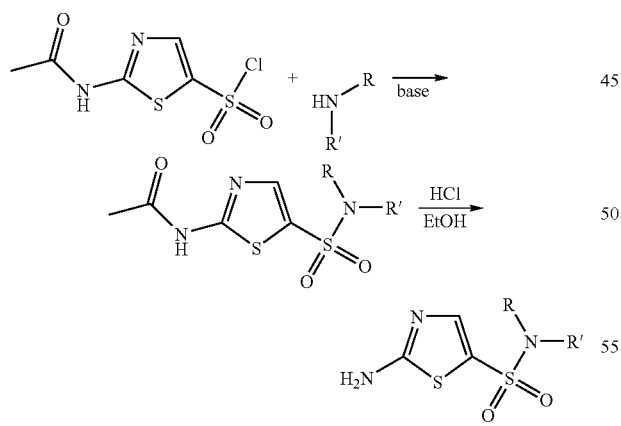

A mixture of an amine, protected amino acid or the like (wherein R and R' are radicals defined according to the invention) is reacted with 2-acetylamino-thiazole-5-sulfonyl chloride prepared as described in *J. Am. Chem. Soc*, 1947, 69, 2063) in the presence of a base such as DIPEA in DCM. N-Deacetylation of the intermediate can be achieved upon heating in the presence of HCl in dioxane/EtOH to give the required sulfonamido-2-aminothiazole.

General Procedure (I)

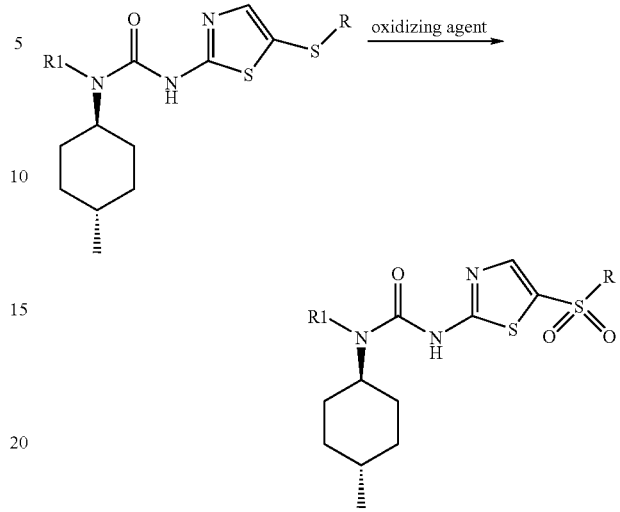

5-Thiosubstituted aminothiazole-urea derivatives can be oxidized with an oxidizing agent such as m-chloroperbenzoic acid in DCM, with oxone and montmorillonite in water/DCM or with hydrogenperoxide in AcOH (*J. Org. Chem.* 1965, 2688-2691) to give the corresponding sulfonyl derivatives.

General Procedure (J)

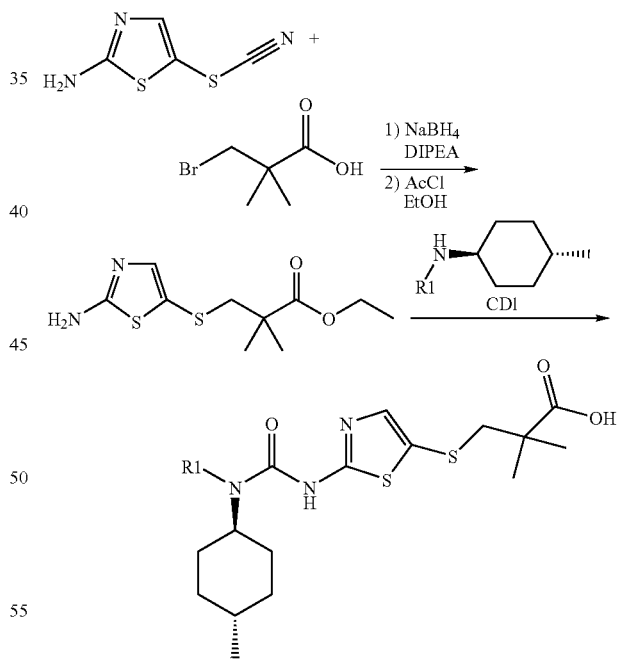

3-(2-Amino-thiazol-5-ylsulfanyl)-2,2-dimethyl-propionic acid ethyl ester can be prepared from 5-thiocyanato-thiazol-2-ylamine by treatment with sodium borohydride in MeOH followed by addition of 3-bromo-2,2-dimethyl-propionic acid. After aqueous work up the intermediate acid can be treated with HCl in EtOH to give the 3-(2-amino-thiazol-5-ylsulfanyl)-2,2-dimethylpropionic acid ethyl ester.

The aminothiazole ester can be coupled to the final urea derivative following the general procedure (A).

General Procedure (K)

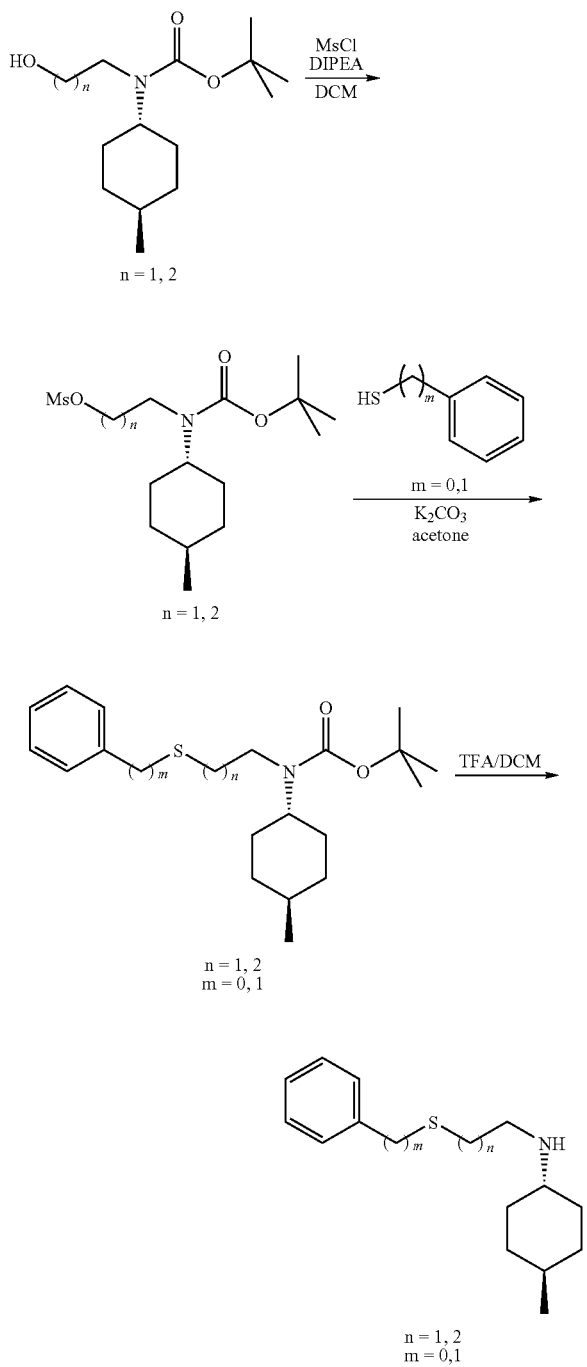

The hydroxypropyl- and hydroxyethyl derivatives, prepared as described in the synthesis of {2-[3-[2-(4-fluoro-2-trifluoromethyl-benzyloxy)-ethyl]-3-(4-trans-methyl-cyclohexyl)-ureido]-thiazol-5-ylsulfanyl}-acetic acid and {2-[3-(4-trans-methyl-cyclohexyl)-3-(3-o-tolyloxy-propyl)-ureido]-thiazol-5-ylsulfanyl}-acetic acid, can be treated with mesyl chloride and DIPEA in DCM to obtain the corresponding mesylate. This can be treated with a thiol like thiophenol og phenyl-methanethiol in acetone using potassium carbonate as base. After removal of the Boc group the secondary amine can be coupled and hydrolysed using the methods described in general procedure (A) to give the final urea thiazole.

Example 1

[2-(3-Cyclohexyl-3-phenethyl-ureido)-thiazol-5-ylsulfanyl]-acetic acid (General Procedure (A) and (B))

(Reductive Amination:

Preparation of Cyclohexyl Phenetylamine.

Phenethylamine (121 mg, 1.0 mmol) in a 2:1 mixture of THF-MeOH (2 mL) was added cyclohexanone (98 mg, 1.0 mmol) and molecular sieves (4 Å, 80 mg). The reaction mixture was shaken for 1 h before NaBH$_3$CN (126 mg, 2.0 mmol) was added. The reaction mixture was shaken for 24 h before it was filtered and the filtrate was concentrated in vacuo to give the intermediate cyclohexyl phenetylamine.

Coupling:

Preparation of: (2-aminothiazol-5-ylsulfanyl)acetic acid ethyl ester

5-Bromo-2-aminothiazole (25 g, 96 mmol) and K$_2$CO$_3$ (26.5 g, 192 mmol) was suspended in DMF (50 mL) and stirred to 0° C. Ethyl thioglycolate (11.6 mL, 96 mmol) was added during 10 min. The reaction mixture was allowed to reach room temperature and stirred for further 16 h. Addition of water (100 mL) and EtOAc (150 mL). Separation of the organic phase followed by extraction of the aqueous phase with EtOAc (2×100 mL). The combined organic phases were washed with aqueous NaHCO3 (2000 mL), brine (2×200 mL) and dried (MgSO4), filtered and evaporated. The crude product was dissolved in a small amount of DCM and purified by flash chromatography (ISCO 330 g silica column, eluent A: heptane/B: 2% TEA in EtOAc. Gradient from 30% B->100% B.) to give 50-65% pure (2-aminothiazol-5-ylsulfanyl)acetic acid ethyl ester as a dark red-brown oil.

$^1$H NMR (CDCl$_3$): δ 7.16 (s, 1H), 5.45 (bs, 2H), 4.26 (q, 2H), 3.39 (s, 2H), 1.28 (t, 3H).

2-Amino-thiazol-5-ylsulfanyl)-acetic acid ethyl ester (218 mg, 1.0 mmol) in DCM (2 mL) was added in sequence CDI (162 mg, 1.0 mmol), DMAP (6 mg, 0.05 mmol) and DIPEA (129 mg, 1.0 mmol) and the mixture was stirred for 1 h before it was added to the intermediate cyclohexyl phenethylamine. The reaction mixture was stirred for 16 h before the volatiles were removed in vacuo.

Hydrolysis:

MeOH (1 mL) was added followed by NaOH (0.50 mL 10 N, 5 mmol) and shaken for 16 h before the mixture was quenched with AcOH (0.286 mL, 5 mmol), whereupon MeOH (0.5 mL) and DMSO (0.5 mL) was added. The mixture was purified on preparative HPLC to give 120 mg (29%) of [2-(3-cyclohexyl-3-phenethyl-ureido)-thiazol-5-ylsulfanyl]-acetic acid.

¹H NMR (400 MHz, DMSO-d₆) δ 7.42 (s, 1H), 7.35-7.25 (m, 4H), 7.24-7.19 (m, 1H), 4.10-3.95 (m, 1H), 3.5 (s, 2H), 3.45-3.35 (m, 2H), 2.85-2.75 (m, 2H), 1.80-1.70 (m, 2H), 1.65-1.40 (m, 5H), 1.40-1.25 (m, 2H), 1.18-1.05 (m, 1H).

HPLC-MS: m/z=420 (M+1), $R_t$=2.1 min

Example 2

[2-(3-Butyl-3-cyclohexyl-ureido)-thiazol-5-ylsulfanyl]-acetic acid

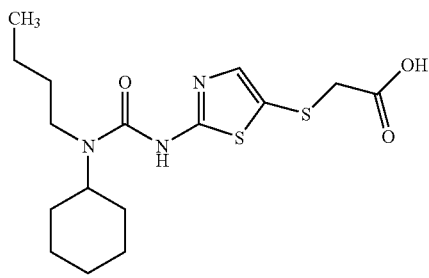

Prepared as described for the synthesis of [2-(3-cyclohexyl-3-phenethyl-ureido)-thiazol-5-ylsulfanyl]-acetic acid, from n-butylamine, cyclohexanone and 2-amino-thiazol-5-ylsulfanyl)-acetic acid ethyl ester.

¹H NMR (400 MHz, DMSO-d₆) δ 7.42 (s, 1H), 4.02-3.90 (m, 1H), 3.49 (s, 2H), 3.25-3.15 (m, 2H), 1.8-1.0 (m, 14H), 0.89 (t, 3H).

HPLC-MS: m/z=372, $R_t$=2.0 min

Example 3

{2-[3-Cyclohexyl-3-(3-methyl-butyl)-ureido]-thiazol-5-ylsulfanyl}-acetic acid

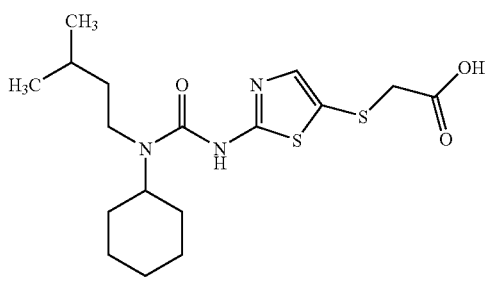

Prepared as described for the synthesis of [2-(3-cyclohexyl-3-phenethyl-ureido)-thiazol-5-ylsulfanyl]-acetic acid, from 3-methyl-butylamine, cyclohexanone and 2-amino-thiazol-5-ylsulfanyl)-acetic acid ethyl ester.

¹H NMR (400 MHz, DMSO-d₆) δ 7.40 (s, 1H), 4.02-3.90 (m, 1H), 3.49 (s, 2H), 3.28-3.18 (m, 2H), 1.80-1.00 (m, 13H), 0.90 (d, 6H).

HPLC-MS: m/z=386, $R_t$=2.1 min

Example 4

{2-[3-Cyclohexyl-3-(2,2-dimethyl-propyl)-ureido]-thiazol-5-ylsulfanyl}-acetic acid

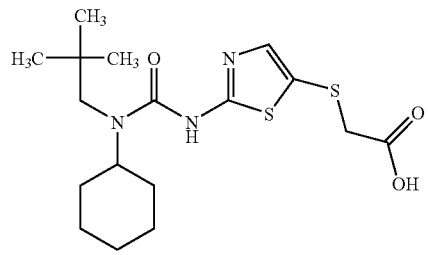

Prepared as described for the synthesis of [2-(3-cyclohexyl-3-phenethyl-ureido)-thiazol-5-ylsulfanyl]-acetic acid, from 3,3-dimethyl-propylamine, cyclohexanone and 2-amino-thiazol-5-ylsulfanyl)-acetic acid ethyl ester.

¹H NMR (400 MHz, DMSO-d₆) δ 7.40 (s, 1H), 3.49 (s, 2H), 3.19 (s, 2H), 2.08-1.85 (m, 2H), 1.80-1.62 (m, 4H), 1.61-1.52 (m, 1H), 1.30-1.00 (m, 3H), 0.91 (s, 9H).

HPLC-MS: m/z=386, $R_t$=2.1 min

Example 5

{2-[3-(2-Cyclohex-1-enyl-ethyl)-3-cyclohexyl-ureido]-thiazol-5-ylsulfanyl}-acetic acid

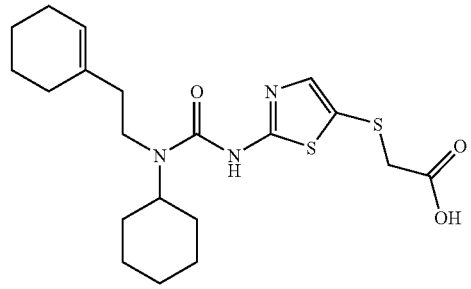

Prepared as described for the synthesis of [2-(3-cyclohexyl-3-phenethyl-ureido)-thiazol-5-ylsulfanyl]-acetic acid, from 2-(1-cyclohexenyl)-ethylamine, cyclohexanone and 2-amino-thiazol-5-ylsulfanyl)-acetic acid ethyl ester.

¹H NMR (400 MHz, DMSO-d₆) δ 7.41 (s, 1H), 4.42 (bs, 1H), 4.0-3.9 (m, 1H), 3.48 (s, 2H), 3.38-3.22 (m, 2H), 2.15-2.05 (m, 2H), 2.0-1.9 (m, 4H), 1.80-1.00 (m, 12H)

HPLC-MS: m/z=424, $R_t$=2.3 min

Example 6

[2-(3-Bicyclo[2.2.1]hept-2-ylmethyl-3-cyclohexyl-ureido)-thiazol-5-ylsulfanyl]-acetic acid

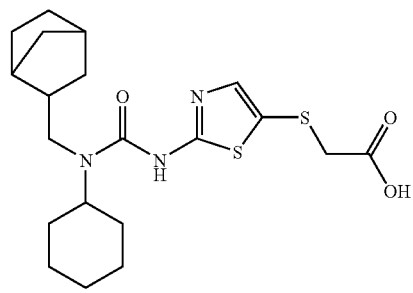

Prepared as described for the synthesis of [2-(3-cyclohexyl-3-phenethyl-ureido)-thiazol-5-ylsulfanyl]-acetic acid, from c-bicyclo[2.2.1]hept-2-yl-methylamine, cyclohexanone and 2-amino-thiazol-5-ylsulfanyl)-acetic acid ethyl ester.

$^1$H NMR (400 MHz, DMSO-d$_6$) δ 7.40 (s, 1H), 3.9-3.7 (m, 1H), 3.49 (s, 2H), 3.40-3.25 (d, 2H), 2.20-1.95 (m, 3H), 1.80-0.70 (m, 20H).

HPLC-MS: m/z=424, R$_t$=2.3 min

Example 7

[2-(3-Bicyclo[2.2.1]hept-5-en-2-ylmethyl-3-cyclohexyl-ureido)-thiazol-5-ylsulfanyl]-acetic acid

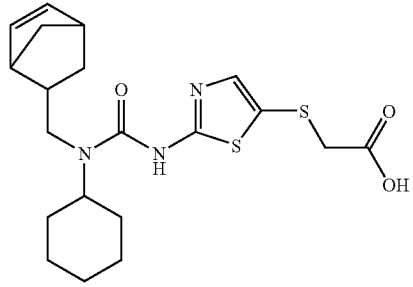

Prepared as described for the synthesis of [2-(3-cyclohexyl-3-phenethyl-ureido)-thiazol-5-ylsulfanyl]-acetic acid, from c-bicyclo[2.2.1]hept-5-en-2-yl-methylamine, cyclohexanone and 2-amino-thiazol-5-ylsulfanyl)-acetic acid ethyl ester.

$^1$H NMR (400 MHz, DMSO-d$_6$) (mixture of two isomers) δ 7.40 (s, 1H), 6.24-6.19 (m, 0.7H), 6.10-6.03 (m, 1.3H), 3.95-3.70 (m, 1H), 3.48 (s, 2H), 3.10-2.88 (m, 2H), 2.80-2.70 (m, 2H), 2.35-2.25 (m, 1H), 1.87-1.00 (m, 11.3H), 0.65-0.55 (m, 0.7H)

HPLC-MS: m/z=422, R$_t$=2.2 min

Example 8

{2-[3-Cyclohexyl-3-(2-cyclohexyl-ethyl)-ureido]-thiazol-5-ylsulfanyl}-acetic acid

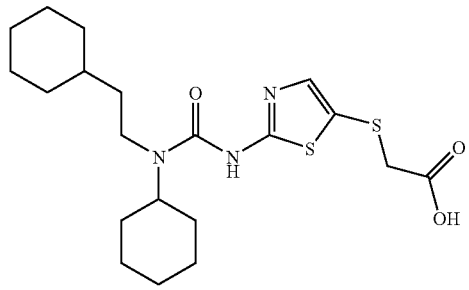

Prepared as described for the synthesis of [2-(3-cyclohexyl-3-phenethyl-ureido)-thiazol-5-ylsulfanyl]-acetic acid, from 2-cyclohexylethylamine, cyclohexanone and 2-amino-thiazol-5-ylsulfanyl)-acetic acid ethyl ester.

HPLC-MS: m/z=426 R$_t$=2.4 min

Example 9

3-[2-(3-Cyclohexyl-3-phenethyl-ureido)-thiazol-5-ylsulfanyl]-propionic acid

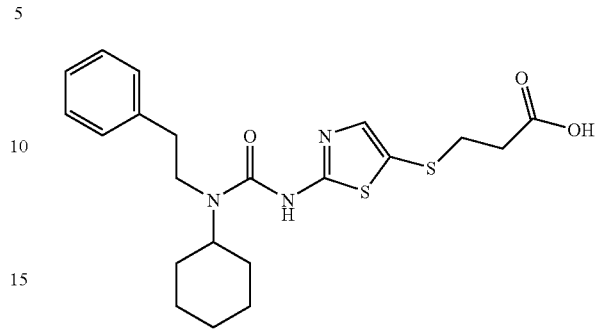

Preparation of 3-(2-amino-thiazol-5-ylsulfanyl)-propionic acid ethyl ester

5-Bromo-2-aminothiazole (25 g, 96 mmol) in DMF (150 mL) was added K$_2$CO$_3$ (26.5 g, 192 mmol) and the mixture was purged with N$_2$ for 5 min. The mixture was cooled to 0° C. on an ice bath before 3-mercaptopropionic acid ethyl ester (12.9 g, 96 mmol) was added dropwise over the course of 30 min. The reaction mixture was stirred for 16 hours before water (400 mL) was added. The aqueous mixture was extracted with Et$_2$O (1×500 mL, 2×250 mL). The combined organic phases was washed with saturated NH$_4$Cl (3×150 mL), dried (MgSO$_4$). The solvent was removed in vacuo to give a dark residue which was purified by column chromatography (SiO$_2$, EtOAc-heptane (1:1)). The solvent was removed in vacuo to give 11 g (49%) of the desired compound.

$^1$H NMR (400 MHz, CDCl$_3$) δ 7.1 (s, 1H), 5.2 (bs, 2H), 4.2 (q, 2H), 2.8 (t, 2H), 2.6 (t, 2H), 1.3 (t, 3H).

3-[2-(3-Cyclohexyl-3-phenethyl-ureido)-thiazol-5-ylsulfanyl]-propionic acid was prepared as described for the synthesis of [2-(3-cyclohexyl-3-phenethyl-ureido)-thiazol-5-ylsulfanyl]-acetic acid, from 2-phenethylamine, cyclohexanone and 2-amino-thiazol-5-ylsulfanyl)-propionic acid ethyl ester.

$^1$H NMR (400 MHz, DMSO-d$_6$) δ 7.41 (s, 1H), 7.45-7.15 (m, 5H), 4.10-3.95 (m, 1H), 3.50-3.40 (m, 2H), 2.87 (t, 2H), 2.78 (m, 2H), 2.5 (t, 2H), 1.8-1.0 (m, 10H)

HPLC-MS: m/z=386, R$_t$=2.1 min

Example 10

3-[2-(3-Butyl-3-cyclohexyl-ureido)-thiazol-5-ylsulfanyl]-propionic acid

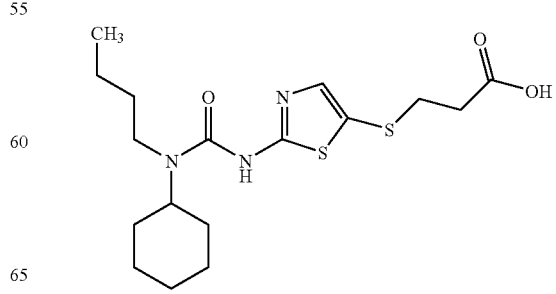

Prepared as described for the synthesis of [2-(3-cyclohexyl-3-phenethyl-ureido)-thiazol-5-ylsulfanyl]-acetic acid, from n-butylamine, cyclohexanone and 2-amino-thiazol-5-ylsulfanyl)-propionic acid ethyl ester.

$^1$H NMR (400 MHz, DMSO-d$_6$) δ 7.40 (s, 1H), 4.05-3.90 (m, 1H), 3.2 (t, 2H), 2.83 (t, 2H), 2.50 (t, 2H), 1.80-1.00 (m, 14H), 0.89 (t, 3H)

HPLC-MS: m/z=434, R$_t$=2.2 min

Example 11

3-{2-[3-Cyclohexyl-3-(3-methyl-butyl)-ureido]-thiazol-5-ylsulfanyl}-propionic acid

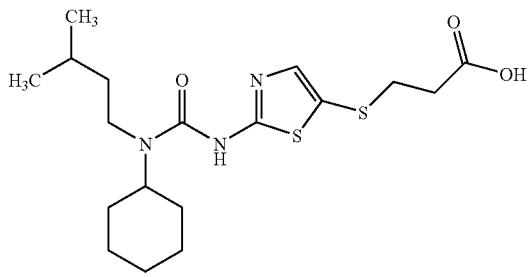

Prepared as described for the synthesis of [2-(3-cyclohexyl-3-phenethyl-ureido)-thiazol-5-ylsulfanyl]-acetic acid, from 3-methylbutylamine, cyclohexanone and 2-amino-thiazol-5-ylsulfanyl)-propionic acid ethyl ester.

$^1$H NMR (400 MHz, DMSO-d$_6$) δ 7.40 (s, 1H), 4.04-3.92 (m, 1H), 3.28-3.18 (m, 2H), 2.83 (t, 2H), 2.50 (t, 2H), 1.80-1.00 (m, 13H), 0.90 (d, 6H)

HPLC-MS: m/z=400, R$_t$=2.2 min

Example 12

3-{2-[3-(trans-4-Methyl-cyclohexyl)-3-phenethyl-ureido]-thiazol-5-ylsulfanyl}-propionic acid

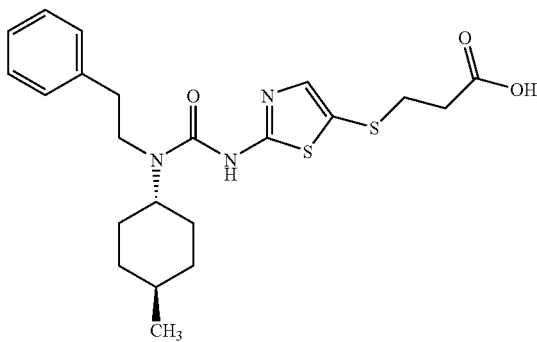

Prepared as described for the synthesis of [2-(3-cyclohexyl-3-phenethyl-ureido)-thiazol-5-ylsulfanyl]-acetic acid, from phenyl acetaldehyde, trans-4-methylcyclohexylamine hydrochloride (prepared via the methode described in *J. Med. Chem.* 1971, vol 14, p. 610) and 2-amino-thiazol-5-ylsulfanyl)-propionic acid ethyl ester. The hydrochloride was added one equivalent DIPEA prior to the reaction.

$^1$H NMR (400 MHz, DMSO-d$_6$) δ 7.42 (s, 1H), 7.35-7.25 (m, 5H), 4.08-3.92 (m, 1H), 3.50-3.35 (m, 2H), 2.87 (t, 2H), 2.82-2.72 (m, 2H), 1.80-0.95 (m, 9H), 0.88 (d, 3H).

HPLC-MS: m/z=448, R$_t$=2.3 min

Example 13

3-{2-[3-Butyl-3-(trans-4-methyl-cyclohexyl)-ureido]-thiazol-5-ylsulfanyl}-propionic acid

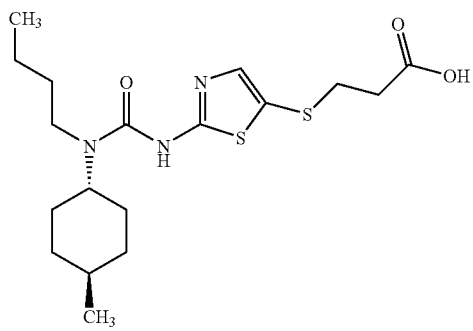

Prepared as described for the synthesis of [2-(3-cyclohexyl-3-phenethyl-ureido)-thiazol-5-ylsulfanyl]-acetic acid, from butyraldehyde, trans-4-methylcyclohexylamine hydrochloride and 2-amino-thiazol-5-ylsulfanyl)-propionic acid ethyl ester. The hydrochloride was added one equivalent DIPEA prior to the reaction.

$^1$H NMR (400 MHz, DMSO-d$_6$) δ 7.40 (s, 1H), 4.02-3.90 (m, 2H), 3.25-3.15 (m, 2H), 2.83 (t, 2H), 2.50 (t, 2H), 1.75-0.95 (m, 13H), 0.92-0.82 (m, 6H)

HPLC-MS: m/z=400, R$_t$=2.3 min

Example 14

3-{2-[3-(3-Methyl-butyl)-3-(trans-4-methyl-cyclohexyl)-ureido]-thiazol-5-ylsulfanyl}-propionic acid

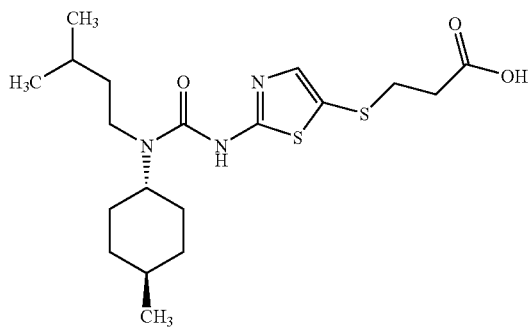

Prepared as described for the synthesis of [2-(3-cyclohexyl-3-phenethyl-ureido)-thiazol-5-ylsulfanyl]-acetic acid, from isovaleraldehyde, trans-4-methylcyclohexylamine hydrochloride and 2-amino-thiazol-5-ylsulfanyl)-propionic acid ethyl ester. The hydrochloride was added one equivalent DIPEA prior to the reaction.

$^1$H NMR (400 MHz, CDCl$_3$) δ 11.2 (bs, 1H), 7.28 (s, 1H), 3.25 (m, 2H), 3.00 (m, 2H), 2.75 (m, 2H), 2.00-1.00 (m, 13H), 0.95-0.87 (m, 9H).

HPLC-MS: m/z=414, R$_t$=2.4 min

Example 15

3-{2-[3-(2-Cyclohex-1-enyl-ethyl)-3-cyclohexyl-ureido]-thiazol-5-ylsulfanyl}-propionic acid

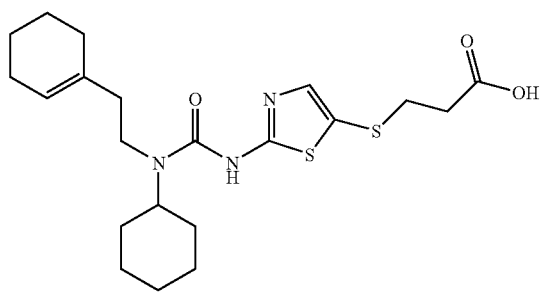

Prepared as described for the synthesis of [2-(3-cyclohexyl-3-phenethyl-ureido)-thiazol-5-ylsulfanyl]-acetic acid, from 2-(1-cyclohexenyl)ethylamine hydrochloride, cyclohexanone and 2-amino-thiazol-5-ylsulfanyl)-propionic acid ethyl ester. The hydrochloride was added one equivalent DIPEA prior to the reaction.

HPLC-MS: m/z=439, $R_t$=2.5 min

Example 16

{2-[3-(3-Methyl-butyl)-3-(trans-4-methyl-cyclohexyl)-ureido]-thiazol-5-ylsulfanyl}-acetic acid

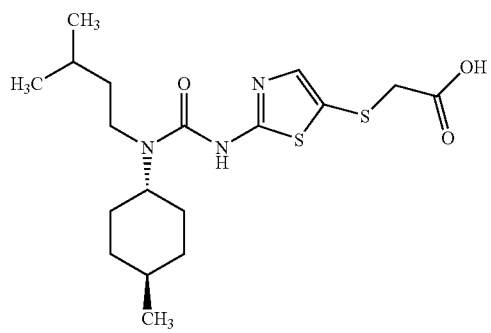

Prepared as described for the synthesis of [2-(3-cyclohexyl-3-phenethyl-ureido)-thiazol-5-ylsulfanyl]-acetic acid, from 4-trans-methyl-cyclohexylamine hydrochloride, isovaleraldehyde and 2-amino-thiazol-5-ylsulfanyl)-acetic acid ethyl ester. The hydrochloride was added one equivalent DIPEA prior to the reaction.

$^1$H NMR (400 MHz, DMSO-$d_6$) δ 7.40 (s, 1H), 4.00-3.95 (m, 1H), 3.48 (s, 2H), 3.25-3.18 (m, 2H), 1.73-1.65 (m, 2H), 1.65-1.44 (m, 5H), 1.40-1.25 (m, 3H), 1.14-1.00 (m, 2H), 0.92-0.84 (m, 9H).

HPLC-MS: m/z=435, $R_t$=2.3 min

Example 17

{2-[3-(trans-4-Methyl-cyclohexyl)-3-phenethyl-ureido]-thiazol-5-ylsulfanyl}-acetic acid

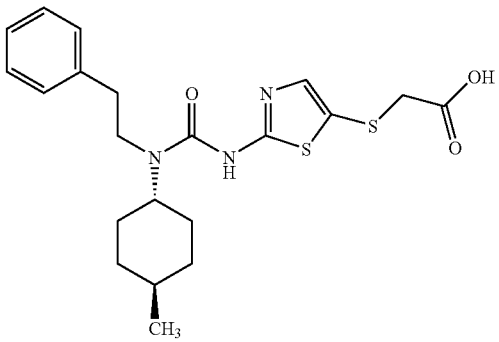

Prepared as described for the synthesis of [2-(3-cyclohexyl-3-phenethyl-ureido)-thiazol-5-ylsulfanyl]-acetic acid, from 4-trans-methyl-cyclohexylamine hydrochloride, phenylacetaldehyde and 2-amino-thiazol-5-ylsulfanyl)-acetic acid ethyl ester. The hydrochloride was added one equivalent DIPEA prior to the reaction.

$^1$H NMR (400 MHz, DMSO-$d_6$) δ 12 (bs, 1H), 7.42 (s, 1H), 7.35-7.25 (m, 4H), 7.23-7.18 (m, 1H), 4.05-3.95 (m, 1H), 3.50 (s, 2H), 3.45-3.35 (m, 2H), 2.82-2.75 (m, 2H), 1.72-1.65 (m, 2H), 1.62-1.50 (m, 4H), 1.40-1.30 (1H), 1.12-1.00 (m, 2H), 0.87 (d, 3H)

HPLC-MS: m/z=400, $R_t$=2.3 min

Example 18

{2-[3-(2-Cyclohex-1-enyl-ethyl)-3-(trans-4-methyl-cyclohexyl)-ureido]-thiazol-5-ylsulfanyl}-acetic acid

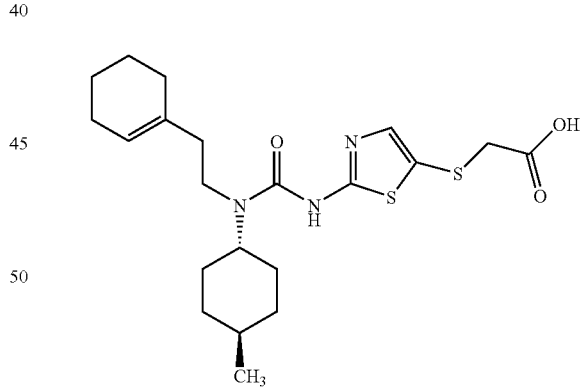

Prepared as described for the synthesis of [2-(3-cyclohexyl-3-phenethyl-ureido)-thiazol-5-ylsulfanyl]-acetic acid, from 4-trans-methyl-cyclohexylamine hydrochloride, cyclohexen-1-yl-acetaldehyde (Prepared according to the procedure given in Oppolzer, W. et al. Tetrahedron, 1985, 41, 17, 3497-3509) and 2-amino-thiazol-5-ylsulfanyl)-acetic acid ethyl ester. The hydrochloride was added one equivalent DIPEA prior to the reaction.

$^1$H NMR (400 MHz, DMSO-$d_6$) δ 12.5 (bs, 1H), 7.40 (s, 1H), 5.42 (s, 1H), 3.48 (s, 2H), 2.12-2.05 (m, 2H), 1.98-1.92 (m, 4H), 1.72-1.65 (m, 2H), 1.64-1.45 (m, 9H), 1.40-1.25 (m, 2H), 1.15-1.00 (m, 2H), 0.88 (d, 3H).

HPLC-MS: m/z=438, $R_t$=2.4 min

Example 19

{2-[3-(3-Methyl-but-2-enyl)-3-(trans-4-methyl-cyclohexyl)-ureido]-thiazol-5-ylsulfanyl}-acetic acid

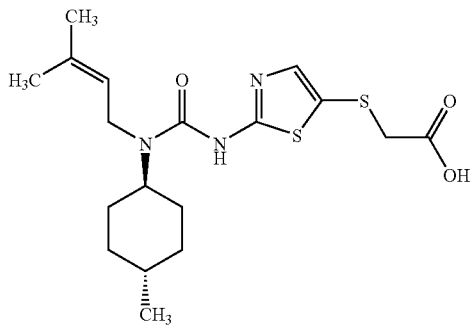

Prepared as described for the synthesis of [2-(3-cyclohexyl-3-phenethyl-ureido)-thiazol-5-ylsulfanyl]-acetic acid, from 4-trans-methyl-cyclohexylamine hydrochloride, 3-methyl-but-2-enal and 2-amino-thiazol-5-ylsulfanyl)-acetic acid ethyl ester. The hydrochloride was added one equivalent DIPEA prior to the reaction.

$^1$H NMR (400 MHz, CDCl$_3$) δ 7.25 (s, 1H), 5.12-5.05 (m, 1H), 4.15-3.95 (m, 1H), 3.92 (d, 2H), 3.32 (s, 2H), 1.80-1.70 (m, 3H), 1.70 (s, 6H), 1.55-1.42 (m, 2H), 1.40-1.24 (m, 2H), 1.20-1.05 (m, 2H), 0.90 (d, 3H).

HPLC-MS: m/z=398, R$_t$=2.1 min

Example 20

3-{2-[3-(3-Methyl-but-2-enyl)-3-(trans-4-methyl-cyclohexyl)-ureido]-thiazol-5-ylsulfanyl}-propionic acid

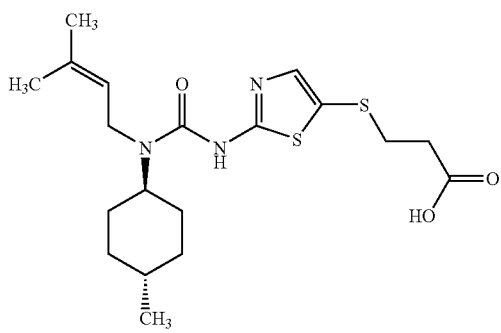

Prepared as described for the synthesis of [2-(3-cyclohexyl-3-phenethyl-ureido)-thiazol-5-ylsulfanyl]-acetic acid, from 4-trans-methyl-cyclohexylamine hydrochloride, 3-methyl-but-2-enal and 2-amino-thiazol-5-ylsulfanyl)-propionic acid ethyl ester. The hydrochloride was added one equivalent DIPEA prior to the reaction.

$^1$H NMR (400 MHz, CDCl$_3$) δ 7.25 (s, 1H), 5.15-5.05 (m, 1H), 3.92 (d, 2H), 3.05-2.95 (m, 2H), 2.75-2.68 (t, 2H), 1.90-1.80 (m, 2H), 1.80-1.70 (m, 2H), 1.70 (s, 3H), 1.68 (s, 3H) 1.60-1.40 (m, 3H), 1.40-1.20 (m, 3H), 0.91 (d, 3H).

HPLC-MS: m/z=412, R$_t$=2.2 min

Example 21

{2-[3-(4-trans-Ethyl-cyclohexyl)-3-(3-methyl-butyl)-ureido]-thiazol-5-ylsulfanyl}-acetic acid (General Procedure (F), (G), (B) and (A, Step 2))

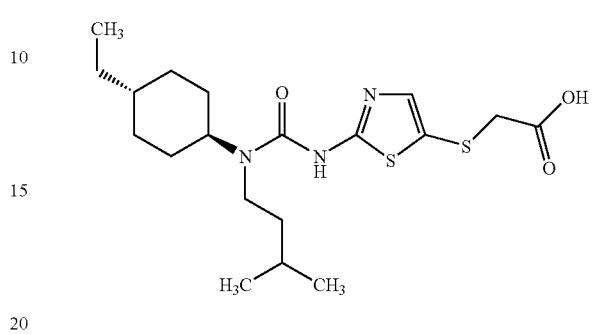

Preparation of trans-4-alkyl-cyclohexylamines

Sodium (45 g, 1.96 mol) was slowly added to a solution of 4-ethylcyclohexanone oxime (33 g, 0.23 mol) (prepared according to lift. R. O. Hutchins et al. J. Org. Chem. 60 (1995) 7396-7405)) in 99.9% ethanol (500 mL) while keeping the temperature below 65° C. The reaction mixture was heated at reflux temperature for 1½ h and then stirred at room temperature for further 16 h. A mixture of water (500 mL) and ethanol (100 mL) was added and the mixture was extracted with diethyl ether (3×250 mL). The combined organic phases was washed with brine (150 mL), dried over anhydrous magnesium sulphate and evaporated to dryness. The residue was dissolved in ethanol (100 mL), pH was adjusted to approx. 3 with 4 N hydrochloric acid (60 mL) and the solution was evaporated to dryness in vacuo to give crude ethylcyclohexylamine. The product was purified by recrystallization from ethanol/acetonitrile (4:1) to give 4-trans-ethylcyclohexylamine, hydrochloride as white crystals.

Preparation of alkyl-(trans-4-alkyl-cyclohexyl)-amine

To a mixture of 4-trans-ethylcyclohexylamine, hydrochloride (1.5 g, 9.2 mmol), dry DMF (40 mL), and potassium carbonate (3.75 g, 27.2 mmol) was added 1-bromo-3-methylbutane (1.125 mL, 9.4 mmol). The mixture was heated at 55° C. for 24 h, filtered, and evaporated to dryness in vacuo after adjusting the pH to 3-4 by adding hydrogen chloride in diethyl ether. The crude product of (4-trans-ethylcyclohexyl)-(3-methylbutyl)-amine, hydrochloride was used in the next step without further purification.

Coupling:

To a solution of (2-amino-thiazol-5-ylsulfanyl)-acetic acid ethyl ester (200 mg, 0.92 mmol) in dry THF (2 mL) was added CDI (152 mg, 0.92 mmol) and DMAP (50 mg, 0.046 mmol). The mixture was stirred at room temperature for 1½ h after which 4-trans-ethylcyclohexylamine, hydrochloride (220 mg, 0.94 mmol) in THF (3 mL) and DIPEA (0.83 mL, 4.77 mmol) were added. Stirring was continued overnight at room temperature. The reaction mixture was evaporated to dryness in vacuo and purified on silica gel (gradient, from heptane: ethyl acetate (9:1) to heptane:ethyl acetate (4:6)) to give 86 mg (yield: 21%) of ethyl {2-[3-(4-trans-ethylcyclohexyl)-3-(3-methyl-butyl)-ureido]-thiazol-5-ylsulfanyl}-acetate.

Hydrolysis:

To a solution of ethyl {2-[3-(4-trans-ethylcyclohexyl)-3-(3-methyl-butyl)-ureido]-thiazol-5-ylsulfanyl}-acetate (86 mg, 0.195 mmol) in dioxan (1 mL) was added 1 N sodium hydroxide (0.75 mL). The mixture was stirred for 4 h at room temperature. 2 N hydrochloric acid (0.38 mL) was added and the mixture was evaporated partly in vacuo to remove dioxan The residue was stirred with water and dried in vacuo to give the title compound as white crystals $^1$H NMR (400 MHz, CDCl$_3$) δ 7.26 (s, 1H), 3.33 (s, 2H), 3.29-3.20 (m, 2H), 1.85-1.75 (m, 4H), 1.70-1.60 (m, 1H), 1.55-1.40 (m, 4H), 1.30-1.20 (m, 3H), 1.18-1.05 (m, 3H), 0.93 (d, 6H), 0.89 (t, 3H)

HPLC-MS: m/z=415, R$_t$=2.4 min

Example 22

{2-[3-(4-trans-Ethyl-cyclohexyl)-3-phenethyl-ureido]-thiazol-5-ylsulfanyl}-acetic acid

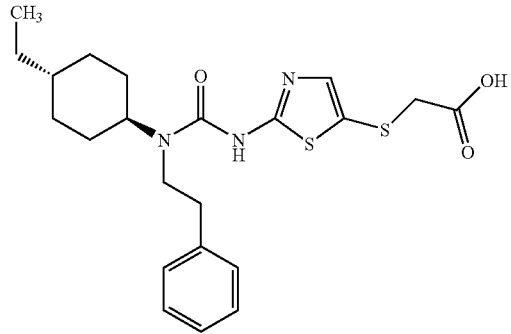

Prepared as described for the synthesis of {2-[3-(4-trans-ethyl-cyclohexyl)-3-(3-methyl-butyl)-ureido]-thiazol-5-yl-sulfanyl}-acetic acid, from 4-trans-ethyl-cyclohexylamine hydrochloride, 2-phenethyl bromide and (2-amino-thiazol-5-ylsulfanyl)-acetic acid ethyl ester.

$^1$H NMR (400 MHz, CDCl$_3$) δ 7.32-7.20 (m, 6H), 3.51 (m, 2H), 3.32 (s, 2H), 2.90 (m, 2H), 1.83 (m, 4H), 1.57-1.49 (m, 2H), 1.25 (m, 3H), 1.12 (m, 3H), 0.89 (t, 3H

HPLC-MS: m/z=448, R$_t$=2.4 min

Example 23

{2-[3-(2-Cyclohexyl-ethyl)-3-(4-trans-ethyl-cyclohexyl)-ureido]-thiazol-5-ylsulfanyl}-acetic acid

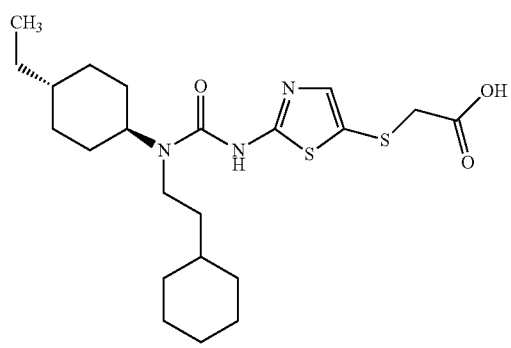

Prepared as described for the synthesis of {2-[3-(4-trans-ethyl-cyclohexyl)-3-(3-methyl-butyl)-ureido]-thiazol-5-yl-sulfanyl}-acetic acid, from 4-trans-ethyl-cyclohexylamine hydrochloride, 2-cyclohexylethyl bromide and (2-amino-thiazol-5-ylsulfanyl)-acetic acid ethyl ester.

$^1$H NMR (400 MHz, CDCl$_3$) δ 7.26 (s, 1H), 3.32 (s, 2H), 3.28 (m, 2H), 1.84-1.64 (m, 10H), 1.47 (m, 4H), 1.34 (m, 1H), 1.25-1.10 (m, 9H), 0.95 (m, 2H), 0.89 (t, 3H);

HPLC-MS: m/z=455, R$_t$=2.7 min

Example 24

3-{2-[3-(4-trans-Ethyl-cyclohexyl)-3-(3-methyl-butyl)-ureido]-thiazol-5-ylsulfanyl}-propionic acid

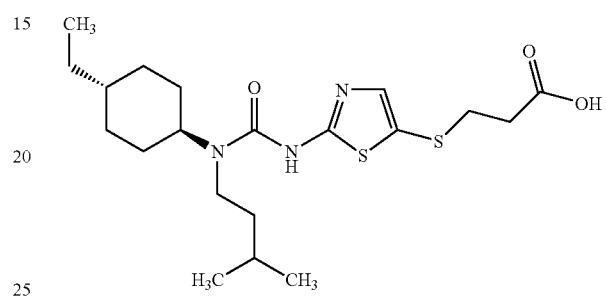

Prepared as described for the synthesis of {2-[3-(4-trans-ethyl-cyclohexyl)-3-(3-methyl-butyl)-ureido]-thiazol-5-yl-sulfanyl}-acetic acid, from 4-trans-ethyl-cyclohexylamine hydrochloride, 1-bromo-3-methylbutane and (2-amino-thiazol-5-ylsulfanyl)-propionic acid ethyl ester.

$^1$H NMR (400 MHz, CDCl$_3$) δ 7.25 (s, 1H), 3.22 (m, 2H), 2.99 (m, 2H), 2.73 (m, 2H), 1.86 (m, 4H), 1.61 (m, 2H), 1.45 (m, 4H), 1.25 (m, 4H), 1.12 (m, 2H), 0.97-0.89 (m, 9H).

HPLC-MS: m/z=429, R$_t$=2.5 min

Example 25

3-{2-[3-(4-trans-Ethyl-cyclohexyl)-3-phenethyl-ureido]-thiazol-5-ylsulfanyl}-propionic acid

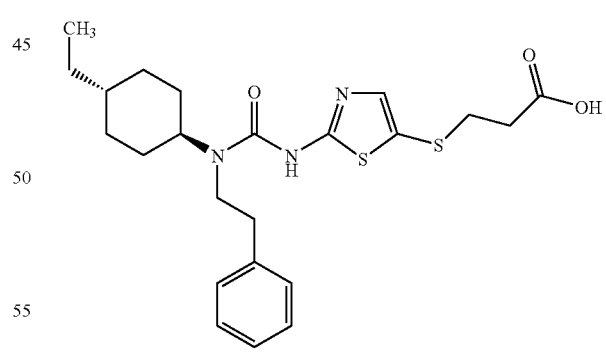

Prepared as described for the synthesis of {2-[3-(4-trans-ethyl-cyclohexyl)-3-(3-methyl-butyl)-ureido]-thiazol-5-yl-sulfanyl}-acetic acid, from 4-trans-ethyl-cyclohexylamine hydrochloride, 2-phenethyl bromide and (2-amino-thiazol-5-ylsulfanyl)-propionic acid ethyl ester.

$^1$H NMR (400 MHz, CDCl$_3$) δ 7.27-7.18 (m, 6H), 3.43 (broad s, 2H), 2.87 (m, 4H), 2.72 (m, 2H), 1.89 (m, 4H), 1.52-1.43 (m, 2H), 1.26-1.09 (m, 5H), 0.88 (m, 3H).

HPLC-MS: m/z=463, R$_t$=2.5 min

Example 26

3-{2-[3-(2-Cyclohexyl-ethyl)-3-(4-trans-ethyl-cyclohexyl)-ureido]-thiazol-5-ylsulfanyl}-propionic acid

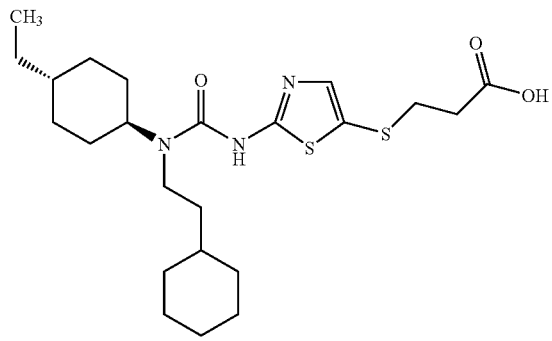

Prepared as described for the synthesis of {2-[3-(4-trans-ethyl-cyclohexyl)-3-(3-methyl-butyl)-ureido]-thiazol-5-ylsulfanyl}-acetic acid, from 4-trans-ethyl-cyclohexylamine hydrochloride, 2-cyclohexylethyl bromide and (2-amino-thiazol-5-ylsulfanyl)-propionic acid ethyl ester.

$^1$H NMR (400 MHz, CDCl$_3$) δ 7.25 (s, 1H), 3.23 (m, 2H), 2.98 (m, 2H), 2.73 (m, 2H), 1.86 (m, 4H), 1.74-1.64 (m, 6H), 1.50-1.42 (m, 4H), 1.28-1.10 (m, 10H), 0.98-0.86 (m, 6H)

HPLC-MS: m/z=469, R$_t$=2.8 min

Example 27

2-{2-[3-(4-trans-Ethyl-cyclohexyl)-3-(3-methyl-butyl)-ureido]-thiazol-5-ylsulfanyl}-2-methyl-propionic acid

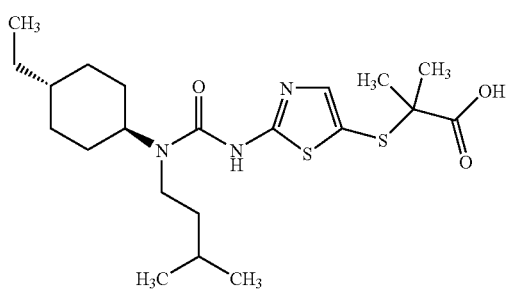

Preparation of 2-(2-amino-thiazol-5-ylsulfanyl)-2-methyl-propionic acid ethyl ester 2-Aminothiazole (35 g, 350 mmol) and sodium thiocyanate (89 g, 1.08 mol) in MeOH (400 mL) was stirred at −10° C. Bromine (18.0 mL, 350 mmol) dissolved in MeOH (100 mL) saturated with NaBr was slowly added keeping the internal temperature between −10 and 0° C. After the addition the mixture was stirred at 0° C. for 3 h and the reaction mixture was poured into ice water (1500 mL). Aqueous NH$_4$OH was added to pH ca 8.5 causing precipitation of light yellow crystals which were isolated by filtration, washed with ice water and dried in a vacuum oven to give 30 g (55%) 5-thiocyanato-thiazol-2-ylamine as light yellow crystals.

Step 2:

In a nitrogen atmosphere 5-thiocyanato-thiazol-2-ylamine (10 g, 64 mmol) dissolved in MeOH (300 mL) was added 2,3-dihydroxy-1,4-dithiolbutane (DTT, 9.8 g, 64 mmol) and stirred at room temperature for 1½ h. Then 2-bromo-2-methyl-propionic acid ethyl ester (13.6 g, 70 mmol) and K$_2$CO$_3$ (10.5 g, 76 mmol) was added and the reaction mixture was stirred for further 16 h. Addition of water (500 mL) and EtOAc (500 mL). Separation of the organic phase followed by extraction of the aqueous phase with EtOAc (2×300 mL). The combined organic phases were washed with water (500 mL) and brine (2×400 mL) and dried (MgSO$_4$), filtered and evaporated.[1] The crude product was dissolved in a small amount of DCM and purified by flash chromatography (heptane/EtOAc 2:1->1:2). Fractions containing the product were pooled and evaporated to a product (ca 14 g) containing impurities of DDT. The crude product was dissolved in diethyl ether (100 mL) and washed with water eight times. The ether phase was dried (MgSO$_4$), filtered and evaporated to give 8.45 g (54%) of 95% pure 2-(2-amino-thiazol-5-ylsulfanyl)-2-methyl-propionic acid ethyl ester as light brown crystals.

[1] As the DTT impurities is not easily removed by flash chromatography it's recommended that the crude product is dissolved in Et2O and subsequently washed with water several times at then purified by flash chromatography.

2-{2-[3-(4-trans-Ethyl-cyclohexyl)-3-(3-methyl-butyl)-ureido]-thiazol-5-ylsulfanyl}-2-methyl-propionic acid was prepared as described for the synthesis of {2-[3-(4-trans-ethyl-cyclohexyl)-3-(3-methyl-butyl)-ureido]-thiazol-5-ylsulfanyl}-acetic acid, from 4-trans-ethyl-cyclohexylamine hydrochloride, 1-bromo-3-methylbutane and 2-(2-amino-thiazol-5-ylsulfanyl)-2-methyl-propionic acid ethyl ester.

$^1$H NMR (400 MHz, CDCl$_3$) δ 7.05 (s, 1H), 3.31 (m, 2H), 1.85 (m, 4H), 1.67 (m, 2H), 1.59 (s, 6H), 1.51 (m, 4H), 1.23 (m, 3H), 1.12 (m, 3H), 0.94 (d, 6H), 0.89 (t, 3H)

HPLC-MS: m/z=442, R$_t$=2.5 min

Example 28

2-{2-[3-(4-trans-Ethyl-cyclohexyl)-3-phenethyl-ureido]-thiazol-5-ylsulfanyl}-2-methyl-propionic acid

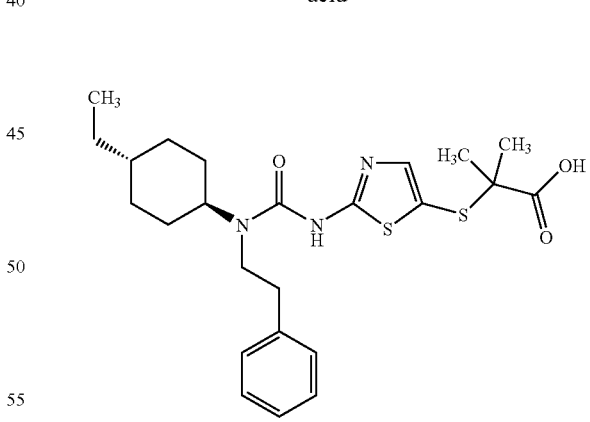

Prepared as described for the synthesis of {2-[3-(4-trans-ethyl-cyclohexyl)-3-(3-methyl-butyl)-ureido]-thiazol-5-ylsulfanyl}-acetic acid, from 4-trans-ethyl-cyclohexylamine hydrochloride, 2-phenethyl bromide and 2-(2-amino-thiazol-5-ylsulfanyl)-2-methyl-propionic acid ethyl ester.

$^1$H NMR (400 MHz, CDCl$_3$) δ 7.31-7.21 (m, 5H), 7.07 (s, 1H), 3.54 (bs, 2H), 2.94 (m, 2H), 1.87 (m, 4H), 1.59 (s, 6H), 1.54 (m, 2H), 1.25-1.20 (m, 4H), 1.13 (broad m, 2H), 0.89 (t, 3H)

HPLC-MS: m/z=477, R$_t$=2.6 min

Example 29

{2-[3-(3-Methyl-butyl)-3-(trans-4-methyl-cyclohexyl)-ureido]-thiazole-5-sulfonylamino}-acetic acid (General Procedure (H) (B) and (A Step 2))

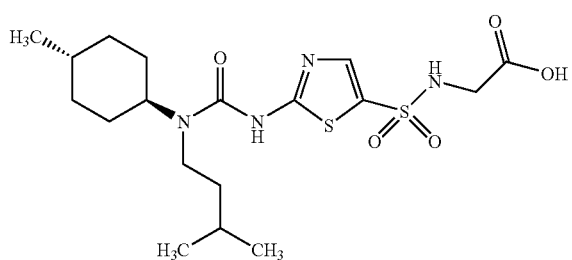

Preparation of 2-Amino-thiazole-5-sulfonic acid amides

Step 1. A mixture of glycine ethylester hydrochloride (15 mmol), 2-acetylamino-thiazole-5-sulfonyl chloride (12 mmol) (prepared as described in *J. Am. Chem. Soc* 69, 2063, 1947), DIPEA (35 mmol) in DCM (50 mL) was stirred at room temperature over night. Addition of water and 1N HCl to pH 2 resulted in precipitation. The precipitate was isolated by filtration, washed with water and dried to give (2-acetylamino-thiazole-5-sulfonylamino)-acetic acid ethyl ester (64%) as crystals. This was suspended in EtOH (15 mL) and added 4N HCl in dioxane (15 mL) and heated for 4 h at 80° C. and then cooled to room temperature. Addition of aqueous NaHCO3 to neutral pH. The organic phase was isolated and the aqueous phase was extracted with $CH_2Cl_2$, and the combined organic phases were dried and concentrated in vacuo to give (2-amino-thiazole-5-sulfonylamino)-acetic acid ethyl ester (80%) as colourless crystals.

Coupling:

An equimolar mixture of 1,1-carbonyldiimidazole, (2-amino-thiazole-5-sulfonylamino)-acetic acid ethyl ester and DMAP (5 mol %) in THF was heated for 5 h at 50-60° C. and then cooled to room temperature. Then (3-methyl-butyl)-(4-methyl-cyclohexyl)-amine (1 equivalent; prepared following the procedure described in the preparation of [2-(3-cyclohexyl-3-phenethyl-ureido)-thiazol-5-ylsulfanyl]-acetic acid) was added and the reaction is stirred overnight at room temperature. The reaction mixture was quenched with water. The organic phase was isolated and the aqueous phase was extracted with $CH_2Cl_2$, and the combined organic phases were dried and concentrated in vacuo. The crude product was dissolved in MeCN and purified using HPLC to give {2-[3-(3-methyl-butyl)-3-(trans-4-methyl-cyclohexyl)-ureido]-thiazole-5-sulfonylamino}-acetic acid ethyl ester as crystals.

Hydrolysis:

{2-[3-(3-methyl-butyl)-3-(trans-4-methyl-cyclohexyl)-ureido]-thiazole-5-sulfonylamino}-acetic acid ethyl ester was dissolved in MeOH and treated with 15 equivalents of 1N NaOH for 2 days at room temperature. MeOH was removed by evaporation. Addition of 1N HCl to pH<1 caused precipitation. The precipitate was isolated by filtration, washed with water and dried to give {2-[3-(3-methyl-butyl)-3-(4-methyl-cyclohexyl)-ureido]-thiazole-5-sulfonylamino}-acetic acid as crystals.

$^1$H NMR (400 MHz, CDCl$_3$+2 dr DMSO) δ 7.80 (s, 1H), 6.68 (br t, 1H), 4.00 (br s, 1H), 3.74 (d, 2H), 3.29-3.23 (m, 2H), 1.80-1.08 (m, 12H), 0.95 (d, 6H), 0.91 (d, 3H).

HPLC-MS: m/z=447, R$_t$=2.13 min

Example 30

3-{2-[3-(3-Methyl-butyl)-3-(trans-4-methyl-cyclohexyl)-ureido]-thiazole-5-sulfonylamino}-propionic acid

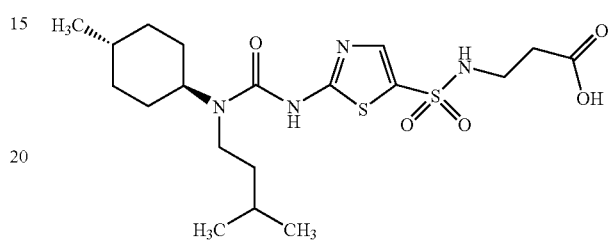

Prepared as described for the preparation of {2-[3-(3-methyl-butyl)-3-(4-methyl-cyclohexyl)-ureido]-thiazole-5-sulfonylamino}-acetic acid using the appropriate amino ester in Step 1.

$^1$H NMR (400 MHz, CDCl$_3$+2dr DMSO) δ 7.80 (s, 1H), 6.38 (br t, 1H), 3.99 (br s, 1H), 3.28-3.21 (m, 4H), 2.55 (t, 2H), 1.80-1.07 (m, 12H), 0.97 (d, 6H), 0.92 (d, 3H).

HPLC-MS: m/z=461, R$_t$=2.13 min

Example 31

(Methyl-{2-[3-(3-methyl-butyl)-3-(trans-4-methyl-cyclohexyl)-ureido]-thiazole-5-sulfonyl}-amino)-acetic acid

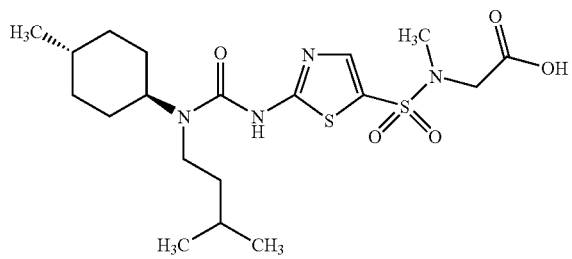

Prepared as described for the preparation of {2-[3-(3-methyl-butyl)-3-(4-methyl-cyclohexyl)-ureido]-thiazole-5-sulfonylamino}-acetic acid using the appropriate amino ester in Step 1.

$^1$H NMR (400 MHz, DMSO) δ 7.89 (s, 1H), 3.97 (br t, 1H), 3.88 (s, 2H), 3.26 (br t, 2H), 2.82 (s, 3H), 1.73-1.01 (m, 12H), 0.90 (d, 6H), 0.88 (d, 3H).

HPLC-MS: m/z=461, R$_t$=2.24 min

Example 32

(S)-1-{2-[3-(3-Methyl-butyl)-3-(trans-4-methyl-cyclohexyl)-ureido]-thiazole-5-sulfonyl}-pyrrolidine-2-carboxylic acid

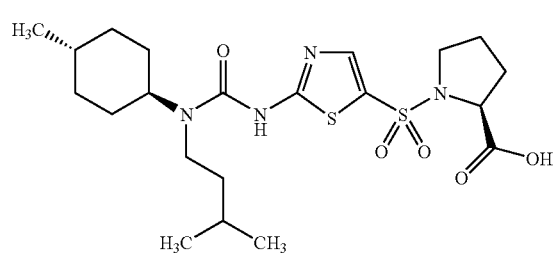

Prepared as described for the preparation of {2-[3-(3-methyl-butyl)-3-(4-methyl-cyclohexyl)-ureido]-thiazole-5-sulfonylamino}-acetic acid using the appropriate amino ester in Step 1.

$^1$H NMR (400 MHz, DMSO) δ 12.75 (br s, 1H), 11.4 (br s, 1H), 7.93 (s, 1H), 4.02 (dd, 1H), 3.97 (brt, 1H), 3.45-3.39 (m, 1H), 3.27-3.18 (m, 3H), 2.05-1.02 (m, 16H), 0.90 (d, 6H), 0.88 (d, 3H).

HPLC-MS: m/z=487, $R_t$=2.27 min

Example 33

{2-[3-(4-trans-tert-Butyl-cyclohexyl)-3-(3-methyl-butyl)-ureido]-thiazol-5-ylsulfanyl}-acetic acid

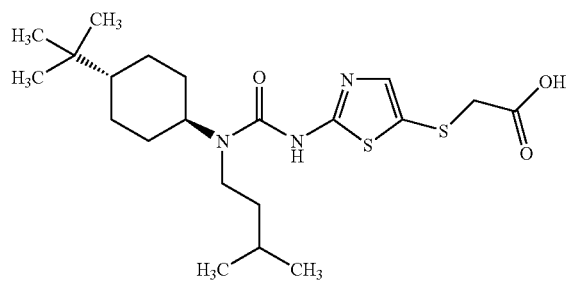

Prepared as described for the synthesis of {2-[3-(4-trans-ethyl-cyclohexyl)-3-(3-methyl-butyl)-ureido]-thiazol-5-yl-sulfanyl}-acetic acid, from 4-trans-tert-butyl-cyclohexylamine hydrochloride, 1-bromo-3-methylbutane and (2-amino-thiazol-5-ylsulfanyl)-acetic acid ethyl ester 1H NMR (400 MHz, CDCl$_3$) δ 7.26 (s, 1H), 3.95 (bs, 1H), 3.32 (s 2H), 3.27 (m, 2H), 1.84 (m, 4H), 1.65 (m, 1H), 1.48 (m, 4H), 1.25 (m, 2H), 0.98 (m, 1H), 0.94 (d, 6H), 0.87 (s, 9H).

HPLC-MS: m/z=442, $R_t$=2.5 min

Example 34

{2-[3-(4-trans-Isopropyl-cyclohexyl)-3-(3-methyl-butyl)-ureido]-thiazol-5-ylsulfanyl}-acetic acid

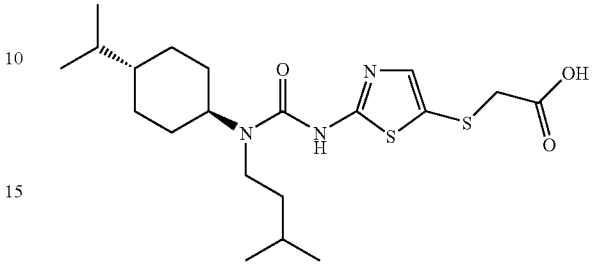

Prepared as described for the synthesis of {2-[3-(4-trans-ethyl-cyclohexyl)-3-(3-methyl-butyl)-ureido]-thiazol-5-yl-sulfanyl}-acetic acid, from 4-trans-isopropyl-cyclohexylamine hydrochloride, 1-bromo-3-methylbutane and (2-amino-thiazol-5-ylsulfanyl)-acetic acid ethyl ester $^1$H NMR (400 MHz, CDCl$_3$) δ 7.22 (s, 1H), 4.02 (broad s, 1H), 3.31 (s 2H), 3.27 (m, 2H), 1.81 (m, 4H), 1.66 (m, 1H), 1.53-1.43 (m, 5H), 1.23 (m, 2H), 1.05 (m, 1H), 0.94 (d, 6H), 0.88 (d, 6H).

HPLC-MS: m/z=428, $R_t$=2.5 min

Example 35

3-{2-[3-(4-trans-tert-Butyl-cyclohexyl)-3-(3-methyl-butyl)-ureido]-thiazol-5-ylsulfanyl}-propionic acid

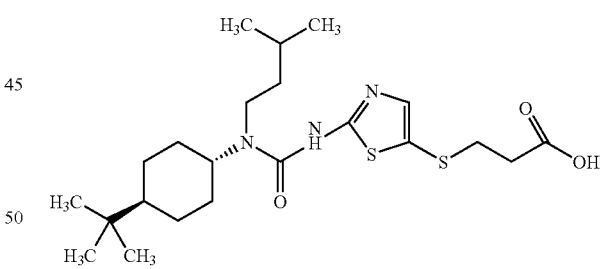

Prepared as described for the synthesis of {2-[3-(4-trans-ethyl-cyclohexyl)-3-(3-methyl-butyl)-ureido]-thiazol-5-yl-sulfanyl}-acetic acid, from 4-trans-tert-butyl-cyclohexylamine hydrochloride, 1-bromo-3-methylbutane and (2-amino-thiazol-5-ylsulfanyl)-propionic acid ethyl ester $^1$H NMR (400 MHz, CDCl$_3$) δ 7.25 (s, 1H), 3.65 (broad s, 1H), 3.21 (m, 2H), 2.99 (broad m, 2H), 2.72 (m, 2H), 1.88 (m, 4H), 1.62 (m, 1H), 1.44 (m, 3H), 1.31 (m, 1H), 0.98 (m, 2H), 0.93 (d, 6H), 0.89 (s, 9H)

HPLC-MS: m/z=456, $R_t$=2.6 min

Example 36

3-{2-[3-(4-trans-Isopropyl-cyclohexyl)-3-(3-methyl-butyl)-ureido]-thiazol-5-ylsulfanyl}-propionic acid

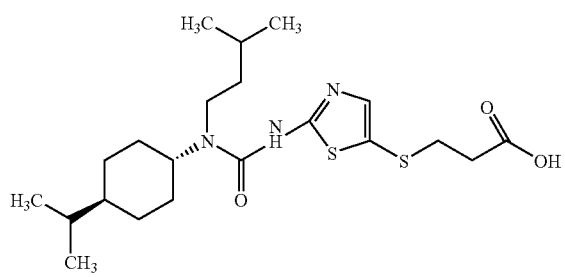

Prepared as described for the synthesis of {2-[3-(4-trans-ethyl-cyclohexyl)-3-(3-methyl-butyl)-ureido]-thiazol-5-ylsulfanyl}-acetic acid, from 4-trans-isopropyl-cyclohexylamine hydrochloride, 1-bromo-3-methylbutane and (2-amino-thiazol-5-ylsulfanyl)-propionic acid ethyl ester.

$^1$H NMR (400 MHz, CDCl$_3$) δ 7.25 (s, 1H), 3.65 (broad s, 1H), 3.21 (m, 2H), 2.99 (broad m, 2H), 2.73 (m, 2H), 1.90 (m, 2H), 1.82 (m, 3H), 1.61 (m, 2H), 1.45 (m, 4H), 1.27 (m, 1H), 1.04 (m, 1H), 0.93 (d, 6H), 0.89 (s, 9H).

HPLC-MS: m/z=442, R$_t$=2.5 min

Example 37

{2-[3-(4-Methyl-cyclohexyl)-3-(3-phenyl-propyl)-ureido]-thiazol-5-ylsulfanyl}-acetic acid

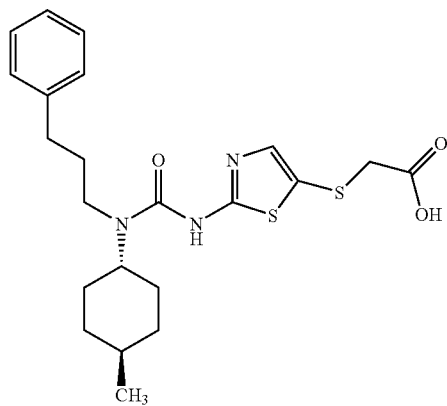

Prepared as described for the synthesis of [2-(3-cyclohexyl-3-phenethyl-ureido)-thiazol-5-ylsulfanyl]-acetic acid using 3-phenylpropionaldehyde, trans-4-methyl-cyclohexylamine and (2-amino-thiazol-5-ylsulfanyl)-acetic acid ethyl ester.

$^1$H NMR (400 MHz, DMSO-d$_6$) δ 7.41 (s, 1H), 7.32-7.25 (m, 5H), 4.10-3.9 (m, 1H), 3.48 (s, 2H), 3.3-3.2 (m, 2H), 2.59 (t, 2H), 1.95-0.95 (m, 11H), 0.87 (d, 3H)

HPLC-MS: m/z=448 (M+1)

Example 38

{2-[3-(3-Methyl-butyl)-3-(trans-4-propoxy-cyclohexyl)-ureido]-thiazol-5-ylsulfanyl}-acetic acid (General Procedure (E), (A) and (B))

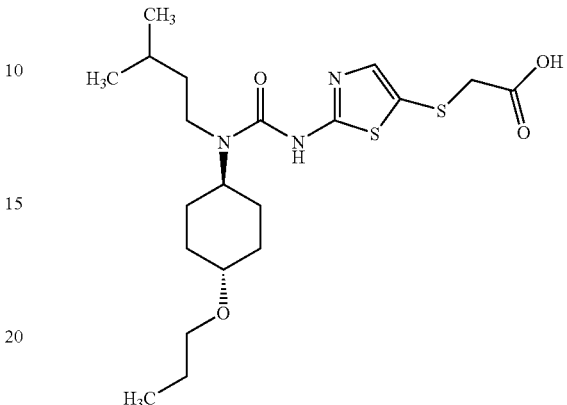

General Synthesis of trans-4-alkoxy-cyclohexylamine Intermediates

Trans 4-aminocyclohexanol (25 g, 0.22 mol) dissolved in water (350 mL) was added potassium carbonate (3.0 g, 0.022 mol) and N-carbethoxyphthalimide (47.6 g, 0.22 mol) and the reaction mixture was stirred for 16 hours. The white precipitate was filtered off, washed with water and dried to give 37.7 g (71%) of trans-2-(4-hydroxycyclohexyl)-isoindole-1,3-dione (J. Med. Chem. 1996, 39, 314-322).

To a solution of trans-2-(4-hydroxycyclohexyl)-isoindole-1,3-dione (13 g, 53 mmol) in dry DMF (50 mL) was added molecular sieves (4 Å, 6 mL). The mixture was stirred for 30 min at rt. NaH (5.3 g 60% in oil, 132.5 mmol) was washed with hexanes before it was added in portions to the reaction mixture. The mixture was stirred for 30 min before propylbromide (48.1 mL, 530 mmol) was added. The reaction mixture was stirred for 16 hours before the reaction mixture was filtered. The filtrate was added water (100 mL) and extracted with Et$_2$O (250 mL). The organic phase was washed with brine (3×50 mL) and dried (MgSO$_4$) and the solvent was removed in vacuo. The crude product was purified by column chromatography (silica gel, heptane-EtOAc (4:1). The first band was collected to give 6.6 g (43%) of trans-2-(4-propyloxycyclohexyl)-isoindole-1,3-dione.

$^1$H-NMR (CDCl$_3$): 7.8 (s, 2H), 7.7 (s, 2H), 4.15 (m, 1H), 3.45 (t, 2H), 3.35 (m, 1H), 2.3 (m, 2H), 2.15 (m, 2H), 1.8 (m, 2H), 1.6 (h, 2H), 1.37 (m, 2H), 0.92 (t, 3H)

Hydrazine hydrate (1.76 g, 55 mmol) was added to a solution of trans-2-(4-propyloxycyclohexyl)-isoindole-1,3-dione (7.90 g, 27.5 mmol) in absolute EtOH (100 mL). The reaction was stirred at 50° C. for 3 h before the reaction mixture was filtered. The solvent was removed in vacuo and Et$_2$O (250 mL) was added after stirring for 30 min the solid was filtered off and the filtrate was added 150 mL 1 N HCl, the phases were separated and the aqueous phase was washed with Et$_2$O (150 mL) before 10 N NaOH was added (until pH=11-12). The aqueous phase was extracted with EtOAc (200 mL+2× 100 mL) and the organic fractions were collected and dried (MgSO$_4$) to give 3.11 g (72%) of trans-4-propoxy-cyclohexylamine.

$^1$H-NMR (CDCl$_3$): 3.4 (t, 2H), 3.18 (m, 1H), 2.7 (m, 1H), 2.0 (m, 2H), 1.85 (m, 2H), 1.55 (h, 2H), 1.4-1.1 (m, 4H), 0.9 (t, 3H).

(Reductive Amination, Coupling and Hydrolysis):

{2-[3-(3-Methyl-butyl)-3-(4-propoxy-cyclohexyl)-ureido]-thiazol-5-ylsulfanyl}-acetic acid was prepared as described for the synthesis of [2-(3-cyclohexyl-3-phenethyl-ureido)-thiazol-5-ylsulfanyl]-acetic acid using isovaleraldehyde, trans-4-propoxy-cyclohexylamine and (2-amino-thiazol-5-ylsulfanyl)-acetic acid ethyl ester.

$^1$H NMR (400 MHz, DMSO-$d_6$) δ 7.40 (s, 1H), 4.1-3.9 (m, 1H), 3.48 (s, 2H), 3.25-3.15 (m, 3H), 2.05-1.95 (m, 2H), 1.7-1.2 (m, 13H), 0.90 (d, 6H), 0.87 (t, 3H).

HPLC-MS: m/z=444 (M+1)

Example 39

{2-[3-(trans-4-tert-Butoxy-cyclohexyl)-3-(3-methyl-butyl)-ureido]-thiazol-5-ylsulfanyl}-acetic acid

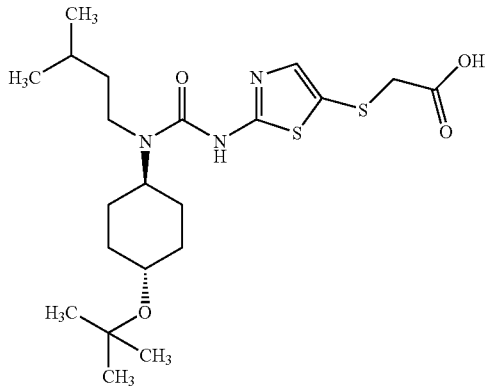

Prepared as described for the synthesis of [2-(3-cyclohexyl-3-phenethyl-ureido)-thiazol-5-ylsulfanyl]-acetic acid using isovaleraldehyde, trans-4-tert-butoxy-cyclohexylamine and (2-amino-thiazol-5-ylsulfanyl)-acetic acid ethyl ester.

$^1$H NMR (400 MHz, DMSO-$d_6$) δ 7.40 (s, 1H), 4.00-3.38 (m, 1H), 3.48 (s, 2H), 3.5-3.3 (m, 1H), 3.25-3.15 (m, 2H), 1.8-1.2 (m, 11H), 1.15 (s, 9H), 0.90 (d, 6H).

HPLC-MS: m/z=458 (M+1)

Example 40

{2-[3-(trans-4-Cyclopropylmethoxy-cyclohexyl)-3-(3-methyl-butyl-ureido]-thiazol-5-ylsulfanyl}-acetic acid

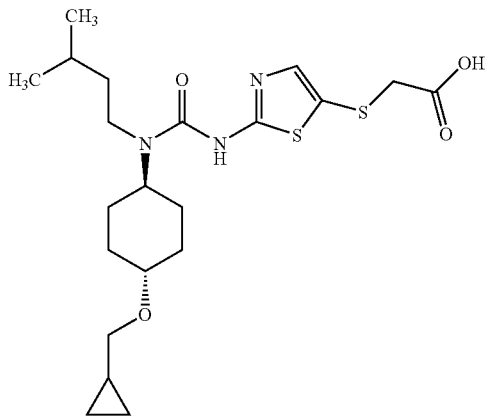

Prepared as described for the synthesis of [2-(3-cyclohexyl-3-phenethyl-ureido)-thiazol-5-ylsulfanyl]-acetic acid using isovaleraldehyde, trans-4-cyclopropylmethoxy-cyclohexylamine (prepared in accordance with the general method given for the preparation of {2-[3-(3-methyl-butyl)-3-(4-propoxy-cyclohexyl)-ureido]-thiazol-5-ylsulfanyl}-acetic acid) and (2-amino-thiazol-5-ylsulfanyl)-acetic acid ethyl ester.

$^1$H NMR (400 MHz, DMSO-$d_6$) δ 7.40 (s, 1H), 4.05-1.90 (m, 1H), 3.48 (s, 1H), 3.23 (d, 2H), 3.25-3.15 (m, 3H), 2.05-1.95 (m, 2H), 1.70-1.15 (m, 9H), 1.0-0.9 (m, 1H), 0.90 (d, 6H), 0.48-0.40 (m, 2H), 0.18-0.10 (m, 2H).

HPLC-MS: m/z=456 (M+1)

Example 41

{2-[3-[trans-4-(2-Methoxy-ethoxy)-cyclohexyl]-3-(3-methyl-butyl)-ureido]-thiazol-5-ylsulfanyl}-acetic acid

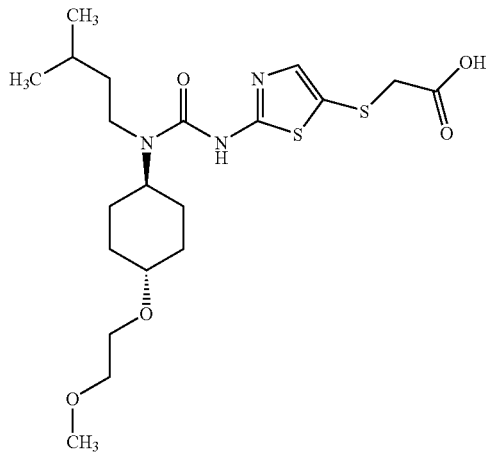

Prepared as described for the synthesis of [2-(3-cyclohexyl-3-phenethyl-ureido)-thiazol-5-ylsulfanyl]-acetic acid using isovaleraldehyde, trans-4-(2-methoxy-ethoxy)-cyclohexylamine (prepared in accordance with the general method given for the preparation of {2-[3-(3-methylbutyl)-3-(4-propoxy-cyclohexyl)-ureido]-thiazol-5-ylsulfanyl}-acetic acid) and (2-amino-thiazol-5-ylsulfanyl)-acetic acid ethyl ester.

$^1$H NMR (400 MHz, DMSO-$d_6$) δ 7.40 (s, 1H), 4.05-3.85 (m, 1H), 3.05-3.38 (m, 4H), 3.49 (s, 2H), 3.25 (s, 3H), 3.28-3.15 (m, 3H), 2.05-1.95 (m, 2H), 1.65-1.15 (m, 10H), 0.90 (d, 6H).

HPLC-MS: m/z=460 (M+1)

Example 42

{2-[3-(trans-4-Benzyloxy-cyclohexyl)-3-(3-methyl-butyl)-ureido]-thiazol-5-ylsulfanyl}-acetic acid

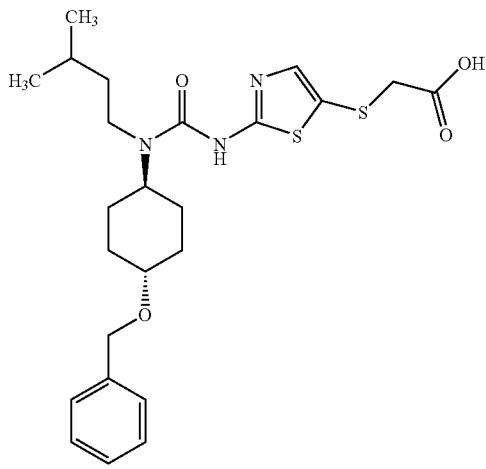

Prepared as described for the synthesis of [2-(3-cyclohexyl-3-phenethyl-ureido)-thiazol-5-ylsulfanyl]-acetic acid using isovaleraldehyde, trans-4-benzyloxy-cyclohexylamine (prepared in accordance with the general method given for the preparation of {2-[3-(3-methyl-butyl)-3-(4-propoxy-cyclohexyl)-ureido]-thiazol-5-ylsulfanyl}-acetic acid) and (2-amino-thiazol-5-ylsulfanyl)-acetic acid ethyl ester.

$^1$H NMR (400 MHz, DMSO-$d_6$) δ 7.41 (s, 1H), 7.38-7.23 (m, 5H), 4.50 (s, 2H); 4.05-3.95 (m, 1H); 3.48 (s, 2H), 3.40-3.25 (s, 1H), 3.25-3.15 (m, 2H); 2.12-2.02 (m, 2H), 1.70-1.28 (m, 9H), 0.88 (d, 6H).

HPLC-MS: m/z=492 (M+1)

Example 43

{2-[3-(trans-4-Methoxymethyl-cyclohexyl)-3-(3-methyl-butyl)-ureido]-thiazol-5-ylsulfanyl}-acetic acid (General Procedure (D), (A) and (B))

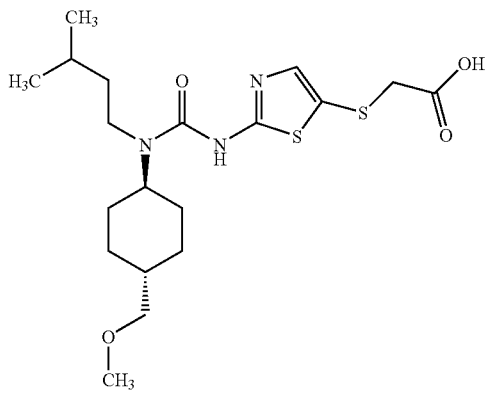

Preparation of trans-4-alkoxymethyl-cyclohexyl amine

A mixture of 4-carboxymethylcyclohexanone (21 g), ethylene glycol (19 g) and benzene (250 mL) was heated at reflux for 20 h with Dean Stark azeotropic removal of water. After cooling the solution was washed with sodium bicarbonate solution, dried over magnesium sulphate and concentrated. The crude ketal was then taken up in diethyl ether (250 mL) and lithium aluminium hydride (7 g) was added. The mixture was stirred overnight and then water (20 mL), 10% sodium hydroxide (30 mL) and water (30 mL) was added carefully. Sodium sulphate (30 g) was then added and the mixture stirred for 20 min. The insoluble material was removed by filtration and the organic phase concentrated in vacuo to give (1,4-dioxaspiro[4.5]dec-8-yl)-methanol (21 g).

$^1$H NMR (400 MHz, CDCl$_3$) δ 1.20-1.80, (m, 10H), 3.45 (d, 2H), 3.95 (s, 4H)

To (1,4-dioxa-spiro[4.5]dec-8-yl)-methanol (10 g) in tetrahydrofuran (300 mL) in an ice bath was added sodium hydride (3.6 g of 60% in mineral oil) and the mixture stirred for 30 min. Methyl iodide 7.8 mL in THF (20 mL) was added dropwise and the reaction was allowed to warm slowly to room temperature overnight. Water (20 mL) was added and the reaction mixture partially concentrated, then partitioned between water (100 mL) and diethyl ether (300 mL). The organic phase was isolated, dried and concentrated in vacuo. The crude was then taken up in tetrahydrofuran (250 mL) and 40 mL of 3N aqueous HCl was added. The reaction was stirred for 2 h at room temperature, partially concentrated and then the crude product was extracted with diethyl ether, dried, concentrated and purified by flash chromatography (4 hexane: 1 ethyl acetate) to give 4-methoxymethyl-cyclohexanone 4.9 g.

$^1$H NMR (400 MHz, CDCl$_3$) δ 1.40-1.55 (m, 2H), 1.98-2.15 (m, 3H), 2.20-2.45 (m, 4H), (d, 2H), 3.36 (d, 4H), 3.31 (s, 3H).

A mixture of 4-methoxymethyl-cyclohexanone (5 g), hydroxylamine hydrochloride (4.7 g), and sodium acetate (5.6 g) in water (125 mL) and methanol (25 mL) was heated to 60° C. for 18 h. ether was added and the organic phase isolated, washed with saturated sodium bicarbonate, dried over magnesium sulphate and concentrated in vacuo. Ethanol was added and then sodium (8 g) was added portion wise. The mixture was then heated to 65° C. for 1.5 h, cooled in an ice bath and water (10 mL) was carefully added. The reaction was partially concentrated, water (30 mL) was added and the aqueous phase was extracted with diethyl ether and concentrated to give the crude product. Addition of 6N HCl afforded the corresponding HCl salt which was recrystallised from acetonitrile to give trans-4-methoxymethyl-cyclohexylamine hydrochloride (3 g).

$^1$H NMR (400 MHz, DMSO-$d_6$) δ 0.90-1.15 (m, 2H), 1.20-1.37 (m, 2H), 1.38-1.54 (m, 1H), 1.73 (d, 2H), 1.95 (d, 2H), 2.80-2.95 (m, 1H), 3.12 (d, 2H), 3.22 (s. 3H), 8.21 (s, 3H).

(Reductive Amination, Coupling and Hydrolysis):

{2-[3-(trans-4-Methoxymethyl-cyclohexyl)-3-(3-methyl-butyl)-ureido]-thiazol-5-ylsulfanyl}-acetic acid was prepared as described for the synthesis of [2-(3-cyclohexyl-3-phenethyl-ureido)-thiazol-5-ylsulfanyl]-acetic acid using, trans-4-methoxymethyl-cyclohexylamine, isovaleraldehyde and (2-amino-thiazol-5-ylsulfanyl)-acetic acid ethyl ester.

$^1$H NMR (400 MHz, DMSO-$d_6$) δ 7.40 (s, 1H), 4.02-3.95 (m, 1H), 3.48 (s, 2H), 3.28-3.17 (m, 2H), 3.23 (s, 3H), 3.13 (d, 2H), 1.80-1.30 (m, 10H), 1.15-0.98 (m, 2H), 0.90 (d, 6H).

HPLC-MS: m/z=430 (M+1)

Example 44

{2-[3-(trans-4-Ethoxymethyl-cyclohexyl)-3-(3-methyl-butyl)-ureido]-thiazol-5-ylsulfanyl}-acetic acid

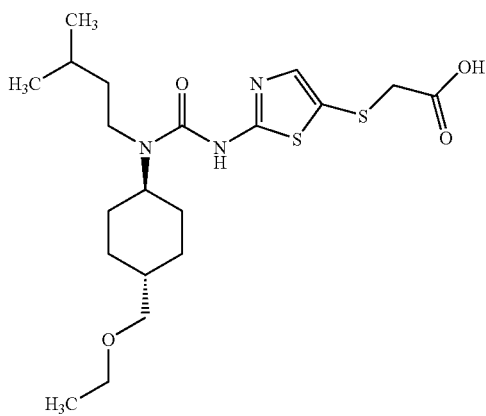

Prepared as described for the synthesis of [2-(3-cyclohexyl-3-phenethyl-ureido)-thiazol-5-ylsulfanyl]-acetic acid using isovaleraldehyde, trans-4-ethoxymethyl-cyclohexylamine (prepared in accordance with the general method given for the preparation of {2-[3-(4-methoxymethyl-cyclohexyl)-3-(3-methyl-butyl)-ureido]-thiazol-5-ylsulfanyl}-acetic acid) and (2-amino-thiazol-5-ylsulfanyl)-acetic acid ethyl ester.

$^1$H NMR (400 MHz, DMSO-d$_6$) δ 7.40 (s, 1H), 4.10-3.90 (m, 1H), 3.48 (s, 2H), 3.38 (q, 2H), 3.26-3.15 (m, 2H), 3.18 (d, 2H), 1.80-1.70 (m, 2H), 1.70-1.30 (m, 9H), 1.10 (t, 3H), 0.90 (d, 6H)

HPLC-MS: m/z=444 (M+1)

Example 45

{2-[3-(trans-4-Cyclopropylmethoxymethyl-cyclohexyl)-3-(3-methyl-butyl)-ureido]-thiazol-5-ylsulfanyl}-acetic acid

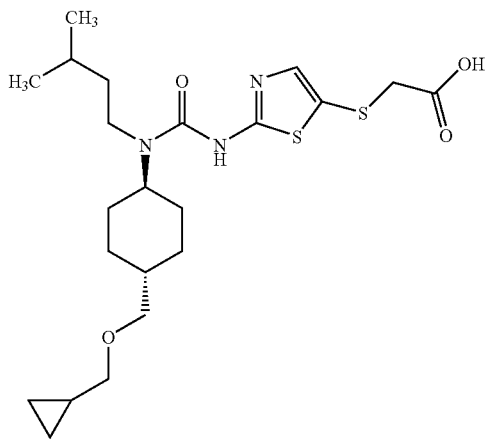

Prepared as described for the synthesis of [2-(3-cyclohexyl-3-phenethyl-ureido)-thiazol-5-ylsulfanyl]-acetic acid using isovaleraldehyde, trans-4-cyclopropyl-methoxymethyl-cyclohexylamine (prepared in accordance with the general method given for the preparation of {2-[3-(4-methoxymethyl-cyclohexyl)-3-(3-methyl-butyl)-ureido]-thiazol-5-ylsulfanyl}-acetic acid) and (2-amino-thiazol-5-ylsulfanyl)-acetic acid ethyl ester.

$^1$H NMR (400 MHz, DMSO-d$_6$) δ 7.40 (s, 1H), 4.05-3.90 (m, 1H), 3.48 (s, 2H), 3.25-3.50 (m, 6H) 1.85-0.95 (m, 13H), 0.90 (d, 6H), 0.50-0.40 (m, 2H), 0.20-0.10 (m, 2H)

HPLC-MS: m/z=470 (M+1)

Example 46

{2-[3-Butyl-3-(trans-4-methyl-cyclohexyl)-ureido]-thiazol-5-ylsulfanyl}-acetic acid

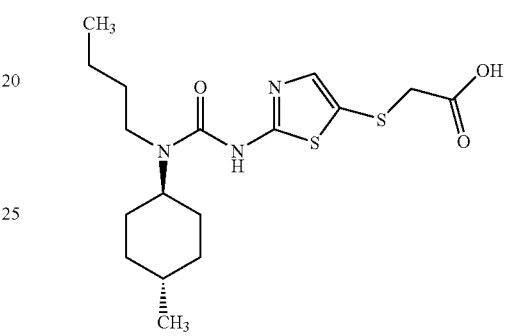

Prepared as described for the synthesis of [2-(3-cyclohexyl-3-phenethyl-ureido)-thiazol-5-ylsulfanyl]-acetic acid using butyraldehyde, trans-4-methyl-cyclohexylamine and (2-amino-thiazol-5-ylsulfanyl)-acetic acid ethyl ester.

$^1$H NMR (400 MHz, DMSO-d$_6$) δ 7.40 (s, 1H), 4.00-3.88 (m, 1H), 3.48 (s, 2H), 3.25-3.15 (m, 2H), 1.75-0.95 (m, 13H), 0.93-0.81 (m, 6H)

HPLC-MS: m/z=386 (M+1)

Example 47

{2-[3,3-Bis-(3-methyl-butyl)-ureido]-thiazol-5-ylsulfanyl}-acetic acid

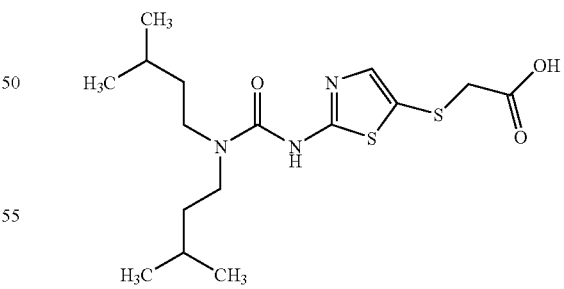

Prepared as described for the synthesis of [2-(3-cyclohexyl-3-phenethyl-ureido)-thiazol-5-ylsulfanyl]-acetic acid using isovaleraldehyde, 3-methylbutylamine and (2-amino-thiazol-5-ylsulfanyl)-acetic acid ethyl ester.

$^1$H NMR (400 MHz, DMSO-d$_6$) δ 7.40 (s, 1H), 3.49 (s, 2H), 3.40-3.20 (m, 4H), 1.60-1.49 (m, 2H), 1.42-1.33 (m, 4H), 0.90 (d, 12H).

HPLC-MS: m/z=374 (M+1)

Example 48

{2-[3-Butyl-3-(3-methyl-butyl)-ureido]-thiazol-5-ylsulfanyl}-acetic acid

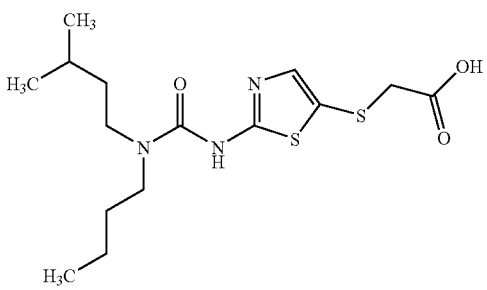

Prepared as described for the synthesis of [2-(3-cyclohexyl-3-phenethyl-ureido)-thiazol-5-ylsulfanyl]-acetic acid using isovaleraldehyde, butylamine and (2-amino-thiazol-5-ylsulfanyl)-acetic acid ethyl ester.

$^1$H NMR (400 MHz, DMSO-$d_6$) δ 7.41 (s, 1H), 3.48 (s, 2H); 3.35-3.2 (m, 4H), 1.60-1.20 (m, 7H), 0.92-0.82 (m, 9H).

HPLC-MS: m/z=360 (M+1)

Example 49

3-{2-[3,3-Bis-(3-methyl-butyl)-ureido]-thiazol-5-ylsulfanyl}-propionic acid

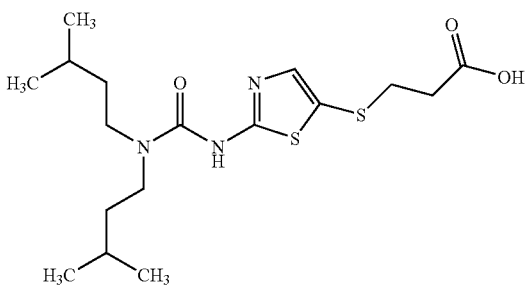

Prepared as described for the synthesis of [2-(3-cyclohexyl-3-phenethyl-ureido)-thiazol-5-ylsulfanyl]-acetic acid using isovaleraldehyde, 3-methyl-butylamine and (2-amino-thiazol-5-ylsulfanyl)-propionic acid ethyl ester.

$^1$H NMR (400 MHz, DMSO-$d_6$) δ 7.39 (s, 1H), 3.40-3.28 (m, 4H), 2.84 (t, 2H), 2.50 (t, 2H), 1.61-1.49 (m, 2H), 1.42-1.32 (m, 4H), 0.89 (d, 6H).

HPLC-MS: m/z=388 (M+1)

Example 50

2-[3-(4-trans-Ethyl-cyclohexyl)-3-(2-phenoxy-ethyl)-ureido]-thiazol-5-ylsulfanyl)-acetic acid

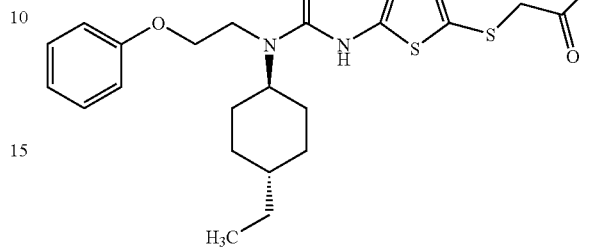

Prepared as described for the synthesis of {2-[3-(4-trans-ethyl-cyclohexyl)-3-(3-methyl-butyl)-ureido]-thiazol-5-yl-sulfanyl}-acetic acid, from 4-trans-ethyl-cyclohexylamine hydrochloride, 2-bromoethoxybenzene and (2-amino-thiazol-5-ylsulfanyl)-acetic acid ethyl ester.

$^1$H NMR (400 MHz, CDCl$_3$) δ 7.30-7.25 (m. 3H), 6.97-6.88 (m, 3H), 4.11 (m, 3H), 3.71 (m, 2H), 3.27 (s, 2H), 1.84 (m, 4H), 1.56 (m, 2H), 1.25-1.10 (m, 7H), 0.88 (m, 4H).

HPLC-MS: m/z=464 (M+1)

Example 51

{2-[3-(4-trans-Ethyl-cyclohexyl)-3-(4-phenoxy-butyl)-ureido]-thiazol-5-ylsulfanyl}-acetic acid

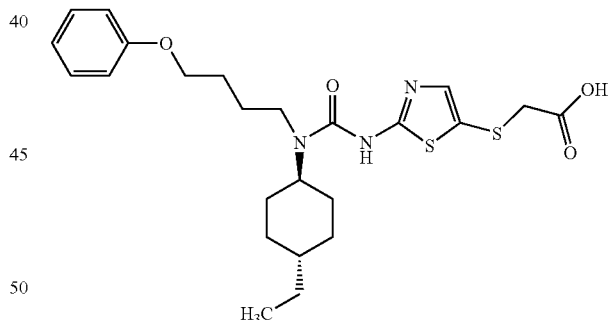

Prepared as described for the synthesis of {2-[3-(4-trans-ethyl-cyclohexyl)-3-(3-methyl-butyl)-ureido]-thiazol-5-yl-sulfanyl}-acetic acid, from 4-trans-ethyl-cyclohexylamine hydrochloride, 4-bromobutoxybenzene and (2-amino-thiazol-5-ylsulfanyl)-acetic acid ethyl ester.

$^1$H NMR (400 MHz, CDCl$_3$) δ 7.30-7.23 (m, 3H), 6.95-6.85 (m, 3H), 3.99 (m, 3H), 3.33 (m, 2H), 3.30 (s, 2H), 1.87-1.75 (m, 8H), 1.50 (m, 2H), 1.23 (m, 2H), 1.08 (m, 2H), 0.88 (t, 3H).

HPLC-MS: m/z=514 (M+1)

Example 52

3-{2-[3-Butyl-3-(3-methyl-butyl)-ureido]-thiazol-5-ylsulfanyl}-propionic acid

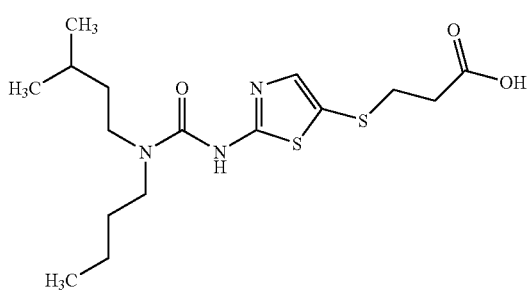

Prepared as described for the synthesis of [2-(3-cyclohexyl-3-phenethyl-ureido)-thiazol-5-ylsulfanyl]-acetic acid using isovaleraldehyde, butylamine and (2-amino-thiazol-5-ylsulfanyl)-propionic acid ethyl ester.

$^1$H NMR (400 MHz, DMSO-$d_6$) 7.39 (s, 1H), 3.80-3.25 (m, 4H), 2.84 (t, 2H), 2.50 (t, 2H), 1.60-1.20 (7H), 0.95-0.84 (m, 9H).

HPLC-MS: m/z=374 (M+1)

Example 53

2-Methyl-2-{2-[3-(3-methyl-butyl)-3-(4-trans-methyl-cyclohexyl)-ureido]-thiazol-5-ylsulfanyl}-propionic acid

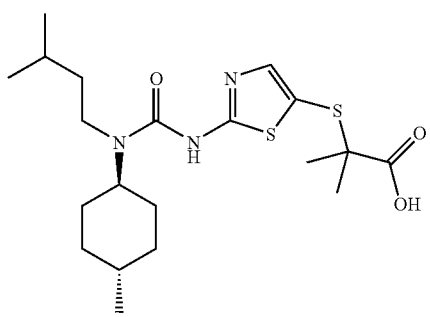

Prepared as described for the synthesis of [2-(3-cyclohexyl-3-phenethyl-ureido)-thiazol-5-ylsulfanyl]-acetic acid, from 4-trans-methyl-cyclohexylamine, isovaleraldehyde and 2-(2-amino-thiazol-5-ylsulfanyl)-2-methyl-propionic acid ethyl ester.

$^1$H NMR (400 MHz, DMSO-$d_6$) δ 7.40 (s, 1H), 3.97 (m, 1H), 3.21 (m, 2H), 1.75-1.25 (m, 10H), 1.39 (s, 6H), 1.15-1.00 (m, 2H), 0.90 (d, 6H), 0.87 (d, 3H)

HPLC-MS: m/z=428

Example 54

2-{2-[3-Cyclohexyl-3-(3-methyl-butyl)-ureido]-thiazol-5-ylsulfanyl}-2-methyl-propionic acid

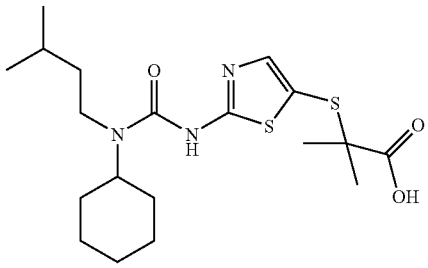

Prepared as described for the synthesis of [2-(3-cyclohexyl-3-phenethyl-ureido)-thiazol-5-ylsulfanyl]-acetic acid, from cyclohexanone, 3-methylbutylamine and 2-(2-amino-thiazol-5-ylsulfanyl)-2-methyl-propionic acid ethyl ester.

$^1$H NMR (400 MHz, DMSO-$d_6$) δ 7.40 (s, 1H), 3.97 (m, 1H), 3.23 (m, 2H), 1.80-1.00 (m, 13H), 1.40 (s, 6H)

HPLC-MS: m/z=415

Example 55

5-[3-(3-Methyl-butyl)-3-(4-trans-methyl-cyclohexyl)-ureido]-1,3,4-thiadiazole-2-carboxylic acid ethyl ester

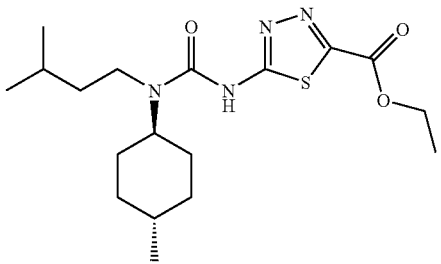

Prepared as described for the synthesis of [2-(3-cyclohexyl-3-phenethyl-ureido)-thiazol-5-ylsulfanyl]-acetic acid, from 4-trans-methyl-cyclohexylamine, isovaleraldehyde and 5-amino-[1,3,4]thiadiazole-2-carboxylic acid ethyl ester.

HPLC-MS: m/z=383

Example 56

{5-[3-(3-Methyl-butyl)-3-(4-trans-methyl-cyclohexyl)-ureido]-1,3,4-thiadiazol-2-ylsulfanyl}-acetic acid ethyl ester

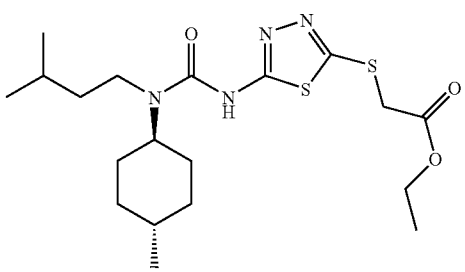

Prepared as described for the synthesis of [2-(3-cyclohexyl-3-phenethyl-ureido)-thiazol-5-ylsulfanyl]-acetic acid, from 4-trans-methyl-cyclohexylamine, isovaleraldehyde and (5-amino-[1,3,4]thiadiazol-2-ylsulfanyl)-acetic acid ethyl ester.

HPLC-MS: m/z=429

Example 57

2-Methyl-2-{5-[3-(3-methyl-butyl)-3-(4-trans-methyl-cyclohexyl)-ureido]-1,3,4-thiadiazol-2-ylsulfanyl}-propionic acid

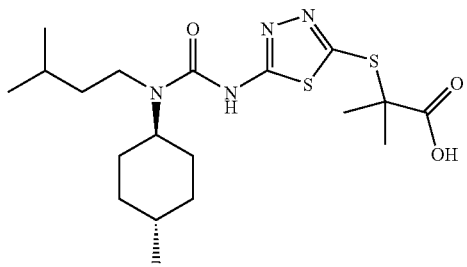

Prepared as described for the synthesis of [2-(3-cyclohexyl-3-phenethyl-ureido)-thiazol-5-ylsulfanyl]-acetic acid, from 4-trans-methyl-cyclohexylamine, isovaleraldehyde and (2-(2-amino-thiazol-5-ylsulfanyl)-2-methyl-propionic acid ethyl ester.

HPLC-MS: m/z=429

Example 58

{5-[3-(3-Methyl-butyl)-3-(4-trans-methyl-cyclohexyl)-ureido]-1,3,4-thiadiazol-2-ylsulfanyl}-acetic acid

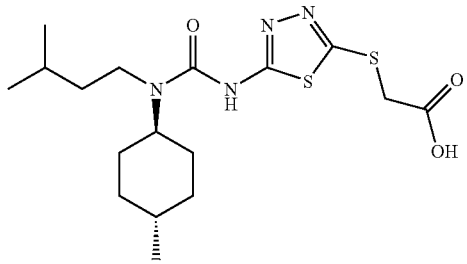

Prepared by hydrolysis of {5-[3-(3-methyl-butyl)-3-(4-trans-methyl-cyclohexyl)-ureido]-1,3,4-thiadiazol-2-ylsulfanyl}-acetic acid ethyl ester described for the synthesis of [2-(3-cyclohexyl-3-phenethyl-ureido)-thiazol-5-ylsulfanyl]-acetic acid.

HPLC-MS: m/z=401

Example 59

3-{5-[3-(3-Methyl-butyl)-3-(4-trans-methyl-cyclohexyl)-ureido]-1,3,4-thiadiazol-2-ylsulfanyl}-propionic acid ethyl ester

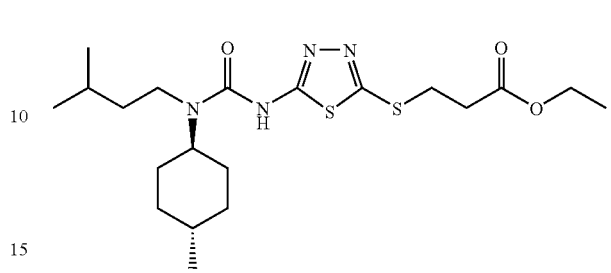

Prepared as described for the synthesis of [2-(3-cyclohexyl-3-phenethyl-ureido)-thiazol-5-ylsulfanyl]-acetic acid, from 4-trans-methyl-cyclohexylamine, isovaleraldehyde and 3-(5-amino-[1,3,4]thiadiazol-2-ylsulfanyl)-propionic acid ethyl ester HPLC-MS: m/z=443

Example 60

3-{5-[3-(3-Methyl-butyl)-3-(4-trans-methyl-cyclohexyl)-ureido]-1,3,4-thiadiazol-2-yl}-propionic acid methyl ester

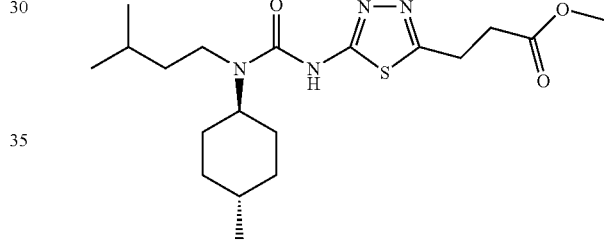

Prepared as described for the synthesis of [2-(3-cyclohexyl-3-phenethyl-ureido)-thiazol-5-ylsulfanyl]-acetic acid, from 4-trans-methyl-cyclohexylamine, isovaleraldehyde and 3-(5-amino-[1,3,4]thiadiazol-2-yl)-propionic acid methyl ester HPLC-MS: m/z=397

Example 61

{2-[3-(1,3-Dimethyl-butyl)-3-(4-trans-methyl-cyclohexyl)-ureido]-thiazol-5-ylsulfanyl}-acetic acid

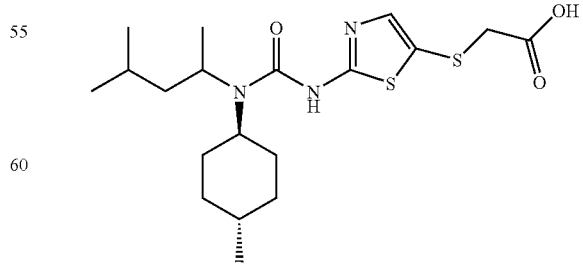

Prepared as described for the synthesis of [2-(3-cyclohexyl-3-phenethyl-ureido)-thiazol-5-ylsulfanyl]-acetic acid from (1,3-dimethyl-butyl)-(4-trans-methyl-cyclohexyl)-amine and (2-amino-thiazol-5-ylsulfanyl)-acetic acid ethyl ester $^1$H NMR (400 MHz, DMSO-d$_6$) δ 7.38 (s, 1H), 3.68-3.55 (m, 1H), 3.50-3.20 (m, 1H), 3.48 (s, 2H), 1.80-0.95 (m, 15H), 0.92-0.80 (m, 9H)

HPLC-MS: m/z=415

Preparation of (1,3-dimethyl-butyl)-(4-trans-methyl-cyclohexyl)-amine 4-trans-methyl-cyclohexylamine hydrochloride (3.74, 24.96 mmol) in anhydrous MeOH (40 mL) was added NaOH (1.0 g, 24.96 mmol) followed by isobutylmethylketone (2.5 g, 24.96 mmol) and the reaction mixture was stirred for 30 min before glacial acetic acid (15 mL), and Pd/C (10%, 375 mg) was added. The reaction mixture was stirred at room temperature under H$_2$ (1 atm) for 18 hours before more isobutylmethylketone (1.25 g, 12.48 mmol) was added. The reaction was then left stirring under H$_2$ for 72 hours before it was filtered through a pad of celite. The filtrate was concentrated in vacuo, dissolved in diethyl ether and washed twice with saturated sodium bicarbonate (50 mL). The organic phase was acidified by adding 1N HCl in diethyl ether (25 mL). The precipitated product was collected by filtration to give 2.9 g of (1,3-dimethyl-butyl)-(4-trans-methyl-cyclohexyl)-amine.

Example 62

2-{2-[3-(1,3-Dimethyl-butyl)-3-(4-trans-methyl-cyclohexyl)-ureido]-thiazol-5-ylsulfanyl}-2-methyl-propionic acid

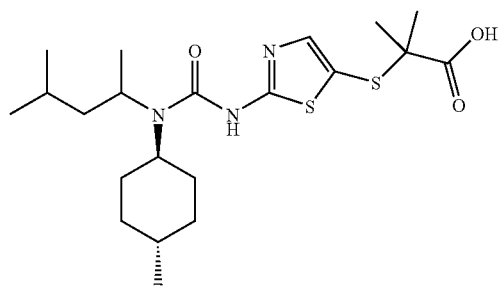

Prepared as described for the synthesis of [2-(3-cyclohexyl-3-phenethyl-ureido)-thiazol-5-ylsulfanyl]-acetic acid from (1,3-dimethyl-butyl)-(4-trans-methyl-cyclohexyl)-amine and (2-(2-amino-thiazol-5-ylsulfanyl)-2-methyl-propionic acid ethyl ester $^1$H NMR (400 MHz, DMSO-d$_6$) δ 7.35 (s, 1H), 3.60-3.10 (m, 2H), 1.72-0.95 (m, 15H), 1.38 (s, 6H), 0.92-0.82 (m, 9H)

HPLC-MS: m/z=443

Example 63

3-{2-[3-(1,3-Dimethyl-butyl)-3-(4-trans-methyl-cyclohexyl)-ureido]-thiazol-5-ylsulfanyl}-propionic acid

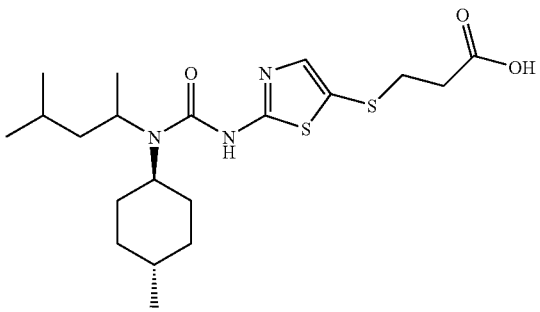

Prepared as described for the synthesis of [2-(3-cyclohexyl-3-phenethyl-ureido)-thiazol-5-ylsulfanyl]-acetic acid from (1,3-dimethyl-butyl)-(4-trans-methyl-cyclohexyl)-amine and (2-amino-thiazol-5-ylsulfanyl)-propionic acid ethyl ester.

$^1$H NMR (400 MHz, DMSO-d$_6$) δ 7.35 (s, 1H), 2.83 (t, 2H), 2.49 (t, 2H), 1.75-0.95 (m, 15H), 0.91-0.82 (m, 9H)

HPLC-MS: m/z=429

Example 64

3-{5-[3-(3-Methyl-butyl)-3-(4-trans-methyl-cyclohexyl)-ureido]-1,3,4-thiadiazol-2-ylsulfanyl}-propionic acid

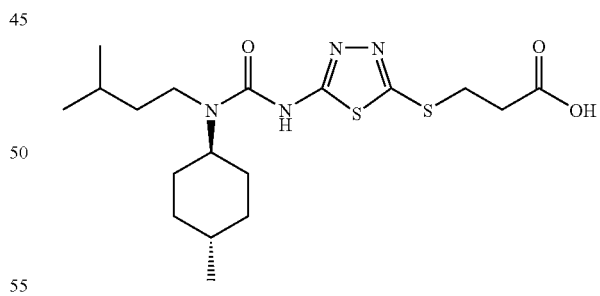

Prepared by hydrolysis of 3-{5-[3-(3-methyl-butyl)-3-(4-trans-methyl-cyclohexyl)-ureido]-1,3,4-thiadiazol-2-ylsulfanyl}-propionic acid ethyl ester as described for the preparation of [2-(3-cyclohexyl-3-phenethyl-ureido)-thiazol-5-ylsulfanyl]-acetic acid HPLC-MS: m/z=415

Example 65

3-{5-[3-(3-Methyl-butyl)-3-(4-trans-methyl-cyclohexyl)-ureido]-1,3,4-thiadiazol-2-yl}-propionic acid

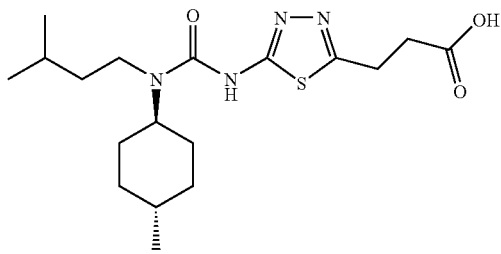

Prepared by hydrolysis of 3-{5-[3-(3-Methyl-butyl)-3-(4-trans-methyl-cyclohexyl)-ureido]-1,3,4-thiadiazol-2-yl}-propionic acid methyl ester as described for the preparation of [2-(3-cyclohexyl-3-phenethyl-ureido)-thiazol-5-ylsulfanyl]-acetic acid HPLC-MS: m/z=383

Example 66

{2-[3-(2-Benzyloxy-ethyl)-3-(4-trans-methyl-cyclohexyl)-ureido]-thiazol-5-ylsulfanyl}-acetic acid

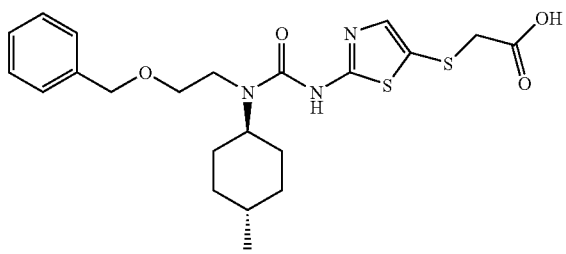

To a solution of 2-benzyloxyethanol (305 mg, 2.0 mmol) and DIPEA (0.69 mL, 4.0 mmol) in DCM (5 mL) cooled on an ice bath was added mesylchloride (0.19 mL, 2.5 mmol). The reaction mixture was stirred for 15 min before the ice bath was removed. After stirring for an additional 45 min the reaction mixture was washed with aqueous HCl (0.1 N, 5 mL). The aqueous phase was extracted with dichloromethane (2×5 mL) and the combined organic phases were dried (MgSO$_4$), filtered and concentrated in vacuo.

The residue was dissolved in acetonitrile (5 mL) before DIPEA (0.34 mL, 2.0 mmol) and 4-trans-methyl-cyclohexylamine (226 mg, 2.0 mmol) were added. The reaction mixture was refluxed for 18 hours before the volatiles were removed in vacuo.

The residue was dissolved in tetrahydrofuran (2 mL) and (2-amino-thiazol-5-ylsulfanyl)-acetic acid ethyl ester (655 mg, 3.0 mmol), carbonyl diimidazole (487 mg, 3.0 mmol) and 4-(dimethylamino)pyridine (12 mg, 0.1 mmol) were added. The reaction mixture was stirred for 2 hours before the volatiles were removed in vacuo.

The residue was dissolved in methanol (2.5 mL) and NaOH (2N, 5 mL, 10 mmol) was added. The mixture was stirred for 2 hours before HCl (1 mL, conc.) was added. The solvent was removed in vacuo before tetrahydrofuran, 5 mL) was added and the mixture was filtered. The filtrate was purified on a preparative HPLC to give 230 mg {2-[3-(2-benzyloxy-ethyl)-3-(4-trans-methyl-cyclohexyl)-ureido]-thiazol-5-ylsulfanyl}-acetic acid.

$^1$H NMR (400 MHz, DMSO-d$_6$) δ 7.41 (s, 1H), 7.35-7.23 (m, 5H), 4.53 (s, 2H), 3.92 (m, 1H), 3.57-3.44 (m, 6H), 1.73-1.45 (m, 6H), 1.35-1.25 (m, 1H), 1.10-0.95 (m, 1H), 0.86 (d, 3H)

HPLC-MS: m/z=465

Example 67

{2-[3-(2-isopropoxy-ethyl)-3-(4-trans-methyl-cyclohexyl)-ureido]-thiazol-5-ylsulfanyl}-acetic acid

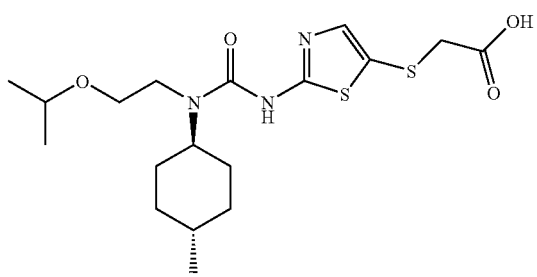

Prepared as described for the synthesis of {2-[3-(2-benzyloxy-ethyl)-3-(4-trans-methyl-cyclohexyl)-ureido]-thiazol-5-ylsulfanyl}-acetic acid using 2-isopropoxyethanol, 4-trans-methyl-cyclohexylamine and (2-amino-thiazol-5-ylsulfanyl)-acetic acid ethyl ester.

$^1$H NMR (400 MHz, DMSO-d$_6$) δ 7.40 (s, 1H), 4.0-3.84 (m, 1H), 3.70-3.20 (m, 7H), 1.80-0.93 (m, 18H) (with the following distinct signal: 1.12 (d, 6H)), 0.86 (d, 3H)

HPLC-MS: m/z=417

Example 68

{2-[3-(2-tert-Butoxy-ethyl)-3-(4-trans-methyl-cyclohexyl)-ureido]-thiazol-5-ylsulfanyl}-acetic acid

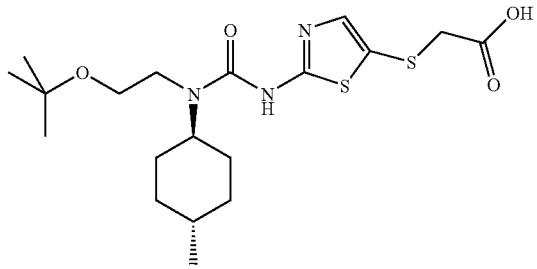

Prepared as described for the synthesis of {2-[3-(2-benzyloxy-ethyl)-3-(4-trans-methyl-cyclohexyl)-ureido]-thiazol-5-ylsulfanyl}-acetic acid using 2-tert-butoxyethanol, 4-trans-methyl-cyclohexylamine and (2-amino-thiazol-5-ylsulfanyl)-acetic acid ethyl ester.

$^1$H NMR (400 MHz, DMSO-d$_6$) δ 7.41 (s, 1H), 3.92 (t, 1H), 3.53-3.33 (m, 6H), 1.75-1.25 (m, 7H), 1.19 (s, 9H), 1.10-0.95 (m, 2H), 0.87 (d, 3H)

HPLC-MS: m/z=431

Example 69

{2-[3-(2-Cyclohexyloxy-ethyl)-3-(4-trans-methyl-cyclohexyl)-ureido]-thiazol-5-ylsulfanyl}-acetic acid

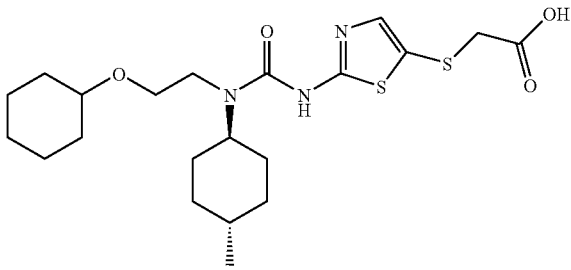

Prepared as described for the synthesis of {2-[3-(2-benzyloxy-ethyl)-3-(4-trans-methyl-cyclohexyl)-ureido]-thiazol-5-ylsulfanyl}-acetic acid using 2-cyclohexyloxyethanol, 4-trans-methyl-cyclohexylamine and (2-amino-thiazol-5-ylsulfanyl)-acetic acid ethyl ester.

HPLC-MS: m/z=457

Example 70

(2-{3-(4-trans-methyl-cyclohexyl)-3-[2-(2,2,2-trifluoro-1-trifluoromethyl-ethoxy)-ethyl]-ureido}-thiazol-5-ylsulfanyl)-acetic acid

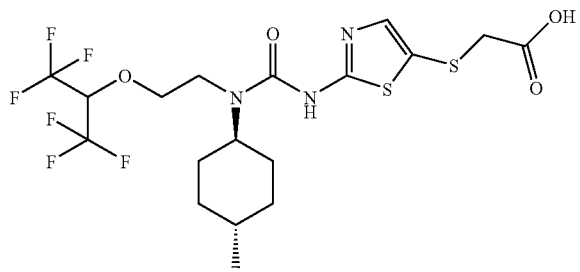

Prepared as described for the synthesis of {2-[3-(2-benzyloxy-ethyl)-3-(4-trans-methyl-cyclohexyl)-ureido]-thiazol-5-ylsulfanyl}-acetic acid using 2-(2,2,2-trifluoro-1-trifluoromethyl-ethoxy)-ethanol, 4-trans-methyl-cyclohexylamine and (2-amino-thiazol-5-ylsulfanyl)-acetic acid ethyl ester.

HPLC-MS: m/z=525

Example 71

{2-[3-(2-Ethoxy-ethyl)-3-(4-trans-methyl-cyclohexyl)-ureido]-thiazol-5-ylsulfanyl}-acetic acid

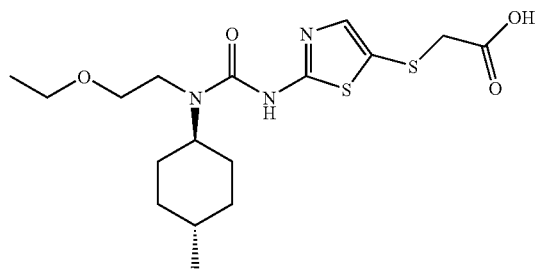

Prepared as described for the synthesis of {2-[3-(2-benzyloxy-ethyl)-3-(4-trans-methyl-cyclohexyl)-ureido]-thiazol-5-ylsulfanyl}-acetic acid using 2-ethoxyethanol, 4-trans-methyl-cyclohexylamine and (2-amino-thiazol-5-ylsulfanyl)-acetic acid ethyl ester.

HPLC-MS: m/z=403

Example 72

{2-[3-(2-Iso-butoxy-ethyl)-3-(4-trans-methyl-cyclohexyl)-ureido]-thiazol-5-ylsulfanyl}-acetic acid

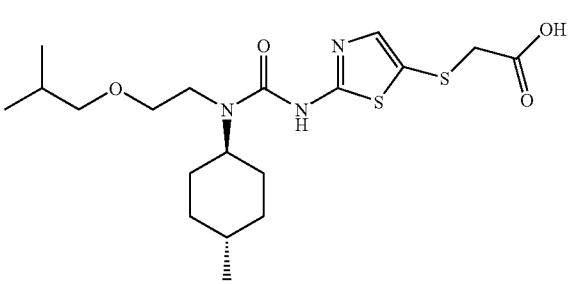

Prepared as described for the synthesis of {2-[3-(2-benzyloxy-ethyl)-3-(4-trans-methyl-cyclohexyl)-ureido]-thiazol-5-ylsulfanyl}-acetic acid using 2-isobutoxyethanol, 4-trans-methyl-cyclohexylamine and (2-amino-thiazol-5-ylsulfanyl)-acetic acid ethyl ester.

HPLC-MS: m/z=431

Example 73

(2-{3-(4-trans-methyl-cyclohexyl)-3-[2-(2,2,2-trifluoro-ethoxy)-ethyl]-ureido}-thiazol-5-ylsulfanyl)-acetic acid

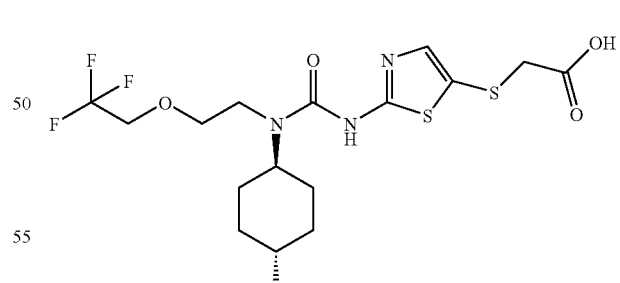

Prepared as described for the synthesis of {2-[3-(2-benzyloxy-ethyl)-3-(4-trans-methyl-cyclohexyl)-ureido]-thiazol-5-ylsulfanyl}-acetic acid using 2-(2,2,2-trifluoroethoxyethanol, 4-trans-methyl-cyclohexylamine and (2-amino-thiazol-5-ylsulfanyl)-acetic acid ethyl ester.

HPLC-MS: m/z=457

Example 74

{2-[3-(3-Methoxy-3-methyl-butyl)-3-(4-trans-methyl-cyclohexyl)-ureido]-thiazol-5-ylsulfanyl}-acetic acid

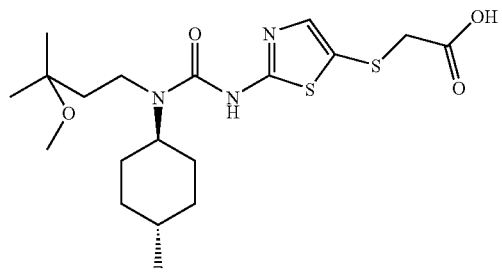

Prepared as described for the synthesis of {2-[3-(2-benzyloxy-ethyl)-3-(4-trans-methyl-cyclohexyl)-ureido]-thiazol-5-ylsulfanyl}-acetic acid using 3-methoxy-3-methylbutan-1-ol, 4-trans-methyl-cyclohexylamine and (2-amino-thiazol-5-ylsulfanyl)-acetic acid ethyl ester.

$^1$H NMR (400 MHz, DMSO-d$_6$) δ 7.41 (s, 1H), 4.04-3.91 (m, 1H), 3.47 (s, 2H), 3.47-3.27 (m, 4H), 3.26-3.16 (m, 3H), 1.75-0.95 (m, 15H), (with following distinct signal: 1.13 (s, 6H)), 0.87 (d, 3H)

HPLC-MS: m/z=431

Example 75

3-{2-[3-(2-Benzyloxy-ethyl)-3-(4-trans-methyl-cyclohexyl)-ureido]-thiazol-5-ylsulfanyl}-propionic acid

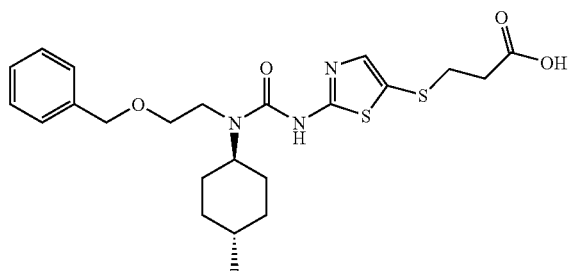

Prepared as described for the synthesis of {2-[3-(2-benzyloxy-ethyl)-3-(4-trans-methyl-cyclohexyl)-ureido]-thiazol-5-ylsulfanyl}-acetic acid using 2-benzyloxyethanol, 4-trans-methyl-cyclohexylamine and (2-amino-thiazol-5-ylsulfanyl)-propionic acid ethyl ester HPLC-MS: m/z=479

Example 76

3-{2-[3-(2-Iso-propoxy-ethyl)-3-(4-trans-methyl-cyclohexyl)-ureido]-thiazol-5-ylsulfanyl}-propionic acid

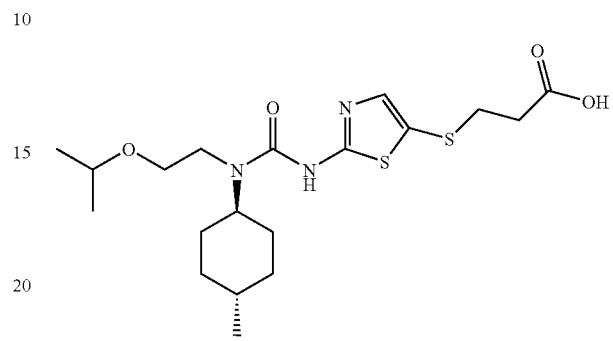

Prepared as described for the synthesis of {2-[3-(2-benzyloxy-ethyl)-3-(4-trans-methyl-cyclohexyl)-ureido]-thiazol-5-ylsulfanyl}-acetic acid using 2-iso-propoxyethanol, 4-trans-methyl-cyclohexylamine and (2-amino-thiazol-5-ylsulfanyl)-propionic acid ethyl ester.

HPLC-MS: m/z=431

Example 77

3-{2-[3-(2-tert-Butoxy-ethyl)-3-(4-trans-methyl-cyclohexyl)-ureido]-thiazol-5-ylsulfanyl}-propionic acid

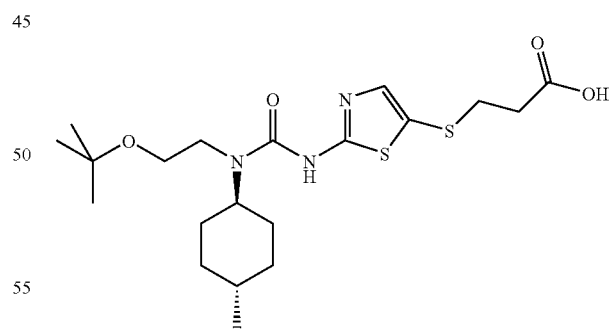

Prepared as described for the synthesis of {2-[3-(2-benzyloxy-ethyl)-3-(4-trans-methyl-cyclohexyl)-ureido]-thiazol-5-ylsulfanyl}-acetic acid using 2-tert-butoxyethanol, 4-trans-methyl-cyclohexylamine and (2-amino-thiazol-5-ylsulfanyl)-propionic acid ethyl ester.

HPLC-MS: m/z=445

Example 78

3-{2-[3-(2-Cyclohexyloxy-ethyl)-3-(4-trans-methyl-cyclohexyl)-ureido]-thiazol-5-ylsulfanyl}-propionic acid

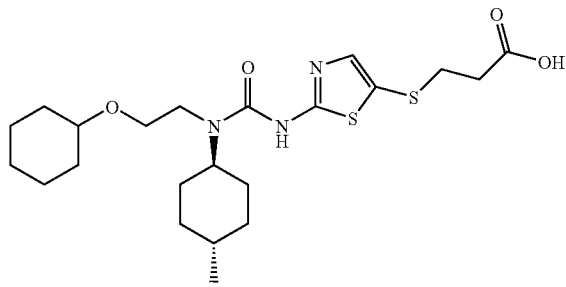

Prepared as described for the synthesis of {2-[3-(2-benzyloxy-ethyl)-3-(4-trans-methyl-cyclohexyl)-ureido]-thiazol-5-ylsulfanyl}-acetic acid using 2-cyclohexyloxyethanol, 4-trans-methyl-cyclohexylamine and (2-amino-thiazol-5-ylsulfanyl)-propionic acid ethyl ester.

HPLC-MS: m/z=471

Example 79

3-(2-{3-(4-trans-methyl-cyclohexyl)-3-[2-(2,2,2-trifluoro-1-trifluoromethyl-ethoxy)-ethyl]-ureido}-thiazol-5-ylsulfanyl)-propionic acid

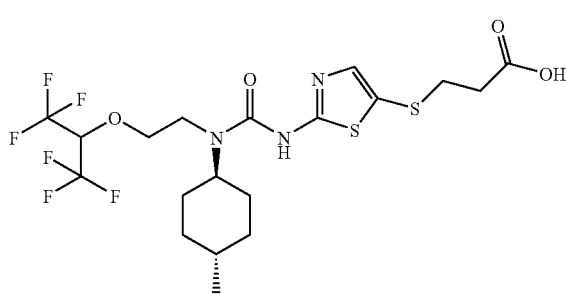

Prepared as described for the synthesis of {2-[3-(2-benzyloxy-ethyl)-3-(4-trans-methyl-cyclohexyl)-ureido]-thiazol-5-ylsulfanyl}-acetic acid using 2-(2,2,2-Trifluoro-1-trifluoromethyl-ethoxy)-ethanol, 4-trans-methyl-cyclohexylamine and (2-amino-thiazol-5-ylsulfanyl)-propionic acid ethyl ester.

HPLC-MS: m/z=539

Example 80

3-{2-[3-(2-Iso-butoxy-ethyl)-3-(4-trans-methyl-cyclohexyl)-ureido]-thiazol-5-ylsulfanyl}-propionic acid

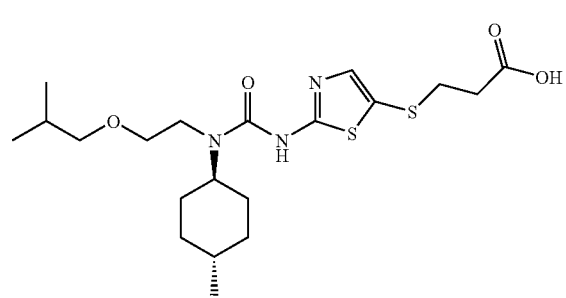

Prepared as described for the synthesis of {2-[3-(2-benzyloxy-ethyl)-3-(4-trans-methyl-cyclohexyl)-ureido]-thiazol-5-ylsulfanyl}-acetic acid using 2-isobutoxyethanol, 4-trans-methyl-cyclohexylamine and (2-amino-thiazol-5-ylsulfanyl)-propionic acid ethyl ester.

HPLC-MS: m/z=444

Example 81

3-(2-{3-(4-trans-methyl-cyclohexyl)-3-[2-(2,2,2-trifluoro-ethoxy)-ethyl]-ureido}-thiazol-5-ylsulfanyl)-propionic acid

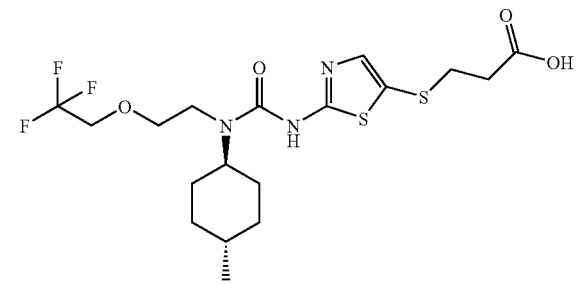

Prepared as described for the synthesis of {2-[3-(2-benzyloxy-ethyl)-3-(4-trans-methyl-cyclohexyl)-ureido]-thiazol-5-ylsulfanyl}-acetic acid using 2-(2,2,2-trifluoroethoxyethanol, 4-trans-methyl-cyclohexylamine and (2-amino-thiazol-5-ylsulfanyl)-propionic acid ethyl ester.

HPLC-MS: m/z=471

Example 82

3-{2-[3-(3-Methoxy-3-methyl-butyl)-3-(4-trans-methyl-cyclohexyl)-ureido]-thiazol-5-ylsulfanyl}-propionic acid

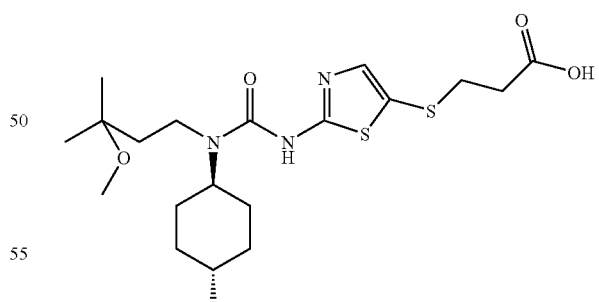

Prepared as described for the synthesis of {2-[3-(2-benzyloxy-ethyl)-3-(4-trans-methyl-cyclohexyl)-ureido]-thiazol-5-ylsulfanyl}-acetic acid using 3-methoxy-3-methylbutan-1-ol, 4-trans-methyl-cyclohexylamine and (2-amino-thiazol-5-ylsulfanyl)-propionic acid ethyl ester.

HPLC-MS: m/z=445

Example 83

{2-[3-(4-trans-methyl-cyclohexyl)-3-(2-phenoxy-ethyl)-ureido]-thiazol-5-ylsulfanyl}-acetic acid

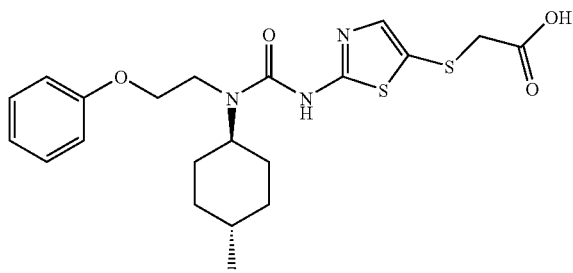

Prepared as described for the synthesis of {2-[3-(2-benzyloxy-ethyl)-3-(4-trans-methyl-cyclohexyl)-ureido]-thiazol-5-ylsulfanyl}-acetic acid using 2-phenoxyethanol, 4-trans-methyl-cyclohexylamine and (2-amino-thiazol-5-ylsulfanyl)-acetic acid ethyl ester.

HPLC-MS: m/z=451

Example 84

{2-[3-(3-Ethoxy-propyl)-3-(4-trans-methyl-cyclohexyl)-ureido]-thiazol-5-ylsulfanyl}-acetic acid

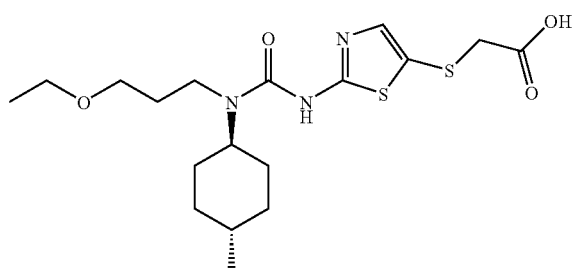

Prepared as described for the synthesis of {2-[3-(2-benzyloxy-ethyl)-3-(4-trans-methyl-cyclohexyl)-ureido]-thiazol-5-ylsulfanyl}-acetic acid using 3-ethoxypropanol, 4-trans-methyl-cyclohexylamine and (2-amino-thiazol-5-ylsulfanyl)-acetic acid ethyl ester.

HPLC-MS: m/z=417

Example 85

{2-[3-(3-Methoxy-butyl)-3-(4-trans-methyl-cyclohexyl)-ureido]-thiazol-5-ylsulfanyl}-acetic acid

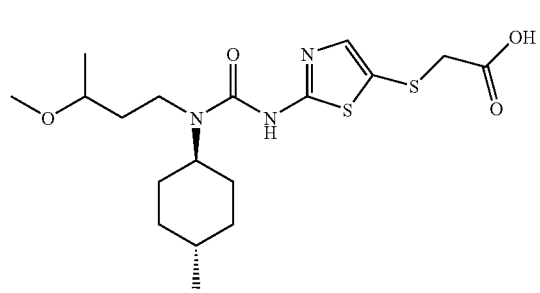

Prepared as described for the synthesis of {2-[3-(2-benzyloxy-ethyl)-3-(4-trans-methyl-cyclohexyl)-ureido]-thiazol-5-ylsulfanyl}-acetic acid using 3-methoxy-butan-1-ol, 4-trans-methyl-cyclohexylamine and (2-amino-thiazol-5-ylsulfanyl)-acetic acid ethyl ester.

HPLC-MS: m/z=417

Example 86

{2-[3-(3-Benzyloxy-propyl)-3-(4-trans-methyl-cyclohexyl)-ureido]-thiazol-5-ylsulfanyl}-acetic acid

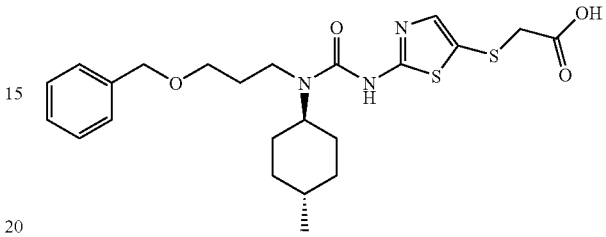

Prepared as described for the synthesis of {2-[3-(2-benzyloxy-ethyl)-3-(4-trans-methyl-cyclohexyl)-ureido]-thiazol-5-ylsulfanyl}-acetic acid using 3-benzyloxypropanol, 4-trans-methyl-cyclohexylamine and (2-amino-thiazol-5-ylsulfanyl)-acetic acid ethyl ester.

HPLC-MS: m/z=479

Example 87

3-{2-[3-(4-trans-methyl-cyclohexyl)-3-(2-phenoxy-ethyl)-ureido]-thiazol-5-ylsulfanyl}-propionic acid

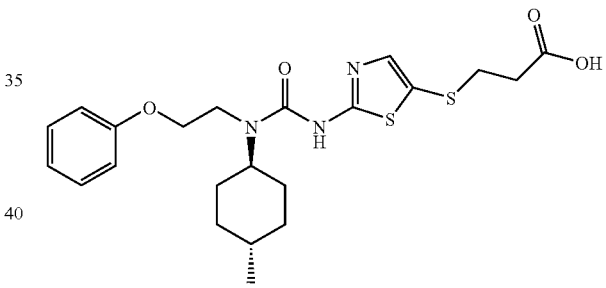

Prepared as described for the synthesis of {2-[3-(2-benzyloxy-ethyl)-3-(4-trans-methyl-cyclohexyl)-ureido]-thiazol-5-ylsulfanyl}-acetic acid using 2-phenoxyethanol, 4-trans-methyl-cyclohexylamine and (2-amino-thiazol-5-ylsulfanyl)-propionic acid ethyl ester.

HPLC-MS: m/z=465

Example 88

3-{2-[3-(3-Ethoxy-propyl)-3-(4-trans-methyl-cyclohexyl)-ureido]-thiazol-5-ylsulfanyl}-propionic acid

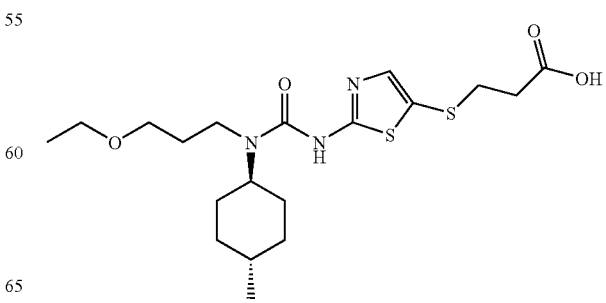

Prepared as described for the synthesis of {2-[3-(2-benzyloxy-ethyl)-3-(4-trans-methyl-cyclohexyl)-ureido]-thiazol-5-ylsulfanyl}-acetic acid using 2-ethoxypropanol, 4-trans-methyl-cyclohexylamine and (2-amino-thiazol-5-ylsulfanyl)-propionic acid ethyl ester.

HPLC-MS: m/z=431

Example 89

{2-[3-(2-Benzyloxy-1-methyl-ethyl)-3-(4-trans-methyl-cyclohexyl)-ureido]-thiazol-5-ylsulfanyl}-acetic acid

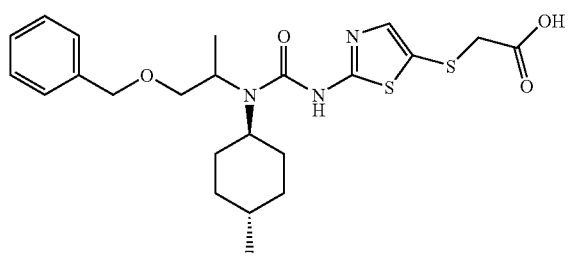

Benzyloxyacetone (0.50 g, 3.0 mmol) and 4-trans-methyl-cyclohexylamine (0.313 g, 2.79 mmol) in THF-MeOH (50 mL, 2:1) and AcOH (5 mL) was added sodium cyanoborohydride (0.26 g, 4.15 mmol) in small portions over 15 min. The reaction mixture was stirred for 16 hours before the solvent was removed in vacuo. The residue was divided between Et$_2$O (150 mL) and aqueous NaOH (10 M, 50 mL). The aqueous phase was extracted twice with Et$_2$O (100 mL), and the combined organic extracts were dried (MgSO$_4$), filtered and dried in vacuo to give (2-benzyloxy-1-methyl-ethyl)-(4-trans-methyl-cyclohexyl)-amine.

{2-[3-(2-Benzyloxy-1-methyl-ethyl)-3-(4-trans-methyl-cyclohexyl)-ureido]-thiazol-5-ylsulfanyl}-acetic acid was then prepared using the procedure described for the synthesis of [2-(3-cyclohexyl-3-phenethyl-ureido)-thiazol-5-ylsulfanyl]-acetic acid from (2-benzyloxy-1-methyl-ethyl)-(4-trans-methyl-cyclohexyl)-amine and (2-amino-thiazol-5-ylsulfanyl)-acetic acid ethyl ester.

$^1$H NMR (400 MHz, DMSO-d$_6$) δ 7.40 (s, 1H), 7.37-7.22 m, 5H), 4.5 (s, 2H), 4.0-3.4 (m, 4H), 1.90-1.48 (m, 6H), 1.39-1.22 (m, 4H), 1.15-0.97 (2H), 0.87 (d, 3H)

HPLC-MS: m/z=478

Example 90

{2-[3-(4-trans-methyl-cyclohexyl)-3-(3-phenoxy-propyl)-ureido]-thiazol-5-ylsulfanyl}-acetic acid

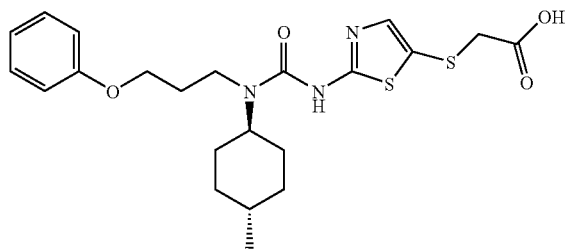

Prepared as described for the synthesis of {2-[3-(2-benzyloxy-ethyl)-3-(4-trans-methyl-cyclohexyl)-ureido]-thiazol-5-ylsulfanyl}-acetic acid using 3-phenoxypropanol, 4-trans-methyl-cyclohexylamine and (2-amino-thiazol-5-ylsulfanyl)-acetic acid ethyl ester.

HPLC-MS: m/z=464

Example 91

3-{2-[3-(2-Benzyloxy-1-methyl-ethyl)-3-(4-trans-methyl-cyclohexyl)-ureido]-thiazol-5-ylsulfanyl}-propionic acid

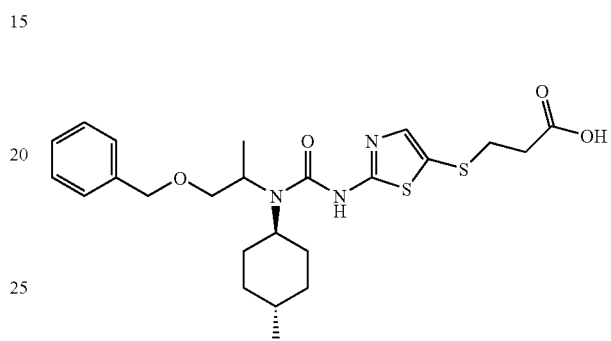

Prepared as described for the synthesis of {2-[3-(2-benzyloxy-1-methyl-ethyl)-3-(4-trans-methyl-cyclohexyl)-ureido]-thiazol-5-ylsulfanyl}-acetic acid using benzyloacetone, 4-trans-methyl-cyclohexylamine and (2-amino-thiazol-5-ylsulfanyl)-propionic acid ethyl ester.

HPLC-MS: m/z=492

Example 92

3-{2-[3-(4-trans-methyl-cyclohexyl)-3-(3-phenoxy-propyl)-ureido]-thiazol-5-ylsulfanyl}-propionic acid

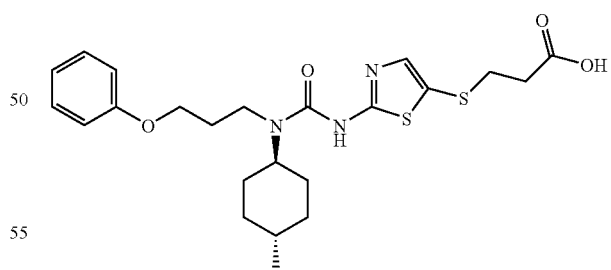

Prepared as described for the synthesis of {2-[3-(2-benzyloxy-ethyl)-3-(4-trans-methyl-cyclohexyl)-ureido]-thiazol-5-ylsulfanyl}-acetic acid using 3-phenoxypropanol, 4-trans-methyl-cyclohexylamine and (2-amino-thiazol-5-ylsulfanyl)-propionic acid ethyl ester.

HPLC-MS: m/z=478

Example 93

{2-[3-[2-(2-Chloro-phenyl)-ethyl]-3-(4-trans-methyl-cyclohexyl)-ureido]-thiazol-5-ylsulfanyl}-acetic acid

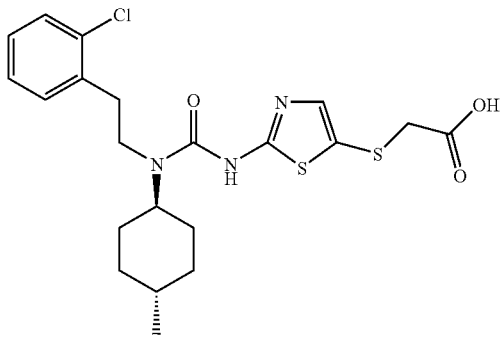

Prepared as described for the synthesis of {2-[3-(2-benzyloxy-ethyl)-3-(4-trans-methyl-cyclohexyl)-ureido]-thiazol-5-ylsulfanyl}-acetic acid using 2-(2-chloro-phenyl)-ethanol, 4-trans-methyl-cyclohexylamine and (2-amino-thiazol-5-yl-sulfanyl)-acetic acid ethyl ester.

$^1$H NMR (400 MHz, DMSO-d$_6$) δ 7.46-7.22 (m, 5H), 4.05-3.92 (m, 1H), 3.50 (s, 2H), 3.49-3.30 (m, 2H), 3.93 (t, 2H), 1.72-1.62 (m, 2H), 1.60-1.44 (m, 4H), 1.38-1.22 (m, 1H), 1.12-1.00 (m, 2H), 0.87 (d, 3H)

HPLC-MS: m/z=468

Example 94

{2-[3-[2-(3-Chloro-phenyl)-ethyl]-3-(4-trans-methyl-cyclohexyl)-ureido]-thiazol-5-ylsulfanyl}-acetic acid

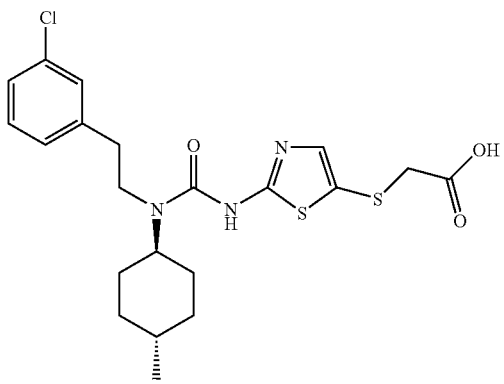

Prepared as described for the synthesis of {2-[3-(2-benzyloxy-ethyl)-3-(4-trans-methyl-cyclohexyl)-ureido]-thiazol-5-ylsulfanyl}-acetic acid using 2-(3-chloro-phenyl)-ethanol, 4-trans-methyl-cyclohexylamine and (2-amino-thiazol-5-yl-sulfanyl)-acetic acid ethyl ester.

$^1$H NMR (400 MHz, DMSO-d$_6$) δ 7.43 (s, 1H), 7.42-7.22 (m, 4H), 4.05-3.95 (m, 1H), 3.50 (s, 2H), 3.49-3.30 (m, 2H), 2.79 (t, 2H), 1.75-1.55 (m, 2H), 1.63-1.50 (m, 4H), 1.15-1.00 (m, 2H), 0.88 (d, 3H)

HPLC-MS: m/z=468

Example 95

{2-[3-[2-(4-Chloro-phenyl)-ethyl]-3-(4-trans-methyl-cyclohexyl)-ureido]-thiazol-5-ylsulfanyl}-acetic acid

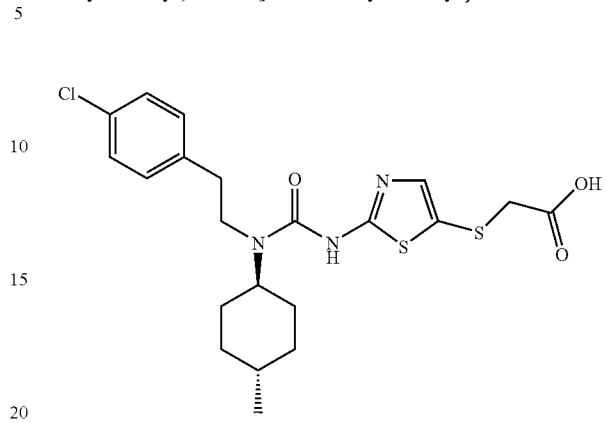

Prepared as described for the synthesis of {2-[3-(2-benzyloxy-ethyl)-3-(4-trans-methyl-cyclohexyl)-ureido]-thiazol-5-ylsulfanyl}-acetic acid using 2-(4-chloro-phenyl)-ethanol, 4-trans-methyl-cyclohexylamine and (2-amino-thiazol-5-yl-sulfanyl)-acetic acid ethyl ester.

$^1$H NMR (400 MHz, DMSO-d$_6$) δ 7.43 (s, 1H), 7.38-7.28 (m, 4H), 4.07-3.92 (m, 1H), 3.50 (s, 2H), 3.46-3.35 (m, 2H), 2.79 (t, 2H), 1.72-1.65 8M, 2H), 1.60-1.50 (m, 4H), 1.40-1.28 (m, 1H), 1.12-0.90 (m, 2H) 0.87 (d, 3H)

HPLC-MS: m/z=469

Example 96

{2-[3-[2-(2-Methoxy-phenyl)-ethyl]-3-(4-trans-methyl-cyclohexyl)-ureido]-thiazol-5-ylsulfanyl}-acetic acid

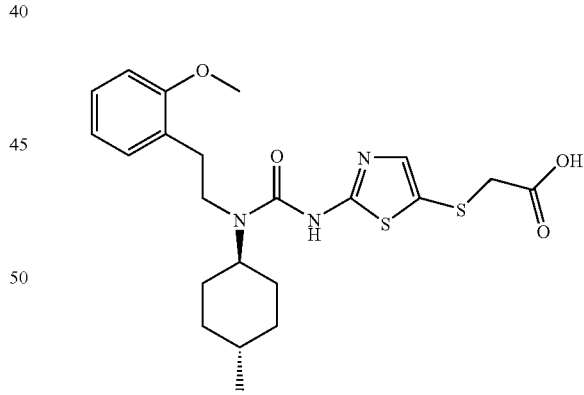

Prepared as described for the synthesis of {2-[3-(2-benzyloxy-ethyl)-3-(4-trans-methyl-cyclohexyl)-ureido]-thiazol-5-ylsulfanyl}-acetic acid using 2-(2-methoxy-phenyl)-ethanol, 4-trans-methyl-cyclohexylamine and (2-amino-thiazol-5-ylsulfanyl)-acetic acid ethyl ester.

$^1$H NMR (400 MHz, DMSO-d$_6$) δ 7.45 (s, 1H), 7.28-7.18 (m, 2H), 7.01-6.98 (m, 1H), 6.92-6.85 (m, 1H), 4.08-3.93 (m, 1H), 3.89 (s, 3H), 3.50 (s, 2H), 3.40-3.30 (m, 2H), 2.80-2.74 (m, 2H), 1.73-1.68 (m, 2H), 1.62-1.52 (m, 4H), 1.40-1.25 (m, 1H), 1.12-1.00 (m, 2H), 0.89 (d, 3H)

HPLC-MS: m/z=464

Example 97

{2-[3-[2-(3-Methoxy-phenyl)-ethyl]-3-(4-trans-methyl-cyclohexyl)-ureido]-thiazol-5-ylsulfanyl}-acetic acid

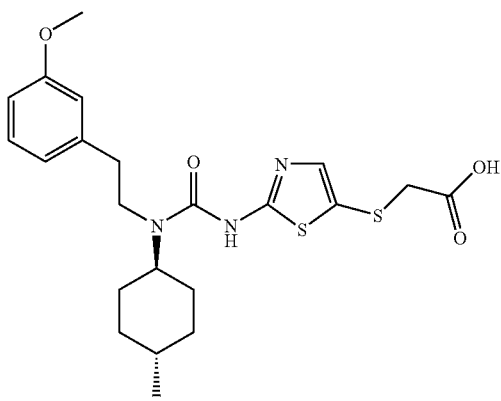

Prepared as described for the synthesis of {2-[3-(2-benzyloxy-ethyl)-3-(4-trans-methyl-cyclohexyl)-ureido]-thiazol-5-ylsulfanyl}-acetic acid using 2-(3-methoxy-phenyl)-ethanol, 4-trans-methyl-cyclohexylamine and (2-amino-thiazol-5-ylsulfanyl)-acetic acid ethyl ester.

$^1$H NMR (400 MHz, CDCl$_3$) δ 7.29-7.19 (m, 2H), 6.90-6.82 (m, 2H), 6.79-6.72 (m, 1H), 3.80 (s, 3H), 3.57-3.45 (m, 2H), 3.32 (s, 2H), 2.92-2.83 (m, 2H), 1.87-1.73 (m, 4H), 1.62-1.48 (m, 2H), 1.42-1.29 (m, 1H), 1.28-1.09 (m, 2H), 0.92 (d, 3H)

HPLC-MS: m/z=464

Example 98

{2-[3-[2-(4-Methoxy-phenyl)-ethyl]-3-(4-trans-methyl-cyclohexyl)-ureido]-thiazol-5-ylsulfanyl}-acetic acid

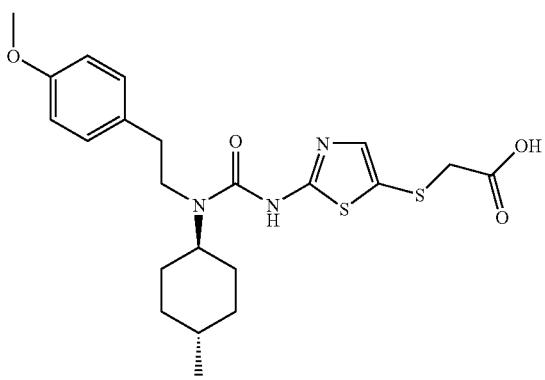

Prepared as described for the synthesis of {2-[3-(2-benzyloxy-ethyl)-3-(4-trans-methyl-cyclohexyl)-ureido]-thiazol-5-ylsulfanyl}-acetic acid using 2-(4-methoxy-phenyl)-ethanol, 4-trans-methyl-cyclohexylamine and (2-amino-thiazol-5-ylsulfanyl)-acetic acid ethyl ester.

$^1$H NMR (400 MHz, CDCl$_3$) δ 7.38 (s, 1H), 7.22 (d, 2H), 6.83 (d, 2H), 4.20-3.90 (m, 1H), 3.79 (s, 3H), 3.55-3.42 (m, 2H), 3.38 (s, 2H), 2.90-2.80 (m, 2H), 1.85-1.72 (m, 4H), 1.62-1.48 (m, 2H), 1.40-1.05 (m, 3H), 0.92 (d, 3H)

HPLC-MS: m/z=464

Example 99

(2-{3-(4-trans-methyl-cyclohexyl)-3-[2-(1-phenyl-ethoxy)-ethyl]-ureido}-thiazol-5-ylsulfanyl)-acetic acid

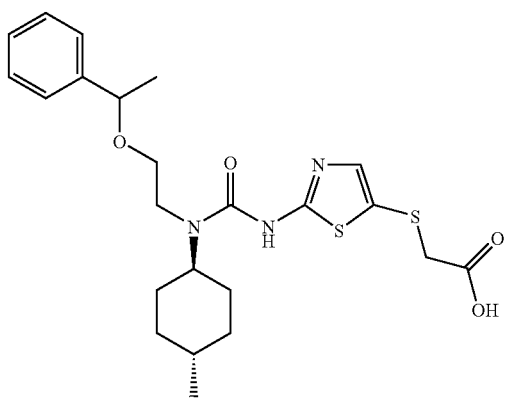

Prepared as described for the synthesis of {2-[3-(2-benzyloxy-ethyl)-3-(4-trans-methyl-cyclohexyl)-ureido]-thiazol-5-ylsulfanyl}-acetic acid using 2-(1-phenyl-ethoxy)-ethanol, 4-trans-methyl-cyclohexylamine and (2-amino-thiazol-5-ylsulfanyl)-acetic acid ethyl ester.

$^1$H NMR (400 MHz, CDCl$_3$) δ 7.39 (s, 1H), 7.37-7.22 (m, 4H), 4.43 (q, 1H), 4.20-4.00 (m, 1H), 3.50-3.40 (m, 4H), 3.38 (s, 2H), 1.78-1.56 (m, 4H), 1.48 (d, 3H) 1.43-1.00 (m, 5H), 0.87 (d, 3H)

HPLC-MS: m/z=478

Example 100

(2-{3-(4-trans-methyl-cyclohexyl)-3-[2-(2-trifluoromethylsulfanyl-benzyloxy)-ethyl]-ureido}-thiazol-5-ylsulfanyl)-acetic acid

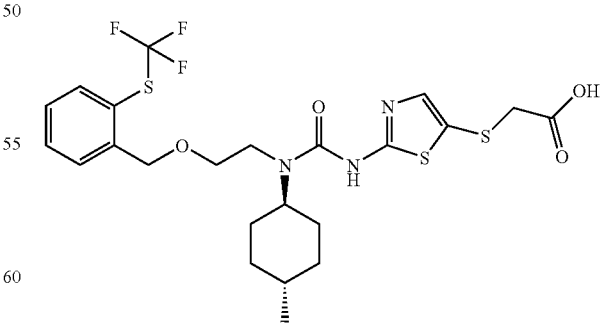

Prepared as described for the synthesis of {2-[3-[2-(4-fluoro-2-trifluoromethyl-benzyloxy)-ethyl]-3-(4-trans-methyl-cyclohexyl)-ureido]-thiazol-5-ylsulfanyl}-acetic acid using 2-trifluoromethylthio-benzylbromide, (2-hydroxyethyl)-(4-trans-methyl-cyclohexyl)-carbamic acid tert-butyl ester and (2-amino-thiazol-5-ylsulfanyl)-acetic acid ethyl ester.

¹H NMR (400 MHz, DMSO-d₆) δ 7.73-7.68 (m, 1H), 7.65-7.61 (m, 1H), 7.59-7.53 (m, 1H), 7.49-7.43 (m, 1H), 7.39 (s, 1H), 4.72 (s, 2H), 3.99-3.87 (m, 1H), 3.63-3.57 (m, 2H), 3.54-3.47 (m, 2H), 3.48 (s, 2H), 1.71-1.46 (m, 6H), 1.36-1.23 (m, 1H), 1.10-0.96 (m, 2H), 0.86 (d, 3H)

HPLC-MS: m/z=564

Example 101

{2-[3-[2-(2-Cyano-benzyloxy)-ethyl]-3-(4-trans-methyl-cyclohexyl)-ureido]-thiazol-5-ylsulfanyl}-acetic acid

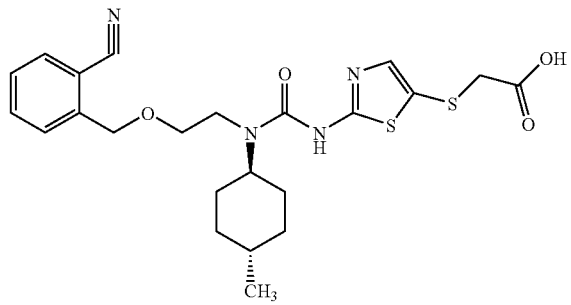

Prepared as described for the synthesis of {2-[3-[2-(4-fluoro-2-trifluoromethyl-benzyloxy)-ethyl]-3-(4-trans-methyl-cyclohexyl)-ureido]-thiazol-5-ylsulfanyl}-acetic acid using 2-cyano-benzylbromide, (2-hydroxy-ethyl)-(4-trans-methyl-cyclohexyl)-carbamic acid tert-butyl ester and (2-amino-thiazol-5-ylsulfanyl)-acetic acid ethyl ester.

¹H NMR (400 MHz, DMSO-d₆) δ 7.85-7.81 (m, 1H), 7.70-7.59 (m, 2H), 7.53-7.46 (m, 1H), 7.39 (s, 1H), 4.69 (s, 2H), 3.99-3.87 (m, 1H), 3.65-3.58 (m, 2H), 3.54-3.46 (m, 2H), 3.48 (s, 2H), 1.72-1.46 (m, 6H), 1.36-1.23 (m, 1H), 1.10-0.95 (m, 2H), 0.86 (d, 3H)

HPLC-MS: m/z=489

Example 102

{2-[3-[2-(4-Fluoro-2-trifluoromethyl-benzyloxy)-ethyl]-3-(4-trans-methyl-cyclohexyl)-ureido]-thiazol-5-ylsulfanyl}-acetic acid

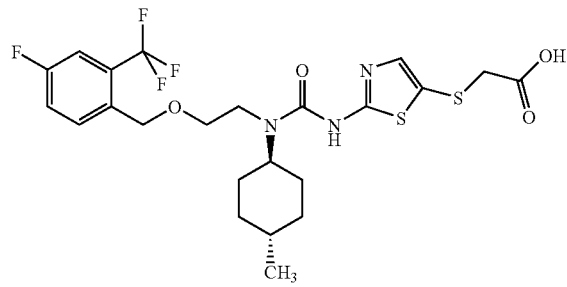

A refluxing solution of 4-trans-methyl-cyclohexylamine hydrochloride (13.9 g, 93 mmol) and potassium carbonate (25.6 g, 186 mmol) in acetonitrile (100 mL) was added a solution of 2-(benzyloxy)-ethylbromide (20 g, 93 mmol) in acetonitrile (50 mL) over the course of 30 min. The mixture was refluxed for 2 hours before it was allowed to reach room temperature whereupon a solution of di-tert-butyl-dicarbonate (1M, THF, 93 mL) was added. The reaction mixture was stirred at room temperature for 18 hours before the volatiles were removed in vacuo. The residue was dissolved in diethyl ether (150 mL) and washed with water (2×100 mL), dried (MgSO₄), filtered and concentrated in vacuo. The residue was purified by flash chromatography (SiO₂, heptane to 10% EtOAc in heptane) to give 23.7 g of (2-benzyloxy-ethyl)-(4-trans-methyl-cyclohexyl)-carbamic acid tert-butyl ester.

This was dissolved in abs. ethanol (250 mL) and Pd/C (10%, 2.0 g) was added. The reaction mixture was stirred under H₂ at room temperature for 4 hours before it was filtered through a pad of Celite and subsequently concentrated in vacuo to give 17.5 g of (2-hydroxy-ethyl)-(4-trans-methyl-cyclohexyl)-carbamic acid tert-butyl ester.

(2-hydroxy-ethyl)-(4-trans-methyl-cyclohexyl)-carbamic acid tert-butyl ester (500 mg, 1.94 mmol) and 4-fluoro-2-trifluoromethyl-benzylbromide (500 mg, 2.33 mmol) in DMF (10 mL) was added NaH (60% in mineral oil, 155 mg, 3.89 mmol) and the reaction mixture was stirred for 2 hours at room temperature. The reaction mixture was divided (caution!) between hexane (50 mL) and water (50 mL). The aqueous phase was extracted twice with hexane (50 mL) and the combined organic fractions were dried (MgSO₄) and concentrated in vacuo. The residue was stirred in a mixture of dichloromethane (5 mL) and trifluoroacetic acid (5 mL) for 2 hours before the volatiles were removed in vacuo. The residue was purified by prep. HPLC to give 500 mg of [2-(4-fluoro-2-trifluoromethyl-benzyloxy)-ethyl]-(4-trans-methyl-cyclohexyl)-amine.

{2-[3-[2-(4-fluoro-2-trifluoromethyl-benzyloxy)-ethyl]-3-(4-trans-methyl-cyclohexyl)-ureido]-thiazol-5-ylsulfanyl}-acetic acid was prepared as described for the synthesis of [2-(3-cyclohexyl-3-phenethyl-ureido)-thiazol-5-ylsulfanyl]-acetic acid from [2-(4-fluoro-2-trifluoromethyl-benzyloxy)-ethyl]-(4-trans-methyl-cyclohexyl)-amine and 5-amino-[1,3,4]thiadiazole-2-carboxylic acid ethyl ester.

¹H NMR (400 MHz, DMSO-d₆) δ 7.78-7.22 (m, 1H), 7.65-7.59 (m, 1H), 7.55-7.48 (m, 1H), 7.40 (s, 1H), 4.65 (s, 2H), 4.00-3.87 (m, 1H), 3.62-3.55 (m, 2H), 3.54-3.48 (m, 2H), 3.48 (s, 2H), 1.72-1.45 (m, 6H), 1.38-1.18 (m, 1H), 1.10-0.95 (m, 2H), 0.87 (d, 3H)

HPLC-MS: m/z=550

Example 103

{2-[3-[2-(4-Fluoro-phenyl)-ethyl]-3-(4-trans-methyl-cyclohexyl)-ureido]-thiazol-5-ylsulfanyl}-acetic acid

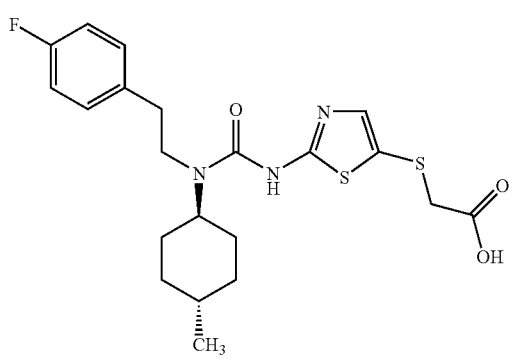

Prepared as described for the synthesis of {2-[3-(2-benzyloxy-ethyl)-3-(4-trans-methyl-cyclohexyl)-ureido]-thiazol-5-ylsulfanyl}-acetic acid using 2-(4-fluoro-phenyl)-ethanol, 4-trans-methyl-cyclohexylamine and (2-amino-thiazol-5-ylsulfanyl)-acetic acid ethyl ester.

$^1$H NMR (400 MHz, CDCl$_3$) δ 7.28-7.22 (m, 3H), 7.02-6.95 (m, 2H), 4.15-3.80 (m, 1H), 3.52-3.40 (m, 2H), 3.33 (s, 2H), 2.92-2.83 (m, 2H), 1.83-1.72 (m, 4H), 1.60-1.43 (m, 2H), 1.43-1.10 (m, 3H), 0.92 (d, 3H)

HPLC-MS: m/z=452

Example 104

{2-[3-[2-(2-Fluoro-6-trifluoromethyl-benzyloxy)-ethyl]-3-(4-trans-methyl-cyclohexyl)-ureido]-thiazol-5-ylsulfanyl}-acetic acid

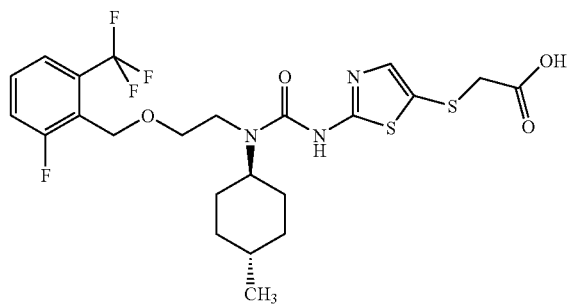

Prepared as described for the synthesis of {2-[3-[2-(4-fluoro-2-trifluoromethyl-benzyloxy)-ethyl]-3-(4-trans-methyl-cyclohexyl)-ureido]-thiazol-5-ylsulfanyl}-acetic acid using 2-fluoro-6-trifluoromethyl-benzylbromide, (2-hydroxy-ethyl)-(4-trans-methyl-cyclohexyl)-carbamic acid tert-butyl ester and (2-amino-thiazol-5-ylsulfanyl)-acetic acid ethyl ester.

HPLC-MS: m/z=550

Example 105

{2-[3-(4-trans-methyl-cyclohexyl)-3-(2-phenyl-propyl)-ureido]-thiazol-5-ylsulfanyl}-acetic acid

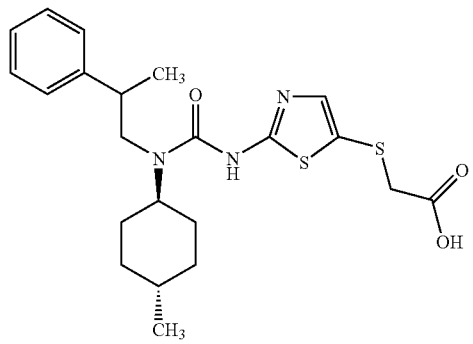

Prepared as described for the synthesis of {2-[3-(2-benzyloxy-ethyl)-3-(4-trans-methyl-cyclohexyl)-ureido]-thiazol-5-ylsulfanyl}-acetic acid using 2-phenyl-propan-1-ol, 4-trans-methyl-cyclohexylamine and (2-amino-thiazol-5-ylsulfanyl)-acetic acid ethyl ester.

$^1$H NMR (400 MHz, CDCl$_3$) δ 7.32-7.12 (m, 6H), 3.85-3.70 (m, 1H), 3.65-3.55 (m, 1H), 3.35 (s, 2H), 3.30-3.08 (m, 2H), 1.80-1.00 (m, 12H, with following distinct signal; 1.31 (d, 3H)), 0.88 (d, 3H)

HPLC-MS: m/z=448

Example 106

{2-[3-[2-(2-Chloro-4-fluoro-benzyloxy)-ethyl]-3-(4-trans-methyl-cyclohexyl)-ureido]-thiazol-5-ylsulfanyl}-acetic acid

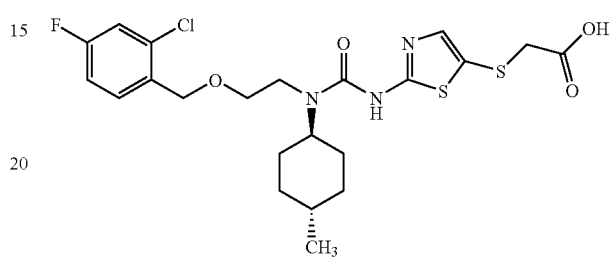

Prepared as described for the synthesis of {2-[3-[2-(4-fluoro-2-trifluoromethyl-benzyloxy)-ethyl]-3-(4-trans-methyl-cyclohexyl)-ureido]-thiazol-5-ylsulfanyl}-acetic acid using 2-chloro-4-fluoro-benzylbromide, (2-hydroxy-ethyl)-(4-trans-methyl-cyclohexyl)-carbamic acid tert-butyl ester and (2-amino-thiazol-5-ylsulfanyl)-acetic acid ethyl ester.

$^1$H NMR (400 MHz, DMSO-d$_6$) δ 7.83-7.76 (m, 1H), 7.71-7.67 (m, 1H), 7.65 (s, 1H), 7.48-7.40 (m, 1H), 4.82 (s, 2H), 4.24-4.12 (m, 1H), 3.88-3.80 (m, 2H), 3.78-3.72 (m, 2H), 3.73 (s, 2H), 1.98-1.47 (m, 8H), 1.37-1.20 (m, 2H), 1.11 (d, 3H)

HPLC-MS: m/z=517

Example 107

{2-[3-[2-(3,4-Dimethoxy-phenyl)-ethyl]-3-(4-trans-methyl-cyclohexyl)-ureido]-thiazol-5-ylsulfanyl}-acetic acid

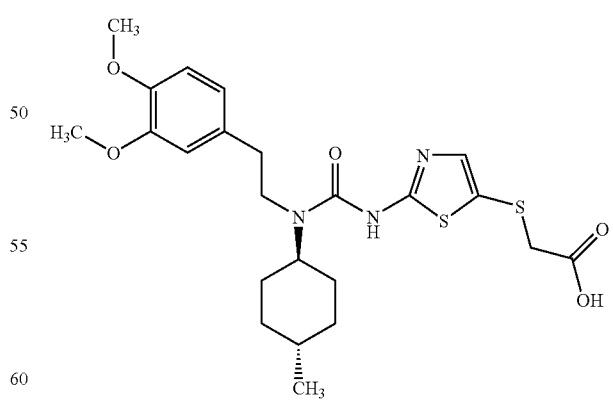

Prepared as described for the synthesis of {2-[3-(2-benzyloxy-ethyl)-3-(4-trans-methyl-cyclohexyl)-ureido]-thiazol-5-ylsulfanyl}-acetic acid using 3,4-dimethoxy-phenyl-ethanol, 4-trans-methyl-cyclohexylamine and (2-amino-thiazol-5-ylsulfanyl)-acetic acid ethyl ester.

¹H NMR (400 MHz, CDCl₃) δ 7.27 (s, 1H), 6.82-6.76 (m, 3H), 3.88 (s, 3H), 3.86 (s, 3H), 3.54-3.44 (m, 2H), 3.32 (s, 2H), 2.89-2.80 (m, 2H), 1.85-1.72 (m, 4H), 1.62-1.48 (m, 2H), 1.42-1.10 (m, 3H), 0.92 (d, 3H)

HPLC-MS: m/z=494

Example 108

{2-[3-(4-trans-methyl-cyclohexyl)-3-(2-p-tolyl-ethyl)-ureido]-thiazol-5-ylsulfanyl}-acetic acid

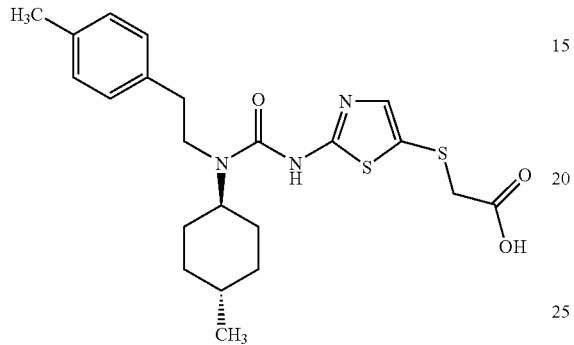

Prepared as described for the synthesis of {2-[3-(2-benzyloxy-ethyl)-3-(4-trans-methyl-cyclohexyl)-ureido]-thiazol-5-ylsulfanyl}-acetic acid using 4-methyl-phenyl-ethanol, 4-trans-methyl-cyclohexylamine and (2-amino-thiazol-5-ylsulfanyl)-acetic acid ethyl ester.

¹H NMR (400 MHz, CDCl₃) δ 7.26 (s, 1H), 7.18 (d, 2H); 7.11 (d, 2H), 4.3-3.8 (m, 1H), 3.52-3.43 (m, 2H), 3.32 (s, 2H), 2.90-2.82 (m, 2H), 2.32 (s, 3H), 1.87-1.72 (m, 4H), 1.62-1.47 (m, 2H), 1.42-1.10 (m, 3H), 0.92 (d, 3H)

HPLC-MS: m/z=448

Example 109

{2-[3-(4-trans-methyl-cyclohexyl)-3-(2-pentafluorophenylmethoxy-ethyl)-ureido]-thiazol-5-ylsulfanyl}-acetic acid

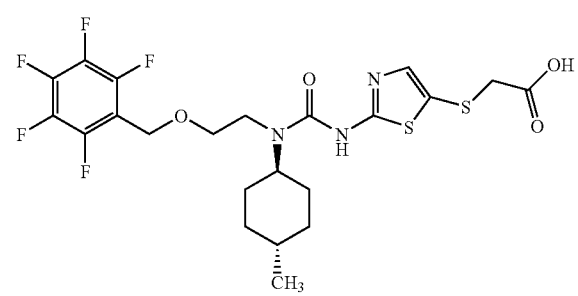

Prepared as described for the synthesis of {2-[3-[2-(4-fluoro-2-trifluoromethyl-benzyloxy)-ethyl]-3-(4-trans-methyl-cyclohexyl)-ureido]-thiazol-5-ylsulfanyl}-acetic acid using 1,2,3,4,5-pentafluoro-benzylbromide, (2-hydroxy-ethyl)-(4-trans-methyl-cyclohexyl)-carbamic acid tert-butyl ester and (2-amino-thiazol-5-ylsulfanyl)-acetic acid ethyl ester.

HPLC-MS: m/z=554

Example 110

(2-{3-(4-trans-methyl-cyclohexyl)-3-[2-(4-trifluoromethyl-phenyl)-ethyl]-ureido}-thiazol-5-ylsulfanyl)-acetic acid

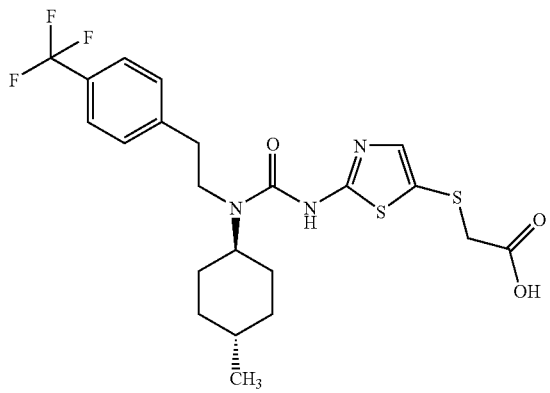

Prepared as described for the synthesis of {2-[3-(2-benzyloxy-ethyl)-3-(4-trans-methyl-cyclohexyl)-ureido]-thiazol-5-ylsulfanyl}-acetic acid using 4-trifluoromethyl-phenyl-ethanol, 4-trans-methyl-cyclohexylamine and (2-amino-thiazol-5-ylsulfanyl)-acetic acid ethyl ester.

¹H NMR (400 MHz, DMSO-d₆) δ 7.67 (d, 2H), 7.52 (d, 2H), 7.43 (s, 1H), 4.05-3.92 (m, 1H), 3.50 (s, 2H), 3.50-3.42 (m, 2H), 2.92-2.85 (m, 2H), 1.73-1.65 (m, 2H), 1.62-1.50 (m, 4H), 1.40-1.25 (m, 1H), 1.13-0.98 (m, 2H), 0.87 (d, 3H)

HPLC-MS: m/z=502

Example 111

{2-[3-[2-(4-Ethoxy-phenyl)-ethyl]-3-(4-trans-methyl-cyclohexyl)-ureido]-thiazol-5-ylsulfanyl}-acetic acid

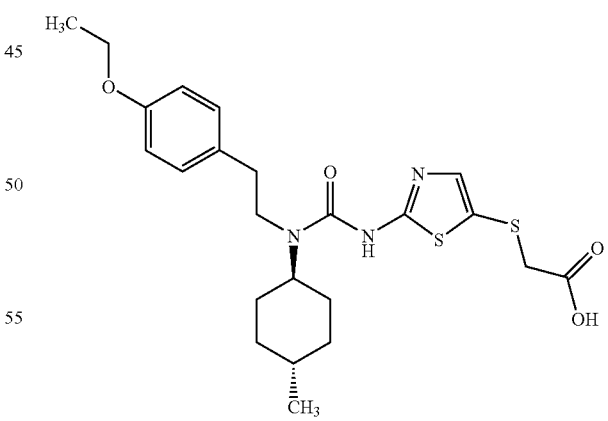

Prepared as described for the synthesis of {2-[3-(2-benzyloxy-ethyl)-3-(4-trans-methyl-cyclohexyl)-ureido]-thiazol-5-ylsulfanyl}-acetic acid using 2-(4-ethoxy-phenyl)-ethanol, 4-trans-methyl-cyclohexylamine and (2-amino-thiazol-5-ylsulfanyl)-acetic acid ethyl ester.

¹H NMR (400 MHz, DMSO-d₆) δ 7.42 (s, 1H), 7.18 (d, 2H), 6.85 (d, 2H), 4.03-3.92 (m, 3H), 3.50 (s, 2H), 3.42-3.40

(m, 2H), 2.75-2.67 (m, 2H), 1.73-1.63 (m, 2H), 1.62-1.59 (m, 4H), 1.39-1.28 (m, 4H), 1.12-1.00 (m, 2H), 0.87 (d, 3H)
HPLC-MS: m/z=478

Example 112

{2-[3-[2-(4-Isopropoxy-phenyl)-ethyl]-3-(4-trans-methyl-cyclohexyl)-ureido]-thiazol-5-ylsulfanyl}-acetic acid

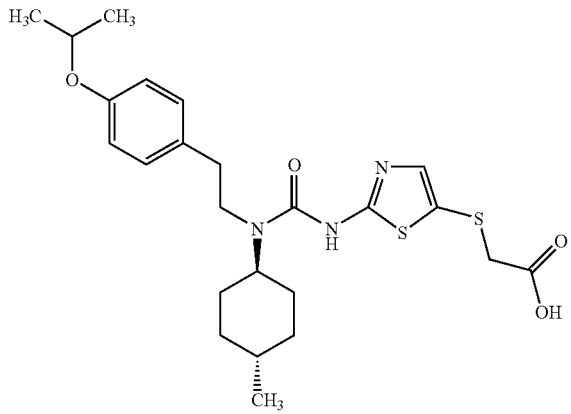

Prepared as described for the synthesis of {2-[3-(2-benzyloxy-ethyl)-3-(4-trans-methyl-cyclohexyl)-ureido]-thiazol-5-ylsulfanyl}-acetic acid using 2-(4-isopropoxy-phenyl)-ethanol, 4-trans-methyl-cyclohexylamine and (2-amino-thiazol-5-ylsulfanyl)-acetic acid ethyl ester.

$^1$H NMR (400 MHz, DMSO-d$_6$) δ 7.43 (s, 1H), 7.17 (d, 2H), 6.83 (d, 2H), 4.57 (h, 1H), 4.02-3.90 (m, 1H), 3.49 (s, 2H), 3.49-3.30 (m, 2H), 2.73-2.65 (m, 2H), 1.73-1.63 (m, 2H), 1.62-1.48 (m, 4H), 1.39-1.29 (m, 1H), 1.25 (d, 6H), 1.12-1.00 (m, 2H), 0.87 (d, 3H)
HPLC-MS: m/z=492

Example 113

(2-{3-(4-trans-methyl-cyclohexyl)-3-[2-(4-propoxy-phenyl)-ethyl]-ureido}-thiazol-5-ylsulfanyl)-acetic acid

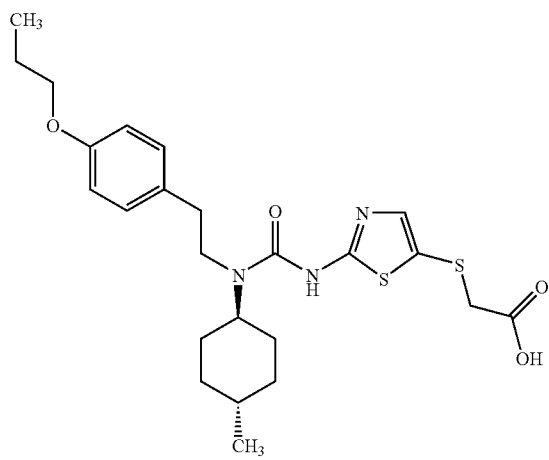

Prepared as described for the synthesis of {2-[3-(2-benzyloxy-ethyl)-3-(4-trans-methyl-cyclohexyl)-ureido]-thiazol-5-ylsulfanyl}-acetic acid using 2-(4-propoxy-phenyl)-ethanol, 4-trans-methyl-cyclohexylamine and (2-amino-thiazol-5-ylsulfanyl)-acetic acid ethyl ester.

$^1$H NMR (400 MHz, DMSO-d$_6$) δ 7.43 (s, 1H), 7.18 (d, 2H), 6.87 (d, 2H), 4.05-3.93 (m, 1H), 3.88 (t, 2H), 3.50 (s, 2H), 3.42-3.30 (m, 2H), 2.75-2.67 (m, 2H), 1.75-1.63 (m, 4H), 1.62-1.48 (m, 4H), 1.40-1.28 (m, 1H), 1.13-1.00 (m, 2H), 0.98 (t, 3H), 0.87 (d, 3H)
HPLC-MS: m/z=492

Example 114

{2-[3-[2-(2-Fluoro-phenyl)-ethyl]-3-(4-trans-methyl-cyclohexyl)-ureido]-thiazol-5-ylsulfanyl}-acetic acid

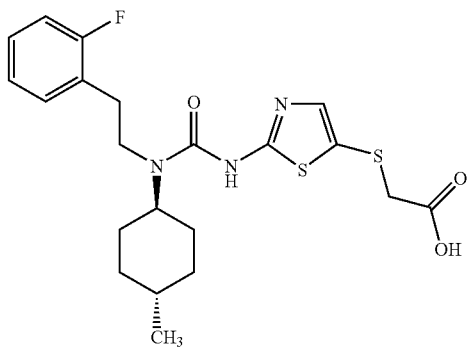

Prepared as described for the synthesis of {2-[3-(2-benzyloxy-ethyl)-3-(4-trans-methyl-cyclohexyl)-ureido]-thiazol-5-ylsulfanyl}-acetic acid using 2-(2-fluoro-phenyl)-ethanol, 4-trans-methyl-cyclohexylamine and (2-amino-thiazol-5-ylsulfanyl)-acetic acid ethyl ester.

$^1$H NMR (400 MHz, DMSO-d$_6$) δ 7.43 (s, 1H), 7.40-7.32 (m, 1H), 7.32-7.22 (m, 1H), 7.19-7.12 (m, 2H), 4.06-3.94 (m, 1H), 3.50 (s, 2H), 3.47-3.38 (m, 2H), 2.88-2.80 (m, 2H), 1.73-1.62 (m, 2H), 1.62-1.42 (m, 4H), 1.38-1.22 (m, 1H), 1.13-0.97 (m, 2H), 0.88 (d, 3H)
HPLC-MS: m/z=452

Example 115

{2-[3-[2-(3-Fluoro-phenyl)-ethyl]-3-(4-trans-methyl-cyclohexyl)-ureido]-thiazol-5-ylsulfanyl}-acetic acid

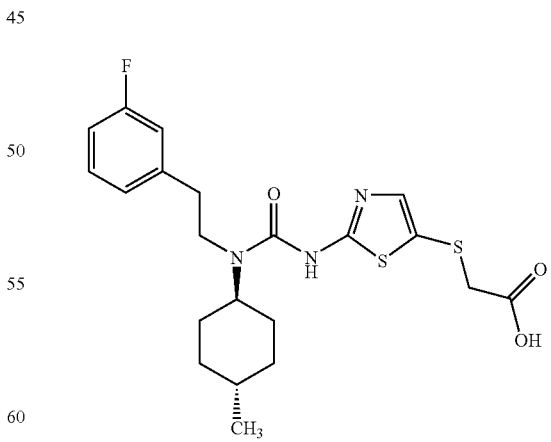

Prepared as described for the synthesis of {2-[3-(2-benzyloxy-ethyl)-3-(4-trans-methyl-cyclohexyl)-ureido]-thiazol-5-ylsulfanyl}-acetic acid using 2-(3-fluoro-phenyl)-ethanol, 4-trans-methyl-cyclohexylamine and (2-amino-thiazol-5-ylsulfanyl)-acetic acid ethyl ester.

¹H NMR (400 MHz, DMDO-d₆) δ 7.42 (s, 1H), 7.38-7.30 (m, 1H), 7.19-7.10 (m, 2H), 7.08-7.00 (m, 1H), 4.05-3.93 (m, 1H), 3.49 (s, 2H), 3.48-3.39 (m, 2H), 2.83-2.77 (m, 2H), 1.73-1.65 (m, 2H), 1.62-1.50 (m, 4H), 1.42-1.29 (m, 1H), 1.15-0.98 (m, 2H), 0.88 (d, 3H)

HPLC-MS: m/z=452

Example 116

{2-[3-[2-(4-Isopropyl-phenyl)-ethyl]-3-(4-trans-methyl-cyclohexyl)-ureido]-thiazol-5-ylsulfanyl}-acetic acid

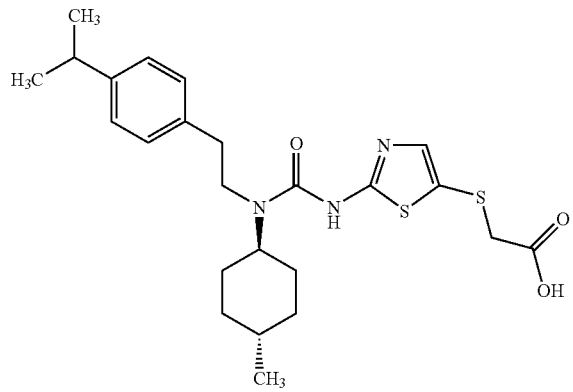

Prepared as described for the synthesis of {2-[3-(2-benzyloxy-ethyl)-3-(4-trans-methyl-cyclohexyl)-ureido]-thiazol-5-ylsulfanyl}-acetic acid using 2-(3-isopropyl-phenyl)-ethanol, 4-trans-methyl-cyclohexylamine and (2-amino-thiazol-5-ylsulfanyl)-acetic acid ethyl ester.

¹H NMR (400 MHz, DMSO-d₆) δ 7.43 (s, 1H) 7.22-7.15 (m, 4H), 4.03-3.90 (m, 1H), 3.50 (s, 2H), 3.45-3.35 (m, 2H), 2.85 (h, 1H), 2.78-2.70 (m, 2H), 1.72-1.64 (m, 2H), 1.63-1.48 (m, 4H), 1.39-1.26 (m, 1H), 1.18 (d, 6H), 1.13-0.98 (m, 2H), 0.87 (d, 3H)

HPLC-MS: m/z=476

Example 117

{2-[3-[2-(3-Fluoro-4-methoxy-phenyl)-ethyl]-3-(4-trans-methyl-cyclohexyl)-ureido]-thiazol-5-ylsulfanyl}-acetic acid

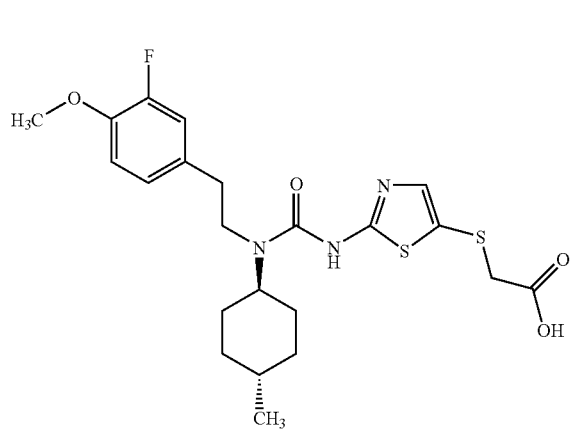

Prepared as described for the synthesis of {2-[3-(2-benzyloxy-ethyl)-3-(4-trans-methyl-cyclohexyl)-ureido]-thiazol-5-ylsulfanyl}-acetic acid using 2-(3-fluoro-4-methoxy-phenyl)-ethanol, 4-trans-methyl-cyclohexylamine and (2-amino-thiazol-5-ylsulfanyl)-acetic acid ethyl ester.

¹H NMR (400 MHz, DMSO-d₆) δ 7.43 (s, 1H), 7.20-7.13 (m, 1H), 7.12-7.00 (m, 2H), 4.04-3.93 (m, 1H), 3.80 (s, 3H), 3.50 (s, 2H), 3.43-3.32 (m, 2H), 2.78-2.68 (m, 2H), 1.73-1.64 (m, 2H), 1.63-1.50 (m, 4H), 1.42-1.28 (m, 1H), 1.12-0.98 (m, 2H), 0.87 (d, 3H)

HPLC-MS: m/z=489

Example 118

{2-[3-[2-(3-Fluoro-benzyloxy)-ethyl]-3-(4-trans-methyl-cyclohexyl)-ureido]-thiazol-5-ylsulfanyl}-acetic acid

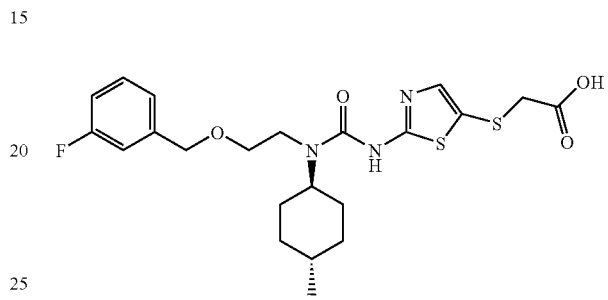

Prepared as described for the synthesis of {2-[3-[2-(4-fluoro-2-trifluoromethyl-benzyloxy)-ethyl]-3-(4-trans-methyl-cyclohexyl)-ureido]-thiazol-5-ylsulfanyl}-acetic acid using 3-fluoro-benzylbromide, (2-hydroxy-ethyl)-(4-trans-methyl-cyclohexyl)-carbamic acid tert-butyl ester and (2-amino-thiazol-5-ylsulfanyl)-acetic acid ethyl ester.

¹H NMR (400 MHz, DMSO-d₆) δ 7.40 (s, 1H), 7.39-7.33 (m, 1H), 7.18-7.05 (m, 3H), 4.55 (s, 2H), 3.99-3.85 (m, 1H), 3.60-3.45 (m, 6H with to following distinct signal (3.49 (s, 2H))

HPLC-MS: m/z=482

Example 119

(2-{3-(4-trans-methyl-cyclohexyl)-3-[2-(3-trifluoromethyl-benzyloxy)-ethyl]-ureido}-thiazol-5-ylsulfanyl)-acetic acid

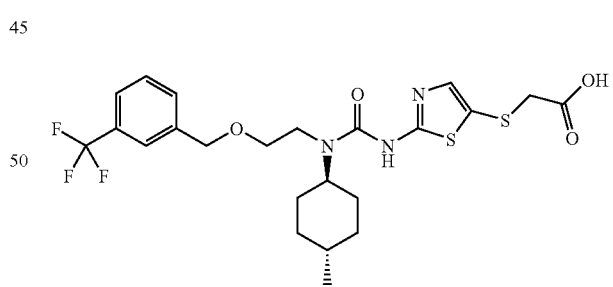

Prepared as described for the synthesis of {2-[3-[2-(4-fluoro-2-trifluoromethyl-benzyloxy)-ethyl]-3-(4-trans-methyl-cyclohexyl)-ureido]-thiazol-5-ylsulfanyl}-acetic acid using 3-trifluoromethyl-benzylbromide, (2-hydroxy-ethyl)-(4-trans-methyl-cyclohexyl)-carbamic acid tert-butyl ester and (2-amino-thiazol-5-ylsulfanyl)-acetic acid ethyl ester.

¹H NMR (400 MHz, DMSO-d₆) δ 7.70-7.52 (m, 4H), 7.39 (s, 1H), 4.63 (s, 2H), 3.98-3.86 m, 1H), 3.62-3.55 (m, 2H), 3.55-33.48 (m, 2H), 3.48 (s, 2H), 1.72-1.62 (m, 2H), 1.62-1.47 (m, 4H), 1.40-1.22 (m, 1H), 1.11-0.96 (m, 2H), 0.87 (d, 3H)

HPLC-MS: m/z=532

Example 120

{2-[3-[2-(4-Methanesulfonyl-benzyloxy)-ethyl]-3-(4-trans-methyl-cyclohexyl)-ureido]-thiazol-5-ylsulfanyl}-acetic acid

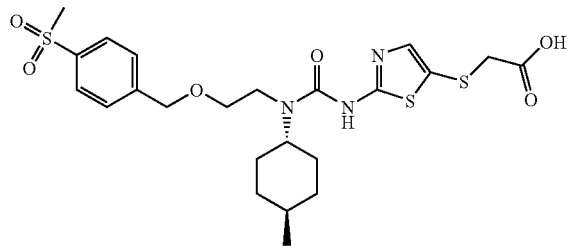

Prepared as described for the synthesis of {2-[3-[2-(4-fluoro-2-trifluoromethyl-benzyloxy)-ethyl]-3-(4-trans-methyl-cyclohexyl)-ureido]-thiazol-5-ylsulfanyl}-acetic acid using 4-methylsulfonyl-benzylbromide, (2-hydroxy-ethyl)-(4-trans-methyl-cyclohexyl)-carbamic acid tert-butyl ester and (2-amino-thiazol-5-ylsulfanyl)-acetic acid ethyl ester.
HPLC-MS: m/z=532

Example 121

(2-{3-(4-trans-methyl-cyclohexyl)-3-[2-(4-trifluoromethyl-benzyloxy)-ethyl]-ureido}-thiazol-5-ylsulfanyl)-acetic acid

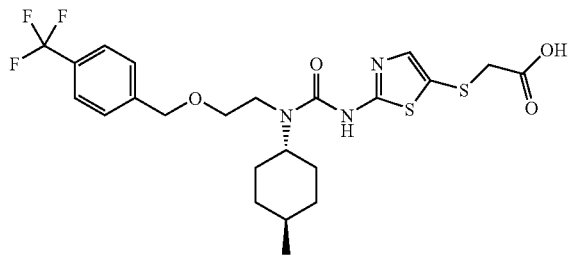

Prepared as described for the synthesis of {2-[3-[2-(4-fluoro-2-trifluoromethyl-benzyloxy)-ethyl]-3-(4-trans-methyl-cyclohexyl)-ureido]-thiazol-5-ylsulfanyl}-acetic acid using 4-trifluoromethyl-benzylbromide, (2-hydroxy-ethyl)-(4-trans-methyl-cyclohexyl)-carbamic acid tert-butyl ester and (2-amino-thiazol-5-ylsulfanyl)-acetic acid ethyl ester.
HPLC-MS: m/z=532

Example 122

(2-{3-(4-trans-methyl-cyclohexyl)-3-[2-(2-trifluoromethyl-benzyloxy)-ethyl]-ureido}-thiazol-5-ylsulfanyl)-acetic acid

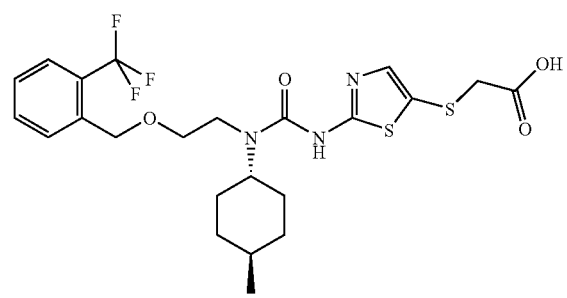

Prepared as described for the synthesis of {2-[3-[2-(4-fluoro-2-trifluoromethyl-benzyloxy)-ethyl]-3-(4-trans-methyl-cyclohexyl)-ureido]-thiazol-5-ylsulfanyl}-acetic acid using 2-trifluoromethyl-benzylbromide, (2-hydroxy-ethyl)-(4-trans-methyl-cyclohexyl)-carbamic acid tert-butyl ester and (2-amino-thiazol-5-ylsulfanyl)-acetic acid ethyl ester.
$^1$H NMR (400 MHz, DMSO-d$_6$) δ 7.74-7.18 (m, 2H), 7.68-7.58 (m, 1H), 7.53-7.47 (m, 1H), 7.40 (s, 1H), 4.69 (s, 2H), 4.00-3.88 (m, 1H), 3.65-3.57 (m, 2H) 3.57-3.49 (m, 2H), 3.49 (s, 2H), 1.72-1.63 (m, 2H), 1.62-1.47 (m, 4H), 1.38-1.20 (m, 1H), 1.10-0.97 (m, 2H), 0.87 (sd, 3H)
HPLC-MS: m/z=532

Example 123

{2-[3-[2-(2-Methoxy-benzyloxy)-ethyl]-3-(4-trans-methyl-cyclohexyl)-ureido]-thiazol-5-ylsulfanyl}-acetic acid

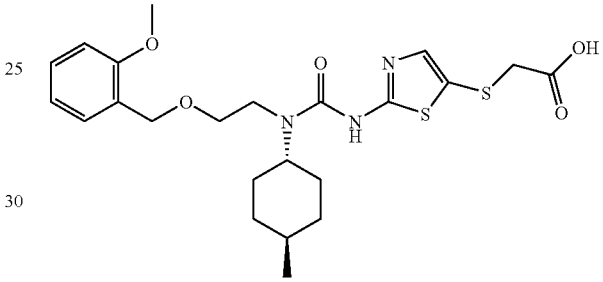

Prepared as described for the synthesis of {2-[3-[2-(4-fluoro-2-trifluoromethyl-benzyloxy)-ethyl]-3-(4-trans-methyl-cyclohexyl)-ureido]-thiazol-5-ylsulfanyl}-acetic acid using 2-methoxy-benzylbromide, (2-hydroxy-ethyl)-(4-trans-methyl-cyclohexyl)-carbamic acid tert-butyl ester and (2-amino-thiazol-5-ylsulfanyl)-acetic acid ethyl ester.
$^1$H NMR (400 MHz, DMSO-d$_6$) δ 7.40 (s, 1H), 7.28-7.20 (m, 1H), 6.92-6.87 (m, 2H), 6.85-6.80 (m, 1H), 4.50 (s, 2H), 3.98-3.85 (m, 1H), 3.8-3.4 (m, 9H, with the following distinct signals; 3.72 (s) and 3.50 (s)), 1.72-1.62 (m, 2H), 1.62-1.42 (m, 4H), 1.38-1.20 (m, 1H), 1.10-0.93 (m, 2H), 0.88 (d, 3H)
HPLC-MS: m/z=494

Example 124

{2-[3-[2-(4-tert-Butyl-benzyloxy)-ethyl]-3-(4-trans-methyl-cyclohexyl)-ureido]-thiazol-5-ylsulfanyl}-acetic acid

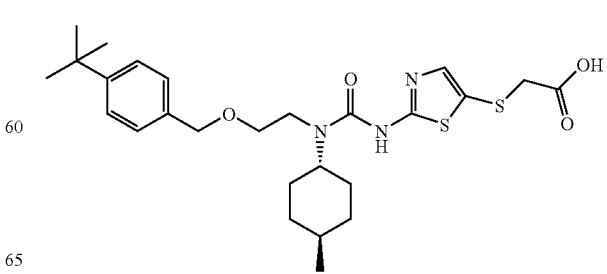

Prepared as described for the synthesis of {2-[3-[2-(4-fluoro-2-trifluoromethyl-benzyloxy)-ethyl]-3-(4-trans-methyl-cyclohexyl)-ureido]-thiazol-5-ylsulfanyl}-acetic acid using 4-tert-butyl-benzylbromide, (2-hydroxy-ethyl)-(4-trans-methyl-cyclohexyl)-carbamic acid tert-butyl ester and (2-amino-thiazol-5-ylsulfanyl)-acetic acid ethyl ester.

HPLC-MS: m/z=520

Example 125

(2-{3-(4-trans-methyl-cyclohexyl)-3-[2-(4-trifluoromethoxy-benzyloxy)-ethyl]-ureido}-thiazol-5-ylsulfanyl)-acetic acid

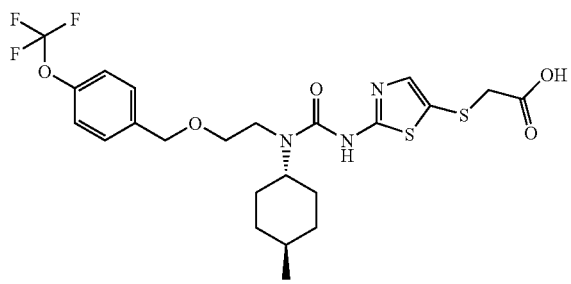

Prepared as described for the synthesis of {2-[3-[2-(4-fluoro-2-trifluoromethyl-benzyloxy)-ethyl]-3-(4-trans-methyl-cyclohexyl)-ureido]-thiazol-5-ylsulfanyl}-acetic acid using 4-trifluoromethoxy-benzylbromide, (2-hydroxy-ethyl)-(4-trans-methyl-cyclohexyl)-carbamic acid tert-butyl ester and (2-amino-thiazol-5-ylsulfanyl)-acetic acid ethyl ester.

HPLC-MS: m/z=548

Example 126

{2-[3-[2-(2,4-Difluoro-benzyloxy)-ethyl]-3-(4-trans-methyl-cyclohexyl)-ureido]-thiazol-5-ylsulfanyl}-acetic acid

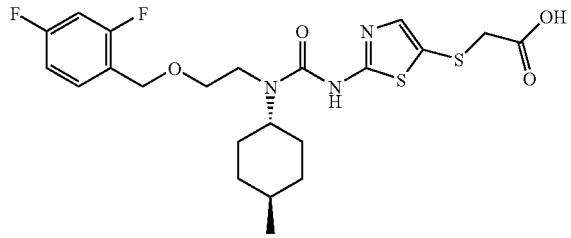

Prepared as described for the synthesis of {2-[3-[2-(4-fluoro-2-trifluoromethyl-benzyloxy)-ethyl]-3-(4-trans-methyl-cyclohexyl)-ureido]-thiazol-5-ylsulfanyl}-acetic acid using 2,4-difluoro-benzylbromide, (2-hydroxy-ethyl)-(4-trans-methyl-cyclohexyl)-carbamic acid tert-butyl ester and (2-amino-thiazol-5-ylsulfanyl)-acetic acid ethyl ester.

HPLC-MS: m/z=500

Example 127

{2-[3-[2-(4-Isopropyl-benzyloxy)-ethyl]-3-(4-trans-methyl-cyclohexyl)-ureido]-thiazol-5-ylsulfanyl}-acetic acid

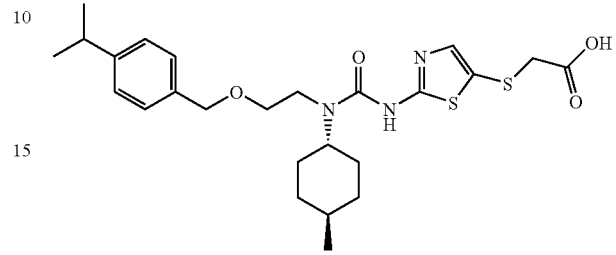

Prepared as described for the synthesis of {2-[3-[2-(4-fluoro-2-trifluoromethyl-benzyloxy)-ethyl]-3-(4-trans-methyl-cyclohexyl)-ureido]-thiazol-5-ylsulfanyl}-acetic acid using 3-isopropyl-benzylbromide, (2-hydroxy-ethyl)-(4-trans-methyl-cyclohexyl)-carbamic acid tert-butyl ester and (2-amino-thiazol-5-ylsulfanyl)-acetic acid ethyl ester.

$^1$H NMR (400 MHz, DMSO-d$_6$) δ 7.40 (s, 1H), 7.28-7.13 (m, 4H), 4.49 (s, 2H), 3.98-3.35 (M, 1H), 3.6-3.3 (m, 4H with the following distinct signal; 3.50 (s, 2H), 2.87 (h, 1H), 1.72-1.60 (m, 2H), 1.60-1.39 (m, 4H), 1.37-1.22 (m, 1H), 1.19 (d, 6H), 1.10-0.94 (m, 2H), 0.85 (d, 3H)

HPLC-MS: m/z=506

Example 128

{2-[3-[2-(4-Fluoro-benzyloxy)-ethyl]-3-(4-trans-methyl-cyclohexyl)-ureido]-thiazol-5-ylsulfanyl}-acetic acid

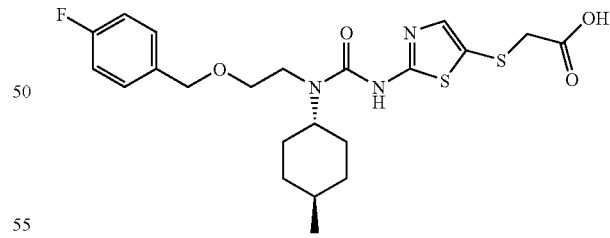

Prepared as described for the synthesis of {2-[3-[2-(4-fluoro-2-trifluoromethyl-benzyloxy)-ethyl]-3-(4-trans-methyl-cyclohexyl)-ureido]-thiazol-5-ylsulfanyl}-acetic acid using 4-fluoro-benzylbromide, (2-hydroxy-ethyl)-(4-trans-methyl-cyclohexyl)-carbamic acid tert-butyl ester and (2-amino-thiazol-5-ylsulfanyl)-acetic acid ethyl ester.

HPLC-MS: m/z=482

Example 129

(2-{3-(4-trans-methyl-cyclohexyl)-3-[2-(3-trifluoromethoxy-benzyloxy)-ethyl]-ureido}-thiazol-5-ylsulfanyl)-acetic acid

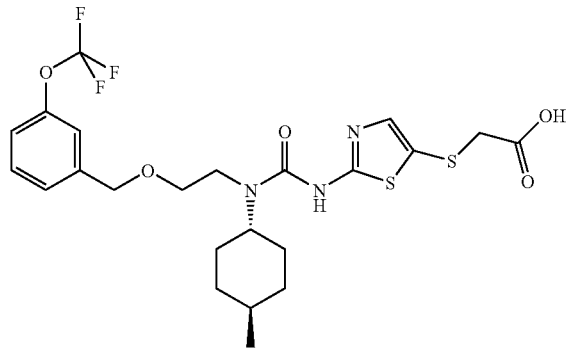

Prepared as described for the synthesis of {2-[3-[2-(4-fluoro-2-trifluoromethyl-benzyloxy)-ethyl]-3-(4-trans-methyl-cyclohexyl)-ureido]-thiazol-5-ylsulfanyl}-acetic acid using 3-trifluoromethyl-benzylbromide, (2-hydroxy-ethyl)-(4-trans-methyl-cyclohexyl)-carbamic acid tert-butyl ester and (2-amino-thiazol-5-ylsulfanyl)-acetic acid ethyl ester.

$^1$H NMR (400 MHz, DMSO-d$_6$) δ 7.50-6.17 (m, 5H, with the following distinct signal; 7.40 (s, 1H), 4.59 (s, 2H), 3.99-3.85 (m, 1H), 3.60-3.55 (m, 2H), 3.55-3.45 (m, 4H with the following distinct signal; 3.49 (s, 2H), 1.72-1.63 (m, 2H), 1.63-1.45 (m, 4H), 1.39-1.22 (m, 1H), 1.10-0.95 (m, 2H), 0.78 (d, 3H)

HPLC-MS: m/z=548

Example 130

{2-[3-[2-(2-Fluoro-benzyloxy)-ethyl]-3-(4-trans-methyl-cyclohexyl)-ureido]-thiazol-5-ylsulfanyl}-acetic acid

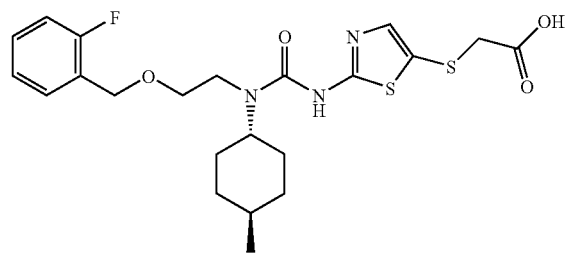

Prepared as described for the synthesis of {2-[3-[2-(4-fluoro-2-trifluoromethyl-benzyloxy)-ethyl]-3-(4-trans-methyl-cyclohexyl)-ureido]-thiazol-5-ylsulfanyl}-acetic acid using 2-fluoro-benzylbromide, (2-hydroxy-ethyl)-(4-trans-methyl-cyclohexyl)-carbamic acid tert-butyl ester and (2-amino-thiazol-5-ylsulfanyl)-acetic acid ethyl ester.

$^1$H NMR (400 MHz, DMSO-d$_6$) δ 7.48-7.30 (m, 3H, with the following distinct signal; 7.40 (s, 1H)), 7.21-7.13 (m, 2H), 4.58 (s, 2H), 3.98-3.83 (m, 1H), 3.60-3.54 (m, 4H, with the following distinct signal 3.49 (s, 2H)), 1.72-1.63 (m, 2H), 1.62-1.38 (m, 4H), 1.38-1.20 (m, 1H), 1.10-0.94 (m, 2H), 0.87 (d, 3H)

HPLC-MS: m/z=482

Example 131

{2-[3-[2-(2-Chloro-benzyloxy)-ethyl]-3-(4-trans-methyl-cyclohexyl)-ureido]-thiazol-5-ylsulfanyl}-acetic acid

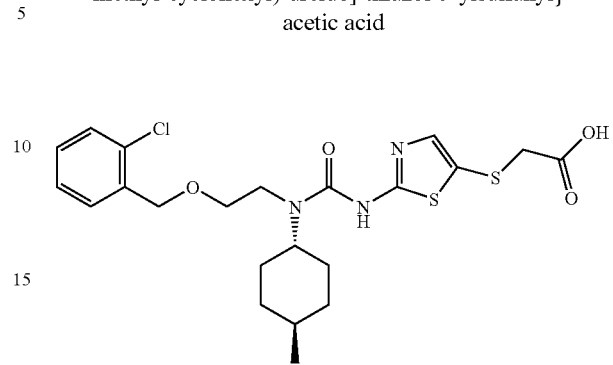

Prepared as described for the synthesis of {2-[3-[2-(4-fluoro-2-trifluoromethyl-benzyloxy)-ethyl]-3-(4-trans-methyl-cyclohexyl)-ureido]-thiazol-5-ylsulfanyl}-acetic acid using 2-chloro-benzylbromide, (2-hydroxy-ethyl)-(4-trans-methyl-cyclohexyl)-carbamic acid tert-butyl ester and (2-amino-thiazol-5-ylsulfanyl)-acetic acid ethyl ester.

$^1$H NMR (400 MHz, DMSO-d$_6$) δ 7.52-7.49 (m, 1H), 7.47-7.41 (m, 1H), 7.40 (s, 1H), 7.34-7.28 (m, 2H), 4.60 (s, 2H), 4.00-3.87 (m, 1H), 3.64-3.58 (m, 2H), 3.50-3.50 (m, 2H), 3.49 (s, 2H), 1.73-1.46 (m, 6H), 1.40-1.20 (m, 1H), 1.12-0.95 (m, 2H), 0.87 (d, 3H)

HPLC-MS: m/z=499

Example 132

{2-[3-[2-(2,3-Difluoro-benzyloxy)-ethyl]-3-(4-trans-methyl-cyclohexyl)-ureido]-thiazol-5-ylsulfanyl}-acetic acid

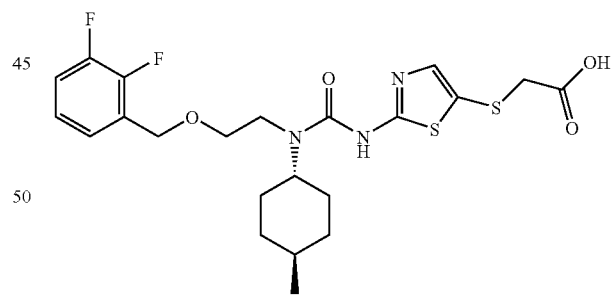

Prepared as described for the synthesis of {2-[3-[2-(4-fluoro-2-trifluoromethyl-benzyloxy)-ethyl]-3-(4-trans-methyl-cyclohexyl)-ureido]-thiazol-5-ylsulfanyl}-acetic acid using 2,3-difluoro-benzylbromide, (2-hydroxy-ethyl)-(4-trans-methyl-cyclohexyl)-carbamic acid tert-butyl ester and (2-amino-thiazol-5-ylsulfanyl)-acetic acid ethyl ester.

$^1$H NMR (400 MHz, DMSO-d$_6$) δ 7.42-7.12 (m, 4H), 4.62 (s, 2H), 3.98-3.85 (m, 1H), 3.62-3.30 (m, 6H) with the following distinct signal: 3.47 (s)), 1.73-1.62 (m, 2H), 1.62-1.20 (m, 5H), 1.12-0.95 (m, 2H), 0.88 (d, 3H)

HPLC-MS: m/z=500

Example 133

{2-[3-[2-(2,6-Difluoro-benzyloxy)-ethyl]-3-(4-trans-methyl-cyclohexyl)-ureido]-thiazol-5-ylsulfanyl}-acetic acid

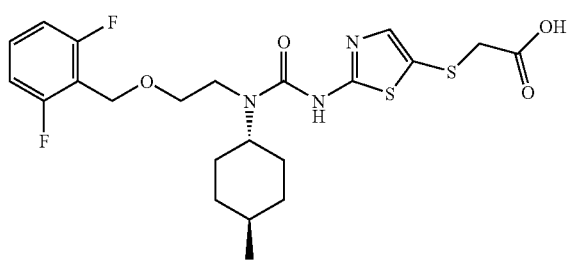

Prepared as described for the synthesis of {2-[3-[2-(4-fluoro-2-trifluoromethyl-benzyloxy)-ethyl]-3-(4-trans-methyl-cyclohexyl)-ureido]-thiazol-5-ylsulfanyl}-acetic acid using 2,6-difluoro-benzylbromide, (2-hydroxy-ethyl)-(4-trans-methyl-cyclohexyl)-carbamic acid tert-butyl ester and (2-amino-thiazol-5-ylsulfanyl)-acetic acid ethyl ester.

HPLC-MS: m/z=500

Example 134

{2-[3-(4-trans-methyl-cyclohexyl)-3-(3-o-tolyloxy-propyl)-ureido]-thiazol-5-ylsulfanyl}-acetic acid

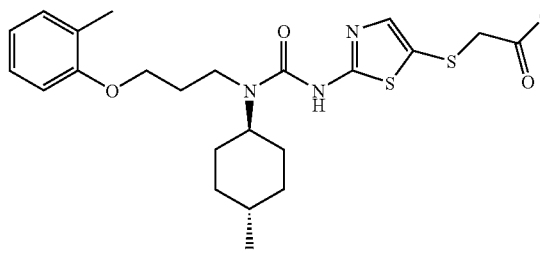

4-Trans-methyl-cyclohexylamine (6.65 g, 44.4 mmol) and potassium carbonate (12.3 g, 88.8 mmol) in acetonitrile (50 mL) was heated to reflux before a solution of (3-bromopropoxymethyl)-benzene (10.2 g, 44.4 mmol) in acetonitrile (25 mL) over a period of 30 min. The reaction mixture was refluxed for 2 hours before the solvent was removed in vacuo. The residue was divided between diethyl ether (100 mL) and aqueous sodium hydroxide (1N, 50 mL). The organic phase was dried (MgSO$_4$), filtered and concentrated in vacuo. The residue was purified using column chromatography (SiO$_2$, heptane-ethyl acetate 1:1) to give 8.4 g (3-benzyloxy-propyl)-(4-methyl-cyclohexyl)-amine. To this was added a solution of bis-tert-butyl-dicarbonate (32 mmol, 1N in THF) and the reaction mixture was stirred at room temperature for 18 hours before the solvent was removed in vacuo. The residue was dissolved in diethyl ether (150 mL) and washed with water (2×100 mL). The organic phase was dried (MgSO$_4$), filtered and concentrated in vacuo to give 10.6 g of (3-benzyloxy-propyl)-(4-methyl-cyclohexyl)-carbamic acid tert-butyl ester. This was subsequently dissolved ethanol (100 mL) and Pd/C (10%, 1 g) was added. The reaction mixture was stirred under H$_2$ (1 atm) for 4 hours. The reaction mixture was filtered throughout a pad of celite and concentrated in vacuo to give 7.9 g of (3-hydroxy-propyl)-(4-methyl-cyclohexyl)-carbamic acid tert-butyl ester.

2-Methyl-phenol (147 mg, 1.36 mmol), triphenylphosphine polystyrene (0.67 g, 3 mmol/g) and diethyl azodicarboxylate (DEAD) (261 mg, 1.5 mmol) in THF was stirred at room temperature for 16 hours before the solid was filtered off. Trifluoro acetic acid (1.5 mL) was added and the reaction mixture was stirred for 1 hour before sodium hydroxide (10%, 5 mL) was added. The mixture was extracted with diethyl ether (3×5 mL), the organic phase dried over MgSO$_4$, filtered and the solvent was removed in vacuo to give (4-trans-methyl-cyclohexyl)-(3-o-tolyloxy-propyl)-amine {2-[3-(4-trans-methyl-cyclohexyl)-3-(3-o-tolyloxy-propyl)-ureido]-thiazol-5-ylsulfanyl}-acetic acid was prepared from (4-trans-methyl-cyclohexyl)-(3-o-tolyloxy-propyl)-amine and (2-amino-thiazol-5-ylsulfanyl)-acetic acid ethyl ester using the procedure described for the synthesis of [2-(3-cyclohexyl-3-phenethyl-ureido)-thiazol-5-ylsulfanyl]-acetic acid.

HPLC-MS: m/z=478

Example 135

{2-[3-[3-(4-Methoxy-phenoxy)-propyl]-3-(4-trans-methyl-cyclohexyl)-ureido]-thiazol-5-ylsulfanyl}-acetic acid

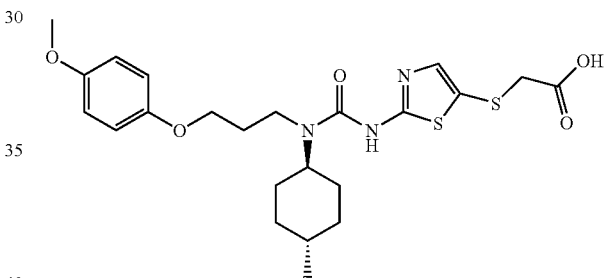

Prepared as described for the synthesis of {2-[3-(4-trans-methyl-cyclohexyl)-3-(3-o-tolyloxy-propyl)-ureido]-thiazol-5-ylsulfanyl}-acetic acid using (3-hydroxy-propyl)-(4-methylcyclohexyl)-carbamic acid tert-butyl ester, 4-methoxy-phenol and (2-amino-thiazol-5-ylsulfanyl)-acetic acid ethyl ester.

HPLC-MS: m/z=494

Example 136

{2-[3-[3-(4-Fluoro-phenoxy)-propyl]-3-(4-trans-methyl-cyclohexyl)-ureido]-thiazol-5-ylsulfanyl}-acetic acid

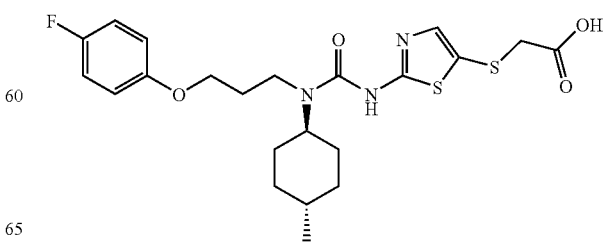

Prepared as described for the synthesis of {2-[3-(4-trans-methyl-cyclohexyl)-3-(3-o-tolyloxy-propyl)-ureido]-thiazol-5-ylsulfanyl}-acetic acid using (3-hydroxy-propyl)-(4-methyl-cyclohexyl)-carbamic acid tert-butyl ester, 4-fluoro-phenol and (2-amino-thiazol-5-ylsulfanyl)-acetic acid ethyl ester.

HPLC-MS: m/z=482

Example 137

{2-[3-[3-(Indan-5-yloxy)-propyl]-3-(4-trans-methyl-cyclohexyl)-ureido]-thiazol-5-ylsulfanyl}-acetic acid

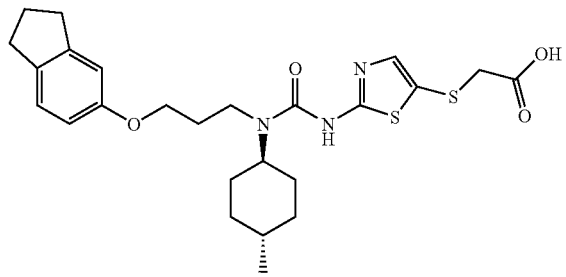

Prepared as described for the synthesis of {2-[3-(4-trans-methyl-cyclohexyl)-3-(3-o-tolyloxy-propyl)-ureido]-thiazol-5-ylsulfanyl}-acetic acid using (3-hydroxy-propyl)-(4-methyl-cyclohexyl)-carbamic acid tert-butyl ester, indane-5-ol and (2-amino-thiazol-5-ylsulfanyl)-acetic acid ethyl ester.

HPLC-MS: m/z=504

Example 138

{2-[3-[3-(3,4-Difluoro-phenoxy)-propyl]-3-(4-trans-methyl-cyclohexyl)-ureido]-thiazol-5-ylsulfanyl}-acetic acid

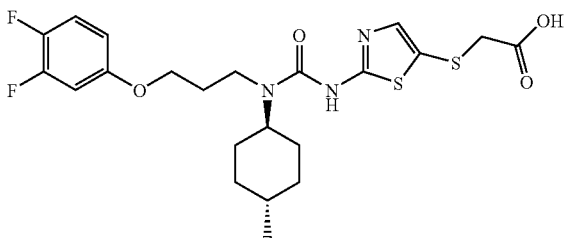

Prepared as described for the synthesis of {2-[3-(4-trans-methyl-cyclohexyl)-3-(3-o-tolyloxy-propyl)-ureido]-thiazol-5-ylsulfanyl}-acetic acid using (3-hydroxy-propyl)-(4-methyl-cyclohexyl)-carbamic acid tert-butyl ester, 3,4-difluorophenol and (2-amino-thiazol-5-ylsulfanyl)-acetic acid ethyl ester.

HPLC-MS: m/z=500

Example 139

{2-[3-[3-(2,4-Difluoro-phenoxy)-propyl]-3-(4-trans-methyl-cyclohexyl)-ureido]-thiazol-5-ylsulfanyl}-acetic acid

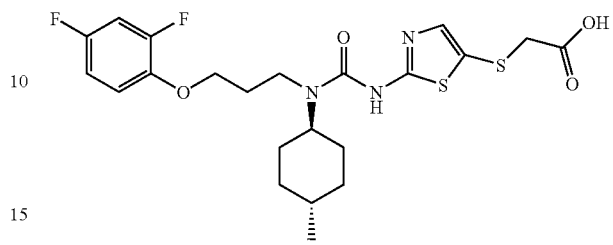

Prepared as described for the synthesis of {2-[3-(4-trans-methyl-cyclohexyl)-3-(3-o-tolyloxy-propyl)-ureido]-thiazol-5-ylsulfanyl}-acetic acid using (3-hydroxy-propyl)-(4-methyl-cyclohexyl)-carbamic acid tert-butyl ester, 2,4-difluorophenol and (2-amino-thiazol-5-ylsulfanyl)-acetic acid ethyl ester.

HPLC-MS: m/z=500

Example 140

{2-[3-[3-(4-tert-Butyl-phenoxy)-propyl]-3-(4-trans-methyl-cyclohexyl)-ureido]-thiazol-5-ylsulfanyl}-acetic acid

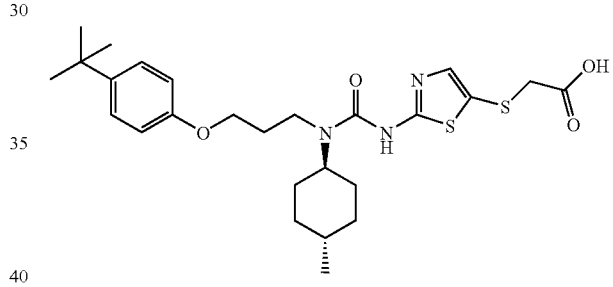

Prepared as described for the synthesis of {2-[3-(4-trans-methyl-cyclohexyl)-3-(3-o-tolyloxy-propyl)-ureido]-thiazol-5-ylsulfanyl}-acetic acid using (3-hydroxy-propyl)-(4-methyl-cyclohexyl)-carbamic acid tert-butyl ester, 4-tert-butylphenol and (2-amino-thiazol-5-ylsulfanyl)-acetic acid ethyl ester.

HPLC-MS: m/z=520

Example 141

{2-[3-[3-(4-Isopropyl-phenoxy)-propyl]-3-(4-trans-methyl-cyclohexyl)-ureido]-thiazol-5-ylsulfanyl}-acetic acid

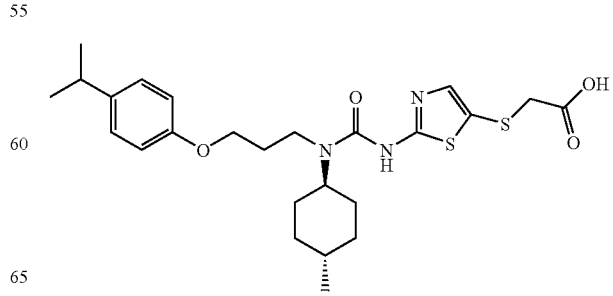

Prepared as described for the synthesis of {2-[3-(4-trans-methyl-cyclohexyl)-3-(3-o-tolyloxy-propyl)-ureido]-thiazol-5-ylsulfanyl}-acetic acid using (3-hydroxy-propyl)-(4-methyl-cyclohexyl)-carbamic acid tert-butyl ester, 4-isopropylphenol and (2-amino-thiazol-5-ylsulfanyl)-acetic acid ethyl ester.
HPLC-MS: m/z=506

Example 142

{2-[3-[3-(3-Acetylamino-phenoxy)-propyl]-3-(4-trans-methyl-cyclohexyl)-ureido]-thiazol-5-ylsulfanyl}-acetic acid

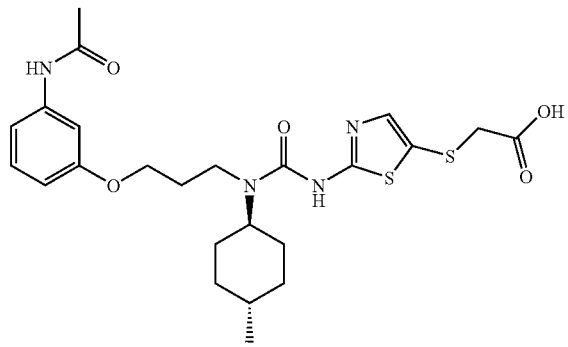

Prepared as described for the synthesis of {2-[3-(4-trans-methyl-cyclohexyl)-3-(3-o-tolyloxy-propyl)-ureido]-thiazol-5-ylsulfanyl}-acetic acid using (3-hydroxy-propyl)-(4-methyl-cyclohexyl)-carbamic acid tert-butyl ester, 3-acetylaminophenol and (2-amino-thiazol-5-ylsulfanyl)-acetic acid ethyl ester.
HPLC-MS: m/z=521

Example 143

{2-[3-[3-(2-Fluoro-phenoxy)-propyl]-3-(4-trans-methyl-cyclohexyl)-ureido]-thiazol-5-ylsulfanyl}-acetic acid

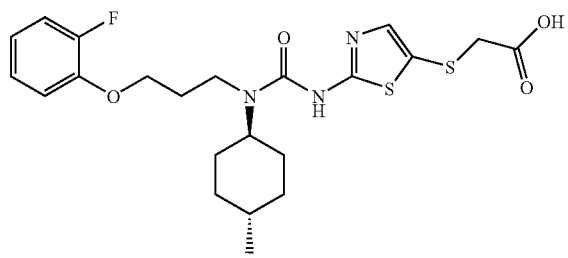

Prepared as described for the synthesis of {2-[3-(4-trans-methyl-cyclohexyl)-3-(3-o-tolyloxy-propyl)-ureido]-thiazol-5-ylsulfanyl}-acetic acid using (3-hydroxy-propyl)-(4-methyl-cyclohexyl)-carbamic acid tert-butyl ester, 2-fluorophenol and (2-amino-thiazol-5-ylsulfanyl)-acetic acid ethyl ester.
$^1$H NMR (400 MHz, DMSO-$d_6$) δ 7.42 (bs, 1H), 7.25-7.09 (m, 3H), 6.97-6.90 (m, 1H), 4.09 (t, 2H), 4.05-3.93 (m, 1H), 3.48 (s, 2H), 3.42-3.32 (m, 2H), 2.02-1.90 (m, 2H), 1.73-1.44 (m, 6H), 1.35-1.21 (m, 1H), 1.12-0.97 (m, 2H), 0.87 (d, 3H)
HPLC-MS: m/z=482

Example 144

{2-[3-[3-(3-Isopropyl-phenoxy)-propyl]-3-(4-trans-methyl-cyclohexyl)-ureido]-thiazol-5-ylsulfanyl}-acetic acid

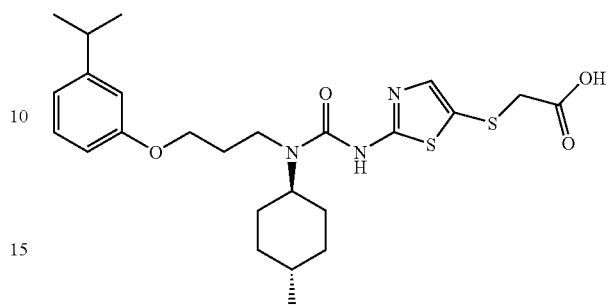

Prepared as described for the synthesis of {2-[3-(4-trans-methyl-cyclohexyl)-3-(3-o-tolyloxy-propyl)-ureido]-thiazol-5-ylsulfanyl}-acetic acid using (3-hydroxy-propyl)-(4-methyl-cyclohexyl)-carbamic acid tert-butyl ester, 2-isopropoxyphenol and (2-amino-thiazol-5-ylsulfanyl)-acetic acid ethyl ester.
HPLC-MS: m/z=506

Example 145

{2-[3-[3-(Benzo[1,3]dioxol-5-yloxy)-propyl]-3-(4-trans-methyl-cyclohexyl)-ureido]-thiazol-5-ylsulfanyl}-acetic acid

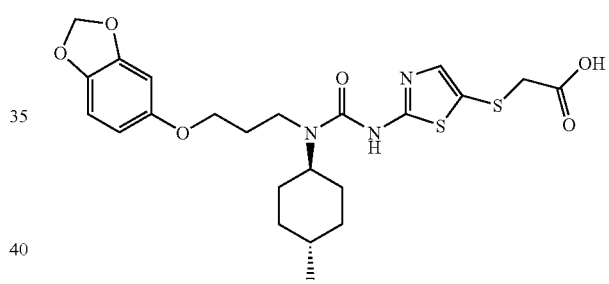

Prepared as described for the synthesis of {2-[3-(4-trans-methyl-cyclohexyl)-3-(3-o-tolyloxy-propyl)-ureido]-thiazol-5-ylsulfanyl}-acetic acid using (3-hydroxy-propyl)-(4-methyl-cyclohexyl)-carbamic acid tert-butyl ester, benzo[1,3]dioxol-5-ol and (2-amino-thiazol-5-ylsulfanyl)-acetic acid ethyl ester.
HPLC-MS: m/z=508

Example 146

(2-{3-(4-trans-methyl-cyclohexyl)-3-[3-(4-trifluoromethoxy-phenoxy)-propyl]-ureido}-thiazol-5-ylsulfanyl)-acetic acid

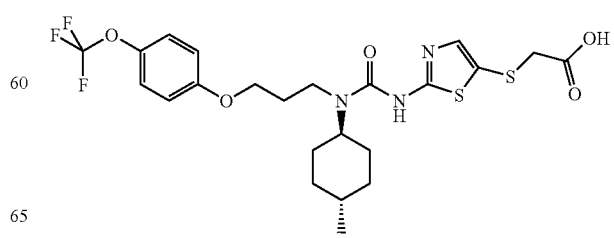

Prepared as described for the synthesis of {2-[3-(4-trans-methyl-cyclohexyl)-3-(3-o-tolyloxy-propyl)-ureido]-thiazol-5-ylsulfanyl}-acetic acid using (3-hydroxy-propyl)-(4-methyl-cyclohexyl)-carbamic acid tert-butyl ester, 4-trifluoromethoxyphenyl and (2-amino-thiazol-5-ylsulfanyl)-acetic acid ethyl ester.

HPLC-MS: m/z=548

Example 147

(2-{3-(4-trans-methyl-cyclohexyl)-3-[3-(3-trifluoromethoxy-phenoxy)-propyl]-ureido}-thiazol-5-ylsulfanyl)-acetic acid

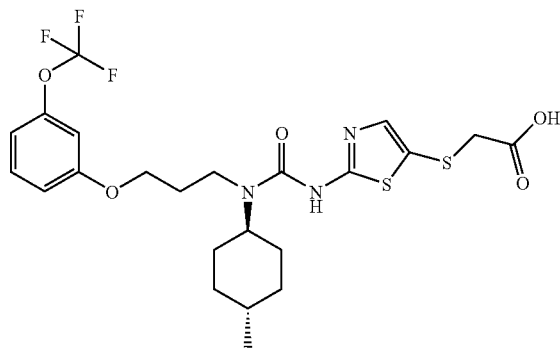

Prepared as described for the synthesis of {2-[3-(4-trans-methyl-cyclohexyl)-3-(3-o-tolyloxy-propyl)-ureido]-thiazol-5-ylsulfanyl}-acetic acid using (3-hydroxy-propyl)-(4-methyl-cyclohexyl)-carbamic acid tert-butyl ester, 3-trifluoromethoxyphenyl and (2-amino-thiazol-5-ylsulfanyl)-acetic acid ethyl ester.

HPLC-MS: m/z=548

Example 148

{2-[3-[3-(3-Fluoro-phenoxy)-propyl]-3-(4-trans-methyl-cyclohexyl)-ureido]-thiazol-5-ylsulfanyl}-acetic acid

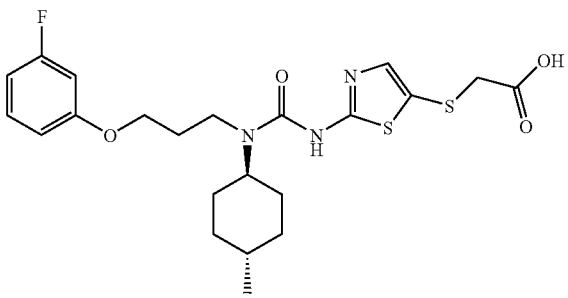

Prepared as described for the synthesis of {2-[3-(4-trans-methyl-cyclohexyl)-3-(3-o-tolyloxy-propyl)-ureido]-thiazol-5-ylsulfanyl}-acetic acid using (3-hydroxy-propyl)-(4-methyl-cyclohexyl)-carbamic acid tert-butyl ester, 3-fluorophenol and (2-amino-thiazol-5-ylsulfanyl)-acetic acid ethyl ester.

HPLC-MS: m/z=482

Example 149

3-{2-[3-[3-(2-Chloro-phenoxy)-propyl]-3-(4-trans-methyl-cyclohexyl)-ureido]-thiazol-5-ylsulfanyl}-propionic acid

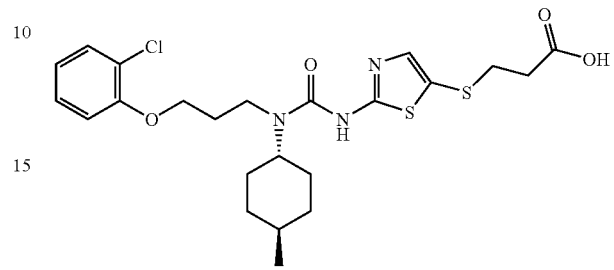

Prepared as described for the synthesis of {2-[3-(4-trans-methyl-cyclohexyl)-3-(3-o-tolyloxy-propyl)-ureido]-thiazol-5-ylsulfanyl}-acetic acid using (3-hydroxy-propyl)-(4-methyl-cyclohexyl)-carbamic acid tert-butyl ester, 2-chlorophenol and (2-amino-thiazol-5-ylsulfanyl)-propionic acid ethyl ester.

$^1$H NMR (400 MHz, DMSO-d$_6$) δ 7.43 (dd, 1H), 7.40 (s, 1H), 7.33-7.27 (m, 1H), 7.17-7.13 (m, 1H), 6.98-6.93 (m, 1H), 4.10 (t, 2H), 4.07-3.96 (m, 1H), 3.45-3.38 (m, 2H), 2.84 (t, 2H), 2.49 (t, 2H), 2.02-1.93 (m, 2H), 1.71-1.46 (6H), 1.35-1.25 (m, 1H), 1.11-0.97 (m, 2H), 0.87 (d, 3H)

HPLC-MS: m/z=512

Example 150

3-{2-[3-[3-(4-Chloro-phenoxy)-propyl]-3-(4-trans-methyl-cyclohexyl)-ureido]-thiazol-5-ylsulfanyl}-propionic acid

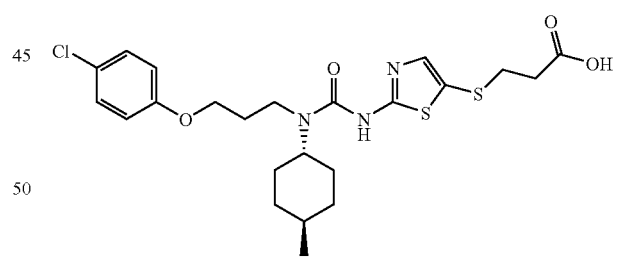

Prepared as described for the synthesis of {2-[3-(4-trans-methyl-cyclohexyl)-3-(3-o-tolyloxy-propyl)-ureido]-thiazol-5-ylsulfanyl}-acetic acid using (3-hydroxy-propyl)-(4-methyl-cyclohexyl)-carbamic acid tert-butyl ester, 4-chlorophenol and (2-amino-thiazol-5-ylsulfanyl)-propionic acid ethyl ester.

$^1$H NMR (400 MHz, DMSO-d$_6$) δ 7.40 (s, 1H), 7.32 (d, 2H)), 6.98 (d, 2H), 4.01 (t, 2H), 4.00-3.93 (m, 1H), 3.47-3.27 (m, 2H), 2.84 (t, 2H), 2.49 (t, 2H), 1.99-1.87 (m, 2H), 1.73-1.42 (m, 6H), 1.38-1.22 (1H), 1.12-0.96 (m, 2H), 0.87 (d, 3H)

HPLC-MS: m/z=512

Example 151

{2-[3-Cyclopentylmethyl-3-(3,4-difluoro-phenyl)-ureido]-thiazol-4-yl}-acetic acid

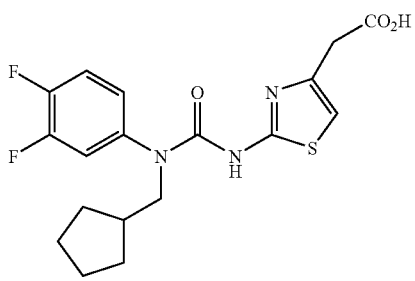

(General Procedure (A) and (B))

Preparation of Secondary Amine:

Preparation of cyclopentylmethyl-(3,4-difluoro-phenyl)-amine-3,4-Difluoroaniline (18.5 mmol) dissolved in 50 ml of THF:MeOH (1:1) was added cyclopentanecarbaldehyde (20.4 mmol) and 3 Å molsieves (5 g) and stirred for 0.5 h at RT. Then NaBH₃CN (37.1 mmol=2 eqv.) was added and the reaction mixture was stirred for 13H at room temperature before it was filtered and the filtrate was concentrated in vacuo to give crude cyclopentylmethyl-(3,4-difluoro-phenyl)-amine.

Coupling:

To a solution of (2-amino-thiazol-4-yl)-acetic acid ethyl ester (1.0 mmol) and cyclopentylmethyl-(3,4-difluoro-phenyl)-amine (1.0 mmol) in dry toluene (10 mL) was added CDI (1.5 mmol) and DMAP (0.05 mmol). The mixture was stirred at 60° C. for 3H an then evaporated to dryness in vacuo. The crude product was purified on silica gel (gradient, from heptane:ethyl acetate (10:1) to heptane:ethyl acetate (3:1)) to give {2-[3-cyclopentylmethyl-3-(3,4-difluoro-phenyl)-ureido]-thiazol-4-yl}-acetic acid ethyl ester.

Hydrolysis:

{2-[3-Cyclopentylmethyl-3-(3,4-difluoro-phenyl)-ureido]-thiazol-4-yl}-acetic acid ethyl ester (0.5 mmol) was dissolved in dioxane (2 mL) and treated with 1N NaOH (2 mL) for 1H at room temperature. Dioxane was removed by evaporation. Addition of 1N HCl to pH 1 caused precipitation. The precipitate was isolated by filtration, washed with water and dried to give the title compound as crystals.

¹H NMR (400 MHz, DMSO-d₆) δ 7.42-7.53 (m, 1H), 7.11-7.22 (m, 1H), 6.75 (s, 1H), 3.67 (d, 1H), 3.50 (s, 1H), 1.87-2.01 (m, 1H), 1.51-1.65 (m, 3H), 1.39-1.50 (m, 1H), 1.11-1.21 (m, 1H)

HPLC-MS: m/z=396, R$_t$=1.9 min

Example 152

{2-[3-Cyclopentylmethyl-3-(3,4-difluoro-phenyl)-ureido]-thiazol-5-ylsulfanyl}-acetic acid

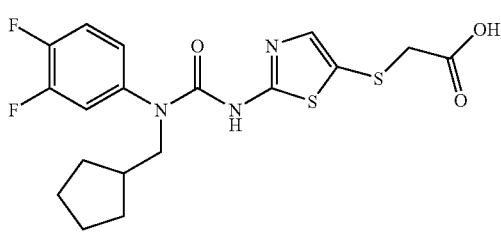

Preparation of (2-aminothiazol-5-ylsulfanyl)acetic acid ethyl ester

5-Bromo-2-aminothiazole (25 g, 96 mmol) and K₂CO₃ (26.5 g, 192 mmol) was suspended in DMF (50 mL) and stirred to 0° C. Ethyl thioglycolate (11.6 mL, 96 mmol) was added during 10 min. The reaction mixture was allowed to reach room temperature and stirred for further 13H. Addition of water (100 mL) and EtOAc (150 mL). Separation of the organic phase followed by extraction of the aqueous phase with EtOAc (2×100 mL). The combined organic phases were washed with aqueous NaHCO3 (2000 mL), brine (2×200 mL) and dried (MgSO4), filtered and evaporated. The crude product was dissolved in a small amount of DCM and purified by flash chromatography (ISCO 330 g silica column, eluent A: heptane/B: 2% TEA in EtOAc. Gradient from 30% B->100% B.) to give 50-65% pure (2-aminothiazol-5-ylsulfanyl)acetic acid ethyl ester as a dark red-brown oil.

¹H NMR (CDCl₃): δ 7.16 (s, 1H), 5.45 (bs, 2H), 4.26 (q, 2H), 3.39 (s, 2H), 1.28 (t, 3H).

The title compound was prepared via {2-[3-cyclopentylmethyl-3-(3,4-difluoro-phenyl)-ureido]-thiazol-5-ylsulfanyl}-acetic acid ethyl ester in a similar manner as described for the synthesis of {2-[3-cyclopentylmethyl-3-(3,4-difluoro-phenyl)-ureido]-thiazol-4-yl}-acetic acid, using 3,4-difluoroaniline, cyclopentanecarbaldehyde and (2-amino-thiazol-5-ylsulfanyl)acetic acid ethyl ester.

¹H NMR (400 MHz, DMSO-d₆) δ 7.44-7.55 (m, 1H), 7.38 (s, 1H), 7.14-7.23 (m, 1H), 3.68 (d, 1H), 3.47-3.53 (m, 1H), 1.88-1.99 (m, 1H), 1.53-1.64 (m, 3H), 1.41-1.50 (m, 1H), 1.12-1.21 (m, 1H)

HPLC-MS: m/z=428, R$_t$=2.5 min

Example 153

2-{2-[3-Cyclopentylmethyl-3-(3,4-difluoro-phenyl)-ureido]-thiazol-5-ylsulfanyl}-2-methyl-propionic acid

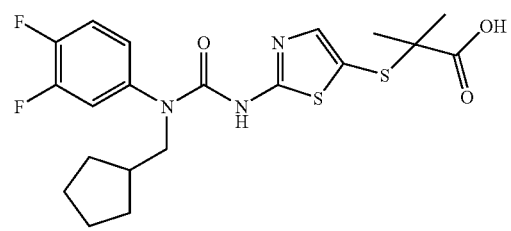

Preparation of 2-(2-amino-thiazol-5-ylsulfanyl)-2-methyl-propionic acid ethyl ester Step 1:

2-Aminothiazole (35 g, 350 mmol) and sodium thiocyanate (89 g, 1.08 mol) in MeOH (400 mL) was stirred at −10° C. Bromine (18.0 mL, 350 mmol) dissolved in MeOH (100 mL) saturated with NaBr was slowly added keeping the internal temperature between −10 and 0° C. After the addition the mixture was stirred at 0° C. for 3H and the reaction mixture was poured into ice water (1500 mL). Aqueous NH₄OH was added to pH ca 8.5 causing precipitation of light yellow crystals which were isolated by filtration, washed with ice water and dried in a vacuum oven to give 30 g (55%) 5-thiocyanato-thiazol-2-ylamine as light yellow crystals.

Step 2:

In a nitrogen atmosphere 5-thiocyanato-thiazol-2-ylamine (10 g, 64 mmol) dissolved in MeOH (300 mL) was added 2,3-dihydroxy-1,4-dithiolbutane (DTT, 9.8 g, 64 mmol) and stirred at room temperature for 1½ h. Then 2-bromo-2-methyl-propionic acid ethyl ester (13.6 g, 70 mmol) and K₂CO₃ (10.5 g, 76 mmol) was added and the reaction mixture was stirred for further 13H. Addition of water (500 mL) and EtOAc (500 mL). Separation of the organic phase followed by extraction of the aqueous phase with EtOAc (2×300 mL). The combined organic phases were washed with water (500 mL) and brine (2×400 mL) and dried (MgSO₄), filtered and evaporated. The crude product was dissolved in a small amount of DCM and purified by flash chromatography (heptane/EtOAc 2:1->1:2). Fractions containing the product were pooled and evaporated to a product containing impurities of DDT. This product was dissolved in diethyl ether (100 mL) and washed with water several times. The ether phase was dried (MgSO₄), filtered and evaporated to give 8.45 g (54%) of 95% pure 2-(2-amino-thiazol-5-ylsulfanyl)-2-methyl-propionic acid ethyl ester as light brown crystals.

The title compound was prepared via 2-{2-[3-cyclopentylmethyl-3-(3,4-difluoro-phenyl)-ureido]-thiazol-5-ylsulfanyl}-2-methyl-propionic acid ethyl ester in a similar manner as described for the synthesis of {2-[3-cyclopentylmethyl-3-(3,4-difluoro-phenyl)-ureido]-thiazol-4-yl}-acetic acid, using 3,4-difluoroaniline, cyclopentanecarbaldehyde and 2-(2-amino-thiazol-5-ylsulfanyl)-2-methyl-propionic acid ethyl ester.

¹H NMR (400 MHz, DMSO-d₆) δ 7.46-7.57 (m, 1H), 7.37 (s, 1H), 7.17-7.26 (m, 1H), 3.68 (d, 1H), 1.88-1.99 (m, 1H), 1.53-1.64 (m, 3H), 1.41-1.49 (m, 1H), 1.39 (s, 3H), 1.12-1.21 (m, 1H)

HPLC-MS: m/z=456, R_t=2.2 min

Example 154

2-({2-[3-Cyclopentylmethyl-3-(3,4-difluoro-phenyl)-ureido]-thiazole-5-sulfonyl}-methyl-amino)-N,N-diethyl-acetamide

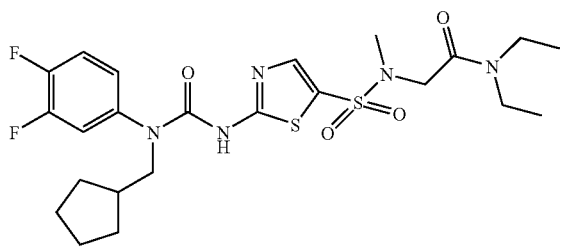

Preparation of 2-[(2-Amino-thiazole-5-sulfonyl)-methyl-amino]-N,N-diethyl-acetamide A mixture of N,N-diethyl-2-methylamino-acetamide (12 mmol), 2-acetylamino-thiazole-5-sulfonyl chloride (12 mmol) (prepared as described in *J. Am. Chem. Soc* 69, 2063, 1947), DIPEA (15 mmol) in DCM (50 mL) was stirred at room temperature over night. The reaction mixture was diluted with DCM (50 mL) washed with 10% aq NaHSO4, water and brine, dried and concentrated to give 2-[(2-acetylamino-thiazole-5-sulfonyl)-methyl-amino]-N,N-diethyl-acetamide (59%) as pale yellow crystals. This was suspended in EtOH (10 mL) and added 8N HCl in dioxane (10 mL) and heated for 3H at 80° C. and then cooled to room temperature and concentrated in vacuo to give 2-[(2-amino-thiazole-5-sulfonyl)-methyl-amino]-N,N-diethyl-acetamide as a hydrochloride as colourless crystals.

The title compound was prepared as described for the synthesis of {2-[3-cyclopentylmethyl-3-(3,4-difluoro-phenyl)-ureido]-thiazol-4-yl}-acetic acid, using 3,4-difluoroaniline, cyclopentanecarbaldehyde and 2-[(2-amino-thiazole-5-sulfonyl)-methyl-amino]-N,N-diethyl-acetamide as a hydrochloride.

¹H NMR (300 MHz, CDCl₃) δ 7.73 (s, 1H), 7.28-7.39 (m, 1H), 7.07-7.21 (m, 1H), 3.95 (s, 1H), 3.71 (d, 1H), 3.30-3.43 (m, 3H), 2.91 (s, 3H), 1.98-2.11 (m, 1H), 1.49-1.76 (m, 3H), 1.24-1.33 (m, 3H), 1.24 (t, 3H), 1.11 (t, 3H), 0.81-0.95 (m, 1H)

HPLC-MS: m/z=544, R_t=2.2 min

Example 155

(S)-1-{2-[3-Cyclopentylmethyl-3-(3,4-difluoro-phenyl)-ureido]-thiazole-5-sulfonyl}-pyrrolidine-2-carboxylic acid

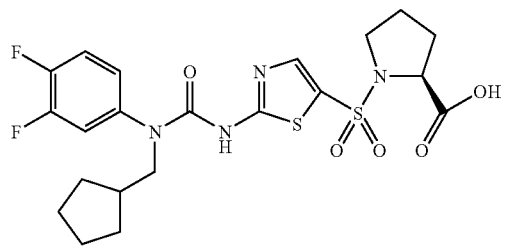

(General Procedure (A), (B) and (H))

Step 1.

A mixture of L-proline methylester hydrochloride (15 mmol), 2-acetylamino-thiazole-5-sulfonyl chloride (12 mmol) (prepared as described in *J. Am. Chem. Soc* 69, 2063, 1947), DIPEA (35 mmol) in DCM (50 mL) was stirred at room temperature over night. Addition of water and 1N HCl to pH 2. Isolation of the organic phase which was washed with water and brine, dried and concentrated to give (S)-1-(2-acetylamino-thiazole-5-sulfonyl)-pyrrolidine-2-carboxylic acid methyl ester as brown crystals. These were suspended in EtOH (15 mL) and added 4N HCl in dioxane (15 mL) and heated for 3H at 80° C. and then cooled to room temperature. Addition of aqueous NaHCO₃ to neutral pH. The organic phase was isolated and the aqueous phase was extracted with CH₂Cl₂, and the combined organic phases were dried and concentrated in vacuo to give (S)-1-(2-amino-thiazole-5-sulfonyl)-pyrrolidine-2-carboxylic acid methyl ester as colourless crystals.

The title compound was prepared via (S)-1-{2-[3-cyclopentylmethyl-3-(3,4-difluoro-phenyl)-ureido]-thiazole-5-sulfonyl}-pyrrolidine-2-carboxylic acid methyl ester in a similar manner as described for the synthesis of {2-[3-cyclopentylmethyl-3-(3,4-difluoro-phenyl)-ureido]-thiazol-4-yl}-acetic acid, using 3,4-difluoroaniline, cyclopentanecarbaldehyde and (S)-1-(2-amino-thiazole-5-sulfonyl)-pyrrolidine-2-carboxylic acid methyl ester.

¹H NMR (400 MHz, DMSO-d₆) δ 7.92 (s, 1H), 7.48-7.60 (m, 1H), 7.19-7.29 (m, 1H), 3.99-4.09 (m, 1H), 3.69 (d, 1H), 3.38-3.46 (m, 1H), 3.17-3.25 (m, 1H), 1.80-2.06 (m, 3H), 1.52-1.72 (m, 3H), 1.42-1.50 (m, 1H), 1.11-1.22 (m, 1H)

HPLC-MS: m/z=515, $R_t$=2.1 min

Example 156

{2-[3-Cyclopentylmethyl-3-(3,4-difluoro-phenyl)-ureido]-thiazole-5-sulfonylamino}-acetic acid

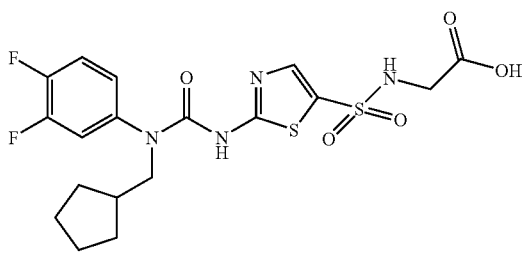

The title compound was prepared via {2-[3-cyclopentylmethyl-3-(3,4-difluoro-phenyl)-ureido]-thiazole-5-sulfonylamino}-acetic acid ethyl ester in a similar manner as described for the synthesis of {2-[3-cyclopentylmethyl-3-(3,4-difluoro-phenyl)-ureido]-thiazol-4-yl}-acetic acid, using 3,4-difluoroaniline, cyclopentanecarbaldehyde and (2-amino-thiazole-5-sulfonylamino)-acetic acid ethyl ester the latter prepared in a similar manner as (S)-1-(2-amino-thiazole-5-sulfonyl)-pyrrolidine-2-carboxylic acid methyl ester.

$^1$H NMR (400 MHz, DMSO-$d_6$) δ 8.25 (t, 1H), 7.76 (s, 1H), 7.48-7.59 (m, 1H), 7.16-7.27 (m, 1H), 3.69 (d, 1H), 3.63 (d, 1H), 1.87-2.00 (m, 1H), 1.53-1.65 (m, 3H), 1.40-1.51 (m, 1H), 1.12-1.23 (m, 1H)

HPLC-MS: m/z=475, $R_t$=1.9 min

Example 157

3-{2-[3-Cyclopentylmethyl-3-(3,4-difluoro-phenyl)-ureido]-thiazole-5-sulfonylamino}-propionic acid

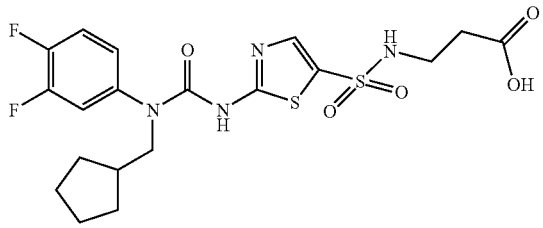

The title compound was prepared via 3-{2-[3-cyclopentylmethyl-3-(3,4-difluoro-phenyl)-ureido]-thiazole-5-sulfonylamino}-propionic acid ethyl ester in a similar manner as described for the synthesis of {2-[3-cyclopentylmethyl-3-(3,4-difluoro-phenyl)-ureido]-thiazol-4-yl}-acetic acid, using 3,4-difluoroaniline, cyclopentanecarbaldehyde and 3-(2-amino-thiazole-5-sulfonylamino)-propionic acid ethyl ester the latter prepared in a similar manner as (S)-1-(2-amino-thiazole-5-sulfonyl)-pyrrolidine-2-carboxylic acid methyl ester.

$^1$H NMR (400 MHz, DMSO-$d_6$) δ 7.84 (t, 1H), 7.78 (s, 1H), 7.57 (s, 1H), 7.49 (dd, 1H), 7.19-7.25 (m, 1H), 3.69 (d, 1H), 2.97-3.04 (m, 1H), 2.41 (t, 1H), 1.89-1.99 (m, 1H), 1.54-1.65 (m, 3H), 1.41-1.50 (m, 1H), 1.12-1.21 (m, 1H)

HPLC-MS: m/z=489, $R_t$=1.9 min

Example 158

{2-[3-Cyclopentylmethyl-3-(4-methanesulfonyl-phenyl)-ureido]-thiazol-4-yl}-acetic acid

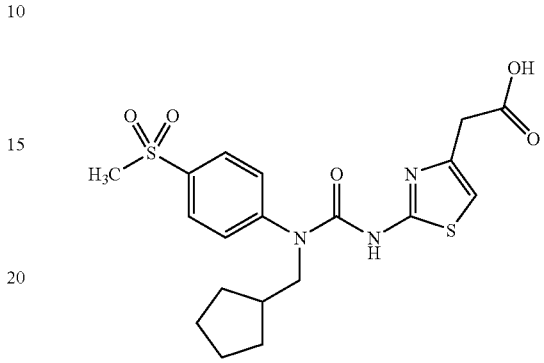

(General Procedure (C) and (A))

Preparation of Secondary Amine:

Preparation of cyclopentylmethyl-(4-methanesulfonyl-phenyl)-amine

Step 1

4-(Methanesulfonyl)aniline hydrochloride (19 mmol) suspended in 25 mL of Et2O was added Et3N (48 mmol) and then a solution cyclopentanecarbonyl chloride (19 mmol) in 25 mL of Et2O was added dropwise during in 10 min. The reaction mixture was stirred for 3 h at RT and then diluted with EtOAc (100 mL) washed with 1N aq HCl, water and aq sat NaHCO₃. The organic phase was dried and concentrated in vacuo to give crude cyclopentanecarboxylic acid (4-methanesulfonyl-phenyl)-amide which was used without further purification.

Step 2:

In a nitrogen atmosphere a solution of cyclopentanecarboxylic acid (4-methanesulfonyl-phenyl)-amide (10 mmol) in THF (20 mL) was added a solution of 1M BH3 in THF (20 mL). The mixture was refluxed for 3H and cooled to RT. Addition of 10 mL of MeOH followed by reflux for 15 min. The mixture was cooled and added water (100 mL) and EtOAc (200 mL). The organic phase was isolated and washed with 1N NaOH, water and brine, dried (MgSO4), filtered and concentrated in vacuo to afford cyclopentylmethyl-(4-methanesulfonyl-phenyl)-amine as a yellow solid.

The title compound was prepared via {2-[3-cyclopentylmethyl-3-(4-methanesulfonyl-phenyl)-ureido]-thiazol-4-yl}-acetic acid ethyl ester employing the coupling and hydrolysis protocol used for the synthesis of {2-[3-cyclopentylmethyl-3-(3,4-difluoro-phenyl)-ureido]-thiazol-4-yl}-acetic acid, using cyclopentylmethyl-(4-methanesulfonyl-phenyl)-amine and (2-amino-thiazol-4-yl)-acetic acid ethyl ester.

$^1$H NMR (400 MHz, DMSO-$d_6$) δ 7.93 (s, 1H), 7.58 (d, 1H), 6.76 (s, 1H), 3.81 (d, 1H), 3.51 (s, 1H), 3.25 (s, 3H), 1.91-2.01 (m, 1H), 1.51-1.62 (m, 3H), 1.39-1.49 (m, 1H), 1.11-1.23 (m, 1H)

HPLC-MS: m/z=438, $R_t$=1.6 min

Example 159

{2-[3-Cyclopentylmethyl-3-(4-methanesulfonyl-phenyl)-ureido]-thiazol-5-ylsulfanyl}-acetic acid

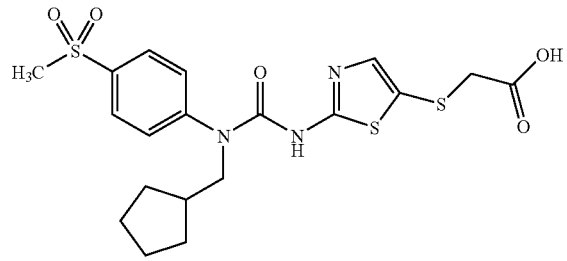

The title compound was prepared via {2-[3-cyclopentylmethyl-3-(4-methanesulfonyl-phenyl)-ureido]-thiazol-5-ylsulfanyl}-acetic acid ethyl ester in a similar manner as described for the synthesis of {2-[3-cyclopentylmethyl-3-(4-methanesulfonyl-phenyl)-ureido]-thiazol-4-yl}-acetic acid, using cyclopentylmethyl-(4-methanesulfonyl-phenyl)-amine and (2-amino-thiazol-5-ylsulfanyl)acetic acid ethyl ester.

$^1$H NMR (400 MHz, DMSO-$d_6$) δ 7.93 (d, 1H), 7.58 (d, 1H), 7.39 (s, 1H), 3.81 (d, 1H), 3.51 (s, 1H), 3.26 (s, 3H), 1.90-2.01 (m, 1H), 1.52-1.62 (m, 3H), 1.40-1.49 (m, 1H), 1.13-1.23 (m, 1H)

HPLC-MS: m/z=470, $R_t$=1.7 min

Example 160

2-{2-[3-Cyclopentylmethyl-3-(4-methanesulfonyl-phenyl)-ureido]-thiazol-5-ylsulfanyl}-2-methyl-propionic acid

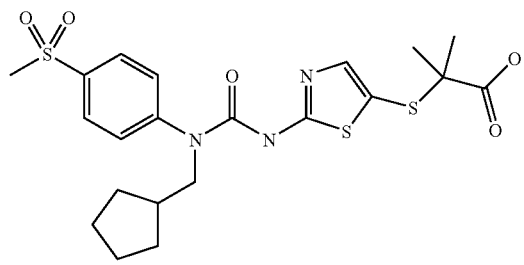

The title compound was prepared via 2-{2-[3-cyclopentylmethyl-3-(4-methanesulfonyl-phenyl)-ureido]-thiazol-5-ylsulfanyl}-2-methyl-propionic acid ethyl ester in a similar manner as described for the synthesis of {2-[3-cyclopentylmethyl-3-(4-methanesulfonyl-phenyl)-ureido]-thiazol-4-yl}-acetic acid, using cyclopentylmethyl-(4-methanesulfonyl-phenyl)-amine and 2-(2-amino-thiazol-5-ylsulfanyl)-2-methyl-propionic acid ethyl ester.

$^1$H NMR (400 MHz, DMSO-$d_6$) δ 7.94 (d, 1H), 7.59 (d, 1H), 7.38 (s, 1H), 3.81 (d, 1H), 3.26 (s, 3H), 1.90-2.01 (m, 1H), 1.52-1.63 (m, 3H), 1.40 (s, 3H), 1.37-1.48 (m, 1H), 1.13-1.24 (m, 1H)

HPLC-MS: m/z=498, $R_t$=1.9 min

Example 161

(S)-1-{2-[3-Cyclopentylmethyl-3-(4-methanesulfonyl-phenyl)-ureido]-thiazole-5-sulfonyl}-pyrrolidine-2-carboxylic acid

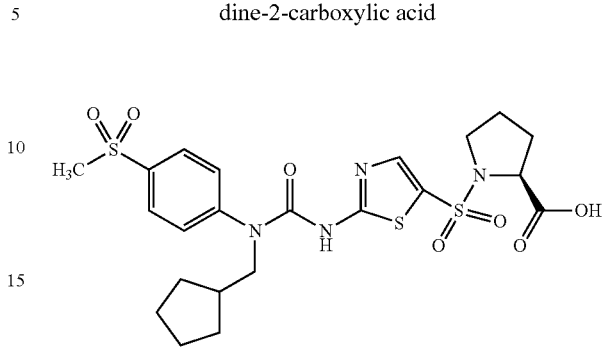

The title compound was prepared via (S)-1-{2-[3-cyclopentylmethyl-3-(4-methanesulfonyl-phenyl)-ureido]-thiazole-5-sulfonyl}-pyrrolidine-2-carboxylic acid methyl ester in a similar manner as described for the synthesis of {2-[3-cyclopentylmethyl-3-(4-methanesulfonyl-phenyl)-ureido]-thiazol-4-yl}-acetic acid, using cyclopentylmethyl-(4-methanesulfonyl-phenyl)-amine and (S)-1-(2-amino-thiazole-5-sulfonyl)-pyrrolidine-2-carboxylic acid methyl ester.

$^1$H NMR (400 MHz, DMSO-$d_6$) δ 7.95 (d, 1H), 7.92 (s, 1H), 7.62 (d, 1H), 4.04 (dd, 1H), 3.82 (d, 1H), 3.37-3.46 (m, 1H), 3.26-3.28 (m, 3H), 3.18-3.25 (m, 1H), 1.80-2.08 (m, 3H), 1.65-1.76 (m, 1H), 1.52-1.64 (m, 3H), 1.40-1.50 (m, 1H), 1.12-1.23 (m, 1H)

HPLC-MS: m/z=557, $R_t$=1.8 min

Example 162

{2-[3-Cyclopentylmethyl-3-(4-methanesulfonyl-phenyl)-ureido]-thiazole-5-sulfonylamino}-acetic acid

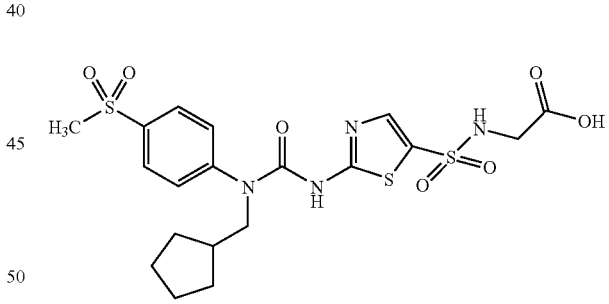

The title compound was prepared via {2-[3-cyclopentylmethyl-3-(4-methanesulfonyl-phenyl)-ureido]-thiazole-5-sulfonylamino}-acetic acid ethyl ester in a similar manner as described for the synthesis of {2-[3-cyclopentylmethyl-3-(4-methanesulfonyl-phenyl)-ureido]-thiazol-4-yl}-acetic acid, using cyclopentylmethyl-(4-methanesulfonyl-phenyl)-amine and (2-amino-thiazole-5-sulfonylamino)-acetic acid ethyl ester the latter prepared in a similar manner as (S)-1-(2-amino-thiazole-5-sulfonyl)-pyrrolidine-2-carboxylic acid methyl ester.

$^1$H NMR (400 MHz, DMSO-$d_6$) δ 7.95 (d, 1H), 7.76 (s, 1H), 7.61 (d, 1H), 3.82 (d, 1H), 3.63 (s, 1H), 3.27 (s, 3H), 1.89-2.02 (m, 1H), 1.52-1.63 (m, 3H), 1.40-1.49 (m, 1H), 1.13-1.24 (m, 1H)

HPLC-MS: m/z=517, $R_t$=1.6 min

Example 163

3-{2-[3-Cyclopentylmethyl-3-(4-methanesulfonyl-phenyl)-ureido]-thiazole-5-sulfonylamino}-propionic acid

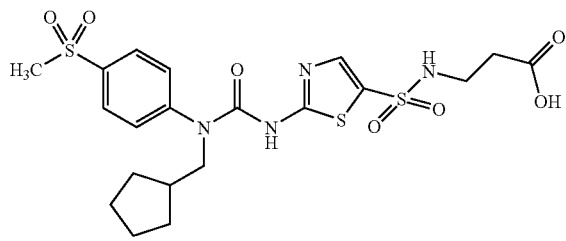

The title compound was prepared via 3-{2-[3-cyclopentyl-methyl-3-(4-methanesulfonyl-phenyl)-ureido]-thiazole-5-sulfonylamino}-propionic acid ethyl ester in a similar manner as described for the synthesis of {2-[3-cyclopentylmethyl-3-(4-methanesulfonyl-phenyl)-ureido]-thiazol-4-yl}-acetic acid, using cyclopentylmethyl-(4-methanesulfonyl-phenyl)-amine and 3-(2-amino-thiazole-5-sulfonylamino)-propionic acid ethyl ester the latter prepared in a similar manner as (S)-1-(2-amino-thiazole-5-sulfonyl)-pyrrolidine-2-carboxylic acid methyl ester.

$^1$H NMR (400 MHz, DMSO-$d_6$) δ 7.95 (d, 1H), 7.86 (t, 1H), 7.78 (s, 1H), 7.62 (d, 1H), 3.82 (d, 1H), 3.27 (s, 3H), 2.97-3.05 (m, 1H), 2.41 (t, 1H), 1.89-2.03 (m, 1H), 1.52-1.63 (m, 3H), 1.39-1.49 (m, 1H), 1.13-1.24 (m, 1H)

HPLC-MS: m/z=531, $R_t$=1.6 min

Example 164

3-{2-[3-Cyclopentylmethyl-3-(3,4-difluoro-phenyl)-ureido]-thiazol-5-ylsulfanyl}-propionic acid

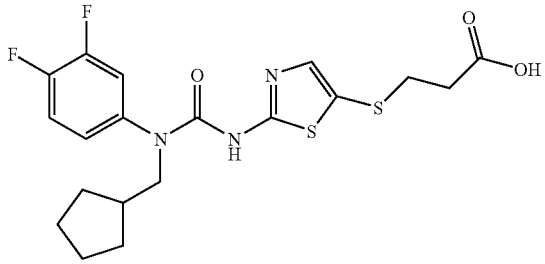

Preparation of 3-(2-amino-thiazol-5-ylsulfanyl)-propionic acid ethyl ester

5-Bromo-2-aminothiazole (25 g, 96 mmol) in DMF (150 mL) was added K$_2$CO$_3$ (26.5 g, 192 mmol) and the mixture was purged with N$_2$ for 5 min. The mixture was cooled to 0° C. on an ice bath before 3-mercaptopropionic acid ethyl ester (12.9 g, 96 mmol) was added dropwise over the course of 30 min. The reaction mixture was stirred for 13 Hours before water (400 mL) was added. The aqueous mixture was extracted with Et$_2$O (1×500 mL, 2×250 mL). The combined organic phases was washed with saturated NH$_4$Cl (3×150 mL), dried (MgSO$_4$). The solvent was removed in vacuo to give a dark residue which was purified by column chromatography (SiO$_2$, EtOAc-heptane (1:1)). The solvent was removed in vacuo to give 11 g (49%) of 3-(2-amino-thiazol-5-ylsulfanyl)-propionic acid ethyl ester.

$^1$H NMR (400 MHz, CDCl$_3$) δ 7.1 (s, 1H), 5.2 (bs, 2H), 4.2 (q, 2H), 2.8 (t, 2H), 2.6 (t, 2H), 1.3 (t, 3H).

The title compound was prepared via 3-{2-[3-cyclopentyl-methyl-3-(3,4-difluoro-phenyl)-ureido]-thiazol-5-ylsulfa-nyl}-propionic acid ethyl ester in a similar manner as described for the synthesis of {2-[3-cyclopentylmethyl-3-(3,4-difluoro-phenyl)-ureido]-thiazol-4-yl}-acetic acid, using 3,4-difluoroaniline, cyclopentanecarbaldehyde and 3-(2-amino-thiazol-5-ylsulfanyl)-propionic acid ethyl ester.

$^1$H NMR (400 MHz, DMSO-$d_6$) 7.43-7.55 (m, 1H), 7.37 (s, 1H), 7.15-7.22 (m, 1H), 3.68 (d, 1H), 2.85 (t, 1H), 2.46-2.50 (m, 1H), 1.88-1.99 (m, 1H), 1.53-1.64 (m, 3H), 1.41-1.50 (m, 1H), 1.11-1.21 (m, 1H)

HPLC-MS: m/z=422, $R_t$=2.1 min

Example 165

3-{2-[3-Cyclopentylmethyl-3-(4-methanesulfonyl-phenyl)-ureido]-thiazol-5-ylsulfanyl}-propionic acid

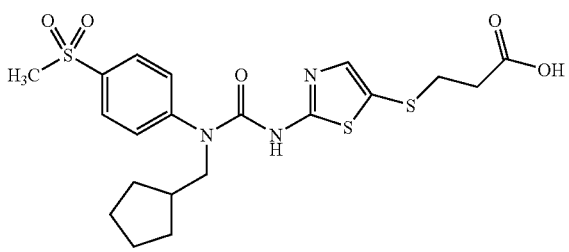

The title compound was prepared via 3-{2-[3-cyclopentyl-methyl-3-(4-methanesulfonyl-phenyl)-ureido]-thiazol-5-yl-sulfanyl}-propionic acid ethyl ester in a similar manner as described for the synthesis of {2-[3-cyclopentylmethyl-3-(4-methanesulfonyl-phenyl)-ureido]-thiazol-4-yl}-acetic acid, using cyclopentylmethyl-(4-methanesulfonyl-phenyl)-amine and 3-(2-amino-thiazol-5-ylsulfanyl)-propionic acid ethyl ester.

$^1$H NMR (400 MHz, DMSO-$d_6$) δ 7.93 (d, 1H), 7.58 (d, 1H), 7.37 (s, 1H), 3.81 (d, 1H), 3.26 (s, 3H), 2.86 (t, 1H), 2.47-2.50 (m, 1H), 1.90-2.01 (m, 1H), 1.52-1.62 (m, 3H), 1.40-1.49 (m, 1H), 1.12-1.23 (m, 1H)

HPLC-MS: m/z=484, $R_t$=1.8 min

Example 166

{2-[3-(3-Acetylamino-phenyl)-3-cyclopentylmethyl-ureido]-thiazol-5-ylsulfanyl}-acetic acid

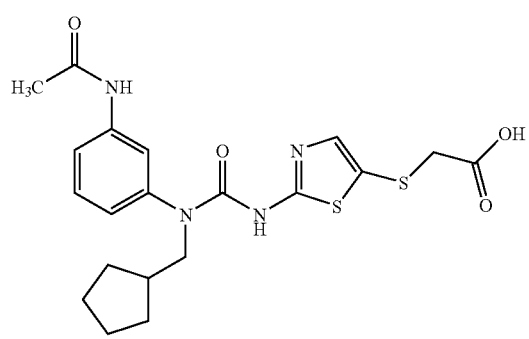

The title compound was prepared via {2-[3-(3-acety-lamino-phenyl)-3-cyclopentylmethyl-ureido]-thiazol-5-yl-sulfanyl}-acetic acid ethyl ester in a similar manner as described for the synthesis of {2-[3-cyclopentylmethyl-3-(3, 4-difluoro-phenyl)-ureido]-thiazol-4-yl}-acetic acid, using N-(3-amino-phenyl)-acetamide, cyclopentanecarbaldehyde and (2-amino-thiazol-5-ylsulfanyl)acetic acid ethyl ester.

$^1$H NMR (400 MHz, DMSO-d$_6$) δ ppm 10.06 (s, 1H), 7.58 (d, 1H), 7.47-7.51 (m, 1H), 7.37 (d, 1H), 7.32 (d, 1H), 6.97 (d, 1H), 3.66 (d, 1H), 3.49 (s, 1H), 2.04 (s, 3H), 1.91-2.01 (m, 1H), 1.53-1.64 (m, 3H), 1.41-1.50 (m, 1H), 1.14-1.24 (m, 1H)

HPLC-MS: m/z=449, R$_t$=1.7 min

Example 167

3-{2-[3-(3-Acetylamino-phenyl)-3-cyclopentylmethyl-ureido]-thiazol-5-ylsulfanyl}-propionic acid

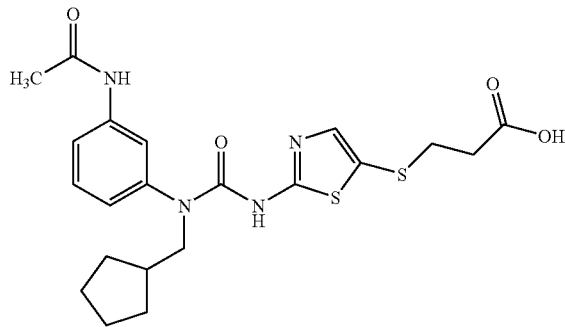

The title compound was prepared via 3-{2-[3-(3-acetylamino-phenyl)-3-cyclopentylmethyl-ureido]-thiazol-5-ylsulfanyl}-propionic acid ethyl ester in a similar manner as described for the synthesis of {2-[3-cyclopentylmethyl-3-(3, 4-difluoro-phenyl)-ureido]-thiazol-4-yl}-acetic acid, using N-(3-amino-phenyl)-acetamide, cyclopentanecarbaldehyde and 3-(2-amino-thiazol-5-ylsulfanyl)-propionic acid ethyl ester.

$^1$H NMR (400 MHz, DMSO-d$_6$) δ ppm 10.07 (s, 1H), 7.57 (d, 1H), 7.50 (s, 1H), 7.30-7.37 (m, 1H), 6.97 (d, 1H), 3.66 (d, 1H), 2.85 (t, 1H), 2.47-2.50 (m, 1H), 2.04 (s, 3H), 1.92-2.01 (m, 1H), 1.53-1.64 (m, 3H), 1.40-1.51 (m, 1H), 1.14-1.24 (m, 1H)

HPLC-MS: m/z=463, R$_t$=1.8 min

Example 168

{2-[3-Cyclopentylmethyl-3-(3-dimethylcarbamoyl-phenyl)-ureido]-thiazol-5-ylsulfanyl}-acetic acid

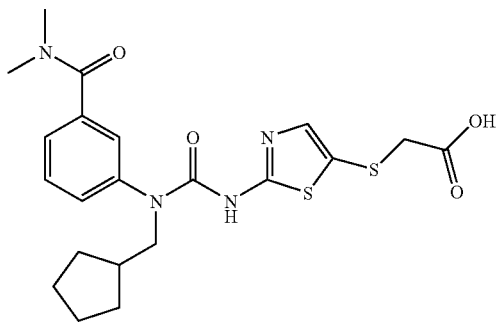

The title compound was prepared via {2-[3-cyclopentylmethyl-3-(3-dimethylcarbamoyl-phenyl)-ureido]-thiazol-5-ylsulfanyl}-acetic acid ethyl ester in a similar manner as described for the synthesis of {2-[3-cyclopentylmethyl-3-(4-methanesulfonyl-phenyl)-ureido]-thiazol-4-yl}-acetic acid, using 3-(cyclopentylmethyl-amino)-N,N-dimethyl-benzamide and (2-amino-thiazol-5-ylsulfanyl)acetic acid ethyl ester $^1$H NMR (400 MHz, DMSO-d$_6$) δ ppm 7.48 (s, 1H), 7.27-7.42 (m, 3H), 3.65-3.77 (m, 1H), 3.49 (s, 1H), 2.97 (s, 3H), 1.87-2.00 (m, 1H), 1.51-1.62 (m, 3H), 1.40-1.48 (m, 1H), 1.12-1.23 (m, 1H).

HPLC-MS: M/Z=463, Rt=1.77 min.

Example 169

3-{2-[3-Cyclopentylmethyl-3-(3-dimethylcarbamoyl-phenyl)-ureido]-thiazol-5-ylsulfanyl}-propionic acid

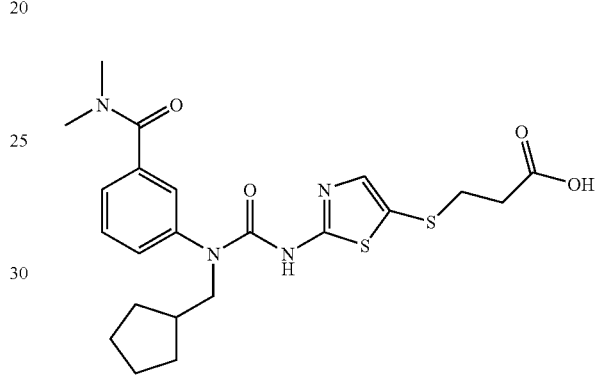

The title compound was prepared via {2-[3-cyclopentylmethyl-3-(3-dimethylcarbamoyl-phenyl)-ureido]-thiazol-5-ylsulfanyl}-propionic acid ethyl ester in a similar manner as described for the synthesis of {2-[3-cyclopentylmethyl-3-(4-methanesulfonyl-phenyl)-ureido]-thiazol-4-yl}-acetic acid, using 3-(cyclopentylmethyl-amino)-N,N-dimethyl-benzamide and (2-amino-thiazol-5-ylsulfanyl) propionic acid ethyl ester 1H NMR (400 MHz, DMSO-d$_6$) δ ppm 7.44-7.51 (m, 1H), 7.30-7.40 (m, 3H), 3.72 (d, 1H), 2.96 (s, 3H), 2.85 (t, 1H), (2.46-2.55, m, 2H), 1.89-1.99 (m, 1H), 1.51-1.62 (m, 3H), 1.36-1.49 (m, 1H), 1.07-1.28 (m, 1H).

HPLC-MS: M/Z=477, R$_t$=1.82 min

Example 170

{2-[3-(3-Carbamoyl-phenyl)-3-cyclopentylmethyl-ureido]-thiazol-5-ylsulfanyl}-acetic acid

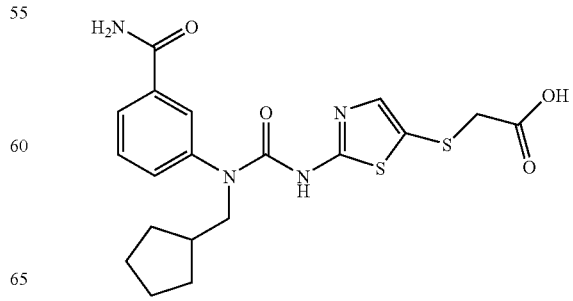

The title compound was prepared via {2-[3-cyclopentylmethyl-3-(3-carbamoyl-phenyl)-ureido]-thiazol-5-ylsulfanyl}-acetic acid ethyl ester in a similar manner as described for the synthesis of {2-[3-cyclopentylmethyl-3-(4-methanesulfonyl-phenyl)-ureido]-thiazol-4-yl}-acetic acid, using 3-(cyclopentylmethyl-amino)-benzamide and (2-amino-thiazol-5-ylsulfanyl)acetic acid ethyl ester 1H NMR (400 MHz, DMSO-$d_6$) δ ppm 8.05 (s, 1H), 7.79-7.85 (m, 1H), 7.43-7.52 (m, 3H), 7.38 (s, 1H), 3.73 (d, 1H), (3.33-3.4 m, 2H), 3.49 (s, 1H), 1.89-1.99 (m, 1H), 1.52-1.64 (m, 3H), 1.40-1.49 (m, 1H), 1.13-1.24 (m, 1H).

HPLC-MS: M/Z=435, Rt=1.65 min

Example 171

3-{2-[3-(3-Carbamoyl-phenyl)-3-cyclopentylmethyl-ureido]-thiazol-5-ylsulfanyl}-propionic acid

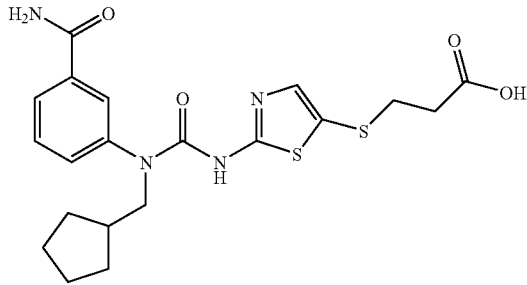

The title compound was prepared via {2-[3-cyclopentylmethyl-3-(3-carbamoyl-phenyl)-ureido]-thiazol-5-ylsulfanyl}-propionic acid ethyl ester in a similar manner as described for the synthesis of {2-[3-cyclopentylmethyl-3-(4-methanesulfonyl-phenyl)-ureido]-thiazol-4-yl}-acetic acid, using 3-(cyclopentylmethyl-amino)-benzamide and (2-amino-thiazol-5-ylsulfanyl) propionic acid ethyl ester 1H NMR (400 MHz, DMSO-$d_6$) δ ppm 8.04 (s, 1H), 7.77-7.87 (m, 1H), 7.41-7.52 (m, 3H), 7.35 (s, 1H), 3.73 (d, 1H), 2.85 (t, 1H), (2.45-2.55, m, 2H), 1.88-2.01 (m, 1H), 1.52-1.64 (m, 3H), 1.40-1.51 (m, 1H), 1.09-1.27 (m, 1H).

HPLC-MS: M/Z=449, Rt=1.71 min.

Example 172

{2-[3-Cyclopentylmethyl-3-(3-methylcarbamoyl-phenyl)-ureido]-thiazol-5-ylsulfanyl}-acetic acid

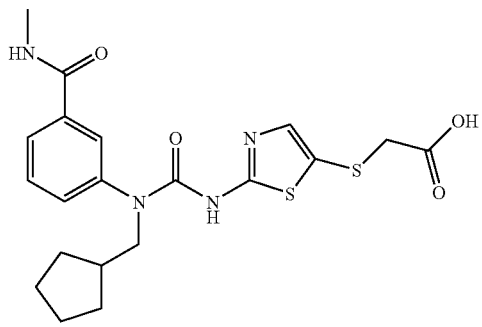

The title compound was prepared via {2-[3-cyclopentylmethyl-3-(3-methylcarbamoyl-phenyl)-ureido]-thiazol-5-ylsulfanyl}-acetic acid ethyl ester in a similar manner as described for the synthesis of {2-[3-cyclopentylmethyl-3-(4-methanesulfonyl-phenyl)-ureido]-thiazol-4-yl}-acetic acid, using 3-(cyclopentylmethyl-amino)-N-methyl-benzamide and (2-amino-thiazol-5-ylsulfanyl)acetic acid ethyl ester 1H NMR (400 MHz, DMSO-$d_6$) δ ppm 8.49 (d, 1H), 7.77-7.81 (m, 1H), 7.75 (s, 1H), 7.42-7.53 (m, 1H), 7.37 (s, 1H), 3.73 (d, 1H), 3.49 (s, 1H), 2.79 (d, 3H), 1.88-1.98 (m, 1H), 1.52-1.63 (m, 3H), 1.39-1.49 (m, 1H), 1.11-1.23 (m, 1H).

HPLC-MS: M/Z=449, Rt=1.71 min

Example 173

3-{2-[3-Cyclopentylmethyl-3-(3-methylcarbamoyl-phenyl)-ureido]-thiazol-5-ylsulfanyl}-propionic acid

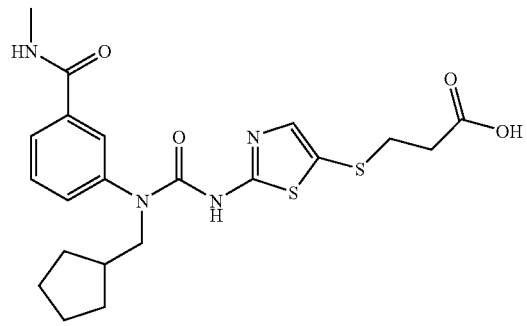

The title compound was prepared via {2-[3-cyclopentylmethyl-3-(3-methylcarbamoyl-phenyl)-ureido]-thiazol-5-ylsulfanyl}-propionic acid ethyl ester in a similar manner as described for the synthesis of {2-[3-cyclopentylmethyl-3-(4-methanesulfonyl-phenyl)-ureido]-thiazol-4-yl}-acetic acid, using 3-(cyclopentylmethyl-amino)-N-methyl-benzamide and (2-amino-thiazol-5-ylsulfanyl) propionic acid ethyl ester 1H NMR (400 MHz, DMSO-$d_6$) δ ppm 8.47-8.53 (m, 1H), 7.77-7.83 (m, 1H), 7.75-7.77 (m, 1H), 7.42-7.54 (m, 1H), 7.35 (s, 1H), 3.73 (d, 1H), 2.85 (t, 1H), 2.79 (d, 3H), 2.46-2.50 (m, 2H), 1.89-1.98 (m, 1H), 1.50-1.64 (m, 3H), 1.40-1.46 (m, 1H), 1.09-1.25 (m, 1H).

HPLC-MS: M/Z=463, Rt=1.78 min

Example 174

{2-[3-Cyclopentylmethyl-3-(3-trifluoromethyl-phenyl)-ureido]-thiazol-5-ylsulfanyl}-acetic acid

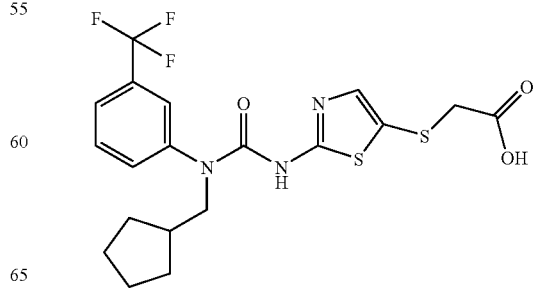

The title compound was prepared via {2-[3-cyclopentylmethyl-3-(3-trifluoromethyl-phenyl)-ureido]-thiazol-5-ylsulfanyl}-acetic acid ethyl ester in a similar manner as described for the synthesis of {2-[3-cyclopentylmethyl-3-(4-methanesulfonyl-phenyl)-ureido]-thiazol-4-yl}-acetic acid, using cyclopentylmethyl-(3-trifluoromethyl-phenyl)-amine and (2-amino-thiazol-5-ylsulfanyl)acetic acid ethyl ester HPLC-MS: M/Z=460, 2, 15 min.

Example 175

{2-[3-Cyclopentylmethyl-3-(4-sulfamoyl-phenyl)-ureido]-thiazol-5-ylsulfanyl}-acetic acid

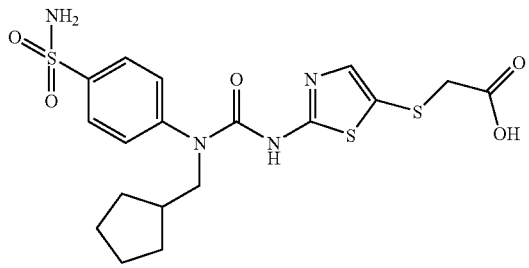

The title compound was prepared via {2-[3-cyclopentylmethyl-3-(4-sulfamoyl-phenyl)-ureido]-thiazol-5-ylsulfanyl}-acetic acid ethyl ester in a similar manner as described for the synthesis of {2-[3-cyclopentylmethyl-3-(4-methanesulfonyl-phenyl)-ureido]-thiazol-4-yl}-acetic acid, using cyclopentylmethyl-(4-sulfamoyl-phenyl)-amine and (2-amino-thiazol-5-ylsulfanyl)acetic acid ethyl ester 1H NMR (400 MHz, DMSO-$d_6$) δ ppm 7.82 (d, 1H), 7.50 (d, 1H), 7.41 (s, 1H), 7.36-7.40 (m, 1H), 3.77 (d, 1H), 3.49 (s, 1H), 1.88-1.98 (m, 1H), 1.51-1.62 (m, 3H), 1.39-1.50 (m, 1H), 1.11-1.21 (m, 1H).

HPLC-MS: M/Z=471, Rt=1.63 min

Example 176

{2-[3-Cyclopentylmethyl-3-(4-fluoro-3-trifluoromethyl-phenyl)-ureido]-thiazol-5-ylsulfanyl}-acetic acid

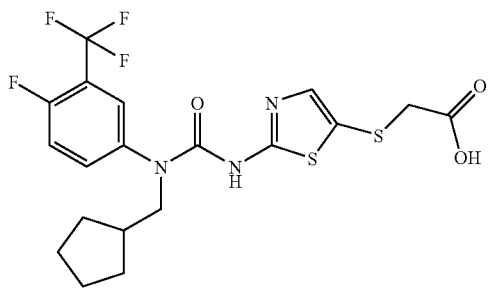

The title compound was prepared via {2-[3-cyclopentylmethyl-3-(4-fluoro-3-trifluoromethyl-phenyl)-ureido]-thiazol-5-ylsulfanyl}-acetic acid ethyl ester in a similar manner as described for the synthesis of {2-[3-cyclopentylmethyl-3-(4-methanesulfonyl-phenyl)-ureido]-thiazol-4-yl}-acetic acid, using cyclopentylmethyl-(4-fluoro-3-trifluoromethyl-phenyl)-amine and (2-amino-thiazol-5-ylsulfanyl)acetic acid ethyl ester 1H NMR (400 MHz, DMSO-$d_6$) δ ppm 7.73-7.77 (m, 1H), 7.67-7.72 (m, 1H), 7.55 (t, 1H), 7.39 (s, 1H), 3.71 (d, 1H), 3.49 (s, 1H), 1.88-1.99 (m, 1H), 1.52-1.63 (m, 3H), 1.40-1.51 (m, 1H), 1.11-1.21 (m, 1H).

HPLC-MS: M/Z=478, Rt=2.19 min

Example 177

{2-[3-Cyclopentylmethyl-3-(4-trifluoromethyl-phenyl)-ureido]-thiazol-5-ylsulfanyl}-acetic acid

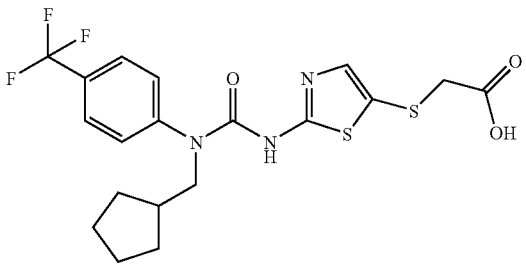

The title compound was prepared via {2-[3-cyclopentylmethyl-3-(4-trifluoromethyl-phenyl)-ureido]-thiazol-5-ylsulfanyl}-acetic acid ethyl ester in a similar manner as described for the synthesis of {2-[3-cyclopentylmethyl-3-(4-methanesulfonyl-phenyl)-ureido]-thiazol-4-yl}-acetic acid, using cyclopentylmethyl-(4-trifluoromethyl-phenyl)-amine and (2-amino-thiazol-5-ylsulfanyl)acetic acid ethyl ester 1H NMR (400 MHz, DMSO-$d_6$) δ ppm 7.76 (d, 1H), 7.54 (d, 1H), 7.39 (s, 1H), 3.78 (d, 1H), 3.50 (s, 1H), 1.89-1.99 (m, 1H), 1.51-1.62 (m, 3H), 1.39-1.50 (m, 1H), 1.12-1.23 (m, 1H).

HPLC-MS: M/Z=457, Rt=2.18 min.

Example 178

{2-[3-Cyclopentylmethyl-3-(4-trifluoromethoxy-phenyl)-ureido]-thiazol-5-ylsulfanyl}-acetic acid

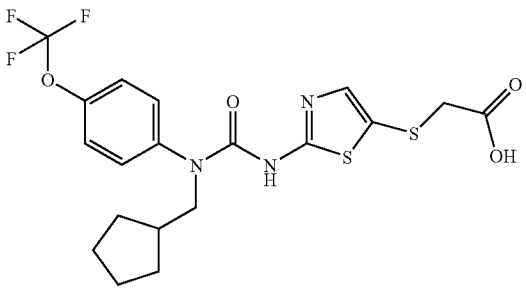

The title compound was prepared via {2-[3-cyclopentylmethyl-3-(4-trifluoromethoxy-phenyl)-ureido]-thiazol-5-ylsulfanyl}-acetic acid ethyl ester in a similar manner as described for the synthesis of {2-[3-cyclopentylmethyl-3-(4-methanesulfonyl-phenyl)-ureido]-thiazol-4-yl}-acetic acid, using cyclopentylmethyl-(4-trifluoromethoxy-phenyl)-amine and (2-amino-thiazol-5-ylsulfanyl)acetic acid ethyl ester 1H NMR (400 MHz, DMSO-d$_6$) δ ppm 7.37-7.46 (m, 3H), 3.71 (d, 1H), 3.49 (s, 1H), 1.88-1.98 (m, 1H), 1.52-1.63 (m, 3H), 1.40-1.51 (m, 1H), 1.12-1.22 (m, 1H).

HPLC-MS: M/Z=476, Rt=2.16 min

Example 179

{2-[3-Cyclopentylmethyl-3-(3-sulfamoyl-phenyl)-ureido]-thiazol-5-ylsulfanyl}-acetic acid

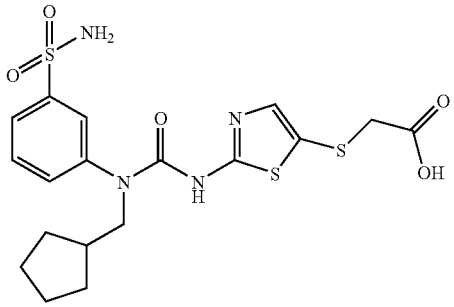

The title compound was prepared via {2-[3-cyclopentylmethyl-3-(3-sulfamoyl-phenyl)-ureido]-thiazol-5-ylsulfanyl}-acetic acid ethyl ester in a similar manner as described for the synthesis of {2-[3-cyclopentylmethyl-3-(4-methanesulfonyl-phenyl)-ureido]-thiazol-4-yl}-acetic acid, using cyclopentylmethyl-(3-sulfamoyl-phenyl)-amine and (2-amino-thiazol-5-ylsulfanyl)acetic acid ethyl ester 1H NMR (400 MHz, DMSO-d$_6$) δ ppm 7.68-7.76 (m, 1H), 7.57-7.62 (m, 1H), 7.50-7.55 (m, 1H), 7.43 (s, 1H), 7.39 (s, 1H), 3.75 (d, 1H), 3.50 (s, 1H), 1.95 (s, 1H), 1.52-1.64 (m, 3H), 1.40-1.51 (m, 1H), 1.13-1.23 (m, 1H).

HPLC-MS: M/Z=471, Rt=1.63 min

Example 180

[2-(3-Benzo[1,3]dioxol-5-yl-3-cyclopentylmethyl-ureido)-thiazol-5-ylsulfanyl]-acetic acid

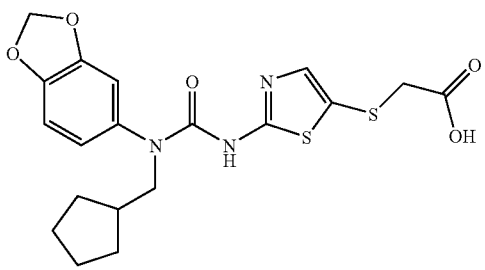

The title compound was prepared via [2-(3-benzo[1,3]dioxol-5-yl-3-cyclopentylmethyl-ureido)-thiazol-5-ylsulfanyl]-acetic acid ethyl ester in a similar manner as described for the synthesis of {2-[3-cyclopentylmethyl-3-(4-methanesulfonyl-phenyl)-ureido]-thiazol-4-yl}-acetic acid, using benzo[1,3]dioxol-5-yl-cyclohexylmethyl-amine and (2-amino-thiazol-5-ylsulfanyl)acetic acid ethyl ester 1H NMR (400 MHz, DMSO-d$_6$) δ ppm 7.36 (s, 1H), 6.91-6.96 (m, 1H), 6.76 (dd, 1H), 6.08 (s, 1H), 3.60 (d, 1H), 3.48 (s, 1H), 1.89-2.00 (m, 1H), 1.52-1.64 (m, 3H), 1.40-1.51 (m, 1H), 1.13-1.24 (m, 1H).

HPLC-MS: M/Z=436, Rt=1.96 min.

Example 181

{2-[3-Cyclopentylmethyl-3-(3-trifluoromethoxy-phenyl)-ureido]-thiazol-5-ylsulfanyl}-acetic acid

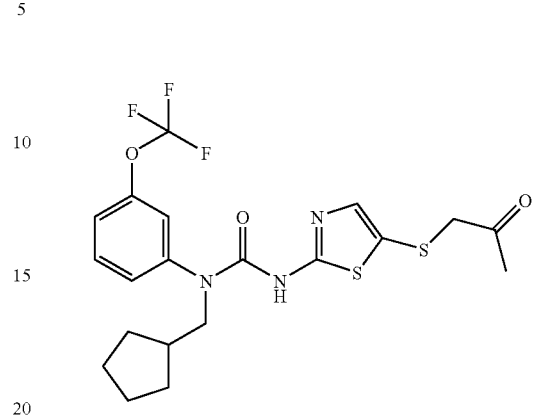

The title compound was prepared via {2-[3-cyclopentylmethyl-3-(3-trifluoromethoxy-phenyl)-ureido]-thiazol-5-ylsulfanyl}-acetic acid ethyl ester in a similar manner as described for the synthesis of {2-[3-cyclopentylmethyl-3-(4-methanesulfonyl-phenyl)-ureido]-thiazol-4-yl}-acetic acid, using cyclopentylmethyl-(3-trifluoromethoxy-phenyl)-amine and (2-amino-thiazol-5-ylsulfanyl)acetic acid ethyl ester 1H NMR (400 MHz, DMSO-d$_6$) δ ppm 7.53 (t, 1H), 7.39 (s, 1H), 7.33-7.37 (m, 1H), 7.30 (d, 1H), 3.74 (d, 1H), 3.50 (s, 1H), 1.88-1.99 (m, 1H), 1.51-1.62 (m, 3H), 1.39-1.50 (m, 1H), 1.10-1.21 (m, 1H).

HPLC-MS: M/Z=476, Rt=2.20 min

Example 182

{2-[3-Cyclopentylmethyl-3-(6-methoxy-pyridin-3-yl)-ureido]-thiazol-5-ylsulfanyl}-acetic acid

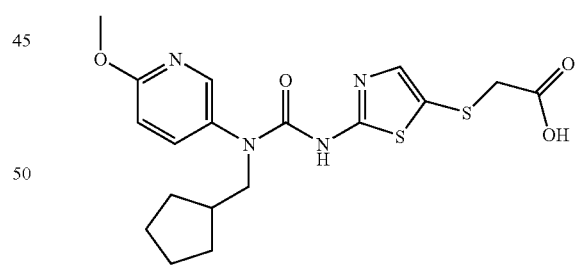

The title compound was prepared via {2-[3-cyclopentylmethyl-3-(6-methoxy-pyridin-3-yl)-ureido]-thiazol-5-ylsulfanyl}-acetic acid ethyl ester in a similar manner as described for the synthesis of {2-[3-cyclopentylmethyl-3-(4-methanesulfonyl-phenyl)-ureido]-thiazol-4-yl}-acetic acid, using cyclopentylmethyl-(6-methoxy-pyridin-3-yl)-amine and (2-amino-thiazol-5-ylsulfanyl)acetic acid ethyl ester 1H NMR (400 MHz, DMSO-d$_6$) δ ppm 8.10 (d, 1H), 7.65 (dd, 1H), 7.37 (s, 1H), 6.87 (d, 1H), 3.88 (s, 3H), 3.64 (d, 1H), 3.49 (s, 1H), 1.87-2.00 (m, 1H), 1.53-1.64 (m, 3H), 1.40-1.51 (m, 1H), 1.11-1.25 (m, 1H).

HPLC-MS: M/Z=423, Rt=1.83 min

Example 183

{2-[3-(6-Acetylamino-pyridin-3-yl)-3-cyclopentylmethyl-ureido]-thiazol-5-ylsulfanyl}-acetic acid

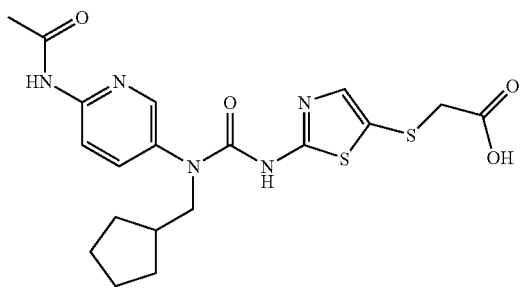

The title compound was prepared via {2-[3-(6-acetylamino-pyridin-3-yl)-3-cyclopentylmethyl-ureido]-thiazol-5-ylsulfanyl}-acetic acid ethyl ester in a similar manner as described for the synthesis of {2-[3-cyclopentylmethyl-3-(4-methanesulfonyl-phenyl)-ureido]-thiazol-4-yl}-acetic acid, using N-[5-(cyclopentylmethyl-amino)-pyridin-2-yl]-acetamide and (2-amino-thiazol-5-ylsulfanyl)acetic acid ethyl ester 1H NMR (400 MHz, DMSO-$d_6$) δ ppm 10.63 (s, 1H), 8.22 (d, 1H), 8.10 (d, 1H), 7.71 (dd, 1H), 7.38 (s, 1H), 3.67 (d, 1H), 3.49 (s, 1H), 2.11 (s, 3H), 1.91-2.00 (m, 1H), 1.53-1.64 (m, 3H), 1.40-1.50 (m, 1H), 1.12-1.22 (m, 1H).

HPLC-MS: M/Z=450, Rt=1.55 min

Example 184

{2-[3-(3-Acetylamino-phenyl)-3-pentyl-ureido]-thiazol-5-ylsulfanyl}-acetic acid

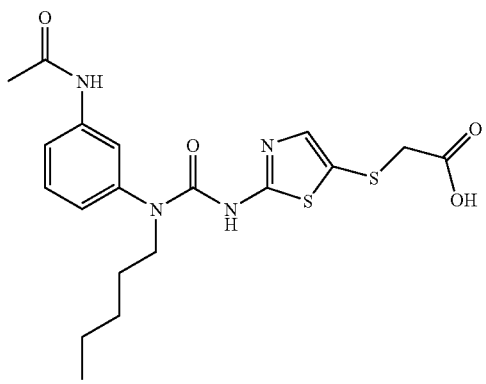

The title compound was prepared via {2-[3-(3-acetylamino-phenyl)-3-pentyl-ureido]-thiazol-5-ylsulfanyl}-acetic acid ethyl ester in a similar manner as described for the synthesis of {2-[3-cyclopentylmethyl-3-(3,4-difluoro-phenyl)-ureido]-thiazol-4-yl}-acetic acid, using N-(3-amino-phenyl)-acetamide, pentanal and (2-amino-thiazol-5-ylsulfanyl)acetic acid ethyl ester.

1H NMR (400 MHz, DMSO-$d_6$) δ ppm 10.05 (s, 1H), 7.57 (d, 1H), 7.50 (s, 1H), 7.31-7.39 (m, 1H), 6.95 (d, 1H), 3.61-3.68 (m, 1H), 3.49 (s, 1H), 2.04 (s, 3H), 1.41-1.49 (m, 1H), 1.20-1.30 (m, 3H), 0.83 (t, 3H).

HPLC-MS: M/Z=437, Rt=1.70 min

Example 185

{2-[3-(3-Acetylamino-phenyl)-3-cyclohexylmethyl-ureido]-thiazol-5-ylsulfanyl}-acetic acid

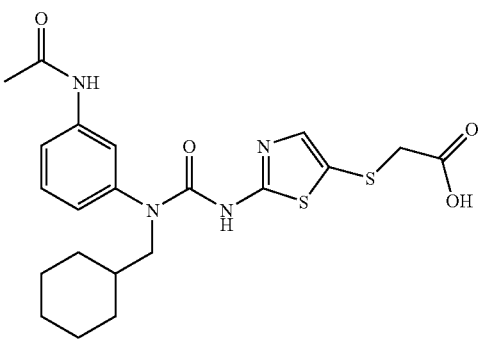

The title compound was prepared via {2-[3-(3-acetylamino-phenyl)-3-cyclohexylmethyl-ureido]-thiazol-5-ylsulfanyl}-acetic acid ethyl ester in a similar manner as described for the synthesis of {2-[3-cyclopentylmethyl-3-(3,4-difluoro-phenyl)-ureido]-thiazol-4-yl}-acetic acid, using N-(3-amino-phenyl)-acetamide, cyclohexylcarbaldehyde and (2-amino-thiazol-5-ylsulfanyl)acetic acid ethyl ester.

HPLC-MS: M/Z=463, Rt=1.80 min

Example 186

{2-[3-(3-Acetylamino-phenyl)-3-(3-methyl-butyl)-ureido]-thiazol-5-ylsulfanyl}-acetic acid

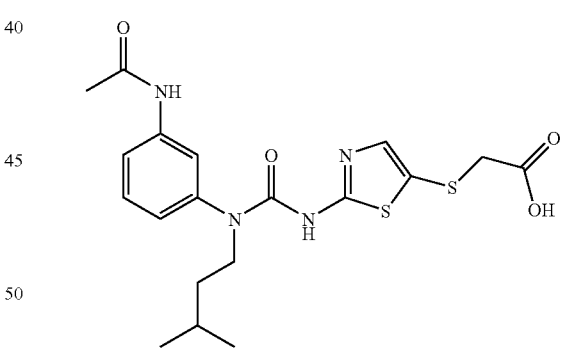

The title compound was prepared via {2-[3-(3-acetylamino-phenyl)-3-(3-methyl-butyl)-ureido]-thiazol-5-ylsulfanyl}-acetic acid ethyl ester in a similar manner as described for the synthesis of {2-[3-cyclopentylmethyl-3-(3,4-difluoro-phenyl)-ureido]-thiazol-4-yl}-acetic acid, using N-(3-amino-phenyl)-acetamide, 3-methylbutanol and (2-amino-thiazol-5-ylsulfanyl)acetic acid ethyl ester.

1H NMR (400 MHz, DMSO-$d_6$) δ ppm 10.05 (s, 1H), 7.57 (d, 1H), 7.47 (s, 1H), 7.31-7.38 (m, 1H), 6.95 (d, 1H), 3.64-3.72 (m, 1H), 3.49 (s, 1H), 2.04 (s, 3H), 1.50-1.60 (m, 1H), 1.31-1.39 (m, 1H), 0.85 (d, 3H).

HPLC-MS: M/Z=437, Rt=1.68 min

Example 187

{2-[3-(3-Acetylamino-phenyl)-3-hexyl-ureido]-thiazol-5-ylsulfanyl}-acetic acid

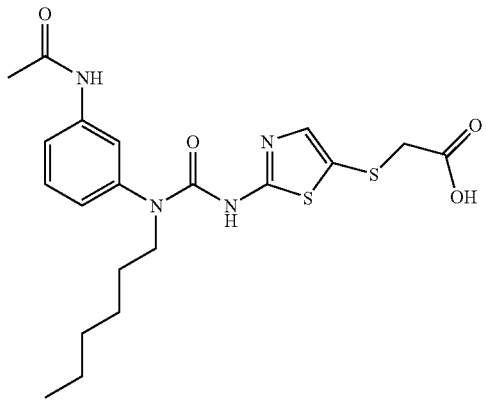

The title compound was prepared via {2-[3-(3-acetylamino-phenyl)-3-hexyl-ureido]-thiazol-5-ylsulfanyl}-acetic acid ethyl ester in a similar manner as described for the synthesis of {2-[3-cyclopentylmethyl-3-(3,4-difluoro-phenyl)-ureido]-thiazol-4-yl}-acetic acid, using N-(3-aminophenyl)-acetamide, hexanal and (2-amino-thiazol-5-ylsulfanyl)acetic acid ethyl ester.

1H NMR (400 MHz, DMSO-$d_6$) δ ppm 10.05 (s, 1H), 7.57 (d, 1H), 7.47 (s, 1H), 7.30-7.39 (m, 1H), 6.94 (d, 1H), 3.59-3.69 (m, 1H), 3.49 (s, 1H), 2.04 (s, 3H), 1.39-1.49 (m, 1H), 1.19-1.29 (m, 3H), 0.80-0.87 (m, 3H).

HPLC-MS: M/Z=451, Rt=1.83 min.,

Example 188

{2-[3-(3-Acetylamino-phenyl)-3-cyclopropylmethyl-ureido]-thiazol-5-ylsulfanyl}-acetic acid

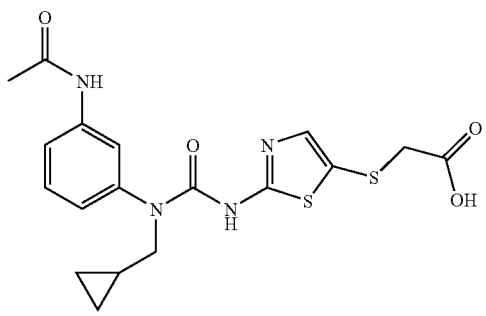

The title compound was prepared via {2-[3-(3-acetylamino-phenyl)-3-cyclopropylmethyl-ureido]-thiazol-5-ylsulfanyl}-acetic acid ethyl ester in a similar manner as described for the synthesis of {2-[3-cyclopentylmethyl-3-(3,4-difluoro-phenyl)-ureido]-thiazol-4-yl}-acetic acid, using N-(3-amino-phenyl)-acetamide, cyclopropanecarboxaldehyde and (2-amino-thiazol-5-ylsulfanyl)acetic acid ethyl ester.

1H NMR (400 MHz, DMSO-$d_6$) δ ppm 10.05 (s, 1H), 7.58 (d, 1H), 7.52 (s, 1H), 7.30-7.39 (m, 1H), 6.97 (d, 1H), 3.55 (d, 1H), 3.49 (s, 1H), 2.04 (s, 3H), 0.91-1.00 (m, 1H), 0.36-0.42 (m, 1H), 0.09-0.15 (m, 1H).

HPLC-MS: M/Z=421, Rt=1.47 min.

Example 189

{2-[3-(3-Acetylamino-phenyl)-3-(3,3-dimethyl-butyl)-ureido]-thiazol-5-ylsulfanyl}-acetic acid

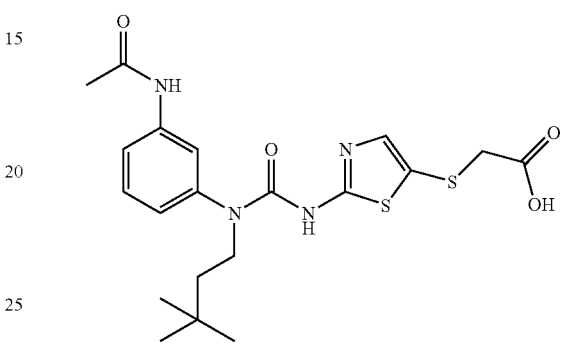

The title compound was prepared via {2-[3-(3-acetylamino-phenyl)-3-(3,3-dimethyl-butyl)-ureido]-thiazol-5-ylsulfanyl}-acetic acid ethyl ester in a similar manner as described for the synthesis of {2-[3-cyclopentylmethyl-3-(3,4-difluoro-phenyl)-ureido]-thiazol-4-yl}-acetic acid, using N-(3-amino-phenyl)-acetamide, 3,3-dimethylbutyraldehyde and (2-amino-thiazol-5-ylsulfanyl)acetic acid ethyl ester.

1H NMR (400 MHz, DMSO-$d_6$) δ ppm 10.05 (s, 1H), 7.59 (d, 1H), 7.45 (s, 1H), 7.31-7.38 (m, 1H), 6.95 (d, 1H), 3.64-3.71 (m, 1H), 3.49 (s, 1H), 2.04 (s, 3H), 1.35-1.44 (m, 1H), 0.87 (s, 9H).

HPLC-MS: M/Z=451, Rt=1.76 min

Example 190

{2-[3-Cyclohexylmethyl-3-(3,4-difluoro-phenyl)-ureido]-thiazol-5-ylsulfanyl}-acetic acid

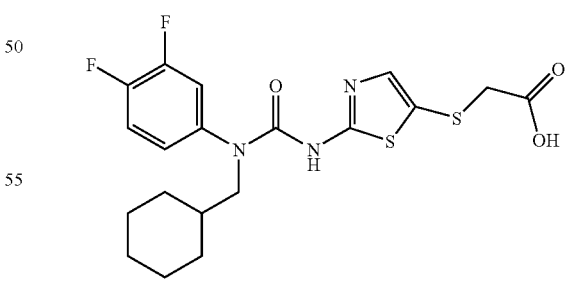

The title compound was prepared via {2-[3-cyclohexylmethyl-3-(3,4-difluoro-phenyl)-ureido]-thiazol-5-ylsulfanyl}-acetic acid ethyl ester in a similar manner as described for the synthesis of {2-[3-cyclopentylmethyl-3-(4-methanesulfonyl-phenyl)-ureido]-thiazol-4-yl}-acetic acid, using cyclohexylmethyl-(3,4-difluorophenyl)-amine and (2-amino-thiazol-5-ylsulfanyl)acetic acid ethyl ester 1H NMR (400 MHz, DMSO-$d_6$) δ ppm 7.45-7.55 (m, 1H), 7.38 (s, 1H), 7.15-7.20 (m, 1H), 3.58 (d, 1H), 3.49 (s, 1H), 1.54-1.69 (m, 3H), 1.35-1.46 (m, 1H), 1.05-1.13 (m, 3H), 0.86-0.97 (m, 1H).

HPLC-MS: M/Z=442, Rt=2.16 min.

Example 191

[2-(3-Benzo[1,3]dioxol-5-yl-3-cyclohexyl methyl-ureido)-thiazol-5-ylsulfanyl]-acetic acid

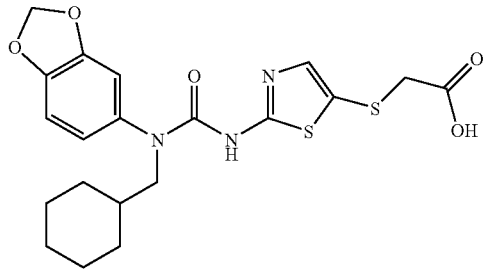

The title compound was prepared via [2-(3-benzo[1,3]dioxol-5-yl-3-cyclohexylmethyl-ureido)-thiazol-5-ylsulfanyl]-acetic acid ethyl ester in a similar manner as described for the synthesis of {2-[3-cyclopentylmethyl-3-(4-methanesulfonyl-phenyl)-ureido]-thiazol-4-yl}-acetic acid, using benzo[1,3]dioxol-5-yl-cyclohexylmethyl-amine and (2-amino-thiazol-5-ylsulfanyl)acetic acid ethyl ester 1H NMR (400 MHz, DMSO-$d_6$) δ ppm 7.36 (s, 1H), 6.93 (s, 1H), 6.93 (d, 1H), 6.76 (dd, 1H), 6.08 (s, 1H), 3.51 (d, 1H), 3.48 (s, 1H), 1.55-1.72 (m, 3H), 1.35-1.46 (m, 1H), 1.06-1.17 (m, 3H), 0.87-0.97 (m, 1H).

HPLC-MS: M/Z=450, Rt=2.08 min

Example 192

{2-[3-Cyclohexylmethyl-3-(6-methoxy-pyridin-3-yl)-ureido]-thiazol-5-ylsulfanyl}-acetic acid

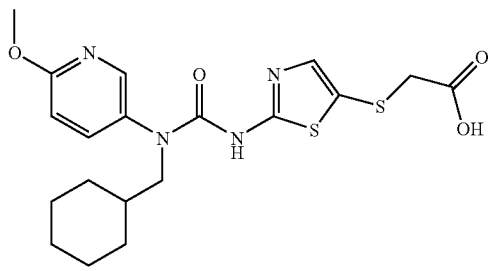

The title compound was prepared via {2-[3-cyclohexylmethyl-3-(6-methoxy-pyridin-3-yl)-ureido]-thiazol-5-ylsulfanyl}-acetic acid ethyl ester in a similar manner as described for the synthesis of {2-[3-cyclopentylmethyl-3-(4-methanesulfonyl-phenyl)-ureido]-thiazol-4-yl}-acetic acid, using cyclohexylmethyl-(6-methoxy-pyridin-3-yl)-amine and (2-amino-thiazol-5-ylsulfanyl)acetic acid ethyl ester.

1H NMR (400 MHz, DMSO-$d_6$) δ ppm 8.09 (d, 1H), 7.64 (dd, 1H), 7.37 (s, 1H), 6.87 (d, 1H), 3.88 (s, 3H), 3.54 (d, 1H), 3.49 (s, 1H), 1.55-1.71 (m, 3H), 1.34-1.45 (m, 1H), 1.06-1.17 (m, 3H), 0.86-0.97 (m, 1H)

HPLC-MS: M/Z=437, Rt=1.96 min.

Example 193

{2-[3-Cyclopentylmethyl-3-(3-ethylcarbamoyl-phenyl)-ureido]-thiazol-5-ylsulfanyl}-acetic acid

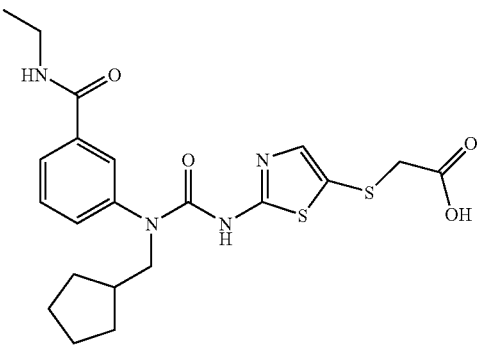

The title compound was prepared via {2-[3-cyclopentylmethyl-3-(3-ethylcarbamoyl-phenyl)-ureido]-thiazol-5-ylsulfanyl}-acetic acid ethyl ester in a similar manner as described for the synthesis of {2-[3-cyclopentylmethyl-3-(4-methanesulfonyl-phenyl)-ureido]-thiazol-4-yl}-acetic acid, using 3-(cyclopentylmethyl-amino)-N-ethyl-benzamide and (2-amino-thiazol-5-ylsulfanyl)acetic acid ethyl ester.

1H NMR (400 MHz, DMSO-$d_6$) δ ppm 8.53 (t, 1H), 7.81 (d, 1H), 7.77 (s, 1H), 7.42-7.56 (m, 1H), 7.37 (s, 1H), 3.73 (d, 1H), 3.49 (s, 1H), 3.26-3.32 (m, 1H), 1.88-1.99 (m, 1H), 1.52-1.63 (m, 3H), 1.39-1.50 (m, 1H), 1.14-1.23 (m, 1H), 1.12 (t, 3H).

HPLC-MS: M/Z=463, Rt=1.75 min.

Example 194

{2-[3-Cyclobutyl methyl-3-(3,4-difluoro-phenyl)-ureido]-thiazol-5-ylsulfanyl}-acetic acid

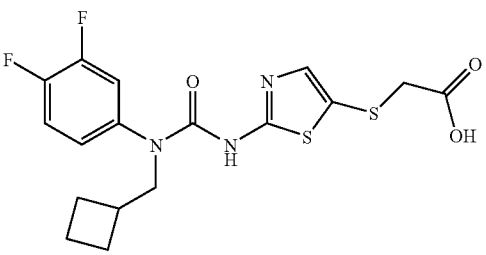

The title compound was prepared via {2-[3-cyclobutylmethyl-3-(3,4-difluoro-phenyl)-ureido]-thiazol-5-ylsulfanyl}-acetic acid ethyl ester in a similar manner as described for the synthesis of {2-[3-cyclopentylmethyl-3-(4-methanesulfonyl-phenyl)-ureido]-thiazol-4-yl}-acetic acid, using cyclobutylmethyl-(3,4-difluorophenyl)-amine and (2-amino-thiazol-5-ylsulfanyl)acetic acid ethyl ester.

1H NMR (400 MHz, DMSO-$d_6$) δ ppm 7.42-7.51 (m, 1H), 7.38 (s, 1H), 7.10-7.16 (m, 1H), 3.75 (d, 1H), 3.49 (s, 1H), 2.35-2.44 (m, 1H), 1.83-1.92 (m, 1H), 1.71-1.82 (m, 1H), 1.55-1.65 (m, 1H).

HPLC-MS: M/Z=414, Rt=1.96 min

Example 195

{2-[3-Cyclopentylmethyl-3-(3-isopropylcarbamoyl-phenyl)-ureido]-thiazol-5-ylsulfanyl}-acetic acid

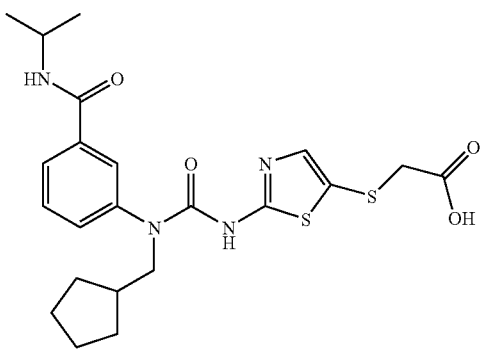

The title compound was prepared via {2-[3-cyclopentylmethyl-3-(3-isopropylcarbamoyl-phenyl)-ureido]-thiazol-5-ylsulfanyl}-acetic acid ethyl ester in a similar manner as described for the synthesis of {2-[3-cyclopentylmethyl-3-(4-methanesulfonyl-phenyl)-ureido]-thiazol-4-yl}-acetic acid, using 3-(cyclopentylethyl-amino)-N-isopropyl-benzamide and (2-amino-thiazol-5-ylsulfanyl)acetic acid ethyl ester.

1H NMR (400 MHz, DMSO-$d_6$) δ ppm 8.26 (d, 1H), 7.78-7.88 (m, 1H), 7.42-7.52 (m, 1H), 7.37 (s, 1H), 4.05-4.16 (m, 1H), 3.73 (d, 1H), 3.49 (s, 1H), 1.88-2.00 (m, 1H), 1.52-1.64 (m, 3H), 1.40-1.51 (m, 1H), 1.18-1.24 (m, 1H), 1.17 (d, 3H)

HPLC-MS: M/Z=477, Rt=1.86 min.

Example 196

(2-{3-[3-(Azetidine-1-carbonyl)-phenyl]-3-cyclopentylmethyl-ureido}-thiazol-5-ylsulfanyl)-acetic acid

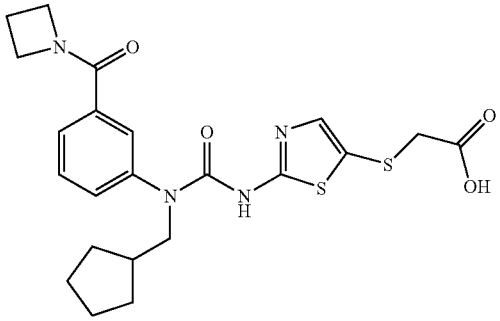

The title compound was prepared via (2-{3-[3-(azetidine-1-carbonyl)-phenyl]-3-cyclopentylmethyl-ureido}-thiazol-5-ylsulfanyl)-acetic acid ethyl ester in a similar manner as described for the synthesis of {2-[3-cyclopentylmethyl-3-(4-methanesulfonyl-phenyl)-ureido]-thiazol-4-yl}-acetic acid, using azetidin-1-yl-[3-(cyclopentylmethyl-amino)-phenyl]-methanone and (2-amino-thiazol-5-ylsulfanyl)acetic acid ethyl ester.

1H NMR (400 MHz, DMSO-$d_6$) δ ppm 7.47-7.55 (m, 3H), 7.42-7.45 (m, 1H), 7.37 (s, 1H), 4.27-4.34 (t, 1H), 4.04 (t, 1H), 3.72 (d, 1H), 3.50 (s, 1H), 2.21-2.29 (m, 1H), 1.89-1.97 (m, 1H), 1.52-1.61 (m, 3H), 1.40-1.49 (m, 1H), 1.12-1.21 (m, 1H)

HPLC-MS: M/Z=475, Rt=1.74 min

Example 197

{2-[3-(3,4-Difluoro-phenyl)-3-(4-methyl-cyclohexylmethyl)-ureido]-thiazol-5-ylsulfanyl}-acetic acid

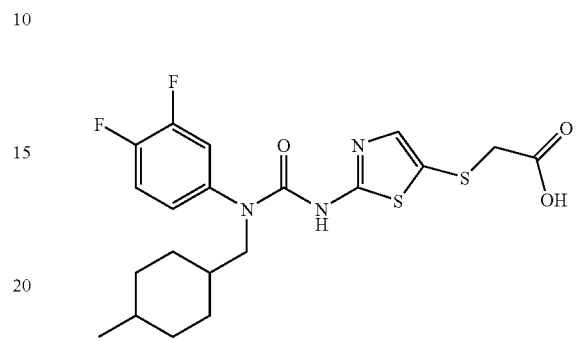

The title compound was prepared via {2-[3-(3,4-difluoro-phenyl)-3-(4-methyl-cyclohexylmethyl)-ureido]-thiazol-5-ylsulfanyl}-acetic acid ethyl ester in a similar manner as described for the synthesis of {2-[3-cyclopentylmethyl-3-(4-methanesulfonyl-phenyl)-ureido]-thiazol-4-yl}-acetic acid, using 4-methyl-cyclohexylmethyl-(3,4-difluorophenyl)-amine and (2-amino-thiazol-5-ylsulfanyl)acetic acid ethyl ester.

HPLC-MS: M/Z=456, Rt=2.29 min

Example 198

{2-[3-(3,4-Difluoro-phenyl)-3-(4-trifluoromethyl-cyclohexylmethyl)-ureido]-thiazol-5-ylsulfanyl}-acetic acid

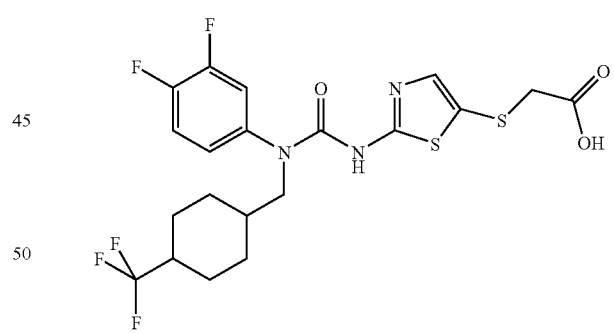

The title compound was prepared via {2-[3-(3,4-difluoro-phenyl)-3-(4-trifluoromethyl-cyclohexylmethyl)-ureido]-thiazol-5-ylsulfanyl}-acetic acid ethyl ester in a similar manner as described for the synthesis of {2-[3-cyclopentylmethyl-3-(4-methanesulfonyl-phenyl)-ureido]-thiazol-4-yl}-acetic acid, using 4-trifluoromethyl-cyclohexylmethyl-(3,4-difluorophenyl)-amine and (2-amino-thiazol-5-ylsulfanyl)acetic acid ethyl ester.

1H NMR (400 MHz, DMSO-$d_6$) δ ppm 7.51-7.58 (m, 1H), 7.44-7.49 (m, 1H), 7.38 (s, 1H), 7.17-7.23 (m, 1H), 3.78 (d, 1H), 3.50 (s, 1H), 2.18-2.30 (m, 1H), 1.65-1.73 (m, 1H), 1.39-1.64 (m, 8H)

HPLC-MS: M/Z=510, Rt=2.20 min

Example 199

{2-[3-(4-tert-Butyl-cyclohexyl methyl)-3-(3,4-difluoro-phenyl)-ureido]-thiazol-5-ylsulfanyl}-acetic acid

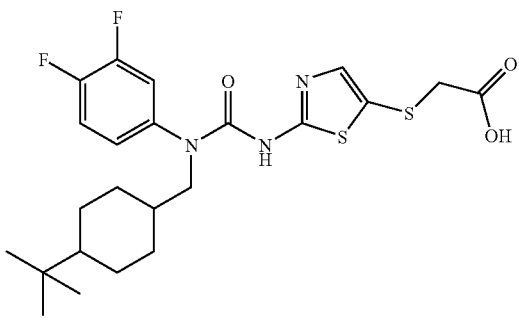

The title compound was prepared via {2-[3-(3,4-difluorophenyl)-3-(4-tert-butyl-cyclohexylmethyl)-ureido]-thiazol-5-ylsulfanyl}-acetic acid ethyl ester in a similar manner as described for the synthesis of {2-[3-cyclopentylmethyl-3-(4-methanesulfonyl-phenyl)-ureido]-thiazol-4-yl}-acetic acid, using 4-tert-butyl-cyclohexylmethyl-(3,4-difluorophenyl)-amine and (2-amino-thiazol-5-ylsulfanyl)acetic acid ethyl ester.

HPLC-MS: M/Z=498, Rt=2.59 min.

Example 200

{2-[3-Cyclopentylmethyl-3-(2,3,4-trifluoro-phenyl)-ureido]-thiazol-5-ylsulfanyl}-acetic acid

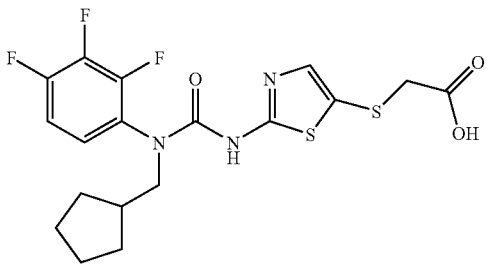

The title compound was prepared via {2-[3-cyclopentylmethyl-3-(2,3,4-trifluoro-phenyl)-ureido]-thiazol-5-ylsulfanyl}-acetic acid ethyl ester in a similar manner as described for the synthesis of {2-[3-cyclopentylmethyl-3-(4-methanesulfonyl-phenyl)-ureido]-thiazol-4-yl}-acetic acid, using cyclopentylmethyl-(2,3,4-trifluorophenyl)-amine and (2-amino-thiazol-5-ylsulfanyl)acetic acid ethyl ester.

HPLC-MS: M/Z=446, Rt=2.59 min.

Example 201

{2-[3-(3-Chloro-4-fluoro-phenyl)-3-cyclopentylmethyl-ureido]-thiazol-5-ylsulfanyl}-acetic acid

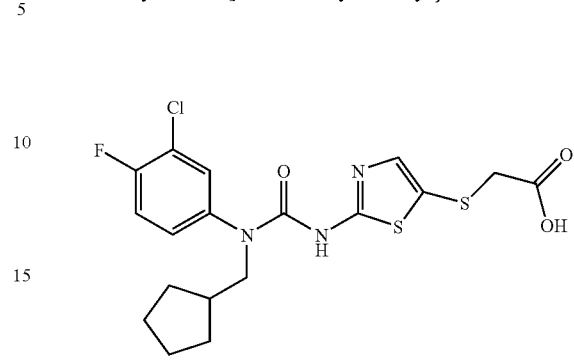

The title compound was prepared via {2-[3-cyclopentylmethyl-3-(3-chloro-4-fluoro-phenyl)-ureido]-thiazol-5-ylsulfanyl}-acetic acid ethyl ester in a similar manner as described for the synthesis of {2-[3-cyclopentylmethyl-3-(4-methanesulfonyl-phenyl)-ureido]-thiazol-4-yl}-acetic acid, using cyclopentylmethyl-(3-chloro-4-fluoro-phenyl)-amine and (2-amino-thiazol-5-ylsulfanyl)acetic acid ethyl ester.

1H NMR (400 MHz, DMSO-$d_6$) δ ppm 7.62 (dd, 1H), 7.45 (t, 1H), 7.38 (s, 1H), 7.32-7.37 (m, 1H), 3.68 (d, 1H), 3.49 (s, 1H), 1.93 (ddd, 1H), 1.52-1.64 (m, 3H), 1.40-1.51 (m, 1H), 1.11-1.21 (m, 1H)

HPLC-MS: M/Z=444, Rt=2.28 min.

Example 202

{2-[3-Cyclopentylmethyl-3-(2,4-difluoro-phenyl)-ureido]-thiazol-5-ylsulfanyl}-acetic acid

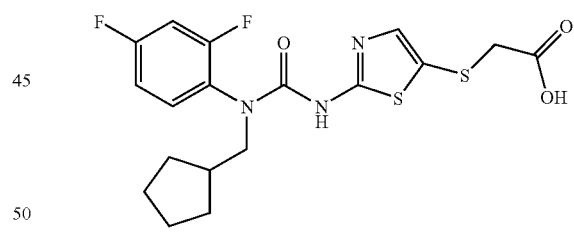

The title compound was prepared via {2-[3-cyclopentylmethyl-3-(2,4-difluoro-phenyl)-ureido]-thiazol-5-ylsulfanyl}-acetic acid ethyl ester in a similar manner as described for the synthesis of {2-[3-cyclopentylmethyl-3-(4-methanesulfonyl-phenyl)-ureido]-thiazol-4-yl}-acetic acid, using cyclopentylmethyl-(2,4-difluorophenyl)-amine and (2-amino-thiazol-5-ylsulfanyl)acetic acid ethyl ester.

1H NMR (400 MHz, DMSO-$d_6$) δ ppm 7.45-7.52 (m, 1H), 7.34-7.41 (m, 1H), 7.14 (t, 1H), 3.62 (d, 1H), 3.50 (s, 1H), 1.86-1.97 (m, 1H), 1.52-1.63 (m, 3H), 1.40-1.51 (m, 1H), 1.12-1.22 (m, 1H) HPLC-MS: M/Z=367, Rt=2.14 min

Example 203

{2-[3-Cyclopentylmethyl-3-(2,3-dichloro-phenyl)-ureido]-thiazol-5-ylsulfanyl}-acetic acid

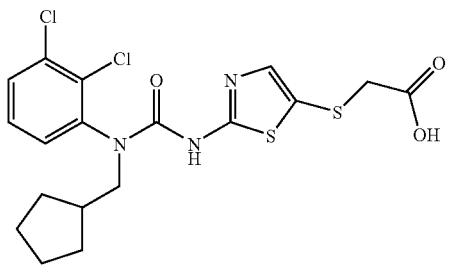

The title compound was prepared via {2-[3-cyclopentylmethyl-3-(2,3-dichloro-phenyl)-ureido]-thiazol-5-ylsulfanyl}-acetic acid ethyl ester in a similar manner as described for the synthesis of {2-[3-cyclopentylmethyl-3-(4-methanesulfonyl-phenyl)-ureido]-thiazol-4-yl}-acetic acid, using cyclopentylmethyl-(2,3-dichlorophenyl)-amine and (2-amino-thiazol-5-ylsulfanyl)acetic acid ethyl ester.

1H NMR (400 MHz, DMSO-$d_6$) δ ppm 7.65 (dd, 1H), 7.40-7.46 (m, 1H), 7.36 (s, 1H), 3.80-3.90 (m, 1H), 3.50 (s, 1H), 1.97 (ddd, 1H), 1.51-1.70 (m, 3H), 1.41-1.51 (m, 1H), 1.12-1.27 (m, 1H)

HPLC-MS: M/Z=460, Rt=2.31 min.

Example 204

{2-[3-Cyclopentylmethyl-3-(3-fluoro-4-methoxy-phenyl)-ureido]-thiazol-5-ylsulfanyl}-acetic acid

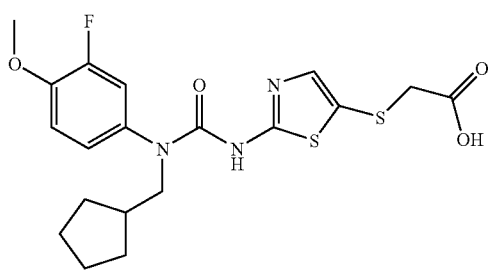

The title compound was prepared via {2-[3-cyclopentylmethyl-3-(3-fluoro-4-methoxy-phenyl)-ureido]-thiazol-5-ylsulfanyl}-acetic acid ethyl ester in a similar manner as described for the synthesis of {2-[3-cyclopentylmethyl-3-(4-methanesulfonyl-phenyl)-ureido]-thiazol-4-yl}-acetic acid, using cyclopentylmethyl-(3-fluoro-4-methoxy-phenyl)-amine and (2-amino-thiazol-5-ylsulfanyl)acetic acid ethyl ester.

1H NMR (400 MHz, DMSO-$d_6$) δ ppm 7.37 (s, 1H), 7.25 (dd, 1H), 7.19 (t, 1H), 7.09 (dd, 1H), 3.87 (s, 3H), 3.63 (d, 1H), 3.49 (s, 1H), 1.87-1.97 (m, 1H), 1.52-1.64 (m, 3H), 1.40-1.50 (m, 1H), 1.12-1.22 (m, 1H)

HPLC-MS: M/Z=304, Rt=2.11 min.

Example 205

{2-[3-(3-Acetylamino-phenyl)-3-benzyl-ureido]-thiazol-5-ylsulfanyl}-acetic acid

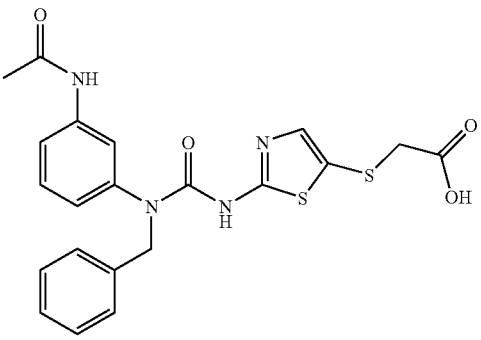

The title compound was prepared via {2-[3-(3-acetylamino-phenyl)-3-benzyl-ureido]-thiazol-5-ylsulfanyl}-acetic acid ethyl ester in a similar manner as described for the synthesis of {2-[3-cyclopentylmethyl-3-(4-methanesulfonyl-phenyl)-ureido]-thiazol-4-yl}-acetic acid, using (3-acetylamino-phenyl)-benzylamine and (2-amino-thiazol-5-ylsulfanyl)acetic acid ethyl ester.

1H NMR (400 MHz, DMSO-$d_6$) δ ppm 9.99 (s, 1H), 7.53 (d, 1H), 7.41 (s, 1H), 7.39 (s, 1H), 7.26-7.33 (m, 1H), 7.20-7.26 (m, 3H), 6.88 (d, 1H), 4.94 (s, 1H), 3.51 (s, 1H), 2.01 (s, 3H)

HPLC-MS: M/Z=457, Rt=1.64 min.

Example 206

{2-[3-(3-Acetylamino-phenyl)-3-phenethyl-ureido]-thiazol-5-ylsulfanyl}-acetic acid

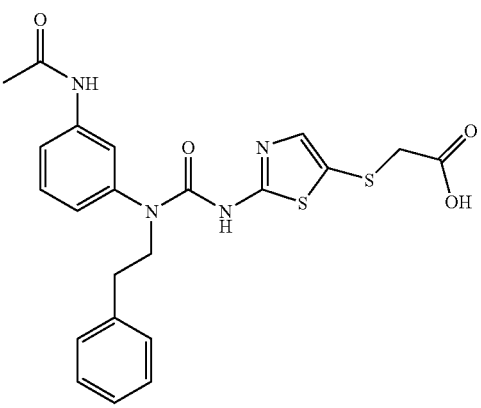

The title compound was prepared via {2-[3-(3-acetylamino-phenyl)-3-phenethyl-ureido]-thiazol-5-ylsulfanyl}-acetic acid ethyl ester in a similar manner as described for the synthesis of {2-[3-cyclopentylmethyl-3-(4-methanesulfonyl-phenyl)-ureido]-thiazol-4-yl}-acetic acid, using (3-acetylamino-phenyl)-phenethylamine and (2-amino-thiazol-5-ylsulfanyl)acetic acid ethyl ester.

HPLC-MS: M/Z=471, Rt=1.82 min.

Example 207

{2-[3-(2-Cyclopentylethyl)-3-(3,4-difluoro-phenyl)-ureido]-thiazol-5-ylsulfanyl}-acetic acid

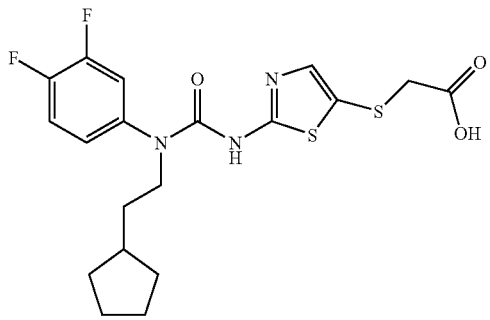

The title compound was prepared via {2-[3-cyclopentylethyl-3-(3,4-difluoro-phenyl)-ureido]-thiazol-5-ylsulfanyl}-acetic acid ethyl ester in a similar manner as described for the synthesis of {2-[3-cyclopentylmethyl-3-(4-methanesulfonyl-phenyl)-ureido]-thiazol-4-yl}-acetic acid, using cyclopentylethyl-(3,4-difluorophenyl)-amine and (2-amino-thiazol-5-ylsulfanyl)acetic acid ethyl ester 1H NMR (400 MHz, DMSO-$d_6$) δ ppm 7.43-7.54 (m, 1H), 7.38 (s, 1H), 7.13-7.19 (m, 1H), 3.63-3.73 (m, 1H), 3.49 (s, 1H), 1.66-1.76 (m, 3H), 1.51-1.56 (m, 1H), 1.43-1.49 (m, 3H), 0.99-1.09 (m, 1H)

HPLC-MS: M/Z=442, Rt=2.31 min.

Example 208

{2-[3-(3,4-Difluoro-phenyl)-3-(trans-4-methyl-cyclohexyl methyl)-ureido]-thiazol-5-ylsulfanyl}-acetic acid

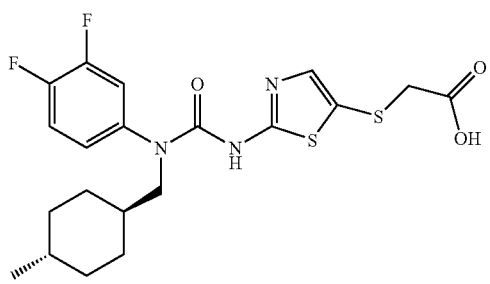

The title compound was prepared via {2-[3-(3,4-difluoro-phenyl)-3-(trans-4-methyl-cyclohexylmethyl)-ureido]-thiazol-5-ylsulfanyl}-acetic acid ethyl ester in a similar manner as described for the synthesis of {2-[3-cyclopentylmethyl-3-(4-methanesulfonyl-phenyl)-ureido]-thiazol-4-yl}-acetic acid, using trans-4-methyl-cyclohexylmethyl-(3,4-difluorophenyl)-amine and (2-amino-thiazol-5-ylsulfanyl)acetic acid ethyl ester 1H NMR (400 MHz, DMSO-$d_6$) δ ppm 7.45-7.55 (m, 1H), 7.39 (s, 1H), 7.15-7.21 (m, 1H), 3.58 (d, 1H), 3.49 (s, 1H), 1.59-1.69 (m, 3H), 1.18-1.39 (m, 1H), 0.86-0.98 (m, 1H), 0.73-0.84 (m, 3H)

HPLC-MS: M/Z=456, Rt=2.39 min

Example 209

{2-[3-(3-Acetylamino-4-fluoro-phenyl)-3-cyclopentylmethyl-ureido]-thiazol-5-ylsulfanyl}-acetic acid

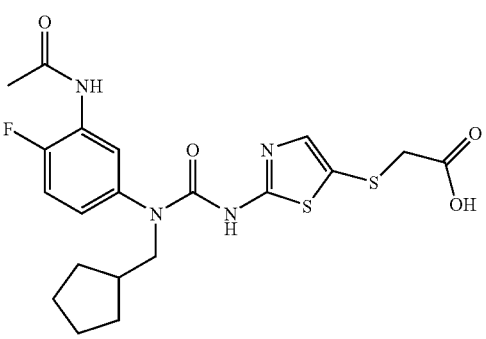

The title compound was prepared via {2-[3-(3-acetylamino-4-fluoro-phenyl)-3-cyclopentylmethyl-ureido]-thiazol-5-ylsulfanyl}-acetic acid ethyl ester in a similar manner as described for the synthesis of {2-[3-cyclopentylmethyl-3-(3,4-difluoro-phenyl)-ureido]-thiazol-4-yl}-acetic acid, using N-(3-amino-4-fluoro-phenyl)-acetamide, cyclopentanecarbaldehyde and (2-amino-thiazol-5-ylsulfanyl)acetic acid ethyl ester.

1H NMR (400 MHz, DMSO-$d_6$) δ ppm 9.85 (s, 1H), 7.90 (d, 1H), 7.37 (s, 1H), 7.24-7.31 (m, 1H), 7.02-7.08 (m, 1H), 3.63 (d, 1H), 3.49 (s, 1H), 2.09 (s, 3H), 1.96 (ddd, 1H), 1.52-1.65 (m, 3H), 1.40-1.51 (m, 1H), 1.12-1.24 (m, 1H)

HPLC-MS: M/Z=467, Rt=1.74 min

Example 210

{2-[3-Cyclopentylmethyl-3-(3-propionylamino-phenyl)-ureido]-thiazol-5-ylsulfanyl}-acetic acid

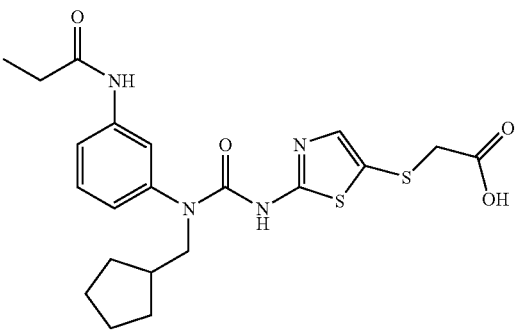

The title compound was prepared via {2-[3-cyclopentylmethyl-3-(3-propionylamino-phenyl)-ureido]-thiazol-5-ylsulfanyl}-acetic acid ethyl ester in a similar manner as described for the synthesis of {2-[3-cyclopentylmethyl-3-(3,4-difluoro-phenyl)-ureido]-thiazol-4-yl}-acetic acid, using N-(3-amino-phenyl)-propionamide, cyclopentanecarbaldehyde and (2-amino-thiazol-5-ylsulfanyl)acetic acid ethyl ester.

1H NMR (400 MHz, DMSO-$d_6$) δ ppm 10.01 (s, 1H), 7.60 (d, 1H), 7.53 (s, 1H), 7.37 (s, 1H), 7.33 (t, 1H), 6.96 (d, 1H), 3.66 (d, 1H), 3.50 (s, 1H), 2.32 (q, 1H), 1.91-2.01 (m, 1H), 1.53-1.64 (m, 3H), 1.40-1.51 (m, 1H), 1.14-1.24 (m, 1H), 1.07 (t, 3H)

HPLC-MS: M/Z=463, Rt=1.82 min.

Example 211

{2-[3-Cyclopentylmethyl-3-(3-isobutyrylamino-phenyl)-ureido]-thiazol-5-ylsulfanyl}-acetic acid

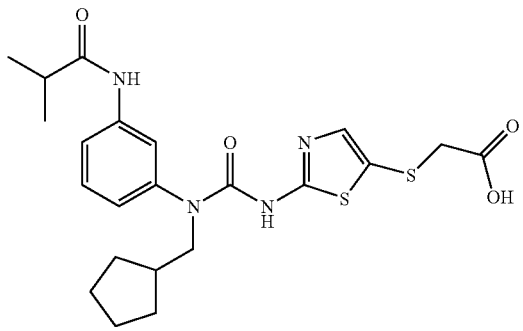

The title compound was prepared via {2-[3-cyclopentylmethyl-3-(3-isobutyrylamino-phenyl)-ureido]-thiazol-5-ylsulfanyl}-acetic acid ethyl ester in a similar manner as described for the synthesis of {2-[3-cyclopentylmethyl-3-(3,4-difluoro-phenyl)-ureido]-thiazol-4-yl}-acetic acid, using N-(3-Amino-phenyl)-isobutyramide, cyclopentanecarbaldehyde and (2-amino-thiazol-5-ylsulfanyl)acetic acid ethyl ester.

1H NMR (400 MHz, DMSO-$d_6$) d ppm 9.96 (s, 1H), 7.62 (d, 1H), 7.54 (s, 1H), 7.37 (s, 1H), 7.33 (t, 1H), 6.96 (d, 1H), 3.66 (d, 1H), 3.49 (s, 1H), 2.54-2.62 (m, 1H), 1.91-2.03 (m, 1H), 1.53-1.64 (m, 3H), 1.40-1.50 (m, 1H), 1.15-1.27 (m, 1H), 1.09 (d, 3H)

HPLC-MS: M/Z=477, Rt=1.92 min.

Example 212

(2-{3-[3-(Cyclopentanecarbonyl-amino)-phenyl]-3-cyclopentylmethyl-ureido}-thiazol-5-ylsulfanyl)-acetic acid

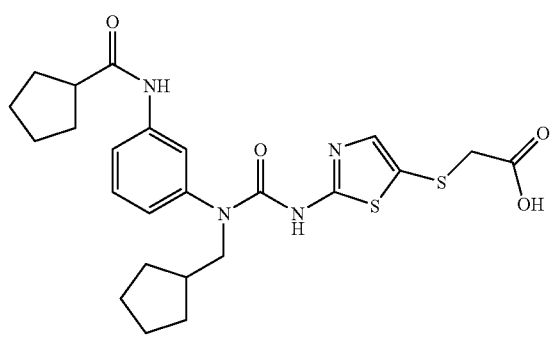

The title compound was prepared via (2-{3-[3-(cyclopentanecarbonyl-amino)-phenyl]-3-cyclopentylmethyl-ureido}-thiazol-5-ylsulfanyl)-acetic acid ethyl ester in a similar manner as described for the synthesis of {2-[3-cyclopentylmethyl-3-(3,4-difluoro-phenyl)-ureido]-thiazol-4-yl}-acetic acid, using cyclopentanecarboxylic acid (3-amino-phenyl)-amide, cyclopentanecarbaldehyde and (2-amino-thiazol-5-ylsulfanyl)acetic acid ethyl ester.

1H NMR (400 MHz, DMSO-$d_6$) δ ppm 10.00 (s, 1H), 7.62 (d, 1H), 7.54 (s, 1H), 7.37 (s, 1H), 7.33 (t, 1H), 6.96 (d, 1H), 3.66 (d, 1H), 3.49 (s, 1H), 2.77 (dq, 1H), 1.91-2.02 (m, 1H), 1.78-1.89 (m, 1H), 1.65-1.71 (m, 3H), 1.53-1.62 (m, 3H), 1.40-1.49 (m, 1H), 1.14-1.25 (m, 1H)

HPLC-MS: M/Z=503, Rt=2.09 min

Example 213

{2-[3-(trans-4-Methyl-cyclohexylmethyl)-3-(2,3,4-trifluoro-phenyl)-ureido]-thiazol-5-ylsulfanyl}-acetic acid

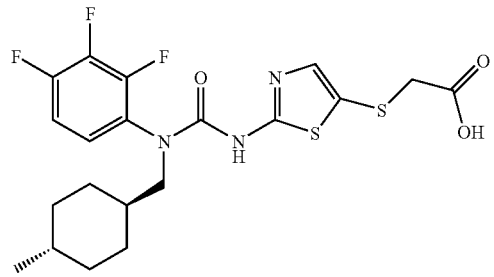

The title compound was prepared via {2-[3-(trans-4-methyl-cyclohexylmethyl)-3-(2,3,4-trifluoro-phenyl)-ureido]-thiazol-5-ylsulfanyl}-acetic acid ethyl ester in a similar manner as described for the synthesis of {2-[3-cyclopentylmethyl-3-(4-methanesulfonyl-phenyl)-ureido]-thiazol-4-yl}-acetic acid, using trans-4-methyl-cyclohexylmethyl-(2,3,4-trifluorophenyl)-amine and (2-amino-thiazol-5-ylsulfanyl)acetic acid ethyl ester.

1H NMR (400 MHz, DMSO-$d_6$) δ ppm 7.31-7.43 (m, 3H), 3.55 (d, 1H), 3.50 (s, 1H), 1.65 (t, 3H), 1.20-1.38 (m, 1H), 0.87-0.99 (m, 1H), 0.83 (d, 3H), 0.74-0.86 (m, 1H)

HPLC-MS: M/Z=474, Rt=2.41 min.

Example 214

{2-[3-Cyclohexylmethyl-3-(2,3,4-trifluoro-phenyl)-ureido]-thiazol-5-ylsulfanyl}-acetic acid

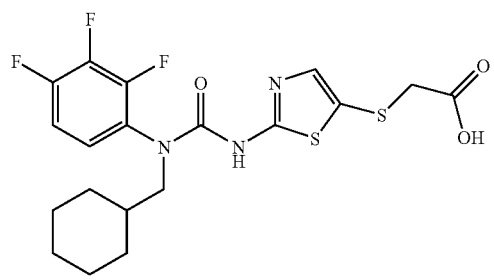

The title compound was prepared via {2-[3-(cyclohexylmethyl)-3-(2,3,4-trifluoro-phenyl)-ureido]-thiazol-5-ylsulfanyl}-acetic acid ethyl ester in a similar manner as described for the synthesis of {2-[3-cyclopentylmethyl-3-(4-methanesulfonyl-phenyl)-ureido]-thiazol-4-yl}-acetic acid, using (methyl-cyclohexylmethyl-(2,3,4-trifluorophenyl)-amine and (2-amino-thiazol-5-ylsulfanyl)acetic acid ethyl ester.

1H NMR (400 MHz, DMSO-d$_6$) δ ppm 7.31-7.44 (m, 3H), 3.55 (d, 1H), 3.50 (s, 1H), 1.56-1.70 (m, 3H), 1.34-1.47 (m, 1H), 1.06-1.20 (m, 3H), 0.85-1.00 (m, 1H)

HPLC-MS: M/Z=460, Rt=2.32 min.

Example 215

{2-[3-Cyclopentylmethyl-3-(2,3-difluoro-phenyl)-ureido]-thiazol-5-ylsulfanyl}-acetic acid

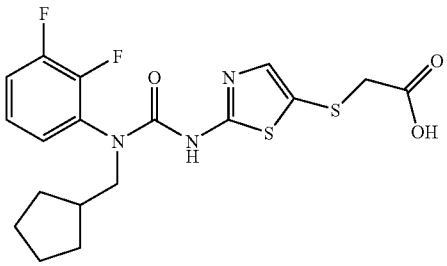

The title compound was prepared via {2-[3-(cyclohexylmethyl)-3-(2,3-difluoro-phenyl)-ureido]-thiazol-5-ylsulfanyl}-acetic acid ethyl ester in a similar manner as described for the synthesis of {2-[3-cyclopentylmethyl-3-(4-methanesulfonyl-phenyl)-ureido]-thiazol-4-yl}-acetic acid, using (methyl-cyclohexylmethyl-(2,3-difluorophenyl)-amine and (2-amino-thiazol-5-ylsulfanyl)acetic acid ethyl ester.

1H NMR (400 MHz, DMSO-d$_6$) δ ppm 7.35-7.46 (m, 1H), 7.21-7.29 (m, 1H), 3.68 (d, 1H), 3.50 (s, 1H), 1.89-2.00 (m, 1H), 1.52-1.63 (m, 3H), 1.40-1.50 (m, 1H), 1.09-1.24 (m, 1H)

HPLC-MS: M/Z=427, Rt=2.07 min

Example 216

{2-[3-Cyclopentylmethyl-3-(4-methoxy-phenyl)-ureido]-thiazol-5-ylsulfanyl}-acetic acid

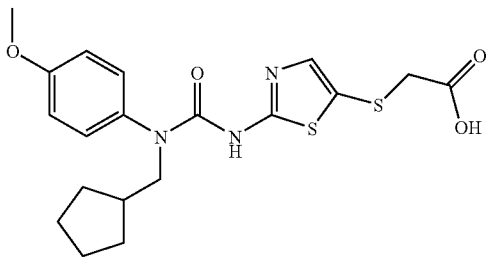

The title compound was prepared via {2-[3-(cyclohexylmethyl)-3-(4-methoxy-phenyl)-ureido]-thiazol-5-ylsulfanyl}-acetic acid ethyl ester in a similar manner as described for the synthesis of {2-[3-cyclopentylmethyl-3-(4-methanesulfonyl-phenyl)-ureido]-thiazol-4-yl}-acetic acid, using (methyl-cyclohexylmethyl-(4-methoxy-phenyl)-amine and (2-amino-thiazol-5-ylsulfanyl)acetic acid ethyl ester.

1H NMR (400 MHz, DMSO-d$_6$) δ ppm 7.36 (s, 1H), 7.22 (d, 1H), 6.98 (d, 1H), 3.78 (s, 3H), 3.62 (d, 1H), 3.49 (s, 1H), 1.87-1.98 (m, 1H), 1.52-1.64 (m, 3H), 1.39-1.50 (m, 1H), 1.13-1.24 (m, 1H)

HPLC-MS: M/Z=422, Rt=2.03 min.

Example 217

{2-[3-(3-Chloro-4-methoxy-phenyl)-3-cyclopentylmethyl-ureido]-thiazol-5-ylsulfanyl}-acetic acid

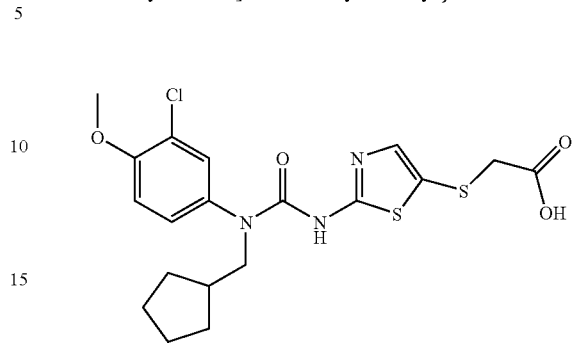

The title compound was prepared via {2-[3-(cyclohexylmethyl)-3-(3-chloro-4-methoxy-phenyl)-ureido]-thiazol-5-ylsulfanyl}-acetic acid ethyl ester in a similar manner as described for the synthesis of {2-[3-cyclopentylmethyl-3-(4-methanesulfonyl-phenyl)-ureido]-thiazol-4-yl}-acetic acid, using (methyl-cyclohexylmethyl-(3-chloro-4-methoxy-phenyl)-amine and (2-amino-thiazol-5-ylsulfanyl)acetic acid ethyl ester.

1H NMR (400 MHz, DMSO-d$_6$) δ ppm 7.41 (d, 1H), 7.37 (s, 1H), 7.25 (dd, 1H), 7.17 (d, 1H), 3.88 (s, 3H), 3.63 (d, 1H), 3.49 (s, 1H), 1.87-1.98 (m, 1H), 1.52-1.64 (m, 3H), 1.40-1.51 (m, 1H), 1.12-1.23 (m, 1H)

HPLC-MS: M/Z=456, Rt=2.16 min.

Example 218

{2-[3-Cyclopentylmethyl-3-(2,2-difluoro-benzo[1,3]dioxol-5-yl)-ureido]-thiazol-5-ylsulfanyl}-acetic acid

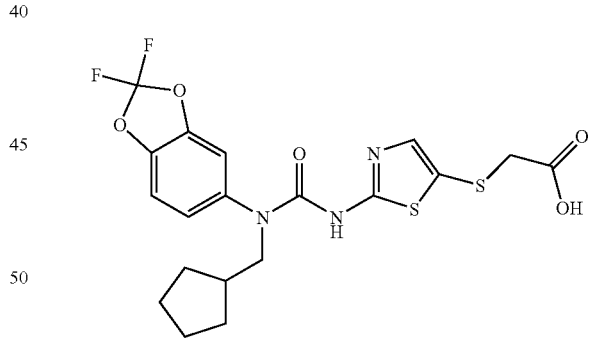

The title compound was prepared via {2-[3-cyclopentylmethyl-3-(2,2-difluoro-benzo[1,3]dioxol-5-yl)-ureido]-thiazol-5-ylsulfanyl}-acetic acid ethyl ester in a similar manner as described for the synthesis of {2-[3-cyclopentylmethyl-3-(4-methanesulfonyl-phenyl)-ureido]-thiazol-4-yl}-acetic acid, using 2,2-difluoro-benzo[1,3]dioxol-5-yl-cyclohexylmethyl-amine and (2-amino-thiazol-5-ylsulfanyl)acetic acid ethyl ester.

1H NMR (400 MHz, DMSO-d$_6$) δ ppm 7.50 (d, 1H), 7.44 (d, 1H), 7.38 (s, 1H), 7.15 (dd, 1H), 3.66 (d, 1H), 3.49 (s, 1H), 1.89-1.99 (m, 1H), 1.54-1.65 (m, 3H), 1.40-1.52 (m, 1H), 1.13-1.23 (m, 1H)

HPLC-MS: M/Z=472, Rt=2.24 min.

Example 219

{2-[3-Cyclopentylmethyl-3-(3-methanesulfonylamino-phenyl)-ureido]-thiazol-5-ylsulfanyl}-acetic acid

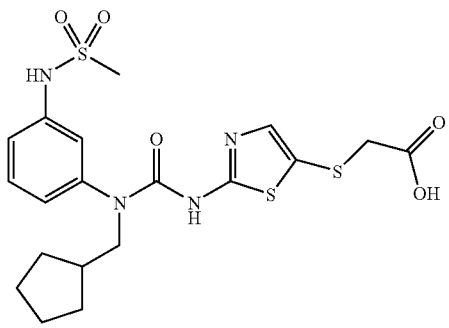

The title compound was prepared via {2-[3-cyclopentylmethyl-3-(3-methanesulfonylamino-phenyl)-ureido]-thiazol-5-ylsulfanyl}-acetic acid ethyl ester in a similar manner as described for the synthesis of {2-[3-cyclopentylmethyl-3-(3,4-difluoro-phenyl)-ureido]-thiazol-4-yl}-acetic acid, using N-(3-Amino-phenyl)-methanesulfonamide, cyclopentanecarbaldehyde and (2-amino-thiazol-5-ylsulfanyl)acetic acid ethyl ester.

1H NMR (400 MHz, DMSO-$d_6$) δ ppm 9.84 (s, 1H), 7.35-7.41 (m, 1H), 7.11-7.18 (m, 1H), 7.04 (d, 1H), 3.65 (d, 1H), 3.50 (s, 1H), 3.04 (s, 3H), 1.91-2.02 (m, 1H), 1.52-1.64 (m, 3H), 1.39-1.50 (m, 1H), 1.13-1.24 (m, 1H)

HPLC-MS: M/Z=485, Rt=1.78 min

Example 220

{2-[3-Cyclopentylmethyl-3-(2,4,6-trifluoro-phenyl)-ureido]-thiazol-5-ylsulfanyl}-acetic acid

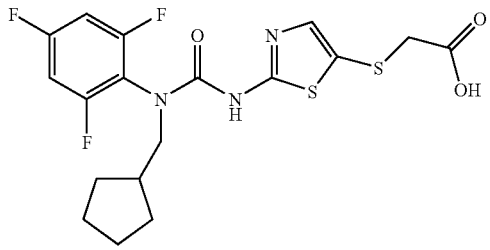

The title compound was prepared via {2-[3-cyclopentylmethyl-3-(2,4,6-trifluoro-phenyl)-ureido]-thiazol-5-ylsulfanyl}-acetic acid ethyl ester in a similar manner as described for the synthesis of {2-[3-cyclopentylmethyl-3-(4-methanesulfonyl-phenyl)-ureido]-thiazol-4-yl}-acetic acid, using cyclopentylmethyl-(2,4,6-trifluorophenyl)-amine and (2-amino-thiazol-5-ylsulfanyl)acetic acid ethyl ester.

1H NMR (400 MHz, DMSO-$d_6$) δ ppm 7.31-7.41 (m, 3H), 3.35-3.61 (m, 3H), 1.89-1.99 (m, 1H), 1.52-1.63 (m, 3H), 1.42-1.50 (m, 1H), 1.13-1.24 (m, 1H)

HPLC-MS: M/Z=446, Rt=2.06 min

Example 221

{2-[3-(3-Chloro-2-fluoro-phenyl)-3-cyclopentylmethyl-ureido]-thiazol-5-ylsulfanyl}-acetic acid

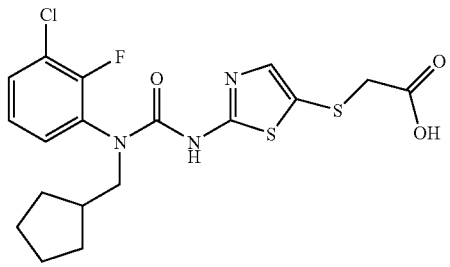

The title compound was prepared via {2-[3-(3-chloro-2-fluoro-phenyl)-3-cyclopentylmethyl-ureido]-thiazol-5-ylsulfanyl}-acetic acid ethyl ester in a similar manner as described for the synthesis of {2-[3-cyclopentylmethyl-3-(4-methanesulfonyl-phenyl)-ureido]-thiazol-4-yl}-acetic acid, using cyclopentylmethyl-(3-chloro-2-fluoro-phenyl)-amine and (2-amino-thiazol-5-ylsulfanyl)acetic acid ethyl ester.

1H NMR (400 MHz, DMSO-$d_6$) δ ppm 7.53-7.62 (m, 1H), 7.35-7.45 (m, 1H), 7.27 (t, 1H), 3.66 (d, 1H), 3.51 (s, 1H), 1.87-1.98 (m, 1H), 1.52-1.64 (m, 3H), 1.42-1.50 (m, 1H), 1.12-1.23 (m, 1H)

HPLC-MS: M/Z=444, Rt=2.11 min

Example 222

{2-[3-Cyclopentylmethyl-3-(4-fluoro-3-methoxy-phenyl)-ureido]-thiazol-5-ylsulfanyl}-acetic acid

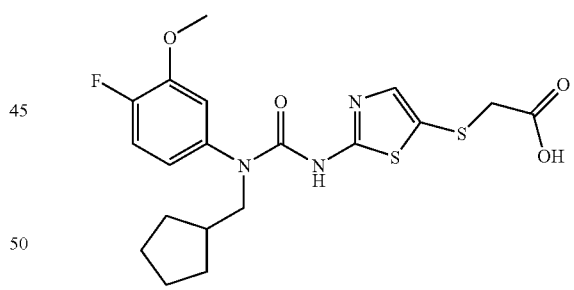

The title compound was prepared via {2-[3-(4-fluoro-3-methoxy-phenyl)-3-cyclopentylmethyl-ureido]-thiazol-5-ylsulfanyl}-acetic acid ethyl ester in a similar manner as described for the synthesis of {2-[3-cyclopentylmethyl-3-(4-methanesulfonyl-phenyl)-ureido]-thiazol-4-yl}-acetic acid, using cyclopentylmethyl-(4-fluoro-3-methoxy-phenyl)-amine and (2-amino-thiazol-5-ylsulfanyl)acetic acid ethyl ester.

1H NMR (400 MHz, DMSO-$d_6$) d ppm 7.38 (s, 1H), 7.24 (dd, 1H), 7.13 (dd, 1H), 6.84-6.90 (m, 1H), 3.83 (s, 3H), 3.66 (d, 1H), 3.49 (s, 1H), 1.90-2.01 (m, 1H), 1.54-1.65 (m, 3H), 1.40-1.51 (m, 1H), 1.13-1.24 (m, 1H)

HPLC-MS: M/Z=440, Rt=2.02 min.

Example 223

{2-[3-Cyclopentylmethyl-3-(2,3-difluoro-4-methoxy-phenyl)-ureido]-thiazol-5-ylsulfanyl}-acetic acid

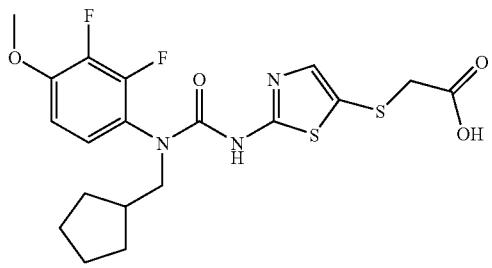

The title compound was prepared via {2-[3-(2,3-difluoro-4-methoxy-phenyl)-3-cyclopentylmethyl-ureido]-thiazol-5-ylsulfanyl}-acetic acid ethyl ester in a similar manner as described for the synthesis of {2-[3-cyclopentylmethyl-3-(4-methanesulfonyl-phenyl)-ureido]-thiazol-4-yl}-acetic acid, using cyclopentylmethyl-(2,3-difluoro-4-methoxy-phenyl)-amine and (2-amino-thiazol-5-ylsulfanyl)acetic acid ethyl ester.

1H NMR (400 MHz, DMSO-$d_6$) δ ppm 7.38 (s, 1H), 7.17-7.25 (m, 1H), 7.02-7.10 (m, 1H), 3.91 (s, 3H), 3.61 (d, 1H), 3.50 (s, 1H), 1.88-1.98 (m, 1H), 1.52-1.64 (m, 3H), 1.40-1.50 (m, 1H), 1.13-1.23 (m, 1H)

HPLC-MS: M/Z=458, Rt=2.07 min.

Example 224

{2-[3-Cyclopentylmethyl-3-(4-isopropoxy-phenyl)-ureido]-thiazol-5-ylsulfanyl}-acetic acid

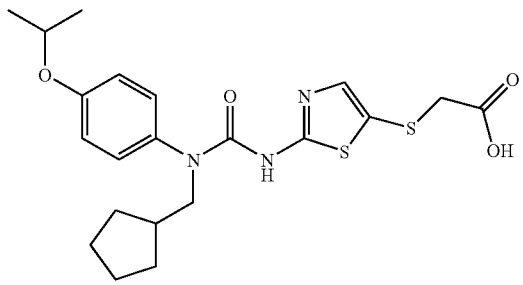

The title compound was prepared via {2-[3-(4-isopropoxy-phenyl)-3-cyclopentylmethyl-ureido]-thiazol-5-ylsulfanyl}-acetic acid ethyl ester in a similar manner as described for the synthesis of {2-[3-cyclopentylmethyl-3-(4-methanesulfonyl-phenyl)-ureido]-thiazol-4-yl}-acetic acid, using cyclopentylmethyl-(4-isopropoxy-phenyl)-amine and (2-amino-thiazol-5-ylsulfanyl)acetic acid ethyl ester.

1H NMR (400 MHz, DMSO-$d_6$) δ ppm 7.36 (s, 1H), 7.19 (d, 1H), 6.95 (d, 1H), 4.57-4.66 (m, 1H), 3.61 (d, 1H), 3.49 (s, 1H), 1.88-1.99 (m, 1H), 1.51-1.65 (m, 3H), 1.39-1.50 (m, 1H), 1.29 (d, 3H), 1.13-1.24 (m, 1H)

HPLC-MS: M/Z=450, Rt=2.18 min.

Example 225

{2-[3-Cyclopentylmethyl-3-(3-fluoro-2-methyl-phenyl)-ureido]-thiazol-5-ylsulfanyl}-acetic acid

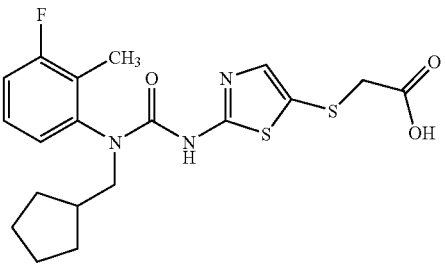

The title compound was prepared via {2-[3-cyclopentylmethyl-3-(3-fluoro-2-methyl-phenyl)-ureido]-thiazol-5-ylsulfanyl}-acetic acid ethyl ester in a similar manner as described for the synthesis of {2-[3-cyclopentylmethyl-3-(4-methanesulfonyl-phenyl)-ureido]-thiazol-4-yl}-acetic acid, using cyclopentylmethyl-(3-fluoro-2-methyl-phenyl)-amine and (2-amino-thiazol-5-ylsulfanyl)acetic acid ethyl ester.

1H NMR (400 MHz, DMSO-$d_6$) δ ppm 7.36 (s, 1H), 7.26-7.32 (m, 1H), 7.14-7.22 (m, 1H), 7.10 (d, 1H), 3.74-3.86 (m, 1H), 3.49 (s, 2H), 3.35-3.43 (m, 1H), 2.04 (d, 3H), 1.92-2.01 (m, 1H), 1.53-1.65 (m, 4H), 1.41-1.51 (m, 2H), 1.14-1.26 (m, 2H)

HPLC-MS: M/Z=424, Rt=2.10 min.

Example 226

{2-[3-(3-Chloro-2-methoxy-phenyl)-3-cyclopentylmethyl-ureido]-thiazol-5-ylsulfanyl}-acetic acid

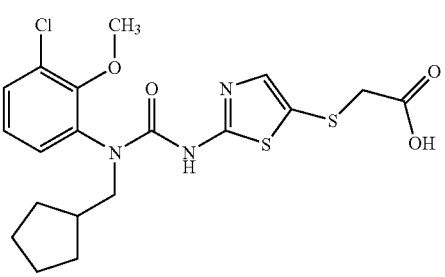

The title compound was prepared via {2-[3-(3-chloro-2-methoxy-phenyl)-3-cyclopentylmethyl-ureido]-thiazol-5-ylsulfanyl}-acetic acid ethyl ester in a similar manner as described for the synthesis of {2-[3-cyclopentylmethyl-3-(4-methanesulfonyl-phenyl)-ureido]-thiazol-4-yl}-acetic acid, using cyclopentylmethyl-(3-chloro-2-methoxy-phenyl)-amine and (2-amino-thiazol-5-ylsulfanyl)acetic acid ethyl ester.

1H NMR (400 MHz, DMSO-$d_6$) δ ppm 7.47-7.51 (m, 1H), 7.37 (s, 1H), 7.23-7.27 (m, 1H), 7.16-7.20 (m, 1H), 3.74 (s, 3H), 3.50 (s, 2H), 1.88-1.98 (m, 1H), 1.53-1.64 (m, 4H), 1.40-1.50 (m, 2H), 1.11-1.22 (m, 2H)

HPLC-MS: M/Z=456, Rt=2.15 min.

Example 227

{2-[3-(3-Chloro-2-methyl-phenyl)-3-cyclopentylmethyl-ureido]-thiazol-5-ylsulfanyl}-acetic acid

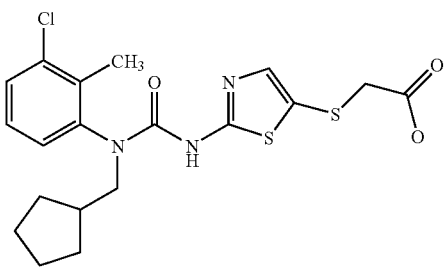

The title compound was prepared via {2-[3-(3-chloro-2-methyl-phenyl)-3-cyclopentylmethyl-ureido]-thiazol-5-ylsulfanyl}-acetic acid ethyl ester in a similar manner as described for the synthesis of {2-[3-cyclopentylmethyl-3-(4-methanesulfonyl-phenyl)-ureido]-thiazol-4-yl}-acetic acid, using cyclopentylmethyl-(3-chloro-2-methyl-phenyl)-amine and (2-amino-thiazol-5-ylsulfanyl)acetic acid ethyl ester 1H NMR (400 MHz, DMSO-$d_6$) δ ppm 7.45 (d, 1H), 7.36 (s, 1H), 7.26-7.31 (m, 1H), 7.21-7.25 (m, 1H), 3.78-3.87 (m, 1H), 3.49 (s, 2H), 2.15 (s, 3H), 1.91-2.01 (m, 1H), 1.53-1.65 (m, 4H), 1.41-1.51 (m, 2H), 1.14-1.26 (m, 2H)

HPLC-MS: M/Z=439, Rt=2.23 min.

Example 228

{2-[3-Cyclopentylmethyl-3-(2-fluoro-3-methyl-phenyl)-ureido]-thiazol-5-ylsulfanyl}-acetic acid

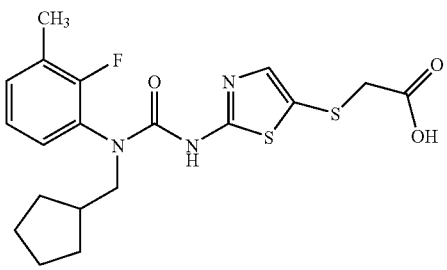

The title compound was prepared via {2-[3-(2-fluoro-3-methyl-phenyl)-3-cyclopentylmethyl-ureido]-thiazol-5-ylsulfanyl}-acetic acid ethyl ester in a similar manner as described for the synthesis of {2-[3-cyclopentylmethyl-3-(4-methanesulfonyl-phenyl)-ureido]-thiazol-4-yl}-acetic acid, using cyclopentylmethyl-(2-fluoro-3-methyl-phenyl)-amine and (2-amino-thiazol-5-ylsulfanyl)acetic acid ethyl ester 1H NMR (400 MHz, DMSO-$d_6$) δ ppm 7.37 (s, 1H), 7.24-7.30 (m, 1H), 7.21 (t, 1H), 7.10-7.17 (m, 1H), 3.62 (d, 2H), 3.49 (s, 2H), 2.26 (d, 3H), 1.88-1.98 (m, 1H), 1.51-1.63 (m, 4H), 1.40-1.49 (m, 2H), 1.13-1.24 (m, 2H)

HPLC-MS: M/Z=424, Rt=2.12 min.

Example 229

{2-[3-[2-(3,4-Difluoro-phenyl)-ethyl]-3-(4-trans-methyl-cyclohexyl)-ureido]-thiazol-5-ylsulfanyl}-acetic acid

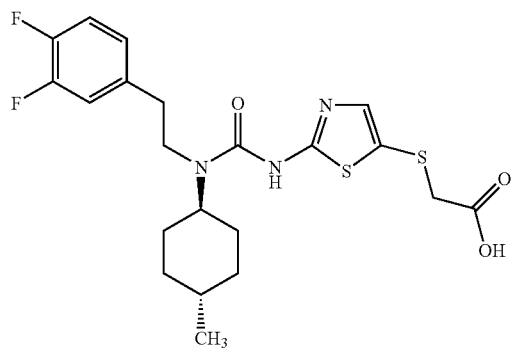

Prepared as described for the synthesis of {2-[3-(2-benzyloxy-ethyl)-3-(4-trans-methyl-cyclohexyl)-ureido]-thiazol-5-ylsulfanyl}-acetic acid using 2-(3,4-difluoro-phenyl)-ethanol, 4-trans-methyl-cyclohexylamine and (2-amino-thiazol-5-ylsulfanyl)-acetic acid ethyl ester.

$^1$H NMR (400 MHz, CDCl$_3$) 7.32 (s, 1H), 7.20-6.94 (m, 3H), 4.18-3.81 (m, 1H), 3.52-3.41 (m, 2H), 3.39 (s, 2H), 2.93-2.78 (m, 2H), 1.87-1.68 (m, 4H), 1.60-1.43 (m, 2H), 1.42-1.10 (m, 3H), 0.92 (d, 3H)

HPLC-MS: m/z=470

Example 230

(2-{3-(4-trans-Methyl-cyclohexyl)-3-[2-(3,4,5-trifluoro-phenyl)-ethyl]-ureido}-thiazol-5-ylsulfanyl)-acetic acid

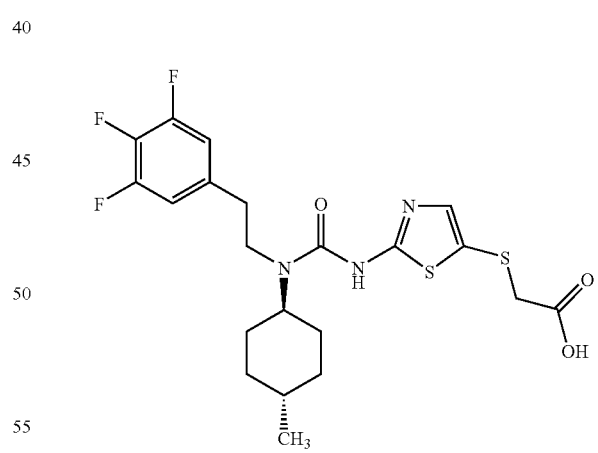

Prepared as described for the synthesis of {2-[3-(2-benzyloxy-ethyl)-3-(4-trans-methyl-cyclohexyl)-ureido]-thiazol-5-ylsulfanyl}-acetic acid using 2-(3,4,5-trifluoro-phenyl)-ethanol, 4-trans-methyl-cyclohexylamine and (2-amino-thiazol-5-ylsulfanyl)-acetic acid ethyl ester.

$^1$H NMR (400 MHz, CDCl$_3$) 7.30 (s, 1H), 7.03-6.85 (m, 2H), 4.14-3.77 (m, 1H), 3.51-3.40 (m, 2H), 3.38 (s, 2H), 2.91-2.78 (m, 2H), 1.87-1.70 (m, 4H), 1.60-1.43 (m, 2H), 1.42-1.10 (m, 3H), 0.92 (d, 3H)

HPLC-MS: m/z=488

Example 231

(2-{3-(4-trans-Methyl-cyclohexyl)-3-[2-(2,4,5-trifluoro-phenyl)-ethyl]-ureido}-thiazol-5-ylsulfanyl)-acetic acid

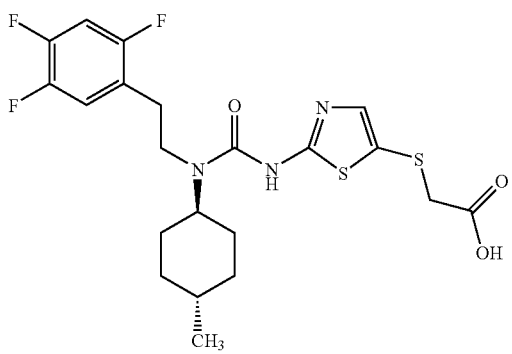

Prepared as described for the synthesis of {2-[3-(2-benzyloxy-ethyl)-3-(4-trans-methyl-cyclohexyl)-ureido]-thiazol-5-ylsulfanyl}-acetic acid using 2-(2,4,5-trifluoro-phenyl)-ethanol, 4-trans-methyl-cyclohexylamine and (2-amino-thiazol-5-ylsulfanyl)-acetic acid ethyl ester.

HPLC-MS: m/z=488

Example 232

(2-{3-(4-trans-Methyl-cyclohexyl)-3-[2-(2,3,4-trifluoro-phenyl)-ethyl]-ureido}-thiazol-5-ylsulfanyl)-acetic acid

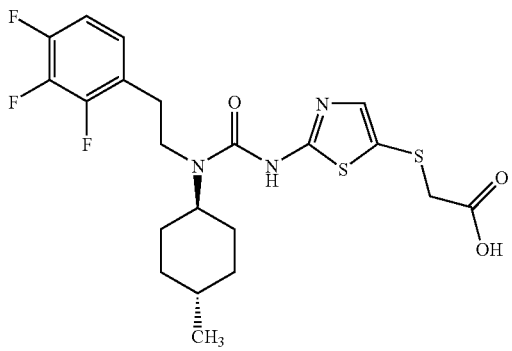

Prepared as described for the synthesis of {2-[3-(2-benzyloxy-ethyl)-3-(4-trans-methyl-cyclohexyl)-ureido]-thiazol-5-ylsulfanyl}-acetic acid using 2-(2,3,4-trifluoro-phenyl)-ethanol, 4-trans-methyl-cyclohexylamine and (2-amino-thiazol-5-ylsulfanyl)-acetic acid ethyl ester.

HPLC-MS: m/z=488

Example 233

2-{2-[3-[2-(2-Chloro-benzyloxy)-ethyl]-3-(4-trans-methyl-cyclohexyl)-ureido]-thiazol-5-ylsulfanyl}-2-methyl-propionic acid

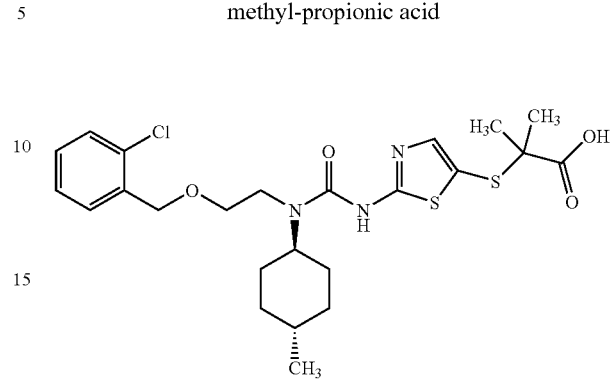

Prepared as described for the synthesis of {2-[3-[2-(4-fluoro-2-trifluoromethyl-benzyloxy)-ethyl]-3-(4-trans-methyl-cyclohexyl)-ureido]-thiazol-5-ylsulfanyl}-acetic acid using 2-chlorobenzylbromide, (2-hydroxy-ethyl)-(4-trans-methyl-cyclohexyl)-carbamic acid tert-butyl ester and 2-(2-amino-thiazol-5-ylsulfanyl)-2-methyl-propionic acid ethyl ester $^1$H NMR (400 MHz, DMSO-$d_6$) 7.53-7.49 (m, 1H), 7.45-7.41 (m, 1H), 7.38 (s, 1H), 7.35-7.27 (m, 2H), 4.62 (s, 2H), 3.99-3.87 (m, 1H), 3.65-3.57 (m, 2H), 3.56-3.49 (m, 2H), 1.73-1.63 (m, 2H), 1.63-1.48 (m, 4H), 1.39 (s, 6H), 1.36-1.22 (m, 1H), 1.11-0.95 (m, 2H), 0.86 (d, 3H)

HPLC-MS: m/z=526

Example 234

2-{2-[3-[2-(2-Fluoro-benzyloxy)-ethyl]-3-(4-trans-methyl-cyclohexyl)-ureido]-thiazol-5-ylsulfanyl}-2-methyl-propionic acid

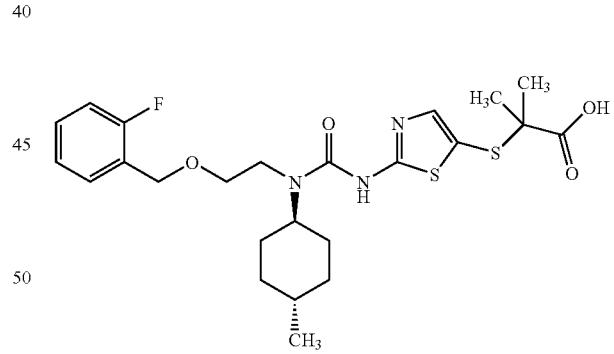

Prepared as described for the synthesis of {2-[3-[2-(4-fluoro-2-trifluoromethyl-benzyloxy)-ethyl]-3-(4-trans-methyl-cyclohexyl)-ureido]-thiazol-5-ylsulfanyl}-acetic acid using 2-fluoro-benzylbromide, (2-hydroxy-ethyl)-(4-trans-methyl-cyclohexyl)-carbamic acid tert-butyl ester and 2-(2-amino-thiazol-5-ylsulfanyl)-2-methyl-propionic acid ethyl ester $^1$H NMR (400 MHz, DMSO-$d_6$) 7.48-7.42 (m, 1H), 7.38 (s, 1H), 7.38-7.31 (m, 1H), 7.21-7.13 (m, 2H), 4.58 (s, 2H), 3.98-3.86 (m, 1H), 3.60-3.54 (m, 2H), 3.52-3.45 (m, 2H), 1.71-1.62 (m, 2H), 1.61-1.45 (m, 4H), 1.39 (s, 6H), 1.36-1.23 (m, 1H), 1.10-0.95 (m, 2H), 0.86 (d, 3H)

HPLC-MS: m/z=510

Example 235

{2-[3-(2-Chloro-3-fluoro-phenyl)-3-cyclopentylmethyl-ureido]-thiazol-5-ylsulfanyl}-acetic acid

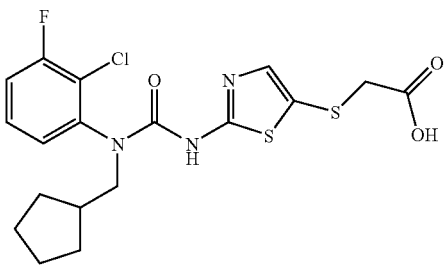

The title compound was prepared via {2-[3-(2-chloro-3-fluoro-phenyl)-3-cyclopentylmethyl-ureido]-thiazol-5-ylsulfanyl}-acetic acid ethyl ester in a similar manner as described for the synthesis of {2-[3-cyclopentylmethyl-3-(4-methanesulfonyl-phenyl)-ureido]-thiazol-4-yl}-acetic acid, using cyclopentylmethyl-(2-chloro-3-fluoro-phenyl)-amine and (2-amino-thiazol-5-ylsulfanyl)acetic acid ethyl ester 1H NMR (400 MHz, DMSO-d$_6$) δ ppm 7.67 (dd, 1H), 7.46 (dd, 1H), 7.41 (d, 1H), 7.37 (s, 1H), 3.63 (d, 2H), 3.50 (s, 2H), 1.87-1.97 (m, 1H), 1.51-1.64 (m, 4H), 1.40-1.50 (m, 2H), 1.11-1.21 (m, 2H)

HPLC-MS: M/Z=425, Rt=1.82 min.

Example 236

{2-[3-(3-Bromo-phenyl)-3-cyclopentylmethyl-ureido]-thiazol-5-ylsulfanyl}-acetic acid

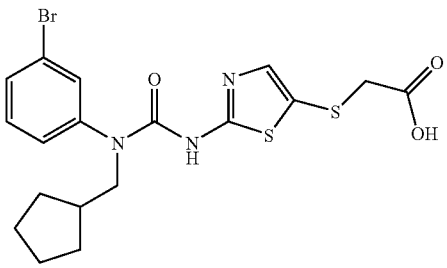

The title compound was prepared via {2-[3-(3-bromo-phenyl)-3-cyclopentylmethyl-ureido]-thiazol-5-ylsulfanyl}-acetic acid ethyl ester in a similar manner as described for the synthesis of {2-[3-cyclopentylmethyl-3-(4-methanesulfonyl-phenyl)-ureido]-thiazol-4-yl}-acetic acid, using cyclopentylmethyl-(3-bromo-phenyl)-amine and (2-amino-thiazol-5-ylsulfanyl)acetic acid ethyl ester 1H NMR (400 MHz, DMSO-d$_6$) δ ppm 7.55 (t, 1H), 7.50 (d, 1H), 7.30-7.39 (m, 3H), 3.71 (d, 2H), 3.50 (s, 2H), 1.88-1.97 (m, 1H), 1.52-1.63 (m, 4H), 1.40-1.49 (m, 2H), 1.12-1.20 (m, 2H)

HPLC-MS: M/Z=470, Rt=2.19 min.

Example 237

{2-[3-(4-Bromo-2-fluoro-phenyl)-3-cyclopentylmethyl-ureido]-thiazol-5-ylsulfanyl}-acetic acid

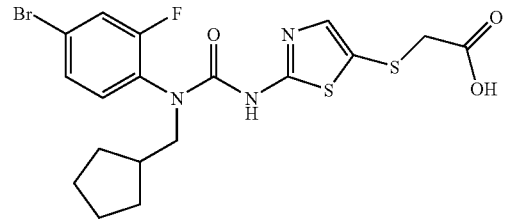

The title compound was prepared via {2-[3-(4-bromo-2-fluoro-phenyl)-3-cyclopentylmethyl-ureido]-thiazol-5-ylsulfanyl}-acetic acid ethyl ester in a similar manner as described for the synthesis of {2-[3-cyclopentylmethyl-3-(4-methanesulfonyl-phenyl)-ureido]-thiazol-4-yl}-acetic acid, using cyclopentylmethyl-(4-bromo-2-fluoro-phenyl)-amine and (2-amino-thiazol-5-ylsulfanyl)acetic acid ethyl ester 1H NMR (400 MHz, DMSO-d$_6$) δ ppm 7.67 (dd, 1H), 7.46 (dd, 1H), 7.41 (d, 1H), 7.37 (s, 1H), 3.63 (d, 2H), 3.50 (s, 2H), 1.87-1.97 (m, 1H), 1.51-1.64 (m, 4H), 1.40-1.50 (m, 2H), 1.11-1.21 (m, 2H)

HPLC-MS: M/Z=488, Rt=2.25 min.

Example 238

{2-[3-(2-Bromo-phenyl)-3-cyclopentylmethyl-ureido]-thiazol-5-ylsulfanyl}-acetic acid

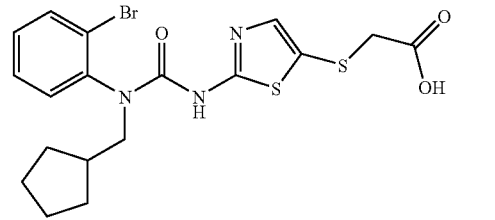

The title compound was prepared via {2-[3-(2-bromo-phenyl)-3-cyclopentylmethyl-ureido]-thiazol-5-ylsulfanyl}-acetic acid ethyl ester in a similar manner as described for the synthesis of {2-[3-cyclopentylmethyl-3-(4-methanesulfonyl-phenyl)-ureido]-thiazol-4-yl}-acetic acid, using cyclopentylmethyl-(2-bromo-phenyl)-amine and (2-amino-thiazol-5-ylsulfanyl)acetic acid ethyl ester 1H NMR (400 MHz, DMSO-d$_6$) δ ppm 7.71-7.76 (m, 1H), 7.40-7.48 (m, 2H), 7.28-7.39 (m, 2H), 3.83-3.99 (m, 1H), 3.50 (s, 2H), 3.21-3.32 (m, 1H), 1.93-2.04 (m, 1H), 1.52-1.71 (m, 4H), 1.41-1.51 (m, 2H), 1.11-1.28 (m, 2H)

HPLC-MS: M/Z=470, Rt=2.18 min.

Example 239

{2-[3-Cyclopentylmethyl-3-(3-methoxy-5-trifluoromethyl-phenyl)-ureido]-thiazol-5-ylsulfanyl}-acetic acid

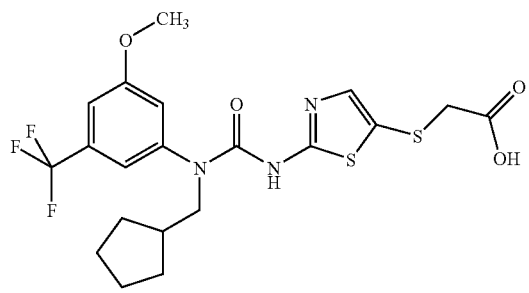

The title compound was prepared via {2-[3-(3-methoxy-5-trifluoromethyl-phenyl)-3-cyclopentylmethyl-ureido]-thiazol-5-ylsulfanyl}-acetic acid ethyl ester in a similar manner as described for the synthesis of {2-[3-cyclopentylmethyl-3-(4-methanesulfonyl-phenyl)-ureido]-thiazol-4-yl}-acetic acid, using cyclopentylmethyl-(3-methoxy-5-trifluoromethyl-phenyl)-amine and (2-amino-thiazol-5-ylsulfanyl)acetic acid ethyl ester 1H NMR (400 MHz, DMSO-$d_6$) δ ppm 7.38 (s, 1H), 7.23 (br. s., 1H), 7.19 (br. s., 2H), 3.85 (s, 3H), 3.74 (d, 2H), 3.50 (s, 2H), 1.89-1.99 (m, 1H), 1.51-1.64 (m, 4H), 1.40-1.50 (m, 2H), 1.12-1.23 (m, 2H)

HPLC-MS: M/Z=490, Rt=2.39 min.

Example 240

{2-[3-(3-Acetyl-phenyl)-3-cyclopentylmethyl-ureido]-thiazol-5-ylsulfanyl}-acetic acid

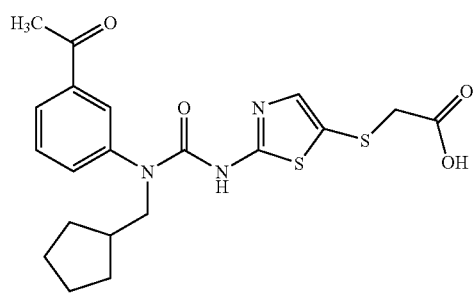

The title compound was prepared via {2-[3-(3-acetyl-phenyl)-3-cyclopentylmethyl-ureido]-thiazol-5-ylsulfanyl}-acetic acid ethyl ester in a similar manner as described for the synthesis of {2-[3-cyclopentylmethyl-3-(4-methanesulfonyl-phenyl)-ureido]-thiazol-4-yl}-acetic acid, using cyclopentylmethyl-(3-acetyl-phenyl)-amine and (2-amino-thiazol-5-ylsulfanyl)acetic acid ethyl ester 1H NMR (400 MHz, DMSO-$d_6$) δ ppm 7.86-7.92 (m, 1H), 7.84 (s, 1H), 7.54-7.60 (m, 2H), 7.37 (s, 1H), 3.75 (d, 2H), 3.50 (s, 2H), 2.60 (s, 3H), 1.88-2.00 (m, 1H), 1.51-1.64 (m, 4H), 1.38-1.50 (m, 2H), 1.12-1.24 (m, 2H)

HPLC-MS: M/Z=434, Rt=2.08 min.

Example 241

{2-[3-(1-Acetyl-2,3-dihydro-1H-indol-6-yl)-3-cyclopentylmethyl-ureido]-thiazol-5-ylsulfanyl}-acetic acid

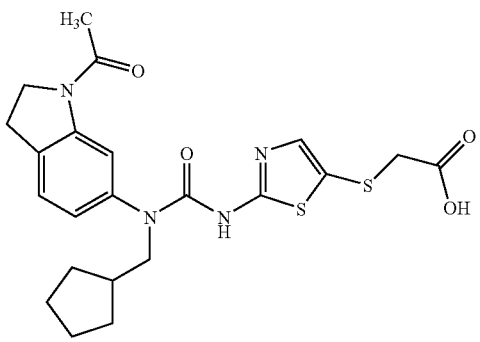

The title compound was prepared via {2-[3-(1-acetyl-2,3-dihydro-1H-indol-6-yl)-3-cyclopentylmethyl-ureido]-thiazol-5-ylsulfanyl}-acetic acid ethyl ester in a similar manner as described for the synthesis of {2-[3-cyclopentylmethyl-3-(4-methanesulfonyl-phenyl)-ureido]thiazol-4-yl}-acetic acid, using 1-[6-(cyclopentylmethyl-amino)-2,3-dihydro-indol-1-yl]-ethanone and (2-amino-thiazol-5-ylsulfanyl)acetic acid ethyl ester 1H NMR (400 MHz, DMSO-$d_6$) ppm 7.92 (d, 1H), 7.35 (s, 1H), 7.26 (d, 1H), 6.92 (dd, 1H), 4.14 (t, 2H), 3.63 (d, 2H), 3.49 (s, 2H), 3.16 (t, 2H), 2.16 (s, 3H), 1.90-2.01 (m, 1H), 1.51-1.65 (m, 4H), 1.39-1.50 (m, 2H), 1.14-1.24 (m, 2H).

HPLC-MS: M/Z=475, Rt=1.82 min.

Example 242

Further Compounds According to the Invention

A non-limiting example of further compounds according to the invention are listed in Table 1. The preparation of the compounds Aa-Bx of general formula (I) of the present invention may be performed according to one or more of the described methods I-K as indicated for each compound in Table 1. Occasionally, the reaction may not be applicable as described to each compound included within the disclosed scope of the invention. The compounds for which this occurs will be readily recognised by those skilled in the art. In these cases the reactions can be successfully performed by conventional modifications known to those skilled in the art, which is, by appropriate protection of interfering groups, by changing to other conventional reagents, or by routine modification of reaction conditions. Alternatively, other reactions disclosed herein or otherwise conventional will be applicable to the preparation of the corresponding compounds of the invention. In all preparative methods, all starting materials are known or may be prepared by a person skilled in the art in analogy with the preparation of similar known compounds or by the General procedures A through K described herein.

TABLE 1

| Compound | Structure | Name | Method |
|---|---|---|---|
| Aa | 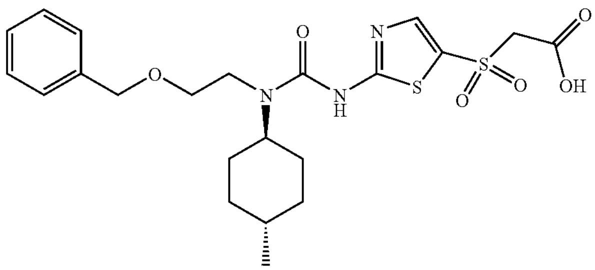 | {2-[3-(2-Benzyloxy-ethyl)-3-(4-methyl-cyclohexyl)-ureido]-thiazole-5-sulfonyl}-acetic acid | (I) |
| Ab | 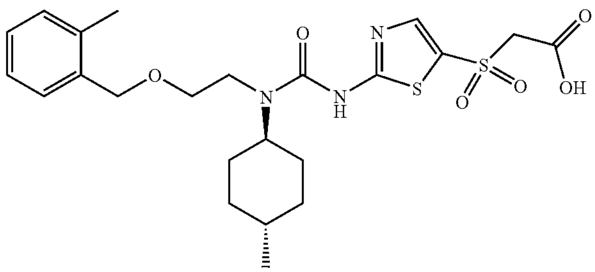 | {2-[3-[2-(2-Methyl-benzyloxy)-ethyl]-3-(4-methyl-cyclohexyl)-ureido]-thiazole-5-sulfonyl}-acetic acid | (I) |
| Ac | 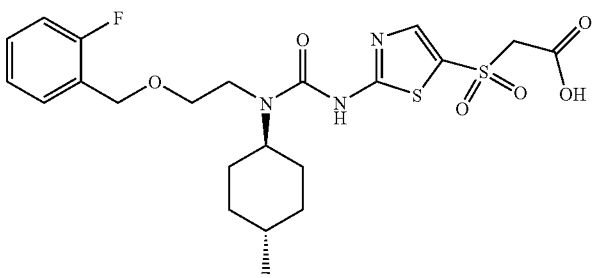 | {2-[3-[2-(2-Fluoro-benzyloxy)-ethyl]-3-(4-methyl-cyclohexyl)-ureido]-thiazole-5-sulfonyl}-acetic acid | (I) |
| Ad | 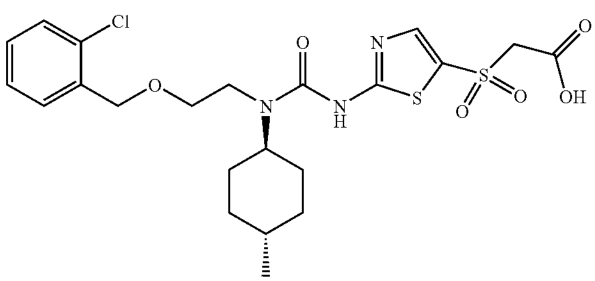 | {2-[3-[2-(2-Chloro-benzyloxy)-ethyl]-3-(4-methyl-cyclohexyl)-ureido]-thiazole-5-sulfonyl}-acetic acid | (I) |
| Ae | 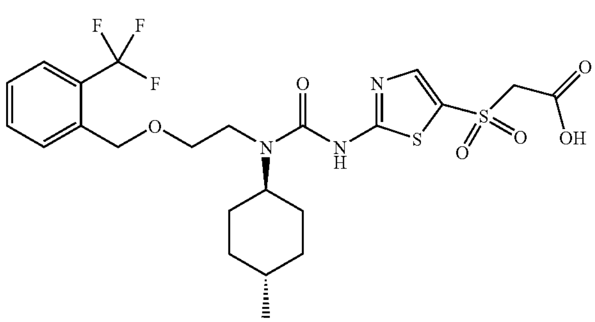 | (2-{3-(4-Methyl-cyclohexyl)-3-[2-(2-trifluoromethyl-benzyloxy)-ethyl]-ureido}-thiazole-5-sulfonyl)-acetic acid | (I) |

TABLE 1-continued

| Compound | Structure | Name | Method |
|---|---|---|---|
| Af | 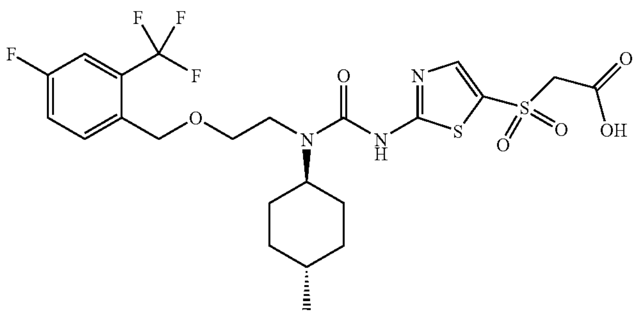 | {2-[3-[2-(4-Fluoro-2-trifluoromethyl-benzyloxy)-ethyl]-3-(4-methyl-cyclohexyl)-ureido]-thiazole-5-sulfonyl}-acetic acid | (I) |
| Ag | 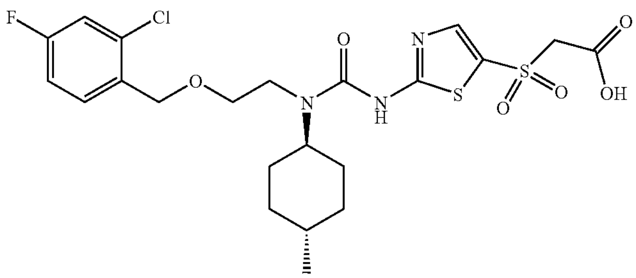 | {2-[3-[2-(2-Chloro-4-fluoro-benzyloxy)-ethyl]-3-(4-methyl-cyclohexyl)-ureido]-thiazole-5-sulfonyl}-acetic acid | (I) |
| Ah | 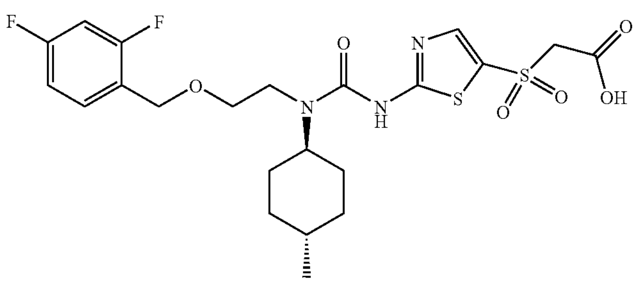 | {2-[3-[2-(2,4-Difluoro-benzyloxy)-ethyl]-3-(4-methyl-cyclohexyl)-ureido]-thiazole-5-sulfonyl}-acetic acid | (I) |
| Ai | 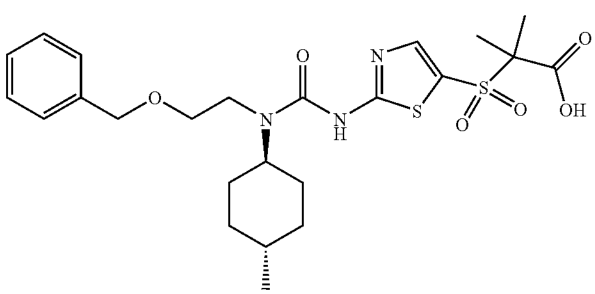 | 2-{2-[3-[2-(2-Benzyloxy-ethyl)-3-(4-methyl-cyclohexyl)-ureido]-thiazole-5-sulfonyl}-2-methyl-propionic acid | (I) |
| Aj | 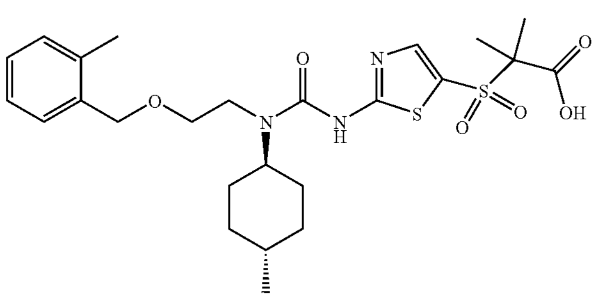 | 2-Methyl-2-{2-[3-[2-(2-methyl-benzyloxy)-ethyl]-3-(4-methyl-cyclohexyl)-ureido]-thiazole-5-sulfonyl}-propionic acid | (I) |

TABLE 1-continued

| Compound | Structure | Name | Method |
|---|---|---|---|
| Ak | 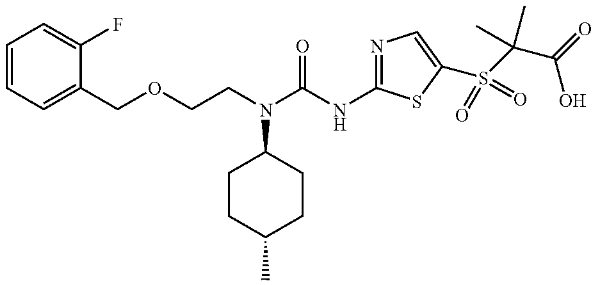 | 2-{2-[3-[2-(2-Fluoro-benzyloxy)-ethyl]-3-(4-methyl-cyclohexyl)-ureido]-thiazole-5-sulfonyl}-2-methyl-propionic acid | (I) |
| Al | 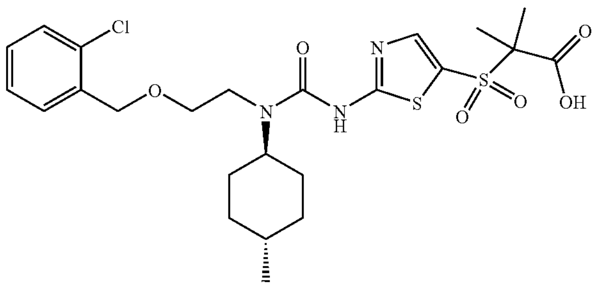 | 2-{2-[3-[2-(2-Chloro-benzyloxy)-ethyl]-3-(4-methyl-cyclohexyl)-ureido]-thiazole-5-sulfonyl}-2-methyl-propionic acid | (I) |
| Am | 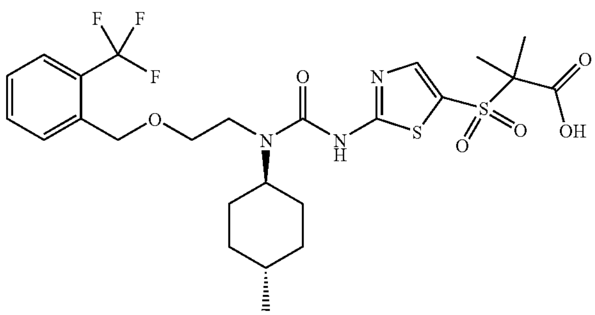 | 2-Methyl-2-(2-{3-(4-methyl-cyclohexyl)-3-[2-(2-trifluoromethyl-benzyloxy)-ethyl]-ureido}-thiazole-5-sulfonyl)-propionic acid | (I) |
| An | 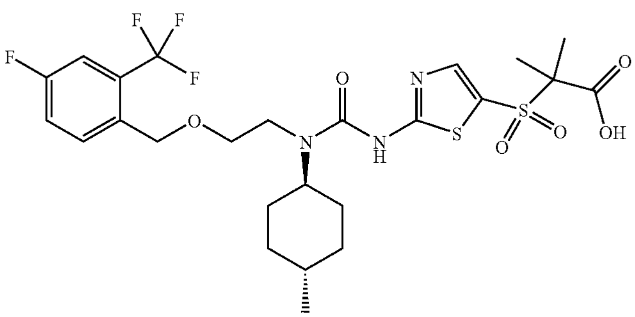 | 2-{2-[3-[2-(4-Fluoro-2-trifluoromethyl-benzyloxy)-ethyl]-3-(4-methyl-cyclohexyl)-ureido]-thiazole-5-sulfonyl}-2-methyl-propionic acid | (I) |
| Ao | 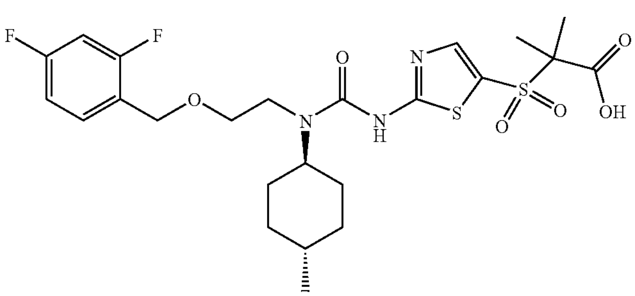 | 2-{2-[3-[2-(2,4-Difluoro-benzyloxy)-ethyl]-3-(4-methyl-cyclohexyl)-ureido]-thiazole-5-sulfonyl}-2-methyl-propionic acid | (I) |

TABLE 1-continued

| Compound | Structure | Name | Method |
|---|---|---|---|
| Ap | 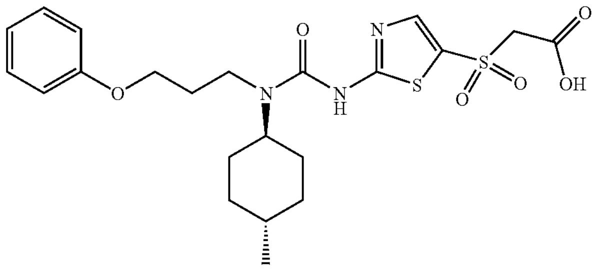 | {2-[3-(4-Methyl-cyclohexyl)-3-(3-phenoxy-propyl)-ureido]-thiazole-5-sulfonyl}-acetic acid | (I) |
| Aq | 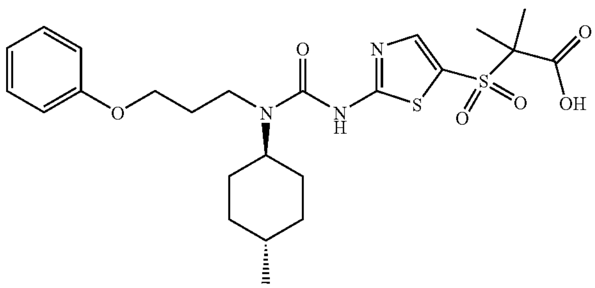 | 2-Methyl-2-{2-[3-(4-methyl-cyclohexyl)-3-(3-phenoxy-propyl)-ureido]-thiazole-5-sulfonyl}-propionic acid | (I) |
| Ar | 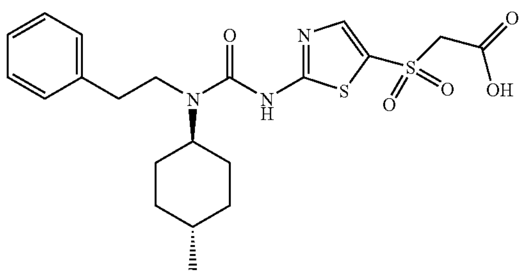 | {2-[3-(4-Methyl-cyclohexyl)-3-phenethyl-ureido]-thiazole-5-sulfonyl}-acetic acid | (I) |
| As | 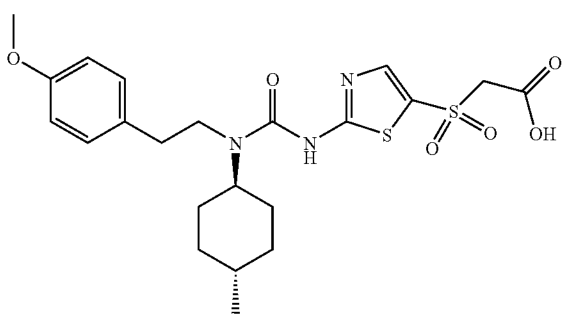 | {2-[3-[2-(4-Methoxy-phenyl)-ethyl]-3-(4-methyl-cyclohexyl)-ureido]-thiazole-5-sulfonyl}-acetic acid | (I) |
| At | 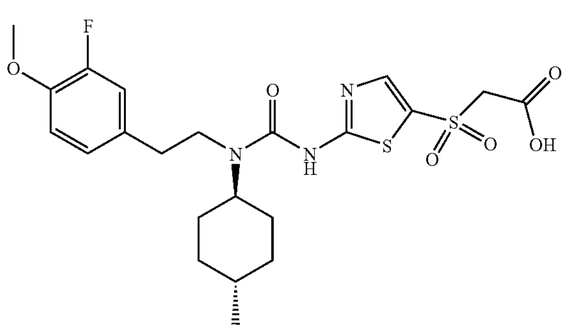 | {2-[3-[2-(3-Fluoro-4-methoxy-phenyl)-ethyl]-3-(4-methyl-cyclohexyl)-ureido]-thiazole-5-sulfonyl}-acetic acid | (I) |

TABLE 1-continued

| Compound | Structure | Name | Method |
|---|---|---|---|
| Au | 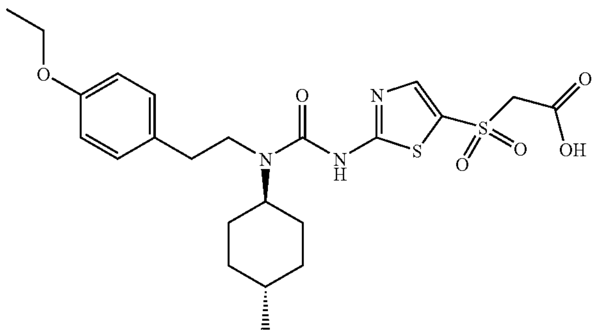 | {2-[3-[2-(4-Ethoxy-phenyl)-ethyl]-3-(4-methyl-cyclohexyl)-ureido]-thiazole-5-sulfonyl}-acetic acid | (I) |
| Av | 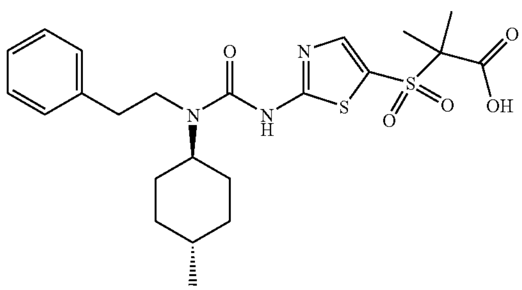 | 2-Methyl-2-{2-[3-(4-methyl-cyclohexyl)-3-phenethyl-ureido]-thiazole-5-sulfonyl}-propionic acid | (I) |
| Aw | 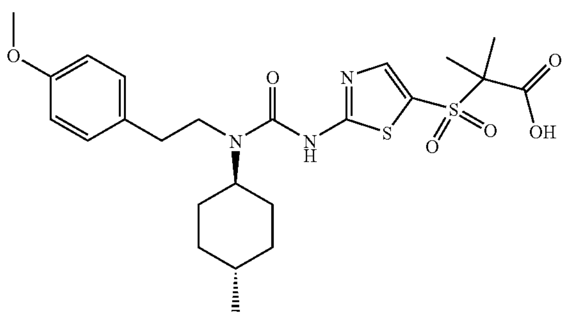 | 2-{2-[3-[2-(4-Methoxy-phenyl)-ethyl]-3-(4-methyl-cyclohexyl)-ureido]-thiazole-5-sulfonyl}-2-methyl-propionic acid | (I) |
| Ax | 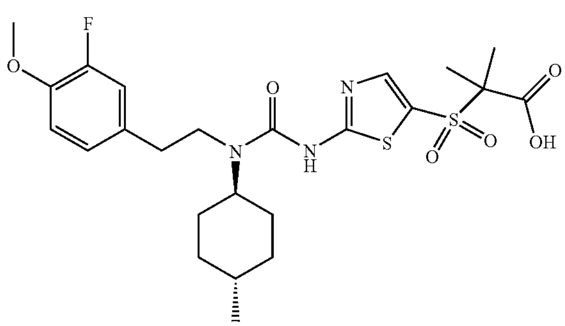 | 2-{2-[3-[2-(3-Fluoro-4-methoxy-phenyl)-ethyl]-3-(4-methyl-cyclohexyl)-ureido]-thiazole-5-sulfonyl}-2-methyl-propionic acid | (I) |

TABLE 1-continued

| Compound | Structure | Name | Method |
|---|---|---|---|
| Ay | 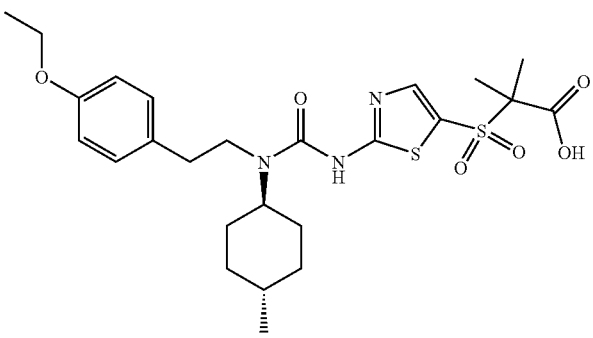 | 2-{2-[3-[2-(3-Fluoro-4-methoxy-phenyl)-ethyl]-3-(4-methyl-cyclohexyl)-ureido]-thiazole-5-sulfonyl}-2-methyl-propionic acid | (I) |
| Az | 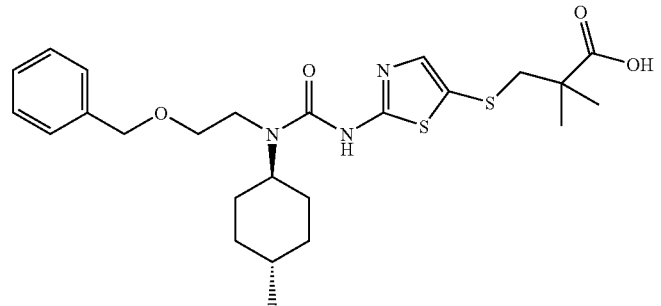 | 3-{2-[3-(2-Benzyloxy-ethyl)-3-(4-methyl-cyclohexyl)-ureido]-thiazol-5-ylsulfanyl}-2,2-dimethyl-propionic acid | (J) |
| Ba | 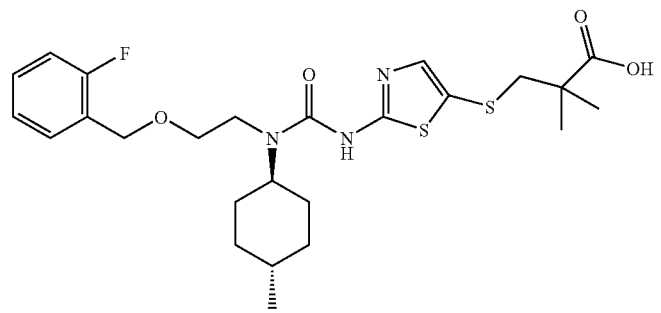 | 3-{2-[3-[2-(2-Fluoro-benzyloxy)-ethyl]-3-(4-methyl-cyclohexyl)-ureido]-thiazol-5-ylsulfanyl}-2,2-dimethyl-propionic acid | (J) |
| Bb | 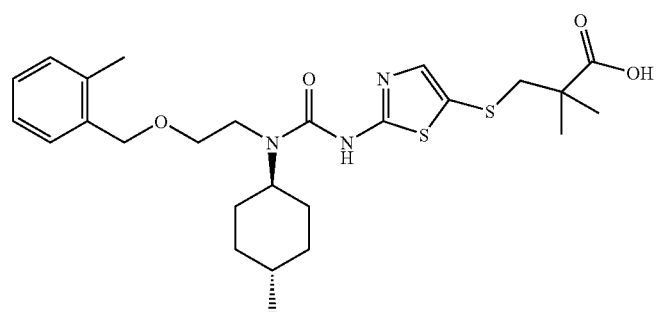 | 2,2-Dimethyl-3-{2-[3-[2-(2-methyl-benzyloxy)-ethyl]-3-(4-methyl-cyclohexyl)-ureido]-thiazol-5-ylsulfanyl}-propionic acid | (J) |

TABLE 1-continued

| Compound | Structure | Name | Method |
|---|---|---|---|
| Bc | 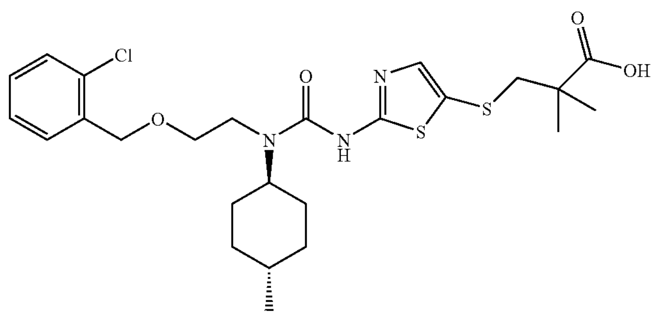 | 3-{2-[3-[2-(2-Chloro-benzyloxy)-ethyl]-3-(4-methyl-cyclohexyl)-ureido]-thiazol-5-ylsulfanyl}-2,2-dimethyl-propionic acid | (J) |
| Bd | 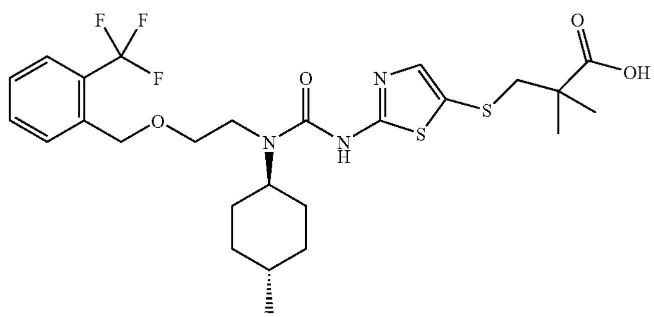 | 2,2-Dimethyl-3-(2-{3-(4-methyl-cyclohexyl)-3-[2-(2-trifluoromethyl-benzyloxy)-ethyl]-ureido}-thiazol-5-ylsulfanyl)-propionic acid | (J) |
| Be | 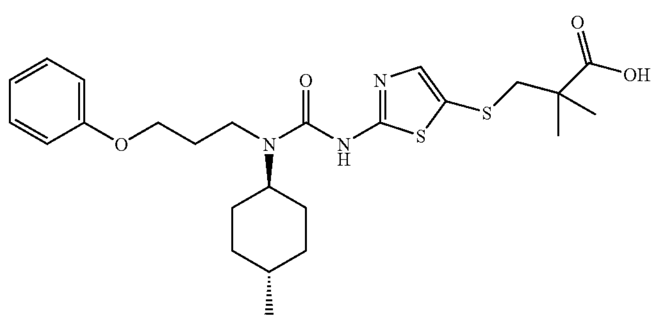 | 2,2-Dimethyl-3-{2-[3-(4-methyl-cyclohexyl)-3-(3-phenoxy-propyl)-ureido]-thiazol-5-ylsulfanyl}-propionic acid | (J) |
| Bf | 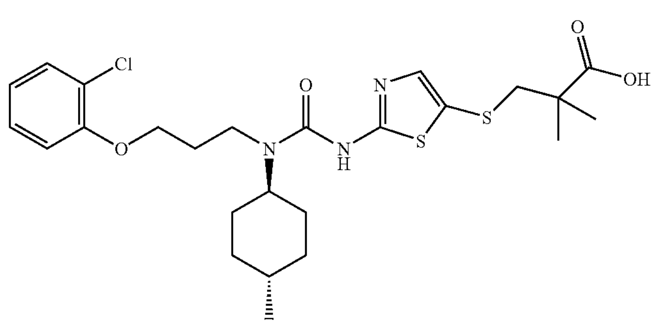 | 3-{2-[3-[3-(2-Chloro-phenoxy)-propyl]-3-(4-methyl-cyclohexyl)-ureido]-thiazol-5-ylsulfanyl}-2,2-dimethyl-propionic acid | (J) |

TABLE 1-continued

| Compound | Structure | Name | Method |
|---|---|---|---|
| Bg | 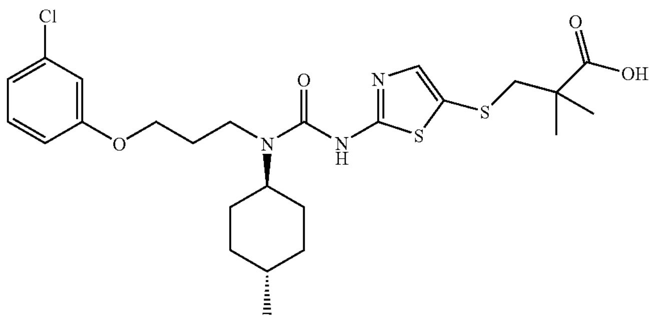 | 3-{2-[3-[3-(3-Chloro-phenoxy)-propyl]-3-(4-methyl-cyclohexyl)-ureido]-thiazol-5-ylsulfanyl}-2,2-dimethyl-propionic acid | (J) |
| Bh | 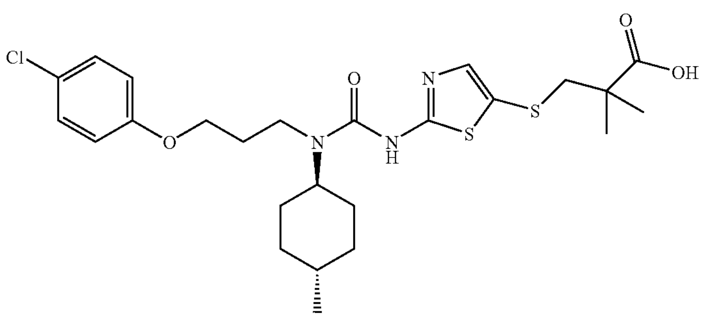 | 3-{2-[3-[3-(4-Chloro-phenoxy)-propyl]-3-(4-methyl-cyclohexyl)-ureido]-thiazol-5-ylsulfanyl}-2,2-dimethyl-propionic acid | (J) |
| Bi | 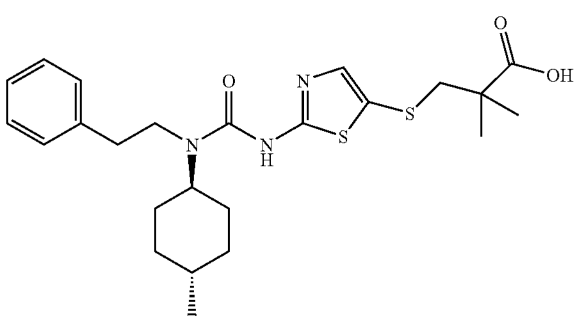 | 2,2-Dimethyl-3-{2-[3-(4-methyl-cyclohexyl)-3-phenethyl-ureido]-thiazol-5-ylsulfanyl}-propionic acid | (J) |
| Bj | 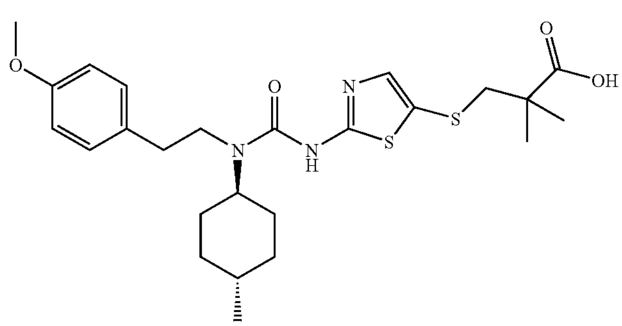 | 3-{2-[3-[2-(4-Methoxy-phenyl)-ethyl]-3-(4-methyl-cyclohexyl)-ureido]-thiazol-5-ylsulfanyl}-2,2-dimethyl-propionic acid | (J) |

TABLE 1-continued

| Compound | Structure | Name | Method |
|---|---|---|---|
| Bk | 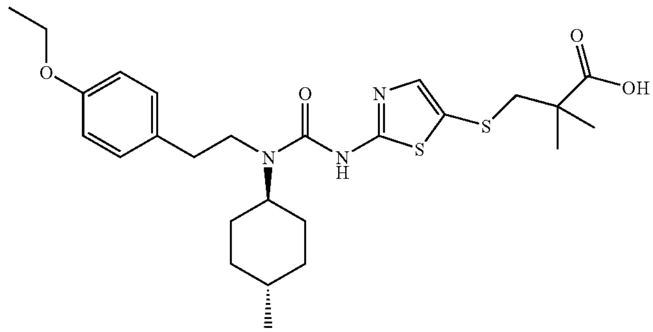 | 3-{2-[3-[2-(4-Ethoxy-phenyl)-ethyl]-3-(4-methyl-cyclohexyl)-ureido]-thiazol-5-ylsulfanyl}-2,2-dimethyl-propionic acid | (J) |
| Bl | 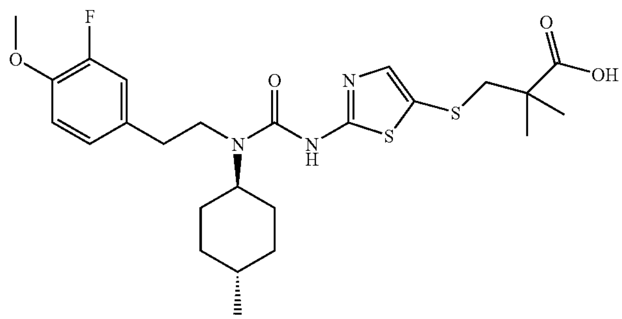 | 3-{2-[3-[2-(3-Fluoro-4-methoxy-phenyl)-ethyl]-3-(4-methyl-cyclohexyl)-ureido]-thiazol-5-ylsulfanyl}-2,2-dimethyl-propionic acid | (J) |
| Bm | 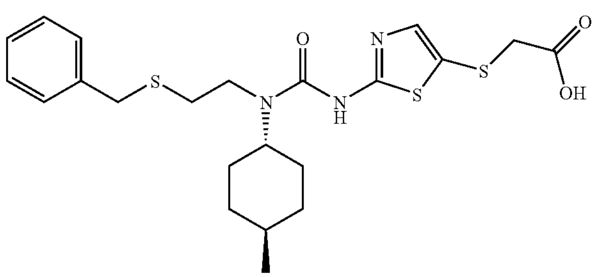 | {2-[3-(2-Benzylsulfanyl-ethyl)-3-(4-methyl-cyclohexyl)-ureido]-thiazol-5-ylsulfanyl}-acetic acid | (K) |
| Bn | 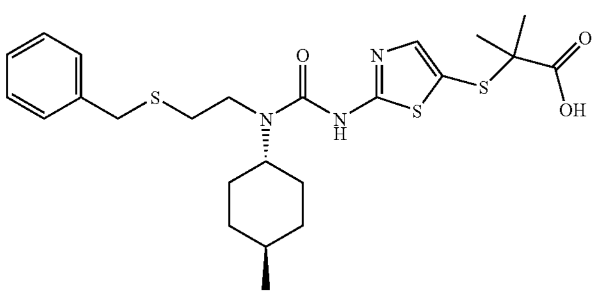 | 2-{2-[3-(2-Benzylsulfanyl-ethyl)-3-(4-methyl-cyclohexyl)-ureido]-thiazol-5-ylsulfanyl}-2-methyl-propionic acid | (K) |
| Bo | 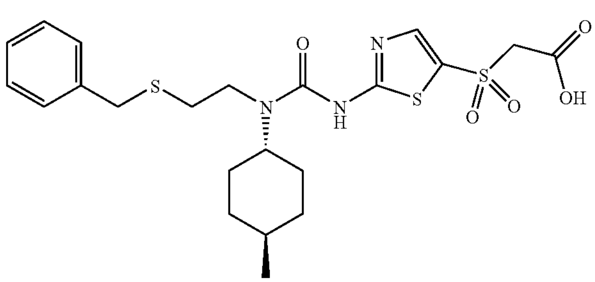 | {2-[3-(2-Benzylsulfanyl-ethyl)-3-(4-methyl-cyclohexyl)-ureido]-thiazole-5-sulfonyl}-acetic acid | (K) + (I) |

TABLE 1-continued

| Compound | Structure | Name | Method |
|---|---|---|---|
| Bp | 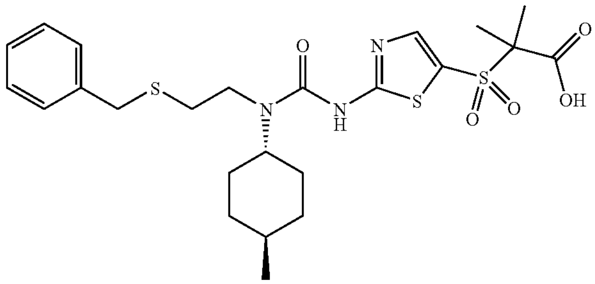 | 2-{2-[3-(2-Benzylsulfanyl-ethyl)-3-(4-methyl-cyclohexyl)-ureido]-thiazole-5-sulfonyl}-2-methyl-propionic acid | (K) + (I) |
| Bq | 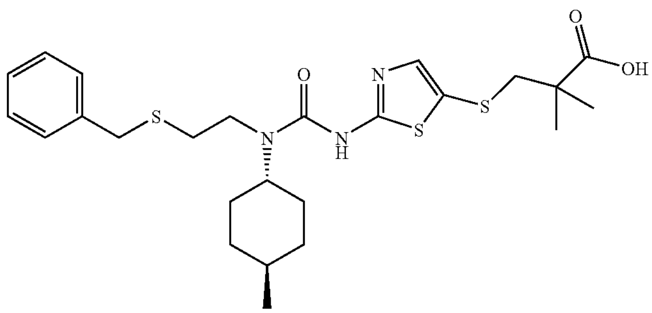 | 3-{2-[3-(2-Benzylsulfanyl-ethyl)-3-(4-methyl-cyclohexyl)-ureido]-thiazol-5-ylsulfanyl}-2,2-dimethyl-propionic acid | (K) + (J) |
| Br | 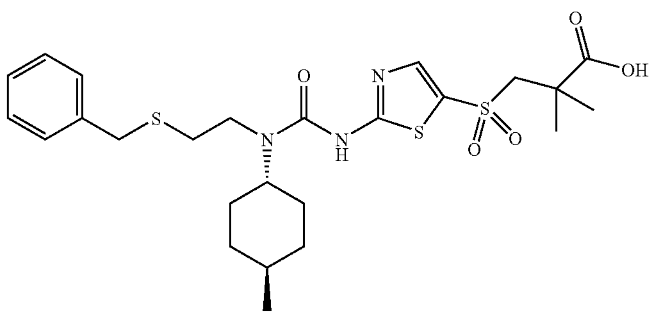 | 3-{2-[3-(2-Benzylsulfanyl-ethyl)-3-(4-methyl-cyclohexyl)-ureido]-thiazole-5-sulfonyl}-2,2-dimethyl-propionic acid | (K) + (I) |
| Bs | 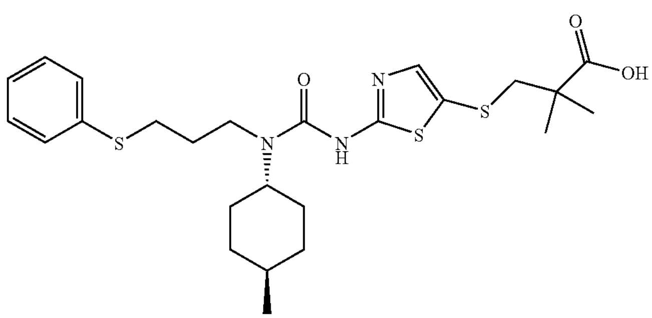 | 2,2-Dimethyl-3-{2-[3-(4-methyl-cyclohexyl)-3-(3-phenylsulfanyl-propyl)-ureido]-thiazol-5-ylsulfanyl}-propionic acid | (K) + (J) |
| Bt | 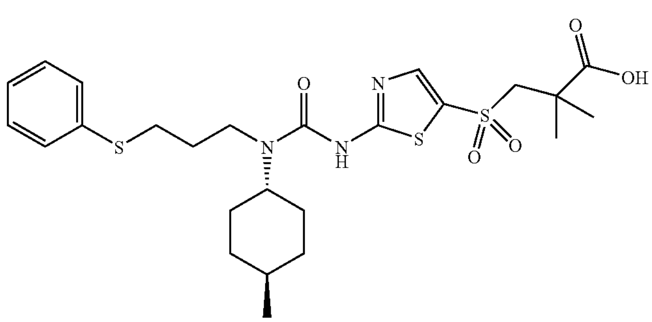 | 2,2-Dimethyl-3-{2-[3-(4-methyl-cyclohexyl)-3-(3-phenylsulfanyl-propyl)-ureido]-thiazole-5-sulfonyl}-propionic acid | (K) + (I) + (J) |

TABLE 1-continued

| Compound | Structure | Name | Method |
|---|---|---|---|
| Bu | 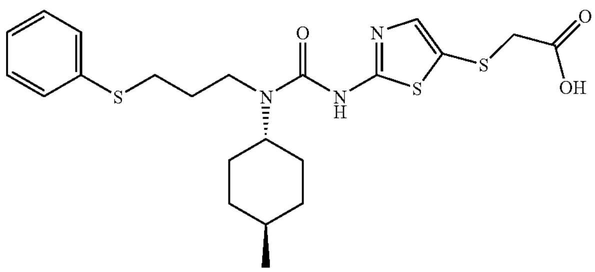 | {2-[3-(4-Methyl-cyclohexyl)-3-(3-phenylsulfanyl-propyl)-ureido]-thiazol-5-ylsulfanyl}-acetic acid | (K) |
| Bv | 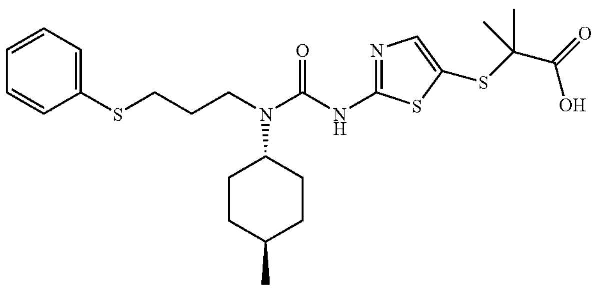 | 2-Methyl-2-{2-[3-(4-methyl-cyclohexyl)-3-(3-phenylsulfanyl-propyl)-uredo]-thiazol-5-ylsulfanyl}-propionic acid | (K) |
| Bw | 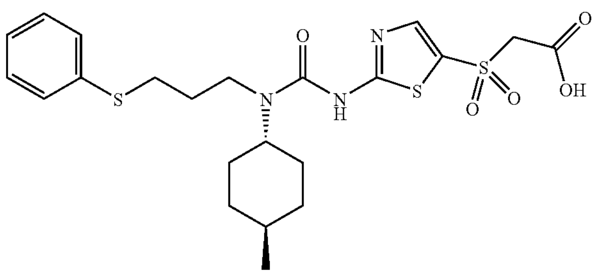 | {2-[3-(4-Methyl-cyclohexyl)-3-(3-phenylsulfanyl-propyl)-ureido]-thiazole-5-sulfonyl}-acetic acid | (K) + (I) |
| Bx | 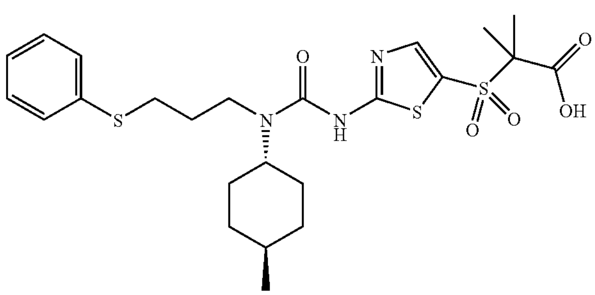 | 2-Methyl-2-{2-[3-(4-methyl-cyclohexyl)-3-(3-phenylsulfanyl-propyl)-ureido]-thiazole-5-sulfonyl}-propionic acid | (K) + (I) |

The invention claimed is:

1. A compound of formula (I)

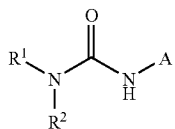

wherein $R^1$ is phenyl optionally substituted with one or more substituents $R^3$, $R^4$, $R^5$ and $R^6$;

$R^2$ is cyclopentylmethyl or cyclohexylmethyl, each of which may optionally be substituted with $R^{30}$;

$R^3$, $R^4$, $R^5$, $R^6$, and $R^{30}$ are independently selected from the group consisting of halogen, nitro, cyano, hydroxy, carboxy, and —$CF_3$; or —$NR^{10}R^{11}$; or $C_{1-6}$alkyl, $C_{2-6}$-alkenyl, $C_{2-6}$-alkynyl, $C_{3-8}$-cycloalkyl, $C_{3-8}$-cycloalkyl-$C_{1-6}$-alkyl, $C_{3-8}$-cycloalkyl-$C_{3-6}$-alkenyl, aryl, aryl-$C_{1-6}$-alkyl, aryl-$C_{2-6}$-alkenyl, heteroaryl-$C_{1-6}$-alkyl, heteroaryl-$C_{2-6}$-alkenyl, heterocyclyl-$C_{1-6}$-alkyl, heterocyclyl-$C_{2-6}$-alkenyl, $C_{1-6}$-alkoxy, $C_{3-6}$-alkenyloxy, $C_{3-8}$-cycloalkoxy, $C_{3-6}$-cycloalkyl-$C_{1-6}$-alkoxy, $C_{3-8}$-cycloalkenyl-$C_{1-6}$-alkoxy, $C_{3-8}$-heterocyclyl-$C_{1-6}$-alkoxy, fused aryl-$C_{3-8}$-cycloalkenyl-$C_{1-6}$-alkoxy, $C_{3-8}$-cycloalkyl-$C_{3-6}$-alkenyloxy, $C_{3-8}$-cycloalkenyl-$C_{3-6}$-alkenyloxy, $C_{3-8}$-heterocyclyl-$C_{3-6}$-alkenyloxy, fused $C_{3-8}$-cycloalkyl-aryloxy, fused heterocyclyl-aryloxy, fused aryl-$C_{3-8}$-cycloalkenyl-$C_{3-6}$-alkenyloxy, aryl-$C_{1-6}$-alkoxy, aryl-$C_{3-6}$-alkenyloxy, heteroaryl, heteroaryl-$C_{1-6}$-alkoxy, heteroaryl-$C_{3-6}$-alkenyloxy, aryloxy, heteroaryloxy, $C_{1-6}$-alkylthio, $C_{3-6}$-alkenylthio, $C_{3-6}$cycloalkyl-$C_{1-6}$-alkylthio, $C_{3-8}$-cycloalkenyl-$C_{1-6}$-alkylthio, $C_{3-8}$-heterocyclyl-$C_{1-6}$-alkylthio, fused aryl-$C_{3-8}$-cycloalkenyl-$C_{1-6}$-alkylthio, $C_{3-8}$-cycloalkyl-$C_{3-6}$-alkenylthio, $C_{3-8}$-cycloalkenyl-$C_{3-6}$-alkenylthio, $C_{3-8}$-heterocyclyl-$C_{3-6}$-alkenylthio, fused aryl-$C_{3-8}$-cycloalkenyl-$C_{3-6}$-alkenylthio, aryl-$C_{1-6}$-alkylthio, aryl-$C_{3-6}$-alkenylthio, heteroaryl-$C_{1-6}$-alkthio, heteroaryl-$C_{3-6}$-alkenylthio, arylthio, heteroarylthio amino-$C_{1-6}$-alkyl, $C_{1-6}$-alkylamino-$C_{1-6}$-alkyl, di-($C_{1-6}$-alkyl)amino-$C_{1-6}$-alkyl, $C_{1-6}$-alkylsulfamoyl, di($C_{1-6}$alkyl)sulfamoyl, $C_{1-6}$-alkylsulfinamoyl and di($C_{1-6}$-alkyl)sulfinamoyl each of which is optionally substituted with one or more substituents independently selected from $R^{12}$; or
—C(O)—$R^{27}$, —S(O)$_2$—$R^{27}$, —C(O)—$NR^{13}R^{14}$, —S(O)$_2$—$NR^{13}R^{14}$, and —$C_{1-6}$-alkyl-C(O)—$NR^{13}R^{14}$; or two substituents selected from $R^3$, $R^4$, $R^5$ and $R^6$ attached to the same or adjacent atoms together may form a radical —O—(CH$_2$)$_{1-3}$—O—;

$R^{10}$ and $R^{11}$ are independently selected from the group consisting of hydrogen, $C_{1-6}$-alkyl, —C(O)—$C_{1-6}$-alkyl, —C(O)—O—$C_{1-6}$-alkyl, —C(O)—$C_{3-8}$-cycloalkyl, carboxy-$C_{1-6}$-alkyl, —C(O)—$C_{1-6}$-alkyl-C(O)OH, —S(O)$_2$—$C_{1-6}$-alkyl, and aryl, each of which is optionally substituted with one or more halogens;

$R^{27}$ is $C_{1-6}$-alkyl, $C_{1-6}$-alkoxy, $C_{2-6}$-alkenyl, $C_{2-6}$-alkynyl, $C_{3-8}$-cycloalkyl, $C_{3-8}$-cycloalkyl-$C_{1-6}$-alkyl, $C_{3-8}$-cycloalkyl-$C_{2-6}$-alkenyl, aryl, aryl-$C_{1-6}$-alkyl, aryloxy-$C_{1-6}$-alkyl, aryl-$C_{2-6}$-alkenyl, heteroaryl, $C_{3-8}$-heterocyclyl, heteroaryl-$C_{1-6}$-alkyl, $C_{3-8}$-heterocyclyl-$C_{1-6}$-alkyl, heteroaryloxy-$C_{1-6}$-alkyl, carboxy-$C_{1-6}$-alkyl, carboxy-$C_{2-6}$-alkenyl, $C_{1-6}$-alkoxy-$C_{1-6}$-alkyl, $C_{1-6}$-alkoxy-$C_{2-6}$-alkenyl, $C_{1-6}$-alkylthio-$C_{1-6}$-alkyl, $R^{10}$HN—$C_{1-6}$-alkyl, $R^{10}R^{11}$—N—$C_{1-6}$-alkyl, $R^{10}R^{11}$—N—$C_{2-6}$-alkenyl, $R^{10}R^{11}$—N—S(O)$_2$—$C_{1-6}$-alkyl, $R^{10}R^{11}$—N—C(O)—$C_{1-6}$-alkyl, $C_{1-6}$-alkyl-C(O)—NH—$C_{1-6}$-alkyl, aryl-C(O)—NH—$C_{1-6}$-alkyl, heteroaryl-C(O)—NH—$C_{1-6}$-alkyl, $C_{3-8}$-cycloalkyl-C(O)—NH—$C_{1-6}$-alkyl, $C_{1-6}$-alkyl-S(O)$_2$—NH—$C_{1-6}$-alkyl, aryl-S(O)$_2$—NH—$C_{1-6}$-alkyl, heteroaryl-S(O)$_2$—NH—$C_{1-6}$-alkyl, or $C_{3-8}$-cycloalkyl-S(O)$_2$—NH—$C_{1-6}$-alkyl, each of which is optionally substituted with one or more substituents independently selected from $R^{12}$;

$R^{12}$ is halogen, cyano, hydroxy, —C(O)—O—$C_{1-6}$-alkyl, carboxy, —CF$_3$, $C_{1-6}$-alkyl, aryl, heteroaryl, $C_{1-6}$-alkoxy, $C_{2-6}$-alkenyloxy, $C_{3-8}$-cycloalkyloxy, $C_{3-8}$-cycloalkenyloxy, $C_{3-8}$-heterocyclyloxy, aryloxy, heteroaryloxy, aryl-$C_{1-6}$-alkoxy, aryl-$C_{1-6}$-alkenyloxy, heteroaryl-$C_{1-6}$-alkoxy, heteroaryl-$C_{1-6}$-alkenyloxy, $C_{3-8}$-cycloalkyl-$C_{1-6}$-alkoxy, $C_{3-8}$-cycloalkyl-$C_{1-6}$-alkenyloxy, $C_{3-8}$-heterocyclyl-$C_{1-6}$-alkoxy, $C_{3-8}$-heterocyclyl-$C_{1-6}$-alkenyloxy, fused aryl-$C_{3-8}$-cycloalkyl-$C_{1-6}$-alkoxy, fused aryl-$C_{3-8}$-cycloalkyl-$C_{1-6}$-alkenyloxy, $C_{1-6}$-alkylthio, $C_{2-6}$-alkenylthio, $C_{3-8}$-cycloalkylthio, $C_{3-8}$-cycloalkenylthio, $C_{3-8}$-heterocyclylthio, arylthio, heteroarylthio, aryl-$C_{1-6}$-alkylthio, aryl-$C_{1-6}$-alkenylhio, heteroaryl-$C_{1-6}$-alkyltio, heteroaryl-$C_{1-6}$-alkenylthio, $C_{3-8}$-cycloalkyl-$C_{1-6}$-alkylthio, $C_{3-8}$-cycloalkyl-$C_{1-6}$-alkenylthio, $C_{3-8}$-heterocyclyl-$C_{1-6}$-alkylthio, $C_{3-8}$-heterocyclyl-$C_{1-6}$-alkenylthio, fused aryl-$C_{3-8}$-cycloalkyl-$C_{1-6}$-alkylthio, fused aryl-$C_{3-8}$-cycloalkyl-$C_{1-6}$-alkenylthio, —$NR^{10}R^{11}$, —S(O)$_2$CH$_3$, —S(O)$_2$CF$_3$ or —S(O)$_2$NH$_2$ each of which is optionally substituted with one or more substituents independently selected from $R^{38}$;

$R^{13}$ and $R^{14}$ are independently selected from the group consisting of hydrogen, $C_{1-6}$-alkyl, hydroxy-$C_{1-6}$-alkyl, carboxy-$C_{1-6}$-alkyl, aryl, and heteroaryl, each of which is optionally substituted with one or more substituents independently selected from $R^{15}$; or $R^{13}$ and $R^{14}$ together with the nitrogen to which they are attached form a 3 to 8 membered heterocyclic ring with the said nitrogen atom, the heterocyclic ring optionally containing one or two further heteroatoms selected from the group consisting of nitrogen, oxygen and sulphur;

$R^{15}$ is halogen, cyano, hydroxy, carboxy, —CF$_3$, $C_{1-6}$-alkyl, —S(O)$_2$CH$_3$, or —S(O)$_2$NH$_2$;

$R^{38}$ is halogen or $C_{1-6}$-alkyl;

A is

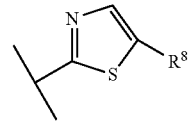

; wherein $R^8$ is selected from the group consisting of methylthio, isopropylthio, ethylthio, and 2-methylpropylthio each of which is substituted with one or more substituents independently selected from $R^{34}$ $R^{34}$ is selected from the group consisting of halogen, nitro, cyano, hydroxy, carboxy, and —CF$_3$; or carboxy-$C_{1-6}$-alkyl, —$C_{1-6}$-alkyl-C(O)—O—$C_{1-6}$-alkyl, —C(O)—O—$C_{1-6}$-alkyl and —C(O)—$C_{1-6}$-alkyl-C(O)—$C_{1-6}$-alkyl each optionally substituted with one or more halogens;

or a salt thereof with a pharmaceutically acceptable acid or base, or a tautomeric form thereof.

2. A compound according to claim 1 which is

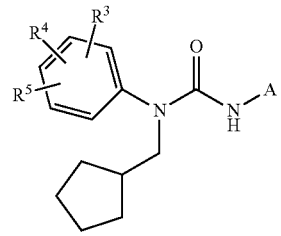

or a salt thereof with a pharmaceutically acceptable acid or base.

3. A compound according to claim 1 wherein $R^3$, $R^4$, $R^5$, $R^6$, and $R^{30}$ are independently selected from the group consisting of halogen, hydroxy, carboxy, and —CF$_3$; or —$NR^{10}R^{11}$; or $C_{1-6}$-alkyl, $C_{2-6}$-alkenyl, $C_{1-6}$-alkoxy, $C_{3-6}$-alkenyloxy, $C_{3-8}$-cycloalkyl, $C_{3-8}$-cycloalkoxy, $C_{3-6}$-cycloalkyl-$C_{1-6}$-alkoxy, $C_{3-8}$-cycloalkenyl-$C_{1-6}$-alkoxy, and phenyl-$C_{1-6}$-alkoxy, each of which is optionally substituted with one or more substituents independently selected from $R^{12}$; or Phenyl, phenoxy, benzyloxy, indanyloxy, benzo[1,3]dioxolyloxy, phenylthio, and benzylthio; or
—C(O)—R$^{27}$, —S(O)$_2$—R$^{27}$, —C(O)—NR$^{13}$R$^{14}$, and —S(O)$_2$—NR$^{13}$R$^{14}$; or
two substituents selected from R$^3$, R$^4$, R$^5$ and R$^6$ attached to the same or adjacent atoms together may form a radical —O—(CH$_2$)$_{1-3}$—O—.

4. A compound according to claim 3 wherein R$^3$, R$^4$, R$^5$, R$^6$, and R$^{30}$ are independently selected from the group consisting of halogen, —CF$_3$, C$_{1-6}$-alkyl, C$_{2-6}$-alkenyl, C$_{1-6}$-alkoxy, phenyl, phenoxy, benzyloxy, indanyloxy, benzo[1,3]dioxolyloxy, phenylthio, benzylthio, phenyl-C$_{1-6}$-alkoxy, C$_{3-8}$-cycloalkyl, C$_{3-8}$-cycloalkoxy, and C$_{3-6}$-cycloalkyl-C$_{1-6}$-alkoxy, each of which is optionally substituted with one or more substituents independently selected from R$^{12}$; or —NR$^{10}$R$^{11}$, —C(O)—R$^{27}$, —S(O)$_2$—R$^{27}$, —C(O)—NR$^{13}$R$^{14}$, and —S(O)$_2$—NR$^{13}$R$^{14}$.

5. A compound according to claim 4 wherein R$^3$, R$^4$, R$^5$ and R$^6$ are independently selected from the group consisting of halogen, CF$_3$, C$_{1-6}$-alkyl, C$_{1-6}$-alkoxy, phenoxy, benzyloxy, phenylthio, benzylthio, C$_{3-8}$-cycloalkyl, C$_{3-8}$-cycloalkoxy, and C$_{3-6}$-cycloalkyl-C$_{1-6}$-alkoxy, each of which is optionally substituted with one or more substituents independently selected from R$^{12}$; or —NR$^{10}$R$^{11}$, —C(O)—R$^{27}$, —S(O)$_2$—R$^{27}$, —C(O)—NR$^{13}$R$^{14}$, and —S(O)$_2$—NR$^{13}$R$^{14}$.

6. A compound according to claim 4 wherein R$^{30}$ is selected from the group consisting of halogen, —CF$_3$, C$_{1-6}$-alkyl, C$_{2-6}$-alkenyl, C$_{1-6}$-alkoxy, phenyl, phenoxy, benzyloxy, phenylthio, benzylthio, C$_{3-8}$-cycloalkyl, C$_{3-8}$-cycloalkoxy, and C$_{3-6}$-cycloalkyl-C$_{1-6}$-alkoxy, each of which is optionally substituted with one or more substituents independently selected from R$^{12}$; or —C(O)—R$^{27}$, —S(O)$_2$—R$^{27}$, —C(O)—NR$^{13}$R$^{14}$, and —S(O)$_2$—NR$^{13}$R$^{14}$.

7. A compound according to claim 4 wherein R$^3$, R$^4$, R$^5$, R$^6$, and R$^{30}$ are independently selected from the group consisting of F, Cl, Br, —CF$_3$, methyl, ethyl, propyl, butyl, isopropyl, tert-butyl, ethenyl, propenyl, butenyl, cyclopropyl, cyclobutyl, cyclopentyl, cyclohexyl, phenyl, methoxy, ethoxy, propoxy, butoxy, isopropoxy, isobutoxy, tert-butoxy, cyclohexyloxy, phenoxy, benzyloxy, indanyloxy, benzo[1,3]dioxolyloxy, cyclopropyl-methoxy, cyclopropyl-ethoxy, cyclopropyl-propoxy, cyclobutyl-methoxy, cyclobutyl-ethoxy, cyclobutyl-propoxy, cyclopentyl-methoxy, cyclopentyl-ethoxy, cyclopentyl-propoxy, cyclohexyl-methoxy, cyclohexyl-ethoxy, cyclohexyl-propoxy, cycloheptyl-methoxy, cycloheptyl-ethoxy, cycloheptyl-propoxy, phenylethoxy, phenylthio and benzylthio, each of which is optionally substituted with one or more substituents independently selected from R$^{12}$; or —NR$^{10}$R$^{11}$, —C(O)—R$^{27}$, —S(O)$_2$—R$^{27}$, —C(O)—NR$^{13}$R$^{14}$, and —S(O)$_2$—NR$^{13}$R$^{14}$.

8. A compound according to claim 7 wherein R$^3$, R$^4$, R$^5$ and R$^6$ are independently selected from the group consisting of F, Cl, Br, —CF$_3$, methyl, ethyl, propyl, isopropyl, methoxy, ethoxy, propoxy, isopropoxy, isobutoxy, tert-butoxy, cyclohexyloxy, phenoxy, benzyloxy, indanyloxy, benzo[1,3]dioxolyloxy, phenylethoxy, phenylthio and benzylthio, each of which is optionally substituted with one or more substituents independently selected from R$^{12}$; and —NR$^{10}$R$^{11}$, —C(O)—R$^{27}$, —S(O)$_2$—R$^{27}$, —C(O)—NR$^{13}$R$^{14}$, or —S(O)$_2$—NR$^{13}$R$^{14}$.

9. A compound according to claim 1 wherein R$^{10}$ and R$^{11}$ are independently selected from the group consisting of hydrogen, C$_{1-6}$-alkyl, —C(O)—C$_{1-6}$-alkyl, carboxy-C$_{1-6}$-alkyl, C(O)—C$_{3-8}$-cycloalkyl, and S(O)$_2$—C$_{1-6}$-alkyl.

10. A compound according to claim 9 wherein R$^{10}$ and R$^{11}$ are independently selected from the group consisting of hydrogen, —C(O)—C$_{1-6}$-alkyl, —C(O)—C$_{3-8}$-cycloalkyl, and S(O)$_2$—C$_{1-6}$-alkyl.

11. A compound according to claim 9 wherein R$^{10}$ and R$^{11}$ are independently selected from the group consisting of hydrogen, methyl, ethyl, propyl, butyl, —C(O)-methyl, —C(O)-ethyl, —C(O)-propyl, —C(O)-isopropyl, —C(O)-butyl, —C(O)-cyclopentyl, —S(O)$_2$-methyl, carboxy-ethyl, carboxy-propyl and carboxy-butyl.

12. A compound according to claim 1 wherein R$^{27}$ is C$_{1-6}$-alkyl, C$_{1-6}$-alkoxy, C$_{2-6}$-alkenyl, C$_{2-6}$-alkynyl, C$_{3-8}$-cycloalkyl, C$_{3-8}$-cycloalkyl-C$_{1-6}$-alkyl, aryl, aryl-C$_{1-6}$-alkyl, aryl-C$_{2-6}$-alkenyl, heteroaryl, heteroaryl-C$_{1-6}$-alkyl, carboxy-C$_{1-6}$-alkyl, C$_{1-6}$-alkoxy-C$_{1-6}$-alkyl, C$_{1-6}$-alkylthio-C$_{1-6}$-alkyl, R$^{10}$HN—C$_{1-6}$-alkyl, R$^{10}$R$^{11}$N—C$_{1-6}$-alkyl, R$^{10}$R$^{11}$N—S(O)$_2$—C$_{1-6}$-alkyl, or R$^{10}$R$^{11}$N—C(O)—C$_{1-6}$-alkyl, each of which is optionally substituted with one or more substituents independently selected from R$^{12}$.

13. A compound according to claim 12 wherein R$^{27}$ is C$_{1-6}$-alkyl, C$_{1-6}$-alkoxy, C$_{3-8}$-cycloalkyl, C$_{3-8}$-cycloalkyl-C$_{1-6}$-alkyl, aryl-C$_{2-6}$-alkenyl, aryl, heteroaryl, aryl-C$_{1-6}$-alkyl, heteroaryl-C$_{1-6}$-alkyl, carboxy-C$_{1-6}$-alkyl, C$_{1-6}$-alkoxy-C$_{1-6}$-alkyl, R$^{10}$HN—C$_{1-6}$-alkyl, R$^{10}$R$^{11}$N—C$_{1-6}$-alkyl, R$^{10}$R$^{11}$N—S(O)$_2$—C$_{1-6}$-alkyl, or R$^{10}$R$^{11}$N—C(O)—C$_{1-6}$-alkyl, each of which is optionally substituted with one or more substituents independently selected from R$^{12}$.

14. A compound according to claim 13 wherein R$^{27}$ is C$_{1-6}$-alkyl, C$_{1-6}$-alkoxy, C$_{3-8}$-cycloalkyl, C$_{3-8}$-cycloalkyl-C$_{1-6}$-alkyl, aryl, heteroaryl-C$_{1-6}$-alkyl, aryl-C$_{1-6}$-alkyl, C$_{1-6}$-alkoxy-C$_{1-6}$-alkyl, carboxy-C$_{1-6}$-alkyl, or heteroaryl, each of which is optionally substituted with one or more substituents independently selected from R$^{12}$.

15. A compound according to claim 14 wherein R$^{27}$ is methyl, ethyl, propyl, n-butyl, isobutyl, 2,2,2-trifluoroethyl, cyclopropyl, cyclopentyl, cyclopropylmethyl, phenyl, pyridyl, thiophene, imidazole, or thiazole, each of which is optionally substituted with one or more substituents independently selected from R$^{12}$.

16. A compound according to claim 15 wherein R$^{27}$ is methyl, ethyl, propyl, n-butyl, isobutyl, 2,2,2-trifluoroethyl, cyclopropyl, cyclopentyl, cyclopropylmethyl, phenyl, pyridyl, thiophene, imidazole, or thiazole.

17. A compound according to claim 16 wherein R$^{27}$ is methyl, ethyl, or propyl.

18. A compound according to claim 1 wherein R$^{12}$ is halogen, —CF$_3$, —CN, C$_{1-6}$-alkyl, C$_{1-6}$-alkoxy, C$_{1-6}$-alkylthio, C$_{2-6}$-alkenyloxy, C$_{3-8}$-cycloalkyloxy, C$_{3-8}$-cycloalkenyloxy, aryloxy, aryl-C$_{1-6}$-alkoxy, aryl-C$_{1-6}$-alkenyloxy, C$_{3-8}$-cycloalkyl-C$_{1-6}$-alkoxy, C$_{3-8}$-cycloalkyl-C$_{1-6}$-alkenyloxy, C$_{3-8}$-heterocyclyl-C$_{1-6}$-alkoxy, or C$_{3-8}$-heterocyclyl-C$_{1-6}$-alkenyloxy, each of which is optionally substituted with one or more substituents independently selected from R$^{38}$; or NR$^{10}$R$^{11}$, or —S(O)$_2$—C$_{1-6}$-alkyl.

19. A compound according to claim 18 wherein R$^{12}$ is halogen, —CF$_3$, —CN, C$_{1-6}$-alkyl, C$_{1-6}$-alkoxy, C$_{1-6}$-alkylthio, C$_{3-8}$-cycloalkyloxy, aryloxy, aryl-C$_{1-6}$-alkoxy, C$_{3-8}$-cycloalkyl-C$_{1-6}$-alkoxy, or C$_{3-8}$-heterocyclyl-C$_{1-6}$-alkoxy, each of which is optionally substituted with one or more substituents independently selected from R$^{38}$; or NR$^{10}$R$^{11}$, or —S(O)$_2$—C$_{1-6}$-alkyl.

20. A compound according to claim 19 wherein R$^{12}$ is F, Cl, Br, —CF$_3$, —CN, methyl, ethyl, propyl, butyl, isopropyl, tert-butyl, methoxy, methylthio, ethoxy, propoxy, butoxy, phenoxy, benzyloxy, cyclopropyl-methoxy, cyclopropylethoxy, cyclobutyl-methoxy, cyclobutyl-ethoxy, cyclopentyl-methoxy, cyclopentyl-ethoxy, cyclohexyl-methoxy, cyclohexyl-ethoxy, —NHC(O)CH$_3$, or —S(O)$_2$—CH$_3$.

21. A compound according to claim 20 wherein R$^{12}$ is F, Cl, Br, —CF$_3$, —CN, methyl, ethyl, isopropyl, tert-butyl, methoxy, methylthio, ethoxy, cyclopropyl-methoxy, —NHC(O)CH$_3$, or —S(O)$_2$—CH$_3$.

22. A compound according to claim 1 wherein R$^{13}$ and R$^{14}$ are independently selected from the group consisting of hydrogen and C$_{1-6}$-alkyl; or R$^{13}$ and R$^{14}$ together with the nitrogen to which they are attached form a 3 to 8 membered heterocyclic ring with the said nitrogen atom.

23. A compound according to claim 1 wherein R$^{15}$ is selected from the group consisting of F, Cl, Br, hydroxy, carboxy, —CF$_3$, and C$_{1-6}$-alkyl.

24. A compound according to claim 1 wherein R$^{38}$ F, Cl, Br, methyl or ethyl.

25. A compound according to claim 1 wherein R$^{34}$ is carboxy, carboxy-C$_{1-6}$-alkyl, or —C(O)—O—C$_{1-6}$-alkyl.

26. A compound according to claim 25 wherein R$^{34}$ is carboxy.

* * * * *

UNITED STATES PATENT AND TRADEMARK OFFICE
CERTIFICATE OF CORRECTION

PATENT NO. : 7,884,210 B2 Page 1 of 1
APPLICATION NO. : 11/994862
DATED : February 8, 2011
INVENTOR(S) : Jesper Lau et al.

It is certified that error appears in the above-identified patent and that said Letters Patent is hereby corrected as shown below:

In column 202, line 57, in Claim 1, delete "$C_{1-6}$alkyl," and insert -- $C_{1-6}$-alkyl, --, therefor.

In column 203, line 6, in Claim 1, delete "$C_{3-6}$cycloalkyl" and insert -- $C_{3-6}$-cycloalkyl --, therefor.

In column 203, line 16, in Claim 1, delete "di($C_{1-6}$alkyl)" and insert -- di($C_{1-6}$-alkyl) --, therefor.

In column 203, line 64, in Claim 1, delete "$C_{1-6}$-alkyltio," and insert -- $C_{1-6}$-alkylthio, --, therefor.

In column 204, line 63, in Claim 3, after "cycloalkoxy," insert -- $C_{3-8}$-cycloalkyl-$C_{1-6}$-alkyl, --.

In column 208, line 4, in Claim 24, delete "$R^{38}$F," and insert -- $R^{38}$ is F, --, therefor.

Signed and Sealed this
Twentieth Day of September, 2011

David J. Kappos
*Director of the United States Patent and Trademark Office*